(12) United States Patent
Cioanta et al.

(10) Patent No.: US 12,364,493 B2
(45) Date of Patent: Jul. 22, 2025

(54) METHOD OF TREATING A BLOOD VESSEL WITH MULTIPLE SHOCK WAVE DISCHARGE POINTS IN A CATHETER BALLOON

(71) Applicant: SANUWAVE, INC., Suwanee, GA (US)

(72) Inventors: Iulian Cioanta, Milton, GA (US); Christopher Cashman, Duluth, GA (US)

(73) Assignee: SANUWAVE, INC., Alpharetta, GA (US)

( * ) Notice: Subject to any disclaimer, the term of this patent is extended or adjusted under 35 U.S.C. 154(b) by 0 days.

(21) Appl. No.: 19/034,430

(22) Filed: Jan. 22, 2025

(65) Prior Publication Data

US 2025/0160863 A1    May 22, 2025

Related U.S. Application Data

(60) Continuation of application No. 18/435,508, filed on Feb. 7, 2024, now Pat. No. 12,239,332, which is a (Continued)

(51) Int. Cl.
*A61B 17/22* (2006.01)
*A61B 17/225* (2006.01)
(Continued)

(52) U.S. Cl.
CPC .. *A61B 17/22012* (2013.01); *A61B 17/22004* (2013.01); *A61B 17/2202* (2013.01);
(Continued)

(58) Field of Classification Search
CPC ........ A61B 17/22012; A61B 17/22004; A61B 17/2202; A61B 17/22022;
(Continued)

(56) References Cited

U.S. PATENT DOCUMENTS

| 4,528,853 A | 7/1985 | Lerch et al. |
| 4,608,983 A | 9/1986 | Mueller et al. |

(Continued)

FOREIGN PATENT DOCUMENTS

| DE | 3038445 C2 | 6/1990 |
| EP | 0 238 772 | 9/1987 |

(Continued)

OTHER PUBLICATIONS

Christ, C., et al., "Boosting skin elasticity and revitalising the dermis in cellulite and connective tissue weakness by means of extracorporeal Acoustic Wave Therapy (AWT)," http://www.cellulite-therapy.com, Jan. 2008, AWT—Acoustic Wave Therapy, Switzerland.

(Continued)

*Primary Examiner* — Eugene T Wu
(74) *Attorney, Agent, or Firm* — Polsinelli PC

(57) ABSTRACT

A target location of a blood vessel is treated by providing an apparatus that includes a catheter and multiple shock wave discharge points positioned within a balloon along the catheter between proximal and distal ends of the catheter, wherein the distal end extends distally beyond the balloon and the proximal end extends proximally beyond the balloon. Shock waves are created by activating an electronic controller connected to an electrode at each shock wave discharge point. The shock waves are applied through the balloon to treat the target location with the shock waves.

29 Claims, 84 Drawing Sheets

Related U.S. Application Data continuation of application No. 18/221,303, filed on Jul. 12, 2023, now Pat. No. 11,925,366, which is a continuation of application No. 17/188,812, filed on Mar. 1, 2021, now abandoned, which is a division of application No. 16/860,544, filed on Apr. 28, 2020, now Pat. No. 11,666,348, which is a division of application No. 14/874,650, filed on Oct. 5, 2015, now Pat. No. 10,639,051, which is a continuation of application No. 14/272,155, filed on May 7, 2014, now Pat. No. 10,058,340, which is a division of application No. 14/036,461, filed on Sep. 25, 2013, now Pat. No. 9,161,768, which is a division of application No. 12/832,932, filed on Jul. 8, 2010, now Pat. No. 8,556,813.

(60) Provisional application No. 61/223,919, filed on Jul. 8, 2009.

(51) Int. Cl.
  *A61B 18/24* (2006.01)
  *A61B 18/26* (2006.01)
  *A61H 9/00* (2006.01)
  *A61H 23/00* (2006.01)
  *G10K 11/28* (2006.01)
  *A61B 17/00* (2006.01)
  *A61B 17/221* (2006.01)
  *A61N 7/00* (2006.01)

(52) U.S. Cl.
  CPC .. *A61B 17/22022* (2013.01); *A61B 17/22029* (2013.01); *A61B 17/225* (2013.01); *A61B 18/245* (2013.01); *A61B 18/26* (2013.01); *A61H 9/0057* (2013.01); *A61H 23/008* (2013.01); *G10K 11/28* (2013.01); *A61B 2017/00867* (2013.01); *A61B 17/22* (2013.01); *A61B 2017/22014* (2013.01); *A61B 2017/22024* (2013.01); *A61B 2017/22025* (2013.01); *A61B 2017/22039* (2013.01); *A61B 2017/22051* (2013.01); *A61B 2017/22054* (2013.01); *A61B 2017/22067* (2013.01); *A61B 2017/22079* (2013.01); *A61B 2017/22082* (2013.01); *A61B 2017/22084* (2013.01); *A61B 2017/2212* (2013.01); *A61B 2017/2253* (2013.01); *A61B 17/2255* (2013.01); *A61H 2201/14* (2013.01); *A61H 2201/1664* (2013.01); *A61N 2007/0008* (2013.01)

(58) Field of Classification Search
  CPC ............ A61B 17/22029; A61B 17/225; A61B 18/245; A61B 18/26; A61B 17/22; A61B 17/2255; A61B 2017/00867; A61B 2017/22014; A61B 2017/22024; A61B 2017/22025; A61B 2017/22039; A61B 2017/22051; A61B 2017/22054; A61B 2017/22067; A61B 2017/22079; A61B 2017/22082; A61B 2017/22084; A61B 2017/2212; A61B 2017/2253; A61H 9/0057; A61H 23/008; A61H 2201/14; A61H 2201/1664; G10K 11/28; A61N 2007/0008

See application file for complete search history.

(56) References Cited

U.S. PATENT DOCUMENTS

| | | |
|---|---|---|
| 4,639,904 A | 1/1987 | Riedlinger |
| 4,696,299 A | 9/1987 | Shene et al. |
| 4,730,614 A | 3/1988 | Lacruche et al. |
| 4,836,191 A | 6/1989 | Noske et al. |
| 4,866,330 A | 9/1989 | Lacruche et al. |
| 4,868,791 A | 9/1989 | Cathignol et al. |
| 4,901,709 A | 2/1990 | Rattner |
| 4,905,672 A | 2/1990 | Schwarze |
| 4,940,050 A | 7/1990 | Forssmann et al. |
| 5,152,768 A | 10/1992 | Bhatta |
| 5,209,221 A | 5/1993 | Riedlinger |
| 5,256,141 A | 10/1993 | Gencheff |
| 5,269,291 A | 12/1993 | Carter |
| 5,301,659 A | 4/1994 | Brisson et al. |
| 5,318,014 A | 6/1994 | Carter |
| 5,362,309 A | 11/1994 | Carter |
| 5,408,363 A | 4/1995 | Kano |
| 5,451,220 A | 9/1995 | Ciervo |
| 5,472,406 A | 12/1995 | De La Torre et al. |
| 5,474,531 A | 12/1995 | Carter |
| 5,509,896 A | 4/1996 | Carter |
| 5,524,620 A | 6/1996 | Rosenschein |
| 5,577,506 A | 11/1996 | Dias |
| 5,609,606 A | 3/1997 | O'Boyle |
| 5,665,053 A | 9/1997 | Jacobs |
| 5,681,336 A | 10/1997 | Clement et al. |
| 5,709,676 A | 1/1998 | Alt |
| 5,788,496 A | 8/1998 | Marlinghaus |
| 6,036,661 A | 3/2000 | Schwarze et al. |
| 6,073,051 A | 6/2000 | Sharkey et al. |
| 6,113,570 A | 9/2000 | Siegel et al. |
| 6,126,619 A | 10/2000 | Peterson et al. |
| 6,186,963 B1 | 2/2001 | Schwarze et al. |
| 6,217,531 B1 | 4/2001 | Reitmajer |
| 6,241,692 B1 | 6/2001 | Tu et al. |
| 6,298,264 B1 | 10/2001 | Zhong et al. |
| 6,361,531 B1 | 3/2002 | Hissong |
| 6,464,660 B2 | 3/2002 | Brisken et al. |
| 6,395,016 B1 | 5/2002 | Oron et al. |
| 6,475,210 B1 | 11/2002 | Phelps et al. |
| 6,478,765 B2 | 11/2002 | Siegel et al. |
| 6,500,134 B1 | 12/2002 | Cassone |
| 6,629,534 B1 | 10/2003 | St. Goar et al. |
| 6,755,821 B1 | 6/2004 | Fry |
| 7,128,719 B2 | 10/2006 | Rosenberg |
| 7,189,209 B1 | 2/2007 | Ogden et al. |
| 7,311,678 B2 | 12/2007 | Spector |
| 7,850,685 B2 | 12/2010 | Kunis et al. |
| 8,040,756 B2 | 10/2011 | Wang et al. |
| 9,421,025 B2 | 8/2016 | Hawkins et al. |
| 2001/0023326 A1 | 9/2001 | Spector |
| 2002/0002345 A1 | 1/2002 | Marlinghaus |
| 2002/0032394 A1 | 3/2002 | Brisken et al. |
| 2002/0072691 A1 | 6/2002 | Thompson |
| 2002/0095147 A1 | 7/2002 | Shadduck |
| 2002/0133099 A1 | 9/2002 | Ein-Gal |
| 2002/0151825 A1 | 10/2002 | Rubenchick et al. |
| 2002/0177889 A1 | 11/2002 | Brisken et al. |
| 2002/0188243 A1 | 12/2002 | Brisken et al. |
| 2003/0181833 A1 | 9/2003 | Faragalla et al. |
| 2003/0225346 A1 | 12/2003 | Ein-Gal |
| 2004/0006288 A1 | 1/2004 | Spector et al. |
| 2004/0010211 A1 | 1/2004 | Spector |
| 2004/0049148 A1 | 3/2004 | Rodriguez |
| 2005/0027198 A1 | 2/2005 | Couvillon |
| 2005/0075588 A1 | 4/2005 | Simnacher et al. |
| 2005/0228370 A1 | 10/2005 | Sterzer et al. |
| 2005/0267488 A1* | 12/2005 | Hare .................. A61B 17/221 606/113 |
| 2006/0241523 A1 | 1/2006 | Spector |
| 2006/0100550 A1 | 5/2006 | Schultheiss et al. |
| 2006/0190022 A1 | 8/2006 | Beyar et al. |
| 2006/0246044 A1 | 11/2006 | Lutz et al. |
| 2006/0265000 A1 | 11/2006 | Azizi |
| 2006/0293708 A1 | 12/2006 | Voss |
| 2007/0016112 A1 | 1/2007 | Schultheiss et al. |
| 2007/0055154 A1 | 3/2007 | Torbati |
| 2007/0055156 A1 | 3/2007 | Desilets et al. |
| 2007/0065420 A1 | 3/2007 | Johnson |
| 2007/0239083 A1 | 10/2007 | Voss |
| 2008/0009885 A1 | 1/2008 | Del Giglio |

(56) References Cited

U.S. PATENT DOCUMENTS

| | | | |
|---|---|---|---|
| 2008/0071198 | A1 | 3/2008 | Ogden |
| 2008/0188866 | A1 | 8/2008 | Karpiel et al. |
| 2008/0269651 | A1 | 10/2008 | Warlick et al. |
| 2008/0275371 | A1 | 11/2008 | Hoffmann |
| 2008/0294127 | A1 | 11/2008 | Blott et al. |
| 2009/0036803 | A1 | 2/2009 | Warlick et al. |
| 2009/0281464 | A1 | 11/2009 | Cioanta et al. |
| 2009/0312768 | A1* | 12/2009 | Hawkins .......... A61B 17/22029 606/128 |
| 2010/0036294 | A1 | 2/2010 | Mantell et al. |
| 2010/0114020 | A1 | 5/2010 | Hawkins et al. |
| 2011/0028868 | A1 | 2/2011 | Spector |
| 2013/0030447 | A1 | 1/2013 | Adams |
| 2013/0345600 | A1 | 12/2013 | Katragadda |

FOREIGN PATENT DOCUMENTS

| | | |
|---|---|---|
| FR | 2673542 | 9/1992 |
| JP | 2004215862 | 8/2004 |
| WO | 9210140 | 6/1992 |
| WO | 9406355 | 3/1994 |
| WO | 9913943 | 3/1999 |
| WO | 9933391 | 7/1999 |
| WO | 0207582 | 1/2002 |
| WO | 2006114783 | 11/2006 |
| WO | 2009152352 A2 | 12/2009 |

OTHER PUBLICATIONS

Kuhn, et al., "Impact of extracorporeal shock waves on the human skin with cellulite: A case study of an unique instance," Clinical Interventions in Aging, 2008, pp. 201-210, vol. 3, Issue 1, Dove Medical Press Ltd., United Kingdom.

Angehrn, et al., Can cellulite be treated with low-energy extracorporeal shock wave therapy?, Clinical Interventions in Aging, 2007, pp. 623-630, vol. 2, Issue 4, Dove Medical Press Ltd., United Kingdom.

"Laser Atherectomy in Peripheral Arterial Disease: Cath Lab Digest talks with Rajesh M. Dave, MD, FACC, FSCAI, Chairman, Endovascular Medicine, Pinnacle Health Heart and Vascular Institute Harrisburg Hospital, Harrisburg, Pennsylvania," Cath Lab Digest, Apr. 2007, pp. 1-12, vol. 15, Issue 4, HMP Publications, LLC, Malvem, PA.

Hoye, et al., " Successful Use of a New Guidewire with Radiofrequency Ablation Capability for the Treatment of Chronic Total Occlusion at the Ostium of the Left Anterior Descending Artery," Cath Lab Digest, Jun. 2005, pp. 33-34, vol. 13, Issue 6, HMP Publications, LLC, Malvem, PA.

Vorwerk, et al., "Chronic venous occlusions in haemodialysis shunts: efficacy of percutaneous treatment," Nephrology Dialysis Transplantation, 1995, pp. 1869-1873, vol. 10, No. 10, European Renal Association—European Dialysis and Transplant Association, United Kingdom.

ESWT (Extracorporeal Shock Wave Therapy) in comparison to UDWT (Unfocused Pressure Wave Therapy), http://www.wolfendoskopi.com.

Lau, M.D., et al., "Vulnerable Plaques: A Brief Review of the Concept and Proposed Approaches to Diagnosis and Treatment," Technology Assessment Prepared for the Agency for Healthcare Research and Quality of the U.S. Dept. of Health and Human Services, Jan. 22, 2004, Tufts-New England Medical Center AHRQ Evidence-based Practice Center, Boston, MA.

Hongbao, et al., "Laser Stabilization of the Vulnerable Plaque to Prevent Heart Attacks," The Journal of American Science, Mar. 2007, pp. 18-27, vol. 3, No. 1, Marsland Press, Lansing, MI.

Ong Lim, M.D., et al., "Vulnerable Plaque," SIS Almanac Online (http://www.sis.org/almanac/vul_plaq.pdf), 2002, Science Innovation Synergy, Seattle, WA.

Cassak, "Vulnerable Plaque Heats Up," In Vivo: The Business & Medicine Report, Oct. 2002, p. 23, Windhover Information, Inc. Norwalk, CT.

"Vulnerable Plaque," http://texasheart.org/HIC/Topics/Cond/vulplaq.cfm#, Texas Heart Institute, Houston, TX.

European Patent Office Communication from EP 10 797 881.9-1659; Jan. 20, 2015.

Extended European Search Report from EP 16186021.8-1659; Nov. 21, 2016.

Judgement; Final Written Decision issued on Jul. 20, 2020 in IPR2019-00408, 62 pages.

Watson, J. et al. (1999) Physiological Effects of Endermologie®: A Preliminary Report,. Aesthetic Surgery Journal. 19(1): 27-33.

Goldenstedt, C. et al. (2008) Delivery by shock waves of active principle embedded in gelatin-based capsules. Ultrasonics Sonochemistry. 15(5): 808-814.

Notice of Allowance dated Apr. 3, 2024, in U.S. Appl. No. 17/937,446.

Office Action dated Feb. 29, 2024, in U.S. Appl. No. 17/937,446.

U.S. Appl. No. 18/918,037, Office Action dated Dec. 5, 2024.

U.S. Appl. No. 18/918,030, Office Action dated Dec. 13, 2024.

U.S. Appl. No. 18/656,316, Final Office Action dated Dec. 19, 2024.

U.S. Appl. No. 18/918,026, Office Action dated Dec. 19, 2024.

Non-Final Office Action issued Jan. 30, 2025 in corresponding U.S. Appl. No. 18/656,345.

Notice of Allowance issued Feb. 24, 2025 in corresponding U.S. Appl. No. 18/798,522.

* cited by examiner

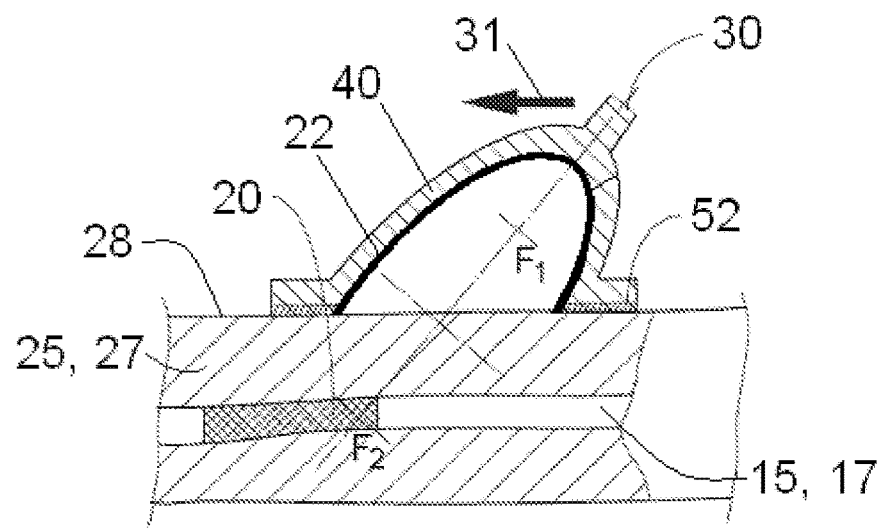
FIG. 5A
FIG. 5B
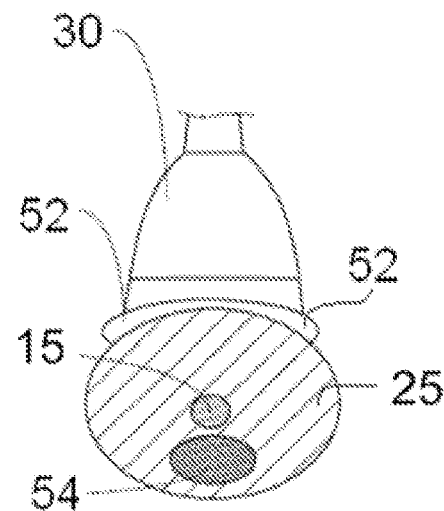
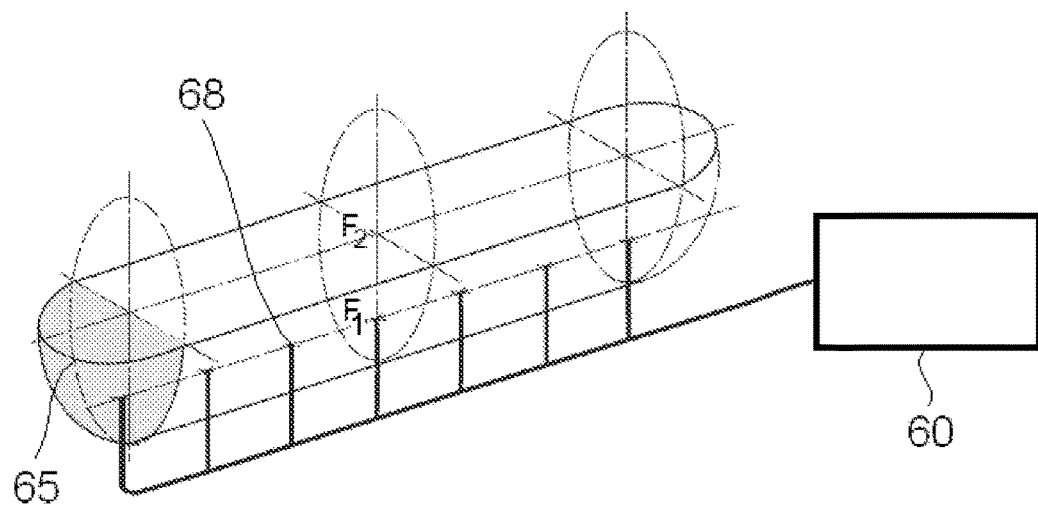
FIG. 6

FIG. 49B
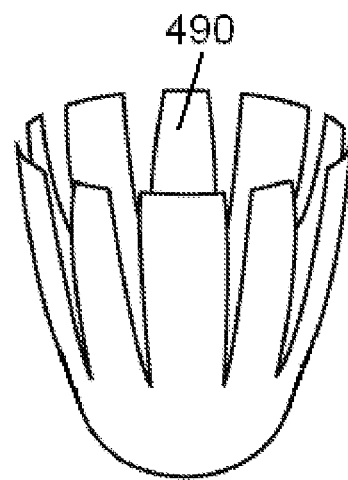
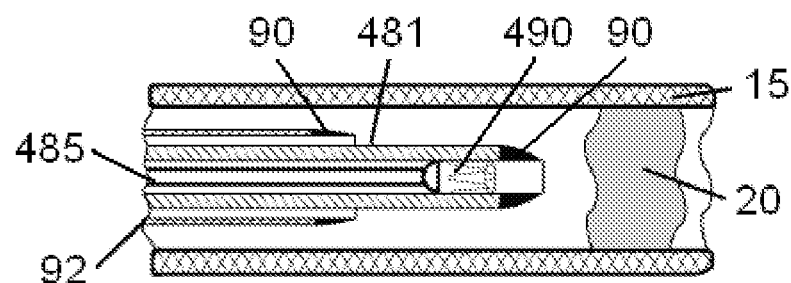
FIG. 49C
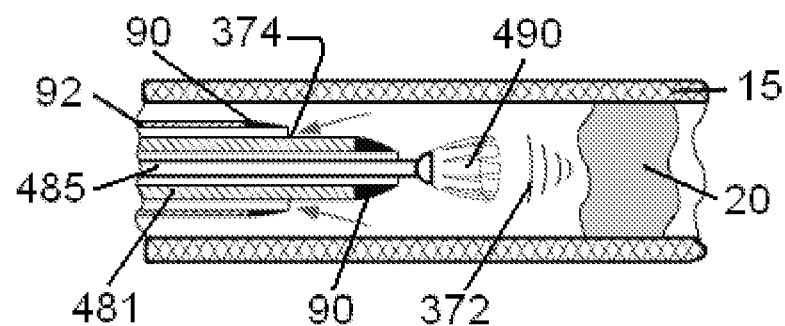
FIG. 49D

572

573

FIG. 58C
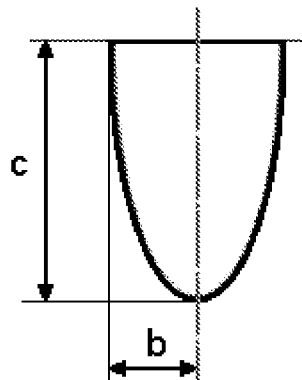
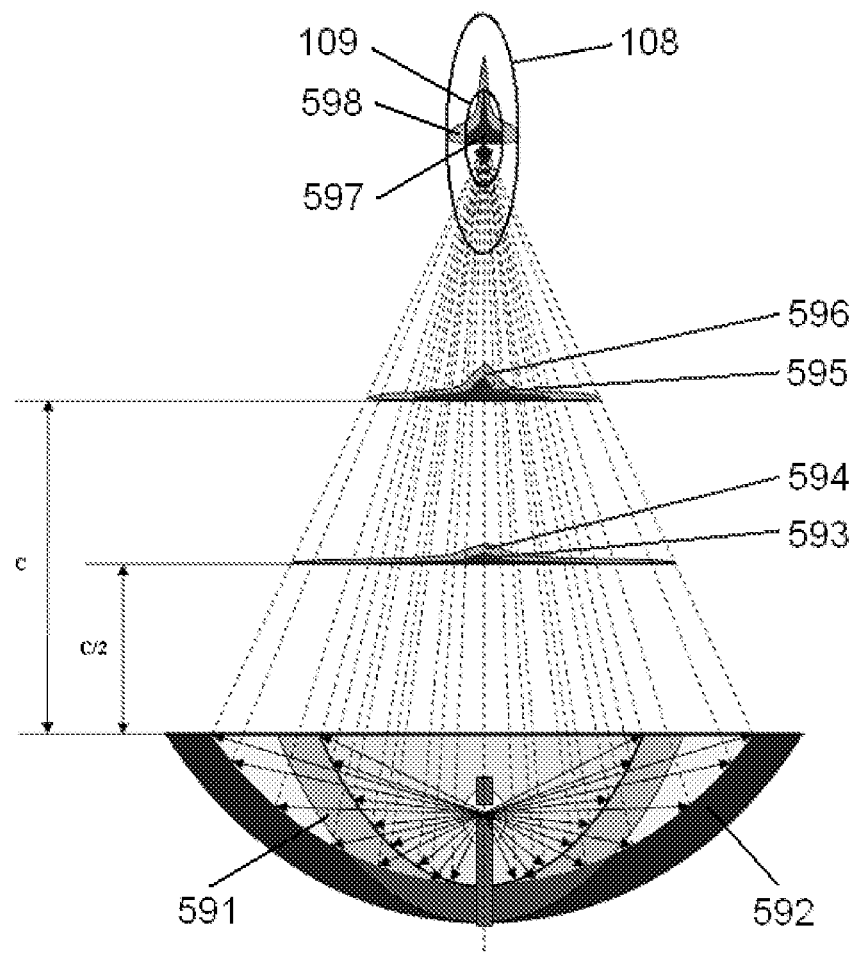
FIG. 59

METHOD OF TREATING A BLOOD VESSEL WITH MULTIPLE SHOCK WAVE DISCHARGE POINTS IN A CATHETER BALLOON

CROSS-REFERENCE TO RELATED APPLICATIONS

The present application is a continuation of U.S. patent application Ser. No. 18/435,508, filed Feb. 7, 2024, which is a continuation of U.S. patent application Ser. No. 18/221,303, filed Jul. 12, 2023, now U.S. Pat. No. 11,925,366, which is a continuation of U.S. patent application Ser. No. 17/188,812, filed Mar. 1, 2021, which is a divisional application of U.S. patent application Ser. No. 16/860,544, filed Apr. 28, 2020, now U.S. Pat. No. 11,666,348, which is a divisional application of U.S. patent application Ser. No. 14/874,650, filed Oct. 5, 2015, now U.S. Pat. No. 10,639,051, which is a continuation application of U.S. patent application Ser. No. 14/272,155, filed May 7, 2014, now U.S. Pat. No. 10,058,340, which is a divisional application of U.S. patent application Ser. No. 14/036,461 filed on Sep. 25, 2013, now U.S. Pat. No. 9,161,768, which is a divisional application of U.S. patent application Ser. No. 12/832,932 filed Jul. 8, 2010, now U.S. Pat. No. 8,556,813, which claims the benefit of priority of U.S. Provisional Application No. 61/223,919 filed Jul. 8, 2009, which are all incorporated herein by reference.

SUMMARY OF THE INVENTION

The efficacy of pressure shock waves for treatment of skin, tissue (soft and hard), and vasculature may be based on a number of factors, including without limitation: (a) cavitation during tensile phase which can break tissue bonds, blood vessels plaque, and other target area; (b) beneficial effects on reducing inflammation in soft tissue. including helping with reducing edema or helping to reduce inflammation after surgical intervention on or close proximity to natural human/animal conduits/lumens or after blood vessels' stenting and angioplasty—technologies that produce inflammation (hyperplasia); (c) pressure shock waves may dissolve lipids which are an important part of the plaque structure or for reducing the effects of cellulite or for reducing body fat in general (body sculpting); (d) pressure shock waves can reduce tissue spasm/contraction and blood vessel's spasm, such as without limitation after stenting and angioplasty; (e) pressure shock waves can act on peripheral nerves to reduce pain or promote nerve regeneration and repair; (f) pressure shock waves produce vessels dilation, which can help with penetration of the vessels' obstructions using guide wires and can enhance blood circulation to the treatment areas; (g) pressure shock waves can stimulate the growth of new capillaries and activate dormant stem cells and angiogenesis factors, which can enhance collateral blood circulation to reduce poor blood circulation; (h) certain dosages may inhibit smooth cells proliferations, which can prevent restenosis (blockage of the vessels that were already treated due to smooth muscle cells proliferations triggered by inflammation produced either by angioplasty or stenting); (i) pressure shock waves can stimulate the growth of hard and soft tissues, which can be used in the treatment of bone fractures, producing bone fusion, repair of tears in cartilage, muscle, skin, ligaments, tendons, and the like; (j) pressure shock waves can reverse hard and soft tissue necrosis through increases blood circulation and recruiting of growth factors; (k) pressure shock waves can prevent adhesions between organs after surgeries in the abdominal, muscular, chest areas, and the like; (l) pressure shock waves can break down scar tissue and fibrotic tissue formed around medical incision; (m) pressure shock waves can be easily transmitted in saline solutions, blood, contrast media, liquid drugs—such liquids and body fluids not only transmit the pressure shock waves, but cavitation may be generated such as to break plaque, break cellular, bacteria and viruses membranes or push DNA inside cells; and (n) pressure shock waves can avoid a thermal effect that can alter tissue in general or blood vessels' cells' structure or increase the risk of blood coagulation. This thermal effect represents the main drawback with treatments for blood vessels using low or high frequency ultrasound (focused or non-focused), radio frequency, microwaves, and the like. The lack of thermal effect recommends this treatment of circulatory problems (lack of coagulation effects and the capacity of destroying plaques) and also for "cold" controlled ablation of unwanted bone or tissue growths, including benign or malignant tumors.

Based on one or more of the foregoing factors, pressure shock wave treatment may be used independently, or in combination with other medical treatments to promote synergetic effects before, during and after other medical therapies. Some examples of pressure shock wave applications include: high energy pressure shock waves to destroy blood vessels plaque; high energy pressure shock waves to penetrate total occlusions of the blood vessels or natural human/animal conduits/lumens; low to medium energy pressure shock waves to treat vulnerable plaque from the blood vessels; high energy pressure shock waves to dissolve blood clots (thrombus or embolus) from the blood vessels or natural human/animal conduits/lumens; low to medium energy pressure shock waves to treat the muscle of the heart (after cardiac infarction) in combination with stem cells; genes or proliferation agents for muscle growth and/or angiogenesis or vasculogenesis; low to medium energy pressure shock waves to improve functionality of muscles that activate heart valves; high energy pressure shock waves to remove fluid accumulation in heart sack; high energy pressure shock waves to help with pacemakers leads extraction by producing their loosening before their removal from heart muscle; low to medium energy pressure shock waves to promote accelerated healing after angioplasty or stenting using metal bare stents or drug eluting stents; low to medium energy pressure shock waves to treat in-stent restenosis (blockage of the blood vessel after stenting due to regrowth of the smooth muscle; high energy pressure shock waves combined with drugs to prevent smooth muscle formation after angioplasty or stenting; high energy pressure shock waves combined with dissolution agents for blood clots (thrombus or embolus) elimination from blood vessels or artificially created shunts/fistulas or from natural human/animal conduits/lumens; high energy pressure shock waves combined with drugs to enhance plaque removal from blood vessels; high energy pressure shock waves combined with drugs to enhance and speed-up the elimination of total occlusions from blood vessels or natural human/animal conduits/lumens; low energy pressure shock waves in combination with drugs to stabilize vulnerable plaque from the blood vessels; low to medium energy pressure shock waves to treat vessel's wall to prevent formation of arterial aneurysms or varicose veins (enlarged and/or twisted veins); low to medium energy pressure shock waves to treat vessel's or natural human/animal conduits/lumens wall for chronic inflammation; medium to high energy pressure shock waves to treat burns, to heal or improve healing of acute and chronic wounds, to enhance blood circulation/perfusion, reduce inflammation and edema and improve cosmetic aspect of the skin; medium to high energy pressure shock waves to break fat cells and produce collagen fibers to reinforce skin for cellulite applications; medium to high energy pressure shock waves to promote body sculpting through fat reduction; low to medium energy pressure shock waves to promote skin rejuvenation through collagen creation and increased blood circulation; low to medium energy pressure shock waves to promote healing of the surgical incisions; medium to high energy pressure shock waves to prevent/eliminate hyperthrophic lesions, organs adhesions, and fibrotic tissue formations or capsular contracture around implants; low to medium energy pressure shock waves to improve the aesthetic aspect of the skin scar tissue (after open surgeries); low to medium energy pressure shock waves to treat tissue in combination with stem cells, genes or proliferation agents for tissue growth and/or angiogenesis or vasculogenesis; medium to high energy pressure shock waves to treat unwanted tissue hyperplasia as benign prostate hyperplasia (BPH) and the like; low and medium energy pressure shock waves to reduce edema and inflammation by pushing the by-products into lymphatic system; medium to high energy pressure shock waves to push excessive accumulation of lymph into lymphatic system, thus preventing lymph-edema; medium to high energy pressure shock waves to promote the repair of lymphatic vessels; medium to high energy pressure shock waves to destroy/crack hard tissues (for example bone spurs, heterotopic ossifications, calcifications, plaque formation on teeth, etc.) due to compressive forces in combination with cavitation microjets; low to medium energy pressure shock waves to stimulate angiogenesis and vasculogenesis; low to medium energy pressure shock waves to treat muscles for pain, tear, contracture and stimulate muscle growth; high energy pressure shock waves to inhibit muscle growth; low and medium energy pressure shock waves to interact at the cellular level, to call for immune system and acute repair mechanism; low and medium energy pressure shock waves to treat interstitial cystitis through cells stimulation and bladder re-epithelialization; low and medium energy pressure shock waves to call in of the stem cells or activate dormant stem cells for tissue repair; low to medium energy pressure shock waves to stimulate stem cells formation at the donor site before harvesting, their proliferation, differentiation and enhance their effects after implantation; medium and high energy pressure shock waves to push DNA fragments, genes, etc., inside cells that can generate different cellular reactions; high energy pressure shock waves to activate and accelerate cellular apoptosis; high energy pressure shock waves and especially cavitation jets can penetrate/break cellular membranes and thus destroying cells using non-heat producing mechanisms (useful to selectively destroy cancer cells); medium to high energy pressure shock waves to kill Gram positive and Gram negative bacteria, viruses or destroy biofilms; medium to high energy pressure shock waves to treat bacterial or abacterial prostatitis (chronic pelvic syndrome), through reduction of inflammation and stimulation of immune system; medium to high energy pressure shock waves to enhance/accelerate the treatment of fungal infections in conjunction with appropriate medication; medium energy pressure shock waves to treat aseptic loosening of human replacement prosthesis; high energy pressure shock waves to help with human replacement prostheses, implants, stents extraction by producing their loosening before their removal from the human body; low to medium energy pressure shock waves to stimulate the growth of soft tissues, which can be used in the repair of tears in cartilage, muscle, skin, ligaments, tendons, and the like; medium to high energy pressure shock waves to stimulate the growth of hard tissues, which can be used in the treatment of acute bone fractures and bone non-unions, to produce backbone fusions, and the like; low to medium pressure shock waves to treat auto-immune diseases as Systemic Lupus Erythematosus, Scleroderma, Crohn's Disease, Dermatomyositis, and the like; medium to high energy pressure shock waves to treat skin infections, high energy pressure shock waves to fragment biodegradable structures in small pieces to allow the easy absorption by the body; low to medium pressure shock waves to reduce pain or promote nerve regeneration and repair; low to medium energy pressure shock waves to kill parasites, harmful micro-organisms, and the like; and medium to high energy pressure shock waves to deliver high concentration drugs inside the tissue from patches and subcutaneous biodegradable pouches.

As used herein, High Energy pressure shock waves generate a flux density higher than 0.3 mJ/mm$^2$.

As used herein, Medium Energy pressure shock waves generate a flux density less than 0.3 mJ/mm$^2$ and higher than 0.1 mJ/mm$^2$.

As used herein, Low Energy pressure shock waves generate a flux density lower than 0.1 mJ/mm$^2$.

The flux density combined with frequency of the shots (1-15 Hz) and the number of shocks per one session (500-50,000) can dictate the energy outcome of shock wave treatments.

In general, High Energy treatments should be able to deliver in one session in the targeted treatment area higher than 1000 Joules of energy, Medium Energy treatments between 100 and 1000 Joules and Low Energy treatments less than 100 Joules.

BRIEF DESCRIPTION OF THE DRAWINGS

FIG. 5A is a schematic diagram of shock wave applicator reflectors' orientations relative to an occlusion target in one embodiment of the present invention.

FIG. 5B is a schematic diagram of a shock wave applicator's orientation relative to a blood vessel target and bone in one embodiment of the present invention.

FIG. 6 is a schematic diagram of an elongated shock wave applicator reflector with multiple discharge points in one embodiment of the present invention.

FIG. 49B is a schematic diagram of an expandable tulip reflector of an intracorporeal shock wave catheter in an open position in one embodiment of the present invention.

FIG. 49C is a schematic diagram of an expandable tulip reflector of an intracorporeal shock wave catheter in closed position in a blood vessel and relative to an occlusion one embodiment of the present invention.

FIG. 49D is a schematic diagram of an expandable tulip reflector of an intracorporeal shock wave catheter in an open position in a blood vessel and relative to an occlusion one embodiment of the present invention.

FIG. 58C is a schematic illustration of a reflector having a large semi-axis (c) and small semi-axis (b) with a c/b ratio greater than 2.0 in one embodiment of the present invention.

FIG. 59 is a schematic diagram illustrating a comparison of focal volumes versus reflector aperture area in one embodiment of the present invention.

FIG. 76B is a schematic diagram of a ball and hinge interconnection between shock applicator system holder in one embodiment of the present invention.

FIG. 77 is a schematic diagram of a ball and hinge interconnection between shock applicator system holder in one embodiment of the present invention.

FIG. 78A is a schematic diagram of an interconnected chain of shock wave applicator system holders in one embodiment of the present invention.

FIG. 78B is a schematic diagram an interconnected chain of shock wave applicator system holders in one embodiment of the present invention.

FIG. 79A is a schematic diagram of a reversed reflector geometry in one embodiment of the present invention.

FIG. 79B is a schematic diagram of a reversed reflector geometry in one embodiment of the present invention.

FIG. 80 is a schematic diagram of reflector including reversed geometry in one embodiment of the present invention.

FIG. 81 is a schematic diagram of a reflector including multiple discharge points in one embodiment of the present invention.

FIGS. 82A-93B are COMSOL simulation graphs showing the propagation of shock wave fronts for resulting from shifting shock wave initiation point ($F_1$) in embodiments of the present invention.

FIG. 94A is a schematic diagram of the focal volume relative to a first position of shock wave discharge location within a reflector in one embodiment of the present invention.

FIG. 94B is a schematic diagram of the focal volume relative to a second position of shock wave discharge location within a reflector in one embodiment of the present invention.

FIG. 95 is a schematic diagram of a shock wave applicator including movable electrode in one embodiment of the present invention.

Figure 96:
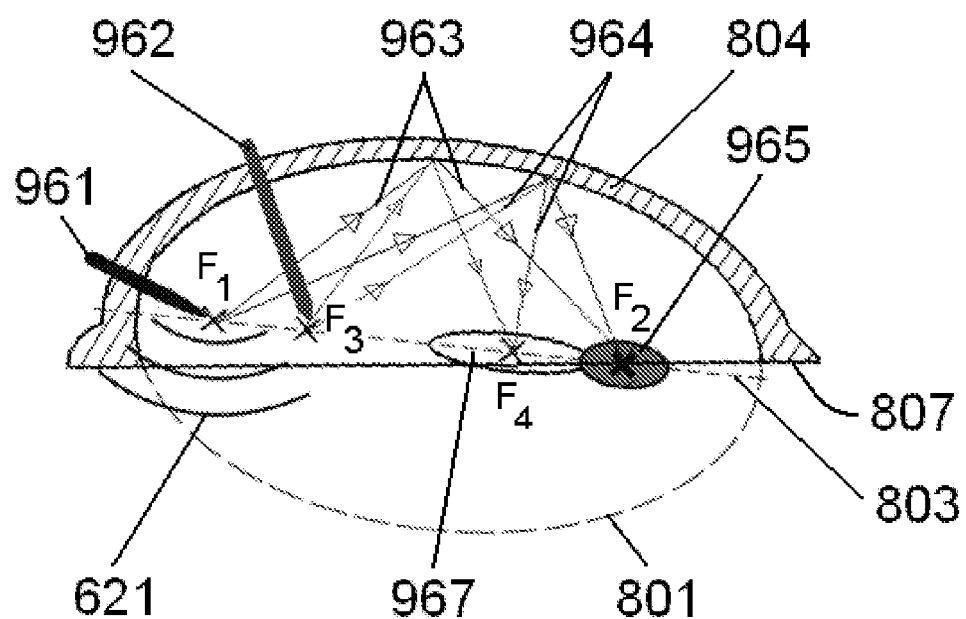

FIG. 96 is a schematic diagram of a reversed reflector with focal point shift in one embodiment of the present invention.

DETAILED DESCRIPTION OF THE INVENTION

In embodiments of the invention, the application of pressure shock waves from the outside of the body (extracorporeal) can be used for a variety of applications that include without limitation:
  removal of leads from heart muscle for pacemakers
  muscle regeneration (heart)—after myocardial infection using only pressure shock waves or in combination with stem cells, genes or proliferation agents for muscle growth and/or angiogenesis or vasculogenesis.
  treatment to improve functionality of muscles that activate heart valves to improve heart valves functioning removal of fluid build-up around heart treatment of total occlusions for all blood vessels dimensions (not limited by the vessel dimension) to eliminate critical limb ischemia (CLI) effects and peripheral arterial disease (PAD) symptoms treatment to inhibit inflammation or smooth muscle formation inside vessels treatment to regenerate circulation to ischemic tissues through elimination of blood vessels stenosis and stimulation of small blood vessels/capillaries formation to reduce the effects or eliminate critical limb ischemia (CLI) effects and peripheral arterial disease (PAD) symptoms removal of blood vessels plaque accumulation enhancement of drug delivery to blood vessels walls stabilization of the vulnerable plaques of the blood vessels, in combination with drugs treatment to reduce inflammation post angioplasty and stenting (bare stents or drug eluting stents) of the blood vessels to promote accelerated healing treatment to reduce chronic inflammation of the blood vessels or other conduits of the human and animal bodies treatment of in-stent restenosis for blood vessels with pressure shock waves alone or combined with drugs to prevent smooth muscle formation after angioplasty or stenting.

removal of blood clots (thrombus or embolus) from blood vessels or natural human/animal conduits/lumens prevention treatment to reduce the blood vessels spasm after angioplasty and stenting or of spasms of the natural/animal conduits/lumens or muscle spasms and contracture (for example produce by cerebral palsy)

treatment of occluded artificial shunts/fistulas-treatment of total occlusions or stenosis of natural human/animal conduits/lumens using only pressure shock waves or in combination with drugs treatment of occluded grafts (bypass grafts—natural or artificial)

treatment for blood clots removal from veins without destroying the valves present in veins treatment of varicose veins treatment to improve cosmetic aspect of the "spider veins"

enhancement of collateral blood flow around compromised vessels treatment of edema and inflammation by pushing the by-products into lymphatic system treatment to push excessive accumulation of lymph into lymphatic system, thus preventing lymph-edema promotion of lymphatic vessels repair treatment of burns, to heal or improve healing of acute and chronic wounds, to enhance blood circulation/perfusion, reduce inflammation and edema and improve cosmetic aspect of the skin cosmetic treatments based on destroying the fat cells and pushing them into lymphatic system for elimination (cellulite, body sculpting, etc.)

treatment to reinforce of the skin through collagen formation and increased blood circulation treatment for skin rejuvenation treatment to improve the cosmetically aspect of the skin scars treatment of internal fibrotic tissue, hyperthrophic lesions, and organ adhesions generated post surgeries or capsular contracture around implants treatment to repair tissues as bones, teeth, cartilage, tendons, ligaments, muscles, etc., which can be used in the treatment of bone fractures, producing spine fusion, repair of partial or total tears in cartilage, muscle, ligaments, tendons, etc.

regeneration of necrotic tissues as necrotic bone, necrotic skin, etc. and restoration of normal blood circulation through angiogenesis and recruiting of growth factors tissue regeneration using only pressure shock waves or in combination with stem cells, genes or proliferation agents for tissue growth and/or angiogenesis or vasculogenesis.

destruction of unwanted hard tissues (for example bone spurs, heterotopic ossifications, calcifications, plaque formation on teeth, etc.)

treatment to destroy cancer tumors or unwanted benign tissue hyperplasia (as benign prostate hyperplasia or BPH) using a "normal body temperature ablation" approach treatment to enhance toxicity of certain drugs used for cancer treatment treatment to activate dormant stem cells for tissue repair treatment to stimulate stem cells formation at the donor site before harvesting treatment of stem cells to enhance their in vitro proliferation treatment of stem cells to promote their differentiation treatment of stem cells to enhance their effects after implantation treatment to stimulate the regeneration of soft tissue as in interstitial cystitis (lining of the bladder wall)

treatment to kill Gram positive and Gram negative bacteria, viruses or destroy biofilms treatment for bacterial or abacterial prostatitis (chronic pelvic syndrome), through reduction of inflammation and stimulation of immune system treatment of fungal infections in conjunction with appropriate medication treatment of pain associated with inflammation and nerve stimulation (analgesic effect)

treatment of nerve degeneration by promoting nerve regeneration and repair targeted treatment for different viruses and bacteria or abnormal cells from the living tissue treatment of ascetic loosening of human replacement prosthesis, to prevent their unwanted movement inside the implantation site in-vitro gene treatment to produce improved genetic material for the treatment of different genetic affliction reduce the symptoms/effects and treat auto-immune diseases as Systemic Lupus Erythematosus, Ankylosing Spondylitis, Crohns Disease, Scleroderma, Dermatomyositis, etc.

loosening of prostheses, stents, implants to allow easy extraction/removal from hard and soft tissue elimination of cysts treatment to kill parasites, harmful micro-organisms, etc.

controlled fragmentation of biodegradable stents in small pieces to allow the easy absorption by the body after their function in the blood vessels was accomplished and to avoid thrombosis of large pieces carried down the blood stream fragmentation of any internal biodegradable structures in small pieces after its functional life was accomplished for easy absorption by the body delivery of high concentration drugs inside the tissue (organs, muscle, bones or dermis) from patches and subcutaneous biodegradable pouches In one embodiment of the invention, extracorporeal pressure shock waves may be used for treatment of a total blood vessel occlusion or a natural human/animal conduit/lumen occlusion.

Total occlusions in the vascular system represent the formation of plaque that totally occludes the blood vessels cross sections or can be produced by accumulation of debris combined with wall inflammation for any natural human or animal conduit or lumen.

For blood vessels, the occlusions can have a soft or a hard cap at their distal or proximal ends. The most difficult to penetrate are the ones with the hard cap. The occlusions with soft cap can be penetrated during manipulation of the guide wires by the physicians. Even so, not all the time will the total occlusions with soft cap be penetrated, due to their long length or distal composition of the occlusion (beyond the soft cap).

Numerous devices were developed to treat total occlusions for blood vessels that can produce critical limb ischemia (reduced blood circulation and thus reduced tissue oxygenation down the blood flow, which can degenerate loss of distal limbs or parts of foot). Also, the blockage of the carotid arteries that bring oxygenated blood to the brain can be damaging or fatal to brain functionality (blockage of blood flow towards the brain can produce brain tissue ischemia, which can generate loss of functionality or death of brain cells).

Figure 1:
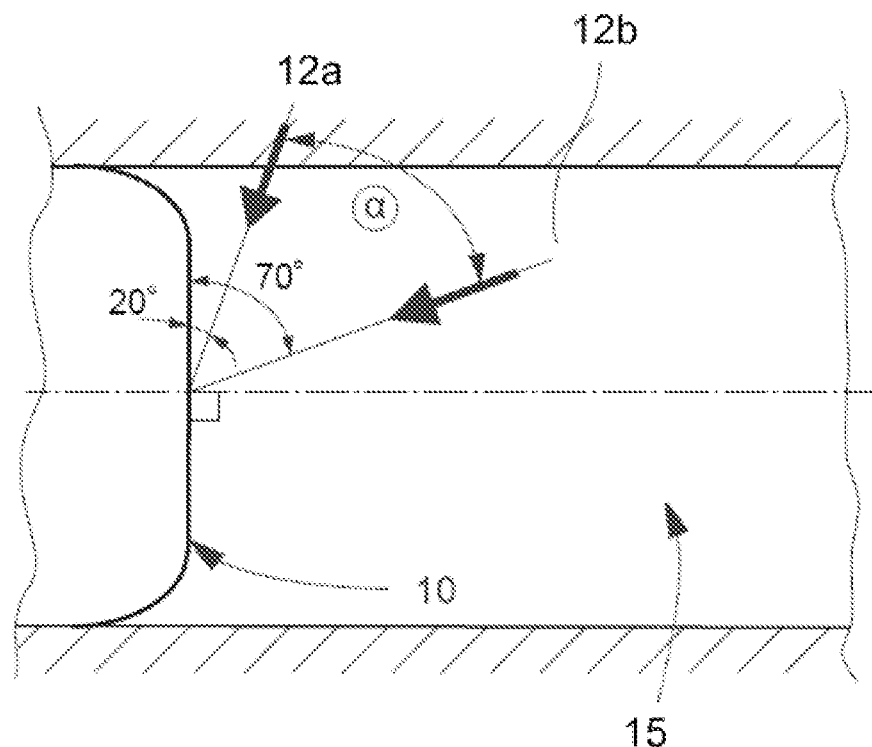
FIG. 1 is a schematic diagram of pressure shock waves applied to an occlusion in one embodiment of the present invention.

Pressure shock waves can offer an extracorporeal approach for treating total occlusions of blood vessels or from any natural human or animal conduits or lumens as non-invasive procedures. Referring to FIG. 1, the destruction of total occlusions is mainly produced by cavitation, which would preferably be directed as perpendicular as possible on the occlusion cap 10. The extracorporeal approach typically directs at angles less than 90° but higher than 20°, depending on the position of the vessels 15 or natural human/animal conduit/lumen relatively to the skin.

The direction, such as direction 12a or 12b, used for focusing the shockwaves at an angle between 20°-70° relative to the surface of the occlusion cap 10, causes cavitation bubbles collapse to be oriented against the occlusion cap 10 and not tangential to it. To produce cavitation in front of the occlusion cap 10, the reflector of the pressure shock waves device may have the focal volume concentrate around the occlusion cap 10 (in other words the occlusion cap 10 intersects the focal volume of the pressure shock waves applicator).

Figure 2:
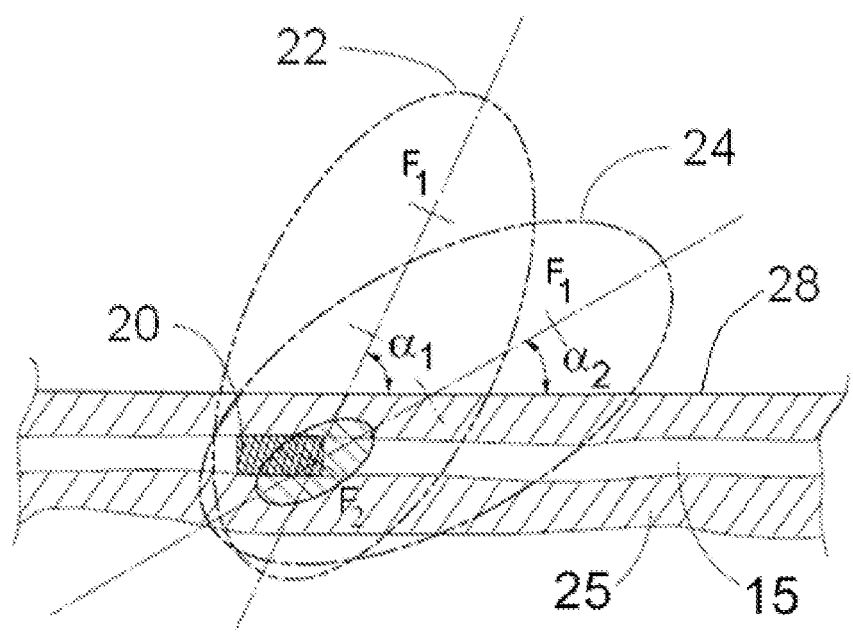
FIG. 2 is a schematic diagram of shock wave applicator reflectors' orientations relative to the skin and an occlusion target in one embodiment of the present invention.

The pressure shock waves applicators can be focused, unfocused or radial. Referring to FIG. 2, the geometry of the reflectors 22, 24 can be part of an ellipsoid, a sphere, a paraboloid or a combination of them. The pressure shock waves can be produced using electrohydraulic, piezoelectric, electromagnetic and by explosive or projectile means.

As can be seen from FIG. 2, when compared with reflector 22 and angle ($\alpha_1$), the reflector 24 with a smaller angle ($\alpha_2$) relatively to the skin 28 is preferred due to a more efficient orientation of the microjets produced by the collapse of cavitation bubbles relatively to the occlusion 20 that needs to be treated. In general the orientations of the cavitation microjets coincide with the direction of the focal line $F_1F_2$. This assumption can be applied for the treatment of any occlusion 20 produced in a blood vessel 15 or any natural human/animal conduit/lumen from a body appendage 25 or a body generally.

As seen from FIGS. 3, 4, 5A and 5B, embodiments of the extracorporeal reflectors to treat occlusions 20 includes inclined geometry to orientate the cavitation towards the occlusion cap 10. As can be seen from FIG. 3, the treatment of occlusion 20 from a blood vessel 15 that has normal blood flow 39 blocked inside the appendage 25 can be performed using confocal opposite applicators 30 and 32. Shock wave applicator 30 includes a housing 40 including a reflector 22 disposed within the housing 40. Shock wave applicator 32 also includes a housing 41 including a reflector 22 disposed within the housing 41. The applicators 30 and 32 can have a longitudinal movement 31 in order to cover the full length of the occlusion 20.

Figure 3:
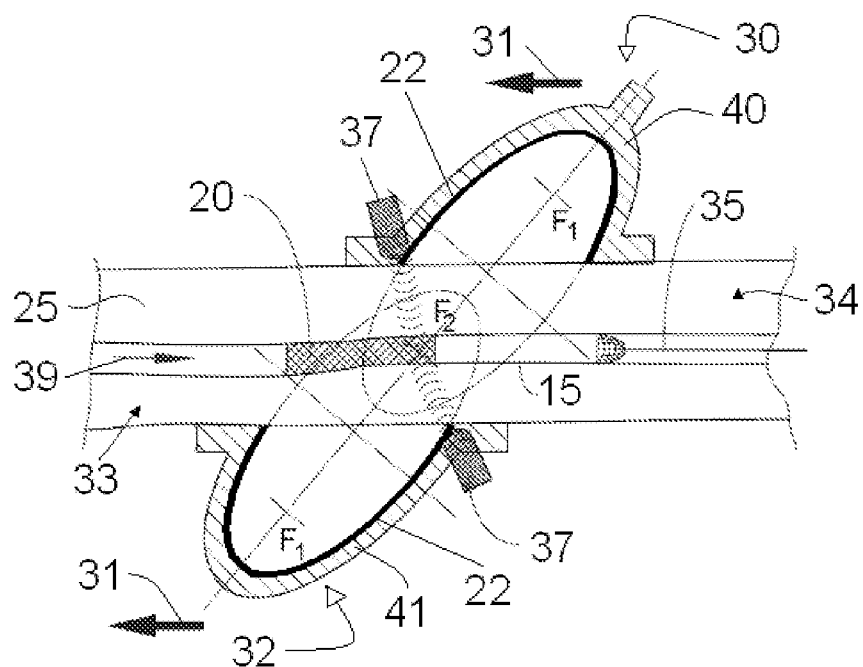
FIG. 3 is a schematic diagram of shock wave applicator reflectors' orientations relative to an occlusion target in one embodiment of the present invention.
Figure 4:
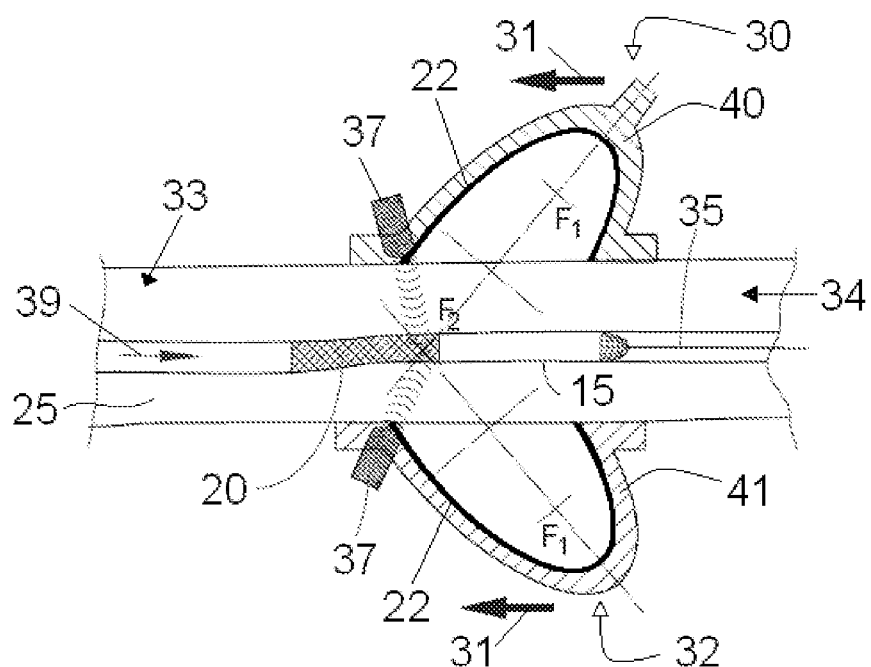
FIG. 4 is a schematic diagram of shock wave applicator reflectors' orientations relative to an occlusion target in one embodiment of the present invention.

Dual applicators 30 and 32 can be used for the treatment of blood vessels 15 from appendages 25, in an opposite position as seen in FIG. 3 or in a mirror position as presented in FIG. 4.

The focal point $F_2$ can be set either in the proximal region 33 or distal region 34 of the occlusion 20 (proximal region 33 is defined in vasculature as the point close to the heart and distal region 34 is defined as the point away from the heart). The correct position of the focal point $F_2$ can be assessed/visualized using ultrasound probes 37 that can detect the super echoic regions produced by the cavitation inside the human/animal body. If the focal point is set in the distal region 34, as seen from FIGS. 3 and 4, to prevent fragment from occlusion 20 to flow down the stream, a debris collection basket 35 has to be installed below the occlusion 20 through a distal incision. The basket 35 in some embodiments is not needed if the fragments are small in size (less 1 mm). If the focal point is set in proximal region 33 to the occlusion 20 (as seen in FIG. 5A), to avoid debris accumulation a suction catheter system can be used to eliminate the debris. The smooth contact of the applicator 30 with the skin 28 is done via a cushion/gel pad 52 that can accommodate the curvature of the body appendages 25 or body generally.

Because the cavitation in blood will develop slower than in water, the number of shocks should be increased accordingly to create the cavitational seeding of the blood in front of occlusion cap 10.

In general, for occlusions 20 of blood vessels 15 or natural human/animal conduits/lumens, in order to work the applicators 30 must be set in a position to avoid the bones 54 (as presented in FIG. 5B), which will produce significant reflection of the pressure shock waves. The pressure shock waves after breaking the occlusion cap 10 can be also applied inside the occlusions 20 to destroy their internal structure and thus restoring the normal passage way. The occlusions 20 of blood vessels 15 can be penetrated by breaking their solid structures (calcifications) or by liquefying the fat trapped inside the occlusion 20.

After the breaking of the occlusions cap 10 from blood vessels 15, penetration of the guide wire through the occlusion 20 occurs, especially if the other cap (the distal one) is not hard. This approach works if the breakage of the occlusion 20 starts from proximal region 33 towards distal region 34.

In case that $F_2$ is set on the proximal end of the occlusion 20 a guide wire might be present, which can potentially reflect the pressure shock waves. In such case the guide wire is retrieved in the proximal region 33 to a safe distance, to not interact with the pressure shock waves.

With long reflector 65 having an elongated shape (FIG. 6) and multiple discharge points 68 a longer occlusion 20 or a larger area (for cosmetic application) can be treated in one position of the applicator 30. For endovascular field (peripheral blood vessels treatments), this shape is indicated for the long femoral artery obstructions or obstructions 20 of the below-the-knee blood vessels 15.

The energy delivered in treatment area of the reflector shown in FIG. 6 is lower than a normal elliptical reflector due to reduction in reflecting area for the focused pressure shock waves (the larger reflective area is available to focus the pressure shock waves, the larger the focal volume is and more energy is found in the focal volume). The decrease in energy delivered to the treatment area with reflector shown in FIG. 6 can be compensated by increasing the number of shocks and/or by increasing the discharge voltage in $F_1$ for the electrohydraulic applicators 30 or the energy setting (in general) for all type of pressure shock waves applicators 30 (electrohydraulic, piezoelectric, electromagnetic and by explosive or projectile means). Also, in cardiovascular applications the penetration depth is dependent on the vessel 15 position inside the human body 27 and can vary from 5-100 mm. For treatment of other natural human or animal conduits or lumens the penetration depth can vary between 30-200 mm. The penetration depth drives the depth of the reflector shape, which can be shallow for superficial application or very deep for application where the focus is deeper inside the human body.

Extracorporeal pressure shock waves may be used to treat occlusions 20, stenosis (reduce of cross section area of a blood vessels 15 or natural human or animal conduits or lumens) and blood clot formation in blood vessels 15 (veins and arteries) or natural human or animal conduits or lumens while avoiding limitations for treatment based on vessel 15 or natural conduit/lumen size. This treatment improves over other procedures used to treat occlusions 20 (invasive procedures) for blood vessels 15 that are physically limited by the catheter dimensions (tubular devices that carry stents inside the human body arteries or have balloons at the distal end that are used to get to the occlusion area). After the occlusions 20 of the blood vessels 15 are opened, other technologies used to re-establish the normal blood vessel cross-section (such as angioplasty and stenting) are also limited by the inability to be used for blood vessels 15 smaller than 2 mm in diameter size.

Bones 54 can be an obstacle for pressure shock waves' penetration/propagation. For treatments in the blood vessels 15 of the head area, the skull bone can be penetrated, although consideration necessarily should be given as to what energy can be used and what is the behavior of pressure shock waves transmitted through the skull bone and their interaction with the brain.

In general, the speed of sound (speed of propagation of the pressure shock waves) is different for each type of human or animal tissue including: skin at 1,600 m/s, water at 1,500 m/s, fat at 1,400 m/s, muscle at 1,600 m/s, bone at 3,500 m/s and dry air at 21° C. is 344 m/s.

Large differences in speed of sound or acoustic impedance (speed of sound multiplied by density of the substance) in different tissue layers (for example between soft tissue and bone or soft tissue and air) may result in reflections of the pressure shock waves. Such reflections can interrupt or change direction of the pressure shock waves and thus their action in the focal volume around $F_2$. This is why bony structures are sought to be avoided in extracorporeal treatment.

Geometries presented in embodiments of the present invention can be used with electrohydraulic, electromagnetic, piezoelectric, or explosive or projectile constructions in order to produce pressure shock waves.

Figure 7:
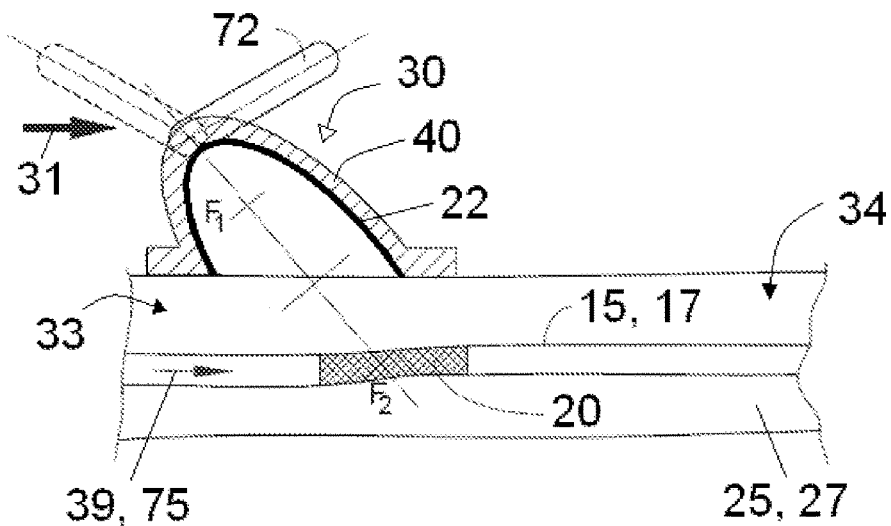
FIG. 7 is a schematic diagram of a shock wave applicator's orientation relative to an occlusion target in one embodiment of the present invention.

An adjustable handle 72, as seen in FIG. 7, can be attached to pressure shock waves applicators 30, to allow an improved ease-of-use for the physicians. A handle also keeps the physician's hands out of the X-ray field in case a C-arm is used to monitor the procedure.

In general, cavitations produced by pressure shock waves, can generate echogenic regions that can be seen using ultrasound in B-mode. Also, contrast medium shows changes in obstructions under X-rays such as a C-arm that goes around the table where the patient is positioned during treatment).

The usual contrast media used for such procedures includes: gas filled liposomes, gas filled lipid bilayers, microbubbles containing liquids, gas emulsions, gas-filled micro-bubbles and micro-bubbles containing suspensions (for example dodecafluropentone).

Any of the above-mentioned contrast media can be used in conjunction with extracorporeal pressure shock waves devices to monitor the progression of treatment and visualize the relative position of the device focal volume to the treatment area as cavitation bubbles developed inside the focal volume produce hyper-echoic regions when monitored with fluoroscopic or ultrasound means.

This type of approach can be used for the treatment of occlusions 20 that block normal flow 75 form any natural human/animal conduit/lumen.

Figure 8A:
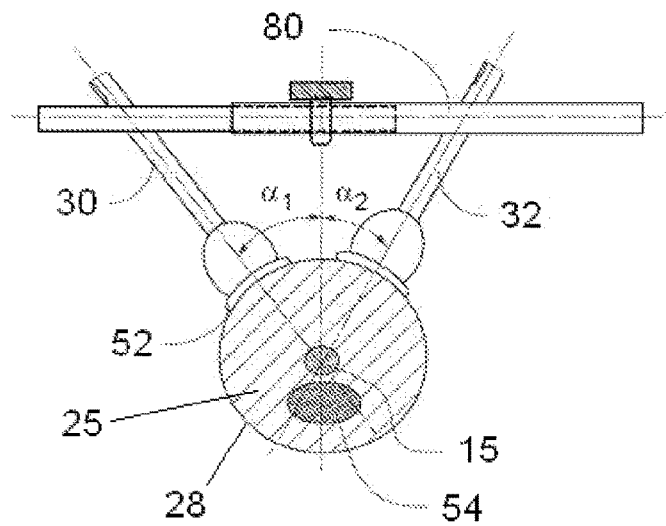
FIG. 8A is a schematic diagram of shock wave applicators with an auxiliary placement device relative to a blood vessel target in one embodiment of the present invention.
Figure 8B:
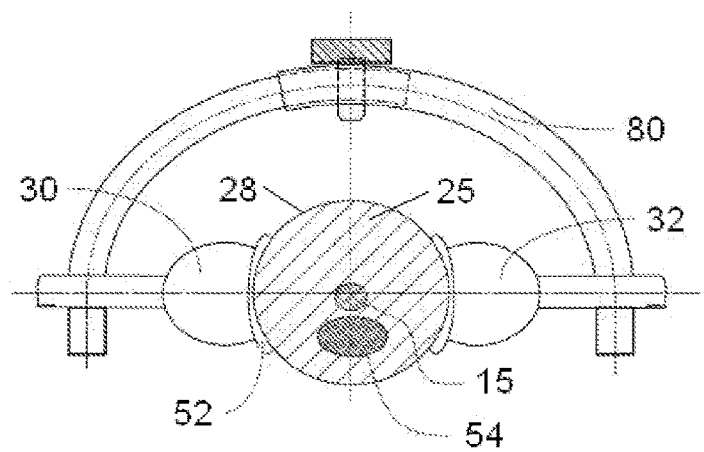
FIG. 8B is a schematic diagram of shock wave applicators with an auxiliary placement device relative to a blood vessel target in one embodiment of the present invention.

Referring to FIGS. 8A and 8B, to increase efficiency of treatment multiple applicators 30, 32 (or more) can be used at the same time and controlled by one central console or individual consoles for each applicator. The choice between one console and multiple consoles is based on the degree of coordination and complexity of the sequence of activation for multiple applicators for treatment.

When multiple reflectors/applicators 30 are utilized, different auxiliary fixtures/devices 80 can be used to keep the applicators 30, 32 or more in place, as seen in FIGS. 8A and 8B.

Based on the position of the blood vessels 15 or natural human/animal conduits/lumens inside the human/animal body, a set of applicators 30 and 32 that contain reflectors with different geometries and angles, such as $\alpha_1$ and $\alpha_2$ that may have same or different values, relative to the skin 28 may be provided to physicians to cover possible treatments.

In vascular applications directed to heavy calcifications of the occlusion cap 10 and very long vascular occlusions 20, a combination of extracorporeal shock wave devices and suction catheter s or distal protection catheters (introduce through the blood vessel 15) may be used in embodiments of the invention.

Figure 9:
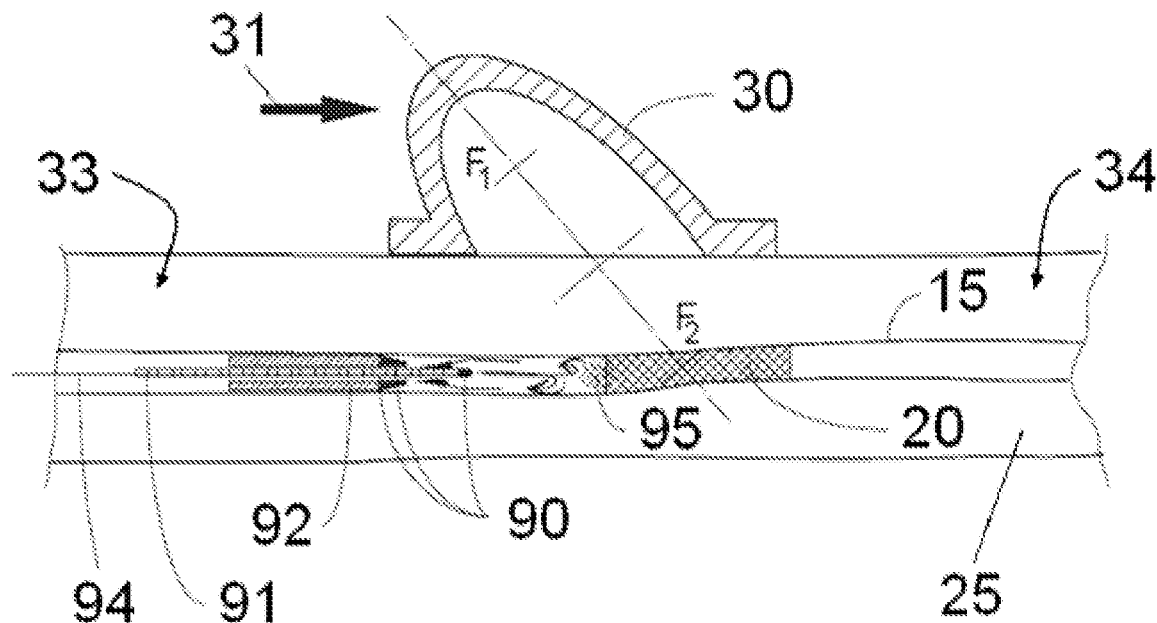
FIG. 9 is a schematic diagram of a shock wave reflectors' orientation relative to a treated occlusion and including debris flushing in one embodiment of the present invention.

As shown in FIG. 9, when the treatment is done at the proximal region/end 33 of a vascular occlusions 20 (closer to heart), the debris 95 generated by shock wave cavitation can be flushed out using a combination of catheters connected to external pumps.

Typically, before starting the extracorporeal session, a guide wire 94 is introduced into vasculature through a small incision in the groin (femoral artery access) or in the arm (brachial artery approach) to allow the movement inside the vasculature of the guide catheter 92 and flush catheter 91 used to flush the debris 95 out of the treated blood vessel 15 from the body appendage 25. Note that for a good visualization of the end of the guide catheter 92 and flush catheter 91 inside the body appendage 25, both catheters have radio-opaque tips 90.

The steps for the treatment in one embodiment of the invention includes:
1) Introduce guide wire 94 into vasculature and advance it until it reaches the occlusion 20.

2) Introduce over the guide wire 94 the guide catheter 92, which is advanced using the guide wire 94 guidance until it reaches a position in the proximal region 33 to occlusion 20.
3) Slide over the guide wire 94 and inside the guide catheter 92 a flush catheter 91.
4) Remove the guide wire 94 and connect the flush catheter 91 to a pump to inject saline solution inside the vessel 15.
5) Connect the guide catheter 92 to another pump that will draw the mixture of blood, saline and debris 95 out of the body appendage 25.
6) Start the extracorporeal pressure shock waves device.
7) Simultaneously start both pumps that activate the flush catheter 91 and guide catheter 92.
8) Continue flushing and pressure shock waves application until occlusion 20 is penetrated.
9) Stop extracorporeal shock wave device.
10) Continue to flush for another 2 minutes.
11) Stop the pumps connected to the flush catheter 91 and guide catheter 92.
12) Disconnect the flush catheter 91 and the guide catheter 92 from the pumps.
13) Remove the flush catheter 91 first.
14) Remove the guide catheter 92.
15) Close the access incision/cut from the femoral or brachial artery.

This approach may be useful for the treatment of occlusions 20 found in the carotid arteries. The large air bubbles or debris 95 may be collected with distal protection devices for carotid arteries interventions. The left and right common carotids supply blood towards the head and branches in the neck area into internal carotids towards the face and external carotids towards brain. For these vessels 15 it is preferable to not allow the flow up stream of debris 95 generated during extracorporeal pressure shock waves treatment, which in the face area can produce local paresis or in the brain can generate strokes. Also, devastating effects can be created by air bubbles larger than 2 mm in size flowing towards the brain (air embolism). The smaller bubbles (less than 2 mm in size) can be dissolved easier in the blood and can pass small vessels as arterioles and capillaries without any problems.

Figure 10:
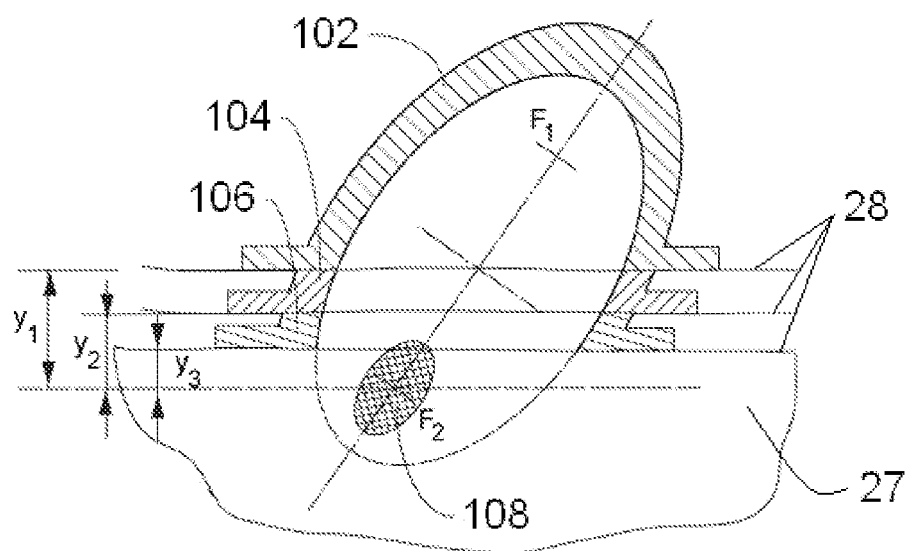
FIG. 10 is a schematic diagram illustrating different treatment depths with a shock wave applicator reflector relative to skin in one embodiment of the present invention.

Referring to FIG. 10, the treatment area can be found at different depths relative to the skin 28 such as with a set of treatment applicators 102, 104 and 106 with different penetration depths ($y_1$, $y_2$, $y_3$ decreasing in respective depth). A set of at least three (3) applicators 102, 104 and 106 may be provided to treat a body 27, including a variety of blood vessels 15 or normal human/animal conduits/lumens or to take into account different human/animal body mass (skinnier or fatter). In this way, treatment can occur to various blood vessels 15 (arteries or veins) or human/animal conduits/lumens, as long as the focal volume 108 intersects the vessel 15 or human/animal conduit/lumen.

Due to inclined geometry of the reflector, in embodiments of the invention it is desirable to equilibrate the applicator 30 from the mass point of view and will not allow the applicator 30 to disengage the treatment area, due to non-equilibrated mass. The consideration of mass distribution may take into account the fact that the physicians should keep their hands out of the treatment regions that might be visualized using an X-ray device (C-arm) and thus avoiding radiation exposure. An appropriate handle design connected to the applicator 30 body may be provided.

Figure 11:
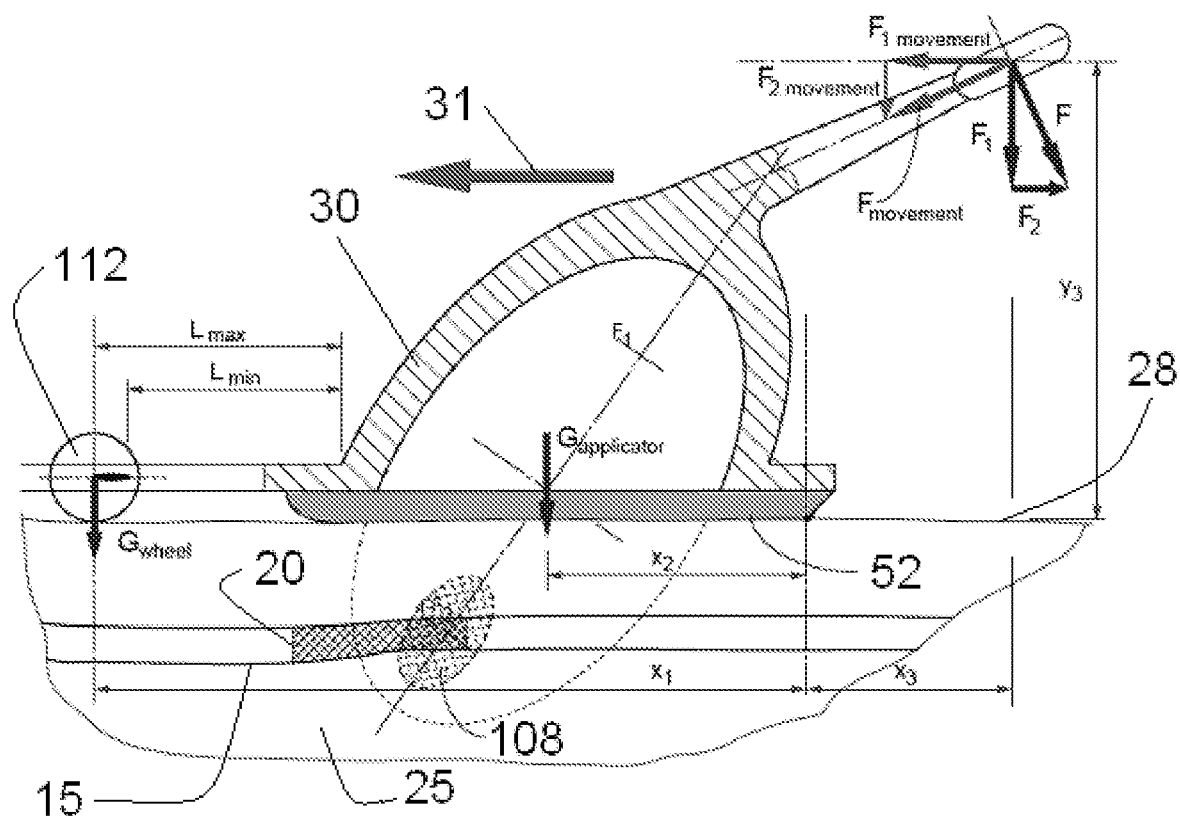
FIG. 11 is a schematic diagram of a movable shock wave applicator including a wheel positioned relative to skin and a target occlusion in one embodiment of the present invention.

Referring to FIG. 11, wheel 112 can be used to equilibrate the momentum of the applicator 30. Note that the position of the wheel 112 can be adjusted between $L_{max}$ and $L_{min}$ as distance away from applicator 30 body.

The equations used to calculate forces for static and dynamic situations includes:

Governing Equation:

$$\text{Total Momentum} = 0$$

Static Situation:

$$G_{wheel} \times x_1 + G_{applicator} \times x_2 = F_1 \times x_3 + F_2 \times y_3$$

Dynamic Situation:

$$G_{wheel} \times x_1 + G_{applicator} \times x_2 + F_{1movement} \times y_3 = F_1 \times x_3 + F_2 \times y_3 + F_{2movement} \times x_3$$

Figure 12A:
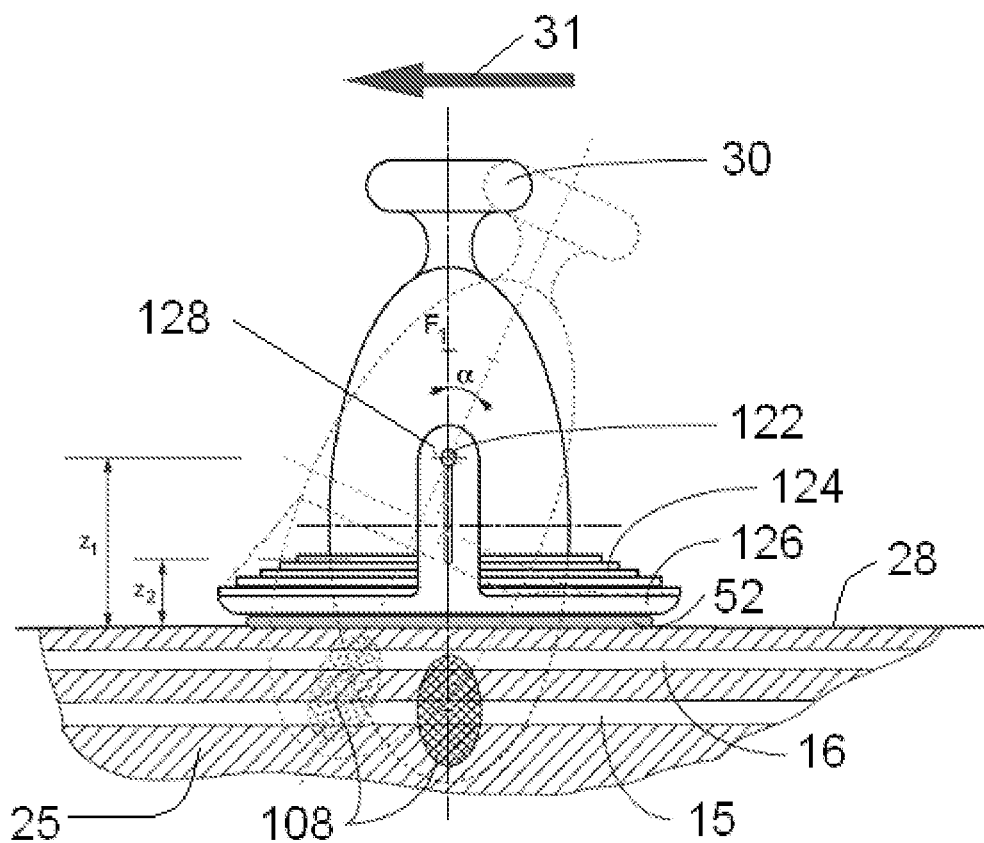
FIG. 12A is a schematic diagram of a pivotable shock wave applicator including bellows in one embodiment of the present invention.
Figure 12B:
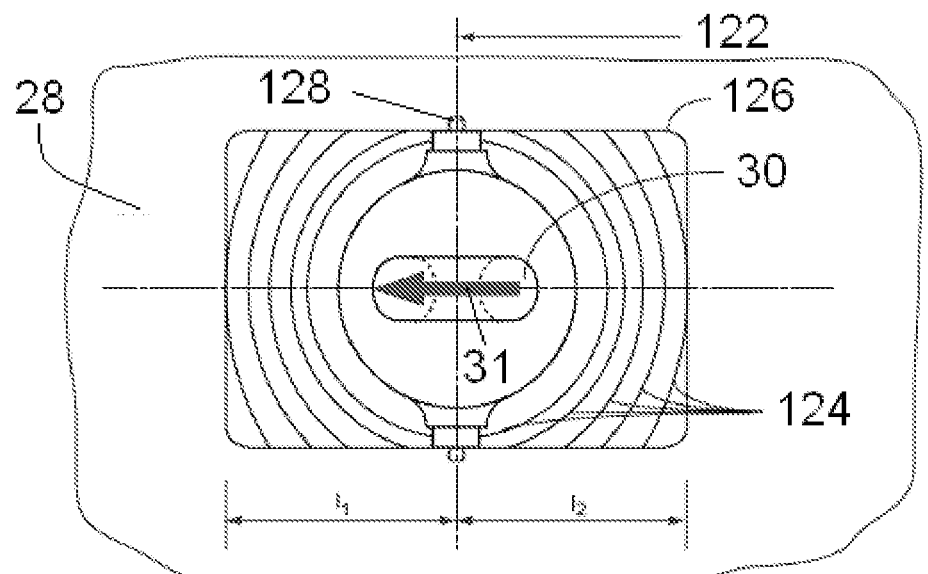
FIG. 12B is a schematic diagram of a bottom plan view of the applicator of FIG. 12A in one embodiment of the present invention.

In embodiments, it is beneficial if an applicator 30 can be created with adjustable angle for the internal axes to treat different blood vessels 15 or natural human/animal conduits/lumens at different depth inside the human appendage 25 or human body generally. As shown in FIGS. 12A and 12B, this approach can be realized by sitting the applicator 30 on a hinge 128 as part of an external frame 126. Note that the pivotal axis 122 provided by the hinge 128 can be moved vertically in between $Z_1$ and $Z_2$. In this way penetration depth can be adjusted and the position of $F_2$ of the focal volume 108 can be adjusted inside the treatment area ($F_2$ is not shown in FIG. 12A). As shown in FIG. 12A, by rotating the applicator 30 around the pivotal axis 122 a different blood vessel 16 or conduit/lumen can be treated, such as a superficial blood vessel or conduit/lumen when compared with vessel 15 or a conduit/lumen. This rotational movement combined with adjustable position for the pivotal axis 122 in between $Z_1$ and $Z_2$, can give multiple treatment options to physicians.

With continuing reference to FIG. 12B, the external frame 126 is longer on the direction of longitudinal movement 31 for the applicator 30 (respectively $l_1 > l_2$) to allow the physician to correctly position of the applicator 30 based on intended treatment procedures. The external frame 126 can have any possible shape. The bellows 124 (connect the frame with the applicator 30 body and keep an enclosed volume of fluid inside the applicator 30) are constructed to fit inside the external frame 126 and for that reason shape for the external frame 126 in an embodiment is circular.

As one shown in FIGS. 8A and 8B, the whole assembly can be positioned in some embodiments in auxiliary fixtures/devices 80 to allow precise alignment of multiple applicators 30, 32.

Figure 13:
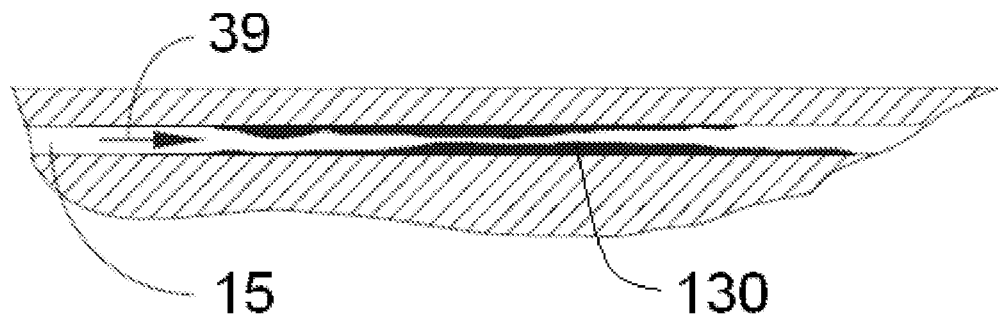
FIG. 13 is a schematic diagram of plaque to be treated in a blood vessel in one embodiment of the present invention.

In further embodiments, extracorporeal pressure shock waves may be used for treatment of stenotic plaque, vulnerable plaque, blood vessels or normal human/animal conduits/lumen. Among plaques 130, stenotic plaque is different from vulnerable plaque in blood vessels 15. The stenotic plaque is relatively stable and it has a thick cap that keeps the accumulation of lipids LDL (bad cholesterol) and cellular debris enclosed between blood vessel wall and the cap (see FIG. 13).

Stenotic plaques can reduce blood flow 39 for organs or body appendages 25 (arms and legs) that translates in ischemia of the affected tissue due to its deprivation of proper nutrients and oxygenation. Ischemic tissue can be a life threatening situation if is affecting the heart (affects normal function of the heart, thus blood circulation in general) or can influence limbs' extremities (can result in amputations due to CLI-critical limb ischemia) or can become a chronic pain in body appendages 25 and especially in legs (known as peripheral arterial disease or PAD that is affecting most of the older population, with debilitating effects for the normal life activities).

The grade of stenosis is indicated based on the percentage of cross-sectional area of blood vessel 15 blocked by the stenotic plaque. That can range from 5-90%, where 5% stenosis is a limited narrowing of the blood vessel 15 and 90% is a severe narrowing. The 5% up to 50% stenosis are kept under observation. After 50% blockage of the blood vessel 15 cross-section, the stenotic vessels need treatment, which today is done with angioplasty (inflate balloons inside the stenosis to dilate the blood vessel 15 and break plaque 130) or stenting (deployment of a stainless steel or nitinol metallic mesh inside the stenosis to keep the blood vessel 15 opened). The disadvantage of both stenting and angioplasty is that they produce post-procedural inflammation, which can generate proliferation of the smooth muscle cells and consequently a re-narrowing of the vessel 15 lumen (cross-section), phenomenon called restenosis. To prevent restenosis drug-eluting stents (DES) were created. These stents have the metallic scaffolding covered with polymers that contain drugs as Paclitaxel or Sirolimus, which prevent inflammation and thus can eliminate or reduce smooth muscle proliferation.

Both stenting and angioplasty procedures are minimally invasive, which makes them acceptable for patients with multiple comorbidities. Some complications with the DES can be generated by the non-epithelialization of the stents in their middle portion, which can produce late thrombus formation that can be life threatening if the stent was placed in coronary arteries (heart) or in carotid arteries.

Recently, a type of angioplasty with the balloons covered with Paclitaxel and Sirolimus was also tried to arrest smooth muscle cells proliferation. In comparison with drug eluting stents the balloons eluting drugs represent a technology yet to be proved.

The angioplasty and stenting of stenoses, with drugs or without drugs have advantages and disadvantages as described. In embodiments, the addition of extracorporeal pressure shock waves technology used independently or in conjunction with angioplasty and stenting may be beneficial.

Vulnerable plaques (see FIG. 13) are vascular plaques that have a very thin cap that makes them prone to be easily cracked, which can let out the mixture of cholesterol and cellulose debris from under the cap. The spilled-out mixture can generate a thrombus (can occlude arteries and thus producing tissue ischemia) or an embolus (can travel distal through the blood vessels 15, which can produce heart attacks for coronaries, pulmonary embolism or strokes for carotids or brain arteries). In the case of a vulnerable plaque the crack of the cap is not dependent on the grade of stenosis. Even 5% reduction of vessel 15 cross-sectional area (stenosis) can be life threatening in the case of vulnerable plaques. This risk associated vulnerable plaques makes such plaques a main target for preventive or acute treatment of stenotic vessels.

Vulnerable plaques are difficult to detect due to the fact that they are asymptomatic, until they erupt and have grave consequences. External methods/technologies that may be used for detection include: MRI (Magnetic Resonance Imaging), CT (Computed Tomography); EBCT (Electron Beam Computed Tomography), Search for inflammatory markers in blood (Interleukins 6, 18, Matrix Metalloproteinase (MMP), C-reactive protein (CRP), etc.) and Ultrasound (look for hypo echoic regions due to LDL presence).

Internal/invasive methods/technologies are described in "Vulnerable Plaques: a Brief Review of the Concept and Proposed Approaches to Diagnosis and Treatment" and "SIS ALMANAC ONLINE-Vulnerable Plaque" citations and can be categorized as follows: Intravascular Ultrasound (IVUS), Angiography, Angioscopy (direct visualization in color of the vessel wall), IVUS Elastography (combination of intravascular ultrasound with radio-frequency measurements), Thermography Catheters (local increase in temp due to the presence of monophages in the vulnerable plaque), Optical Coherence Tomography, Spectroscopy (RAMAN or near infrared) and Intravascular MRI.

Proposed treatments for vulnerable plaques include: drug eluting stents (DES) and medication (ACE inhibitors, beta-blockers, anti-microbial agents, anti-inflammatory agents, inhibitors for MMP, etc.).

In embodiments of the invention, pressure shock waves produced in an extracorporeal manner can be used for the treatment of vulnerable plaques using the mechanisms that include: pressure shock waves to improve endothelial function of the body, decrease the LDL (bad cholesterol) levels, inhibit LDL oxidation, increase reverse cholinesterase transcript, reduce inflammation and inhibit thrombosis.

Because treatments of plaque 130 such as stenotic plaques and vulnerable plaques, blood vessels' inflammations, enlarged or torturous veins (varicose veins), inflammations or degeneration of any natural human/animal conduit/lumen, use the same type of construction of equipment, the described FIGS. 14A-17 apply for both types of blood vessels plaques 130 (stenotic and vulnerable) and for any other specific treatment of the blood vessels 15 wall (arteries/veins) or natural human/animal conduits/lumens wall.

Note that the major difference in between the treatment of blood vessels 15 generally and of blood vessels 15 that have plaques 130 is the setting for the pressure shock waves. For chronic inflammation of the blood vessels 15 wall and enlarged or torturous veins (varicose veins) the energy used is low to medium, for stenotic plaques the setting for energy will be high and for vulnerable plaques the energy used is low to medium (promotes tissue growth on the plaque cap). For electromagnetic, piezoelectric and electrohydraulic or projectile pressure shock waves applicators 30 the settings for treating vulnerable plaques will produce flux density of $\leq 0.2$ mJ/mm$^2$ in one or more embodiments.

For stenotic plaques 130 the energy flux density should be $\geq 0.3$ mJ/mm$^2$ to produce the elimination of the plaque in one or more embodiments.

For chronic inflammation of the blood vessels 15 or any natural human/animal conduits/lumens and for enlarged and/or torturous veins (varicose veins) the energy flux density should be $>0.1$ mJ/mm$^2$ and $\leq 0.3$ mJ/mm$^2$ in one or more embodiments.

Also, the treatment of inflammation for blood vessels 15 or human/animal conduits/lumens, enlarged or torturous veins (varicose veins) or for vascular plaques 130 (stenotic or vulnerable) can be done independently with extracorporeal pressure shock waves devices or in synergy with different drugs or other medical devices.

In embodiments of the invention, extracorporeal pressure shock waves are not limited by vessel 15 or conduit or lumen size in order to treat inflammation for blood vessels 15 or human/animal conduits/lumens, enlarged or torturous veins (varicose veins), stenosis (reduce of cross section area of blood vessels), blood clots formation in blood vessels 15 (veins and arteries) or human/animal conduits/lumens. Avoiding such limitation is useful for blood vessels 15 where comparative angioplasty and stenting (invasive procedures) are physically limited by the catheter dimensions (tubular devices that carry the stents inside the human body or have balloons at the distal end that are used to reopen the blood vessel 15 in the stenotic area). Thus, angioplasty and stenting cannot be done for vessels 15 smaller than 2 mm in diameter size.

Figure 14A:
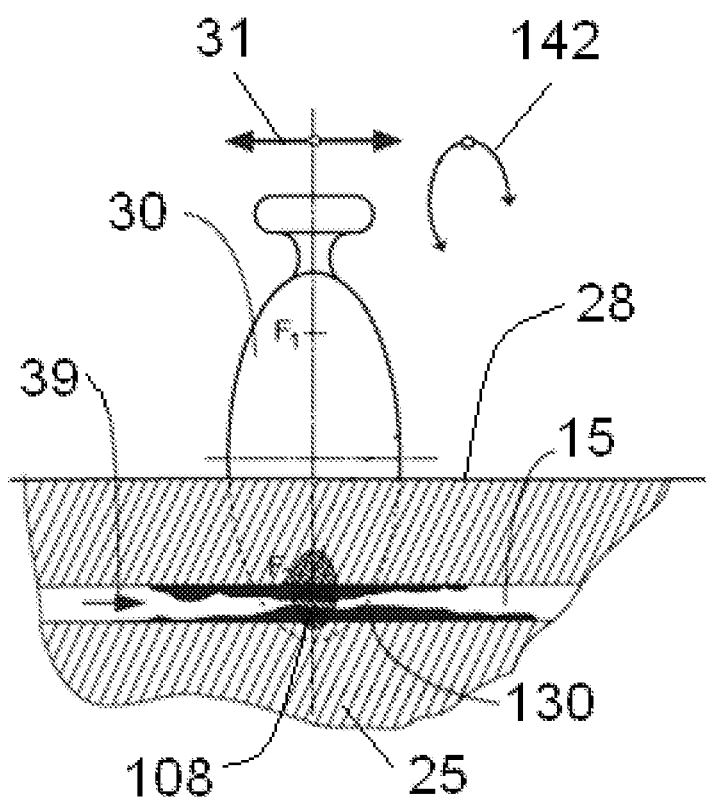
FIG. 14A is a schematic diagram of a shock wave applicator positioned to treat vascular plaque in one embodiment of the present invention.

Referring to FIG. 14A, for the treatment of any type of plaques 130 (stenotic or vulnerable) or blockages of the arteries, veins, natural human/animal conduits/lumens due to blood clots (thrombus or embolus), the focus of the pressure shock waves should be done on the vessel 15 or conduit/lumen wall in front of the targeted area and as perpendicular possible to the vessel 15 or conduit/lumen wall.

Figure 14B:
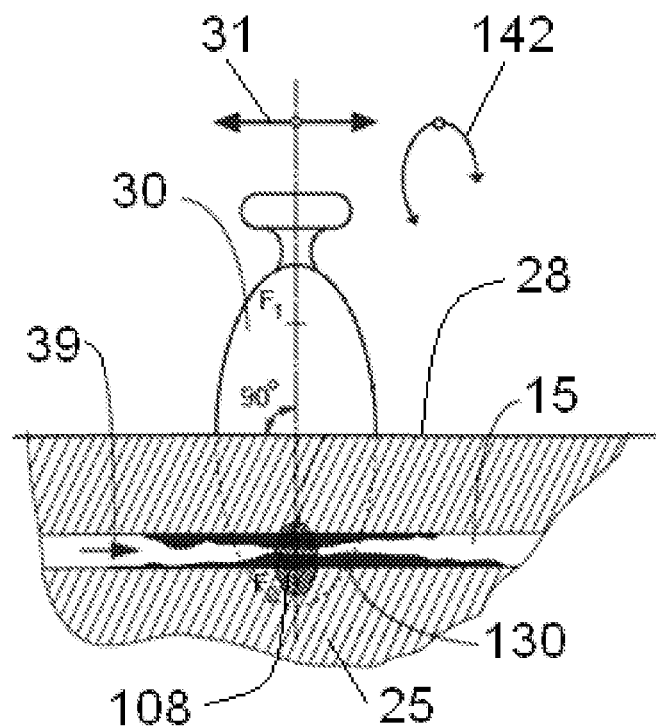
FIG. 14B is a schematic diagram of a shock wave applicator positioned to treat vascular plaque in one embodiment of the present invention.

When there is no patient risk in generating debris 95 down the flow stream 39 inside a blood vessel 15 or a natural conduit/lumen (for example blood vessels of the limbs present lower risk of debris 95 blocking small vessels compared with neck, brain, or heart vessels), applicator 30 can be focused on plaque 130 or in front of the plaque 130 as shown in FIG. 14B. In one illustrated embodiment, a 90° angle is provided in between the direction of the applicator 30 and vessel 15 or conduit/lumen walls. Also, a long focal volume 108 can cover the whole vessel 15 or conduit/lumen cross-sections, which can give action from cavitation and/or by the compressive forces both on the surface of the plaques 130 and on the lipids trapped inside the plaques 130. As shown in FIGS. 14A and 14B, a variable penetration is helpful to apply treatment correctly, particularly for big vessels 15 or natural conduits or lumens (large diameter) or for the vessels 15 or conduits/lumens that change penetration relative to the skin 28 on their path inside an appendage 25 or body generally.

The approach presented in FIGS. 14A and 14B can be used to eliminate blood vessels 15 or natural human/animal conduits/lumens spasm (especially when catheters, guide wires 94, stents, balloons, or other invasive medical devices, etc. are used to navigate through vessels 15 or conduits/lumens or stretch them). A similar approach can be also applied to reduce the chronic inflammation of the blood vessels 15 and other natural conduits/lumens of the human/animal bodies, which can have debilitating effects in the long term.

Figure 15A:
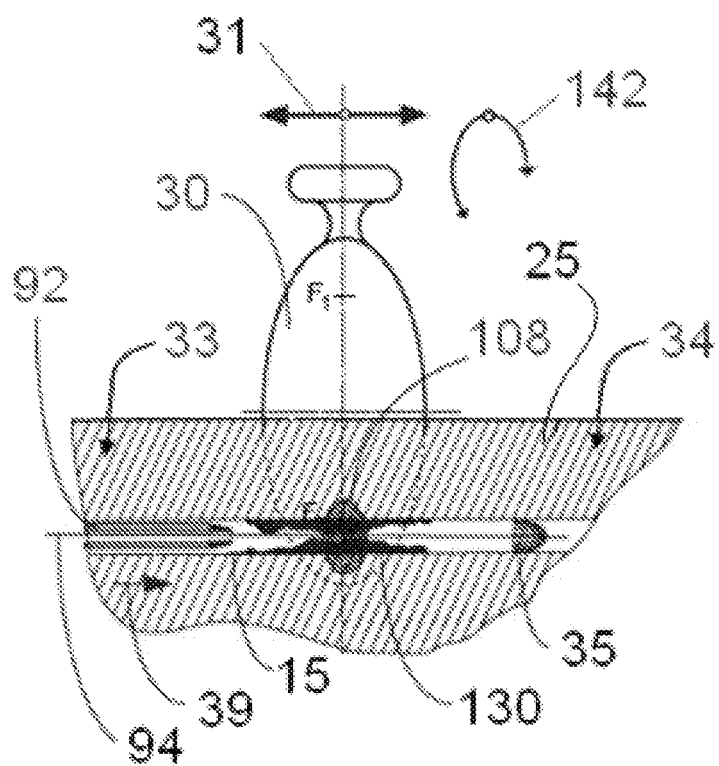
FIG. 15A is a schematic diagram of a shock wave applicator and debris basket positioned to treat vascular plaque in one embodiment of the present invention.
Figure 15B:
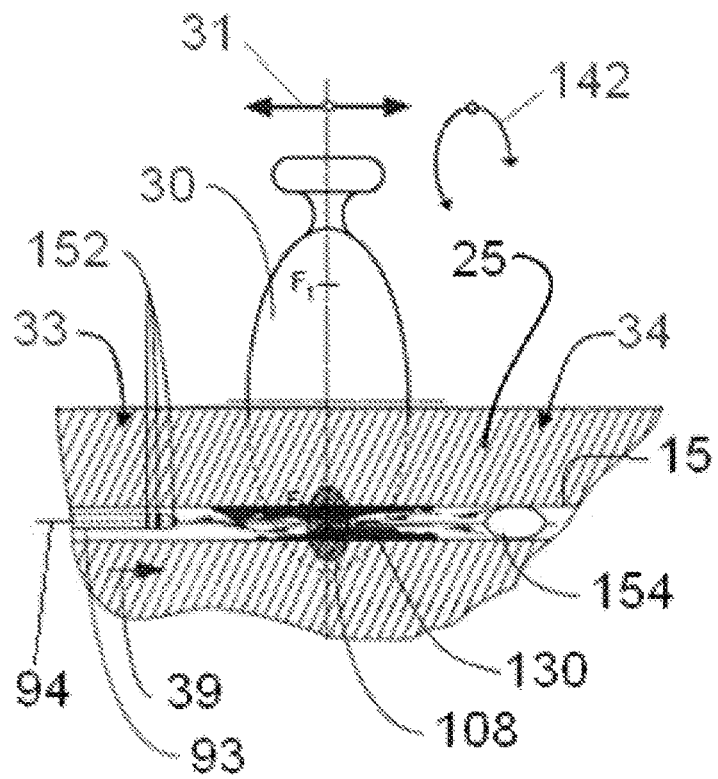
FIG. 15B is a schematic diagram of a shock wave applicator and occlusion balloon positioned to treat vascular plaque in one embodiment of the present invention.

Referring to FIGS. 15A and 15B, in order to cover the entire stenotic region, applicator 30 can have longitudinal movement 31 combined with transversal movement 142. For arteries that can pose the risk for the blood flow 39 carrying debris 95 (plaque fragments, blood clots, etc.) from the stenotic area in sensitive areas (brain or heart) the pressure shock waves may be delivered with the use of distal protection devices (such as baskets 35 or occlusion balloons 154).

The distal protection system preferably is able to pass the plaques 130 (stenotic or vulnerable) towards the distal region 34 of the plaque 130, to protect the smaller vessels down the flow 39 to be blocked by debris 95 (not shown in FIGS. 15A and 15B) and/or embolus from the plaques 130 and thus seeking to prevent tissue ischemia (lack of oxygen and nutrients).

For distal protection, either basket devices 35 (see FIG. 15A) or balloon occlusion 154 devices (see FIG. 15B) can be used. The main difference is that the baskets 35 have a mesh with pores ≥10 μm that collect debris 95 larger than 10 μm and in the same time allow the normal blood flow 39 to take place. The balloon occlusion 154 devices use guide wires 94 with balloons on their distal end. The balloon guide wire 94 is positioned to allow the inflation of the occlusion balloon 154 after stenotic area. In this way the debris 95 are collected around the proximal surface of the balloon. This solution completely blocks the blood flow 39 during procedure. The collected debris 95 can be extracted using:

Passive extraction as presented in FIG. 15B. Practically, a suction catheter 93 is positioned in such way to allow the suction of blood column with collected debris 95. The suction is created by connecting the proximal end of the suction catheter 93 to a syringe.

Active extraction as presented in FIG. 9. In this case the collected debris 95 around the proximal end of the occlusion balloon 154 is stirred by the active flush produced by the flush catheter 91 and collected by the guide catheter 92, which thus has a dual role—to guide the flush catheter 91 inside the vasculature and also to collect through active suction the debris 95. In this case dedicated pumps need to be used to drive the flush catheter 91 and the guide catheter 92.

The disadvantage of the catheter system that uses the occlusion balloon 154 is given by the complete blockage of blood flow 39 during action, which can be restrictive, especially for the treatment of carotids or heart arteries.

In an embodiment for visualization inside the human body, the suction catheter 93 from FIG. 15B has radio-opaque markers 152 that can be seen using fluoroscopy, which helps with the correct positioning of these devices inside the blood vessels 15 or natural conduits/lumens 17. The occlusion balloon 154 from both FIGS. 15A and 15B are filled with contrast agent that makes them visible under fluoroscopy.

Figure 16A:
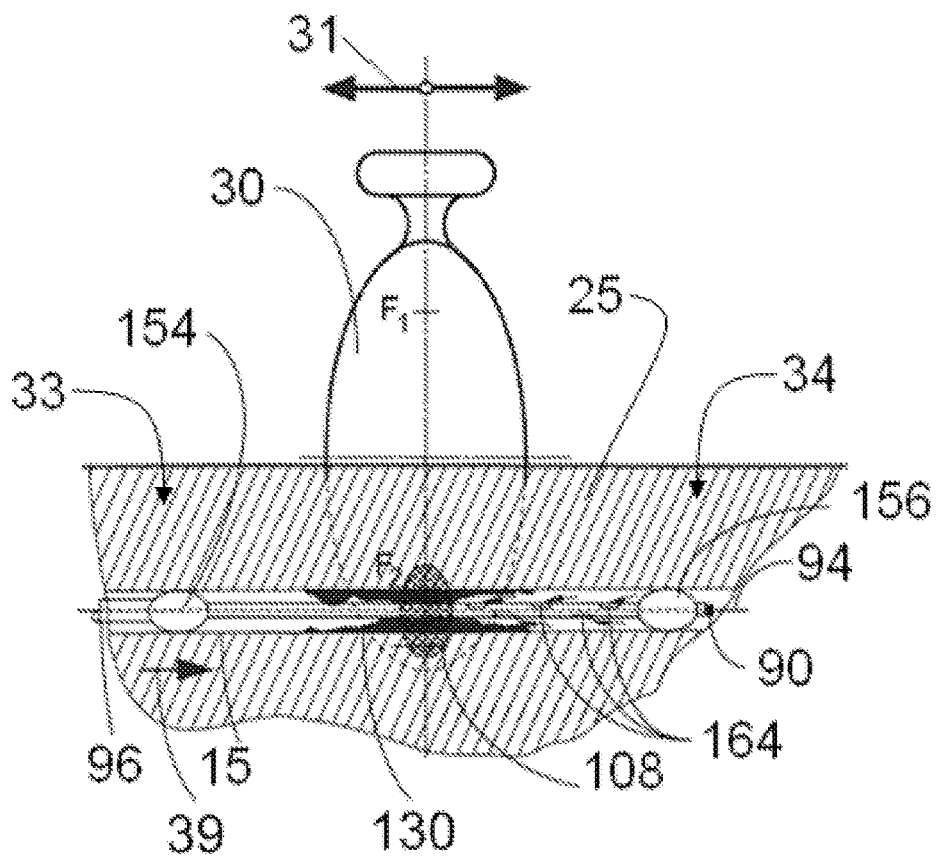
FIG. 16A is a schematic diagram of a shock wave applicator and occlusion balloons positioned to treat vascular plaque in one embodiment of the present invention.
Figure 16B:
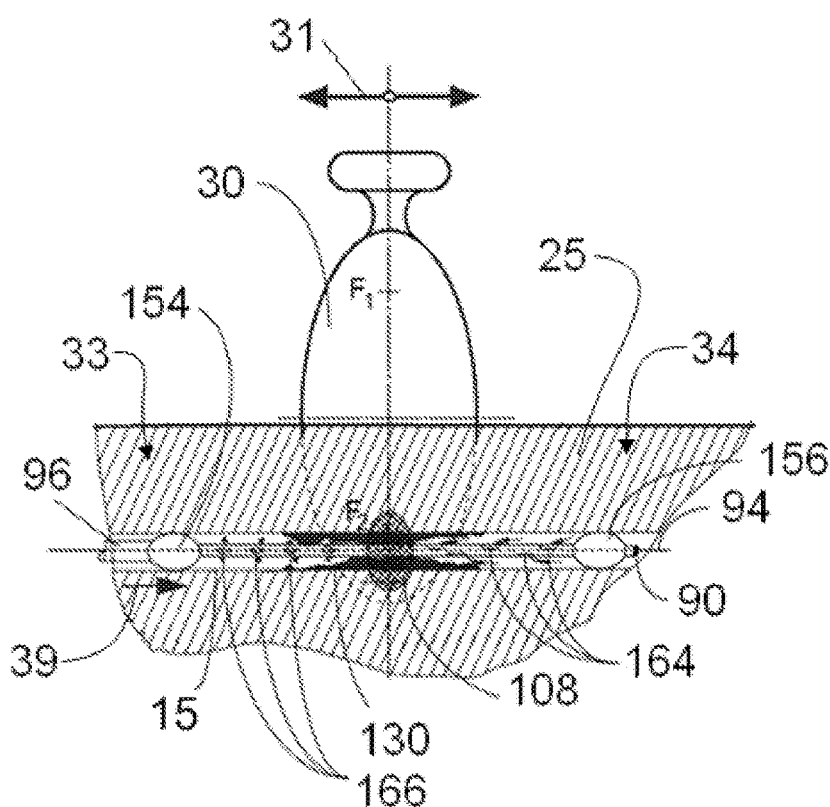
FIG. 16B is a schematic diagram of a shock wave applicator and occlusion balloons positioned to treat vascular plaque in one embodiment of the present invention.

Sometimes is desired that a totally enclosed space be created in the treatment area from a body appendage 25 or body, as shown in FIGS. 16A and 16B. This closure can be accomplished with the use of an occlusion catheter 96 that uses two balloons-first balloon 154 in the proximal region 33 to the plaques 130 (stenotic or vulnerable) or targeted area 145 and the second balloon 156 in the distal region 34 to the plaque 130, 135 or targeted area.

The newly created space can be emptied from blood (in case of blood vessels 15) or any other body fluid (for natural conduits/lumens) and medical saline solution can be introduced. This saline solution should be able to create much faster cavitation bubbles than the blood or any other body fluid, which can facilitate the cavitation action of the pressure shock waves inside the focal volume 108. After the shock wave treatment, the occlusion balloon 154 will be deflated letting the blood flow 39 or body fluid normal flow 75 to get in the protected space and finally the occlusion balloon 156 is deflated and the occlusion catheter 96 can be retrieved over the guide wire 94. As can be seen from FIG. 16A, before deflation of the occlusion balloon 156 a passive suction via suction holes 164 (using a medical syringe attached to the occlusion catheter 96) can be applied to collect any debris 95 (not shown in FIGS. 16A and 16B) trapped proximal to the balloon 156.

In some cases besides the saline solution, drugs in liquid form can also be added in the occluded space via drug delivery holes 166 (see FIG. 16B), which can help with plaque 130 (stenotic or vulnerable) and/or blood clots (thrombus or embolus) elimination or for any treatment of the blood vessel 15 wall or natural human/animal conduit/lumen wall that required specific high dosage medication that is not recommended to be administered systemically. The advantage of delivering a high concentration substances added in the saline solution is that will have a high probability of affecting vessel 15 walls (including plaques 130) or natural human/animal conduit/lumen wall from the targeted area 145 and in a synergetic effect with the pressure shock waves. For example, the pressure shock waves can open micro-cracks in the plaques 130 or blood vessels 15 walls or conduit/lumen walls and thus allowing the penetration of substances/drugs inside the plaque 130 or vessel 15 walls or conduit/lumen walls.

For removal/dissolution of the blood clots from veins using extracorporeal pressure shock waves, as sole treatment or in combination with specific drugs, the big advantage is given by the fact that the pressure shock waves treatment can be done without affecting the valves present in veins.

Substances/drugs that can be added in the saline solution in non-limiting below, although embodiments include: heparin, tacrolimus, beta blockers, paclytaxel, thrombolitic substances, ACE inhibitors, cyclosporin, antibiotics, antimicrobial agents, sirolimus, anti-inflammatory drugs, other tissue growth inhibitors and the like.

The use of pressure shock waves alone or with drugs in an enclosed space that contains the stenotic regions or targeted treatment area is applicable to the embodiments presented in FIGS. 16A and 16B.

Furthermore, the pressure shock waves can be used to reduce post-procedural inflammation after angioplasty (balloons inflated inside the stenotic region) or stenting of a blood vessel 15 or any natural conduit/lumen.

Figure 17:
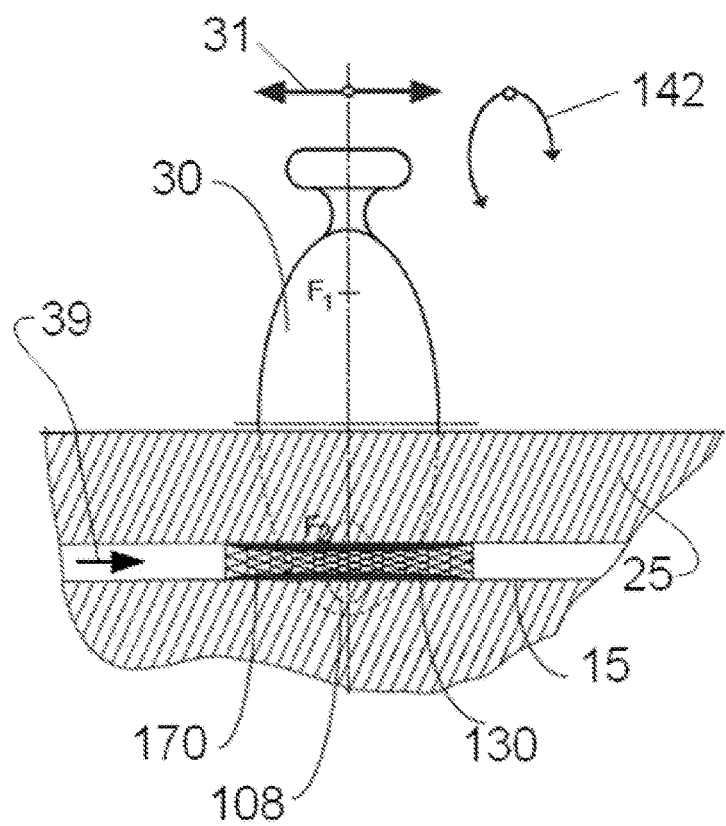
FIG. 17 is a schematic diagram of a shock wave applicator positioned to treat tissue in blood vessel with a stent in one embodiment of the present invention.

Referring to FIG. 17, stents 170 are open structures that allow pressure shock waves to travel through them. Due to the nature of the stents 170 (metallic or plastic meshes) there will be interference between pressure shock waves and stents 170, which will affect the focusing of the pressure shock waves and finally their efficiency. For treatment of tissue from a blood vessel 15 or a natural human/animal conduit/lumen inside a body appendage 25 or body generally with the stents 170 incorporated therein, the focus is preferably on the soft tissue around the stent 170. In some embodiments, an applicator 30 with a very large focal volume 108 (FIG. 17) is used.

When compared with stenotic plaques, vulnerable plaques 135 may be treated with similar approaches, with the distinction that low energy settings will be used (low spark discharge voltages or energy actuation for electromagnetic, piezoelectric or projectile devices) combined with lower number of shocks (minimum 100, and maximum 1500). The same principles apply for the treatment of a stent in a targeted area 145 of a natural human/animal conduit/lumen. Also, the focus of the pressure shock waves should be on blood vessel 15 walls or conduit/lumen walls. Where no debris 95 is generated by the process in one or more embodiments, the distal protection is not necessary. The treatment can be done in one enclosed space, with pressure shock waves only (see FIG. 16A), or with addition of drugs (see FIG. 16B). The synergetic effect between highly compressive waves and cavitation that push the drugs inside the tissue (due to cavitation microjets) can help to thicken the cap of the vulnerable plaques and thus preventing their rupture.

An advantage of extracorporeal pressure shock waves usage in treatment of blood vessels 15 or natural human/animal conduits/lumens is that it can be performed without any major inconvenience to the patient. The treatments can be administered in one or more sessions and at different or equal time intervals. If restenosis occurs, the shock wave treatment can be applied immediately without any kind of surgery or invasive procedure in various embodiments.

Based on their efficacy, pressure shock waves delivered extracorporeally can also be used as prophylactic treatments, such as to prevent plaque 130 (stenotic or vulnerable) formation for patients genetically prone to develop vascular disease. The time intervals can be from 1 day to 30 days or more. A combination of pressure shock waves delivered extracorporeally with invasive means (catheters, guide wires 94) can be more complicated for the patient. In any case, if the pressure shock waves can enhance drug delivery or help to achieve the targeted goal, it is still beneficial to the patient. Introduction of guide wires 94, guide catheters 92, diagnostic catheters, flush catheters 91, inside the vasculature (via femoral or brachial access) represent minimal invasive procedures that are practiced conventionally. Furthermore, for natural human or animal conduits or lumens the use of any invasive means in conjunction with extracorporeal pressure shock waves is even less complicated when compared with the blood vessels 15. In general, if a metallic structure (stent 170, guide wires 94, catheters made of metallic hypo tubes, etc.) is present in the focal volume 108 of the shock wave devices, the structure will be an interference, which usually moves the focal point $F_2$ proximal to the structures. This phenomenon may be used to move $F_2$ from inside the vessels 15 or conduits/lumens to their wall.

Figure 18:
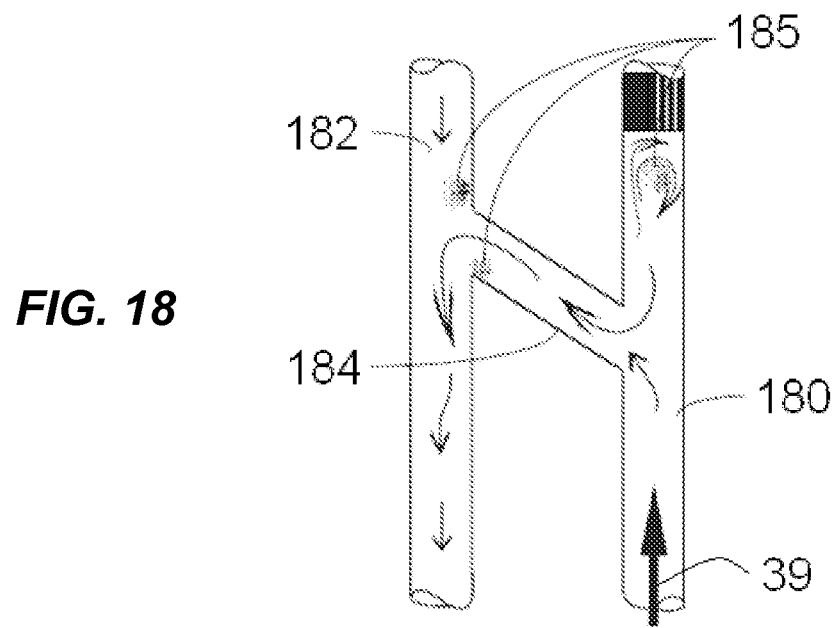
FIG. 18 is a schematic diagram of an artery and vein with an artificial vessel in one embodiment of the present invention.

Extracorporeal treatment may also be used to treat shunts/fistulas between an artery and a vein using harvested vessels, grafts and/or stents, and for thrombus/embolus elimination from blood vessels or natural human/animal conduits/lumens. In general, when a slow blood flow 39 occurs in the vasculature due to occlusions 20 or stenosis, there is an increased chance of thrombosis. Also, when foreign objects are flowing or sitting in the vasculature, the body reaction is to clot blood around them using the thrombosis mechanism. As shown in FIG. 18, in cases where an artificial material is used to create an alternative conduit for the blood flow 39 using artificial vessels 184 or grafts made of DRACON, PTFE, etc., thrombosis may occur too. The thrombosis risk is elevated with shunts (fistulas), which are created between an artery 180 and a vein 182 in a compromised vasculature due to hemodialysis, for example. Through shunts the blood can slowly move from the arteries 180 to the veins 182. Due to big difference in velocity between the blood flow 39 in the arteries 180 and the veins 182 (very slow in veins 182 compared to arteries 180) vortexes are created and dead spaces, which can entrap blood and thus creating blood clots prone areas 185, as can be seen from FIG. 18. Furthermore, due to slow moving blood and due to the contact with a foreign substance/material, the distal area of the shunts represents the perfect environment to create additional blood clots prone areas 185.

In these cases, stents 170 might be used to open the shunt (not shown in FIG. 18). Even in the presence of the stents 170 inside the shunts, there are zones where blood clots prone areas 185 are formed in the metallic mesh of the stent 170 due to the same big difference in velocity between the blood in the arteries 180 and the veins 182 and the presence of foreign material of the stent 170. The blood clots from the stents 170 can grow in size and thus blocking the shunt (artificial vessel 184).

Blood clots (thrombus or embolus) can also be created during the injury/trauma of a vessel 15 or of a natural human/animal conduit/lumen or in the case of rupture of the cap of plaques 130. To repair the rupture/trauma the organism brings clotting agents that promote the formation of a blood clot (thrombus) that can grow in size to a sufficient dimension to block the active blood circulation 39 from blood vessels 15 or the normal fluid flow from natural conduit/lumen or can travel through the vessel 15 or conduit/lumen in the form of embolus until it reaches a smaller diametric dimension of the vessel 15 or conduit/lumen, where it produces a blockage.

To eliminate blood clots from natural blood vessels 15 (arteries 180 and veins 182) or artificial vessels 184 (shunts or bypass harvested vessels) or from natural human/animal conduits/lumens the pressure shock waves generated externally (extracorporeal) can be used to break this coagulated blood (lysis of the blood). The pressure shock waves can be used alone or in combination with thrombolytic drugs. For blood clots formed inside natural vessels 15 or natural human/animal conduits/lumens any approach as presented in FIG. 14A, 14B, 15A, 15B, 16A, 16B or 17 might be used.

The extracorporeal treatment using pressure shock waves for blood clots formed in shunts or bypasses using artificial vessels 184 or natural/harvested vessels 15 is possible due to the fact that in these cases the shunts made of artificial vessels 184 or natural/harvested vessels 15 are placed immediately under or closer to the skin 28.

For blood clots formed in shunts or bypass artificial vessels 184, reflectors 22 with elliptical geometries can be used that produce superficial penetration (10 to 30 mm), reflectors that have the semi axis ratio of b/c≥1.1 and b/c≤1.6. Spherical or parabolic ($y^2=2px$) reflectors 22 can be also used due to the superficial treatment necessary for these situations.

The detailed treatment choices for shunts are identical in embodiments of the invention to those presented on FIG. 14A, 14B, 15A, 15B, 16A, 16B or 17.

Figure 19:
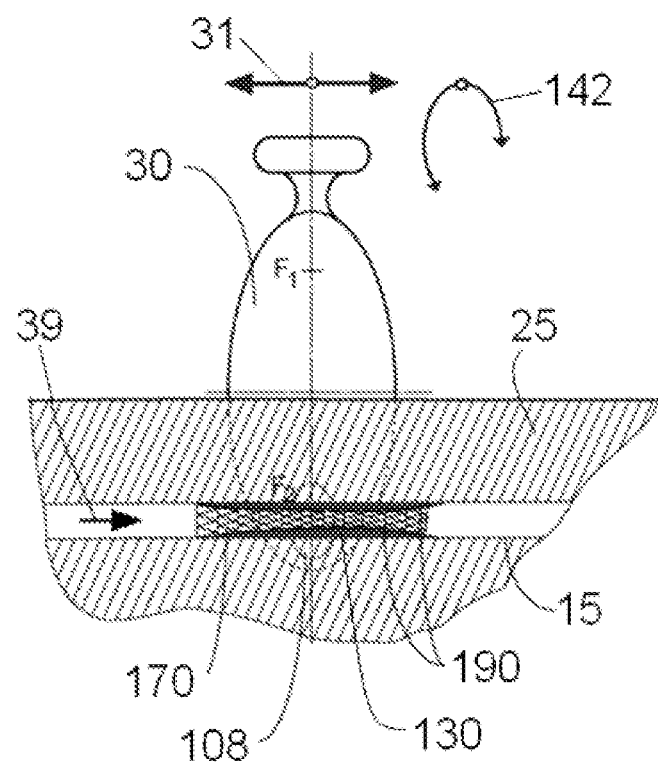
FIG. 19 is a schematic diagram of a shock wave applicator positioned to treat in-stent restenosis in one embodiment of the present invention.

Extracorporeal pressure shock waves may also be used for the treatment of in-stent restenosis. After stenting of stenotic regions, there is a relatively high potential that the tissue will grow back through the stent 170 and produce a new stenotic region that can reduce the blood flow 39 from a blood vessel 15 or the normal fluid flow from a natural human/animal conduit/lumen. This phenomenon is called in-stent (inside the stent 170) restenosis 190, as shown in FIG. 19. This new stenotic region that incorporates a stent 170 underneath it is very difficult to treat, due to the reduced vessel 15 or conduit/lumen 17 diameters. Sometimes for blood vessels stents 170 angioplasty balloons are used to push the new formed tissue and the stent 170 radially away from the axis of the vessel 15 or conduit/lumen. Although this approach can be successful in short term, it does not offer a preferable long-term solution. For blood vessels 15 used with drug eluting stents (DES) in-stent restenosis 190 is often reduced when compared to bare metal stents 170.

The use of non-invasive (extracorporeal) pressure shock waves may provide a solution for in-stent restenosis. The inflammation and tissue proliferation may be arrested immediately after the stenting procedure using the approach presented in FIG. 17 to reduce post procedural inflammation, smooth muscle growth and finally in-stent restenosis 190. If the in-stent restenosis 190 was produced, then the pressure shock waves can be used to treat this chronic target location, as shown in FIG. 19.

The pressure shock waves are delivered in embodiments in the stenotic area developed inside the stent 170. The focal point $F_2$ of the focal volume 108, where the pressure shock waves are concentrated, should be inside the stenotic plaque 130 of a blood vessel 15 or targeted area of a natural conduit/lumen. Minimal interference with the metallic mesh of the stent 170 may be provided. If the pressure shock waves pass through the stent 170 (highly possible) then consideration might be given to the shift of the $F_2$ away from the stent 170.

Depending on the type of vessel 15 or conduit/lumen treated and its position inside the body or body appendage 25, this procedure will be implemented distal protection to capture debris 95 generated during procedure, as presented in FIGS. 15A and 15B. Also, an enclosed treatment space approach can be used (especially for combination of pressure shock waves and drugs), as shown in FIGS. 16A and 16B.

In further embodiments, extracorporeal pressure shock waves can be used to treat the heart in non-limiting examples such as: treatment of muscles that activates the heart valves to strengthen them, eliminate any excess pericardial fluid accumulation from the pericardial cavity (pathologic, accidents or due to heart surgical intervention); treat ischemic muscle that resulted after a myocardial infarction episode; revascularization of heart muscle, 2-3 weeks before stem cells genes or growth factors applications (injection) in the ischemic tissue that resulted after a myocardial infection; adjunct treatment during injection of stem cells, genes or growth factors into tissue; in general for tissue regeneration and in particular for myocardial infarction ischemic tissue, auxiliary treatment post injection of stem cells, genes or growth factors into tissue; in general for tissue regeneration and revascularization, and in particular for myocardial infarction ischemic tissue regeneration; and treatment for destroying internal fibrotic/scarring tissue and regrowth of viable heart muscle and treatment after heart surgery or coronary interventions to enhance healing.

Challenges of treating the heart tissue, pericardium and pericardial cavity using pressure shock waves (extracorporeal) include factors such as: chest ribs bone in front of the pressure shock waves (they obstruct the penetration of pressure shock waves towards heart); the presence of the lungs behind the heart can interfere with the treatment of the posterior tissue of the heart; pressure shock waves change dramatically their speed at the boundaries where the sound speed changes (soft tissue to air) and in this way can produce lung hemorrhagic lesions; and breast tissue in front of the heart can also produce variable penetration depth.

Figure 20:
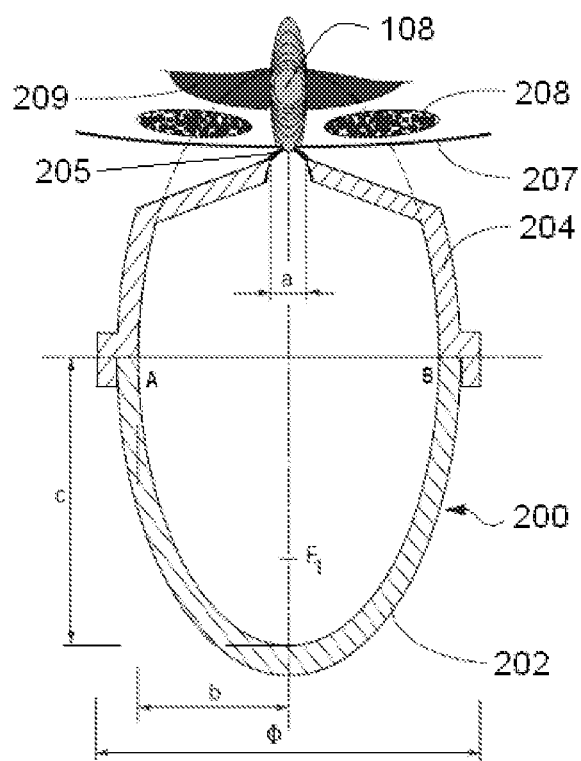
FIG. 20 is a schematic diagram of a shock wave applicator having an elongated aperture and positioned for treatment of a heart in one embodiment of the present invention.

To avoid the interference of the bony structure of the rib cage, reflectors 200 as shown in FIG. 20 may be small in size to be placed in between the ribs, with an aperture (a) that allows pressure shock waves to focus in $F_2$ and with a diameter of the focal volume 108 of the order of 1-2 cm or less.

With continuing reference to FIG. 20, the effective treatment of the heart 209 muscle can be accomplished by designing special heart applicators 200 with small elongated apertures to match the openings between ribs 208 and with deep reflectors to allow the necessary penetration to reach the heart 209 tissue, when heart applicators 200 are maintained in contact with the patient chest 207.

The dimension of the reflector largest diameter @ is 10-40 mm, which produces a mini-reflector. Due to its reduced dimension the discharge in $F_1$, in embodiments the voltage applied for electromagnetic or piezoelectric approach is reduced to 1-14 kV or even lower. To overcome the reduction in energy delivered with each shock, one embodiment uses 80-90% of the ellipsoid (increased reflective area surface), compared with classic approach where only 50% of the ellipsoid surface is used to focus the pressure shock waves.

The use of 80-90% of the ellipsoid surface is done by combining a lower shell 202 with a distinctive upper shell 204, which together form most of the internal surface of the ellipsoid. This embodiment provides a much higher efficiency in shock transmission and focusing. The top portion of the heart applicator 200 has a membrane 205 on top of a small aperture (a) of 5-10 mm that is constructed to fit the intervertebrae openings and concentrates the reflected waves towards the focal volume 108 without interference.

Minimal interference is preferable in points A and B to allow distortion of the signal between compression and tensile phase. That can be realized through a small difference in size of the connection between upper shell 204 and the lower shell 202.

Figure 21A:
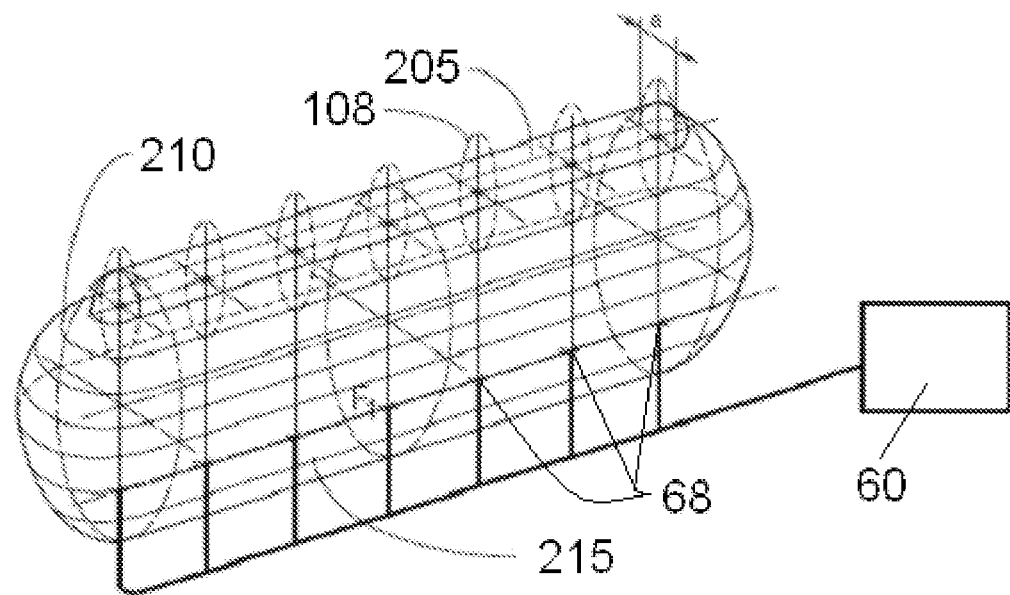
FIG. 21A is a schematic diagram of an elongated shock wave applicator reflector with multiple discharge points in one embodiment of the present invention.
Figure 21B:
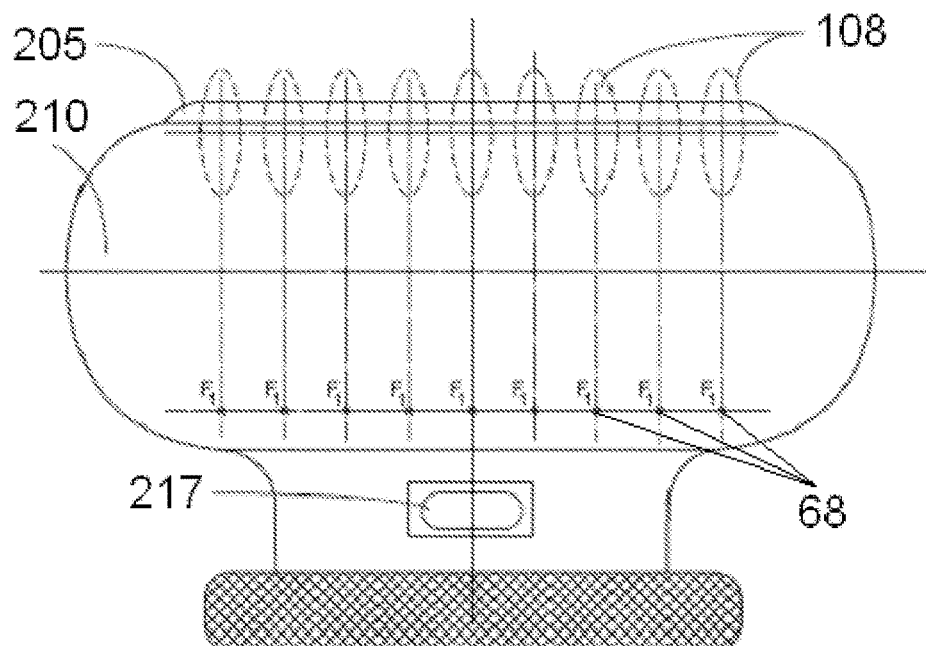
FIG. 21B is a schematic diagram of an elongated shock wave applicator reflector with multiple discharge points and activation button in one embodiment of the present invention.

An elongated applicator 210, shown in FIGS. 21A and 21B, can increase efficiency of the treatment and the triggering of the pressure shock waves in multiple $F_1$ (discharge points 68), which can be done in the same time or sequential using a shock wave generator 60 based on the needs of the treatment. The cross section of the reflecting surface 215 of the special elongated applicator 210 can be an ellipse (as presented in FIG. 21A) or can be a parabola, a circle or any combination of these geometries. The actuation/control of the special elongated applicator 210 can be done using the actuation button 217. The reflecting surface 215 can be also created using piezoelectric elements as crystals, thin films or fibers. Finally, the aperture in the membrane 205 area is preferably comparable with intervertebral openings to avoid interference of the pressure shock waves with rib cage bones.

Figure 22:
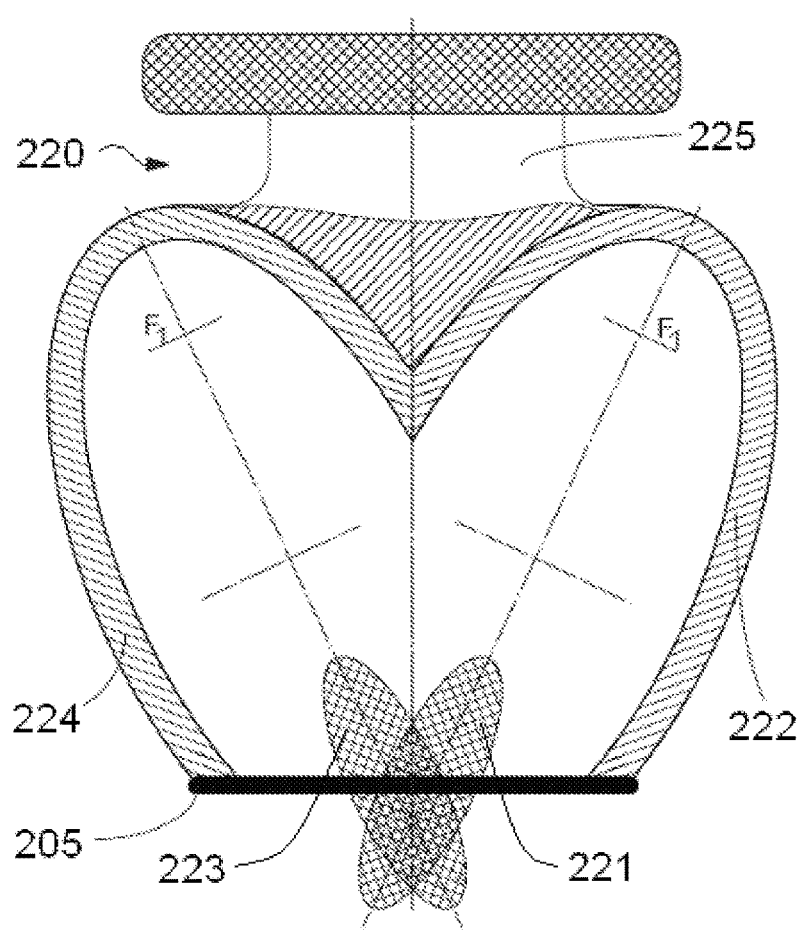
FIG. 22 is a schematic diagram of a shock wave applicator with angled reflectors' portions' geometries in one embodiment of the present invention.

A reflector with angled geometries is shown in the embodiment of FIG. 22 as a multi-reflectors' applicator 220. To create this applicator embodiment, three pieces (first reflector portion 222, second reflector portion 224 and top piece 225) are assembled together to achieve the illustrated enclosed space used to focus pressure shock waves confocal in the treatment area. The focal volumes (first reflector focal volume 221 and second reflector focal volume 223) have controlled length to avoid penetrating inside the heart chambers. Also, the aperture in the membrane 205 is preferably comparable with the intervertebral openings, as described with reference to FIGS. 20, 21A and 21B.

Figure 23A:
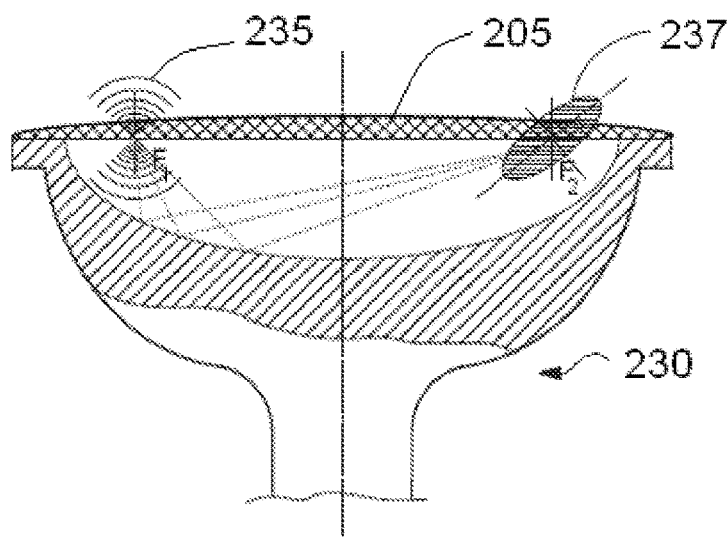
FIG. 23A is a schematic diagram of a shock wave applicator including a reversed ellipsoid reflector in one embodiment of the present invention.
Figure 23B:
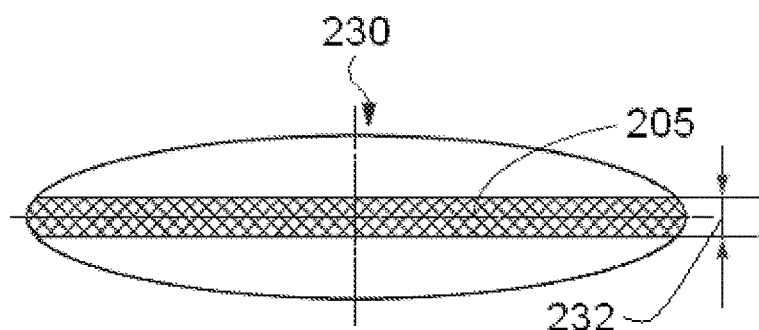
FIG. 23B is a schematic diagram of a top plan view of an aperture of a shock wave applicator including a reversed ellipsoid reflector in one embodiment of the present invention.

A reversed reflector 230 for cardio application is illustrated in FIGS. 23A and 23B. The geometry of the reversed reflector 230 is created in embodiments by slicing an ellipsoid longitudinally and not transversal as it was done with the classic approach for a reflector geometry. Reversed reflectors 230 are able to generate radial waves 235 and focused waves that are directed in focal volume 237, acting in sequential manner on the treatment area. Such design can increase treatment efficiency. Contact with the body 27 occurs via membrane 205 covering the aperture 232 of the reversed reflector 230. As described with reference to FIGS. 20, 21A and 21B, the aperture 232 preferably matches the distance in between ribs 208, for an efficient treatment of the heart 209 using extracorporeal pressure shock waves.

Figure 24A:
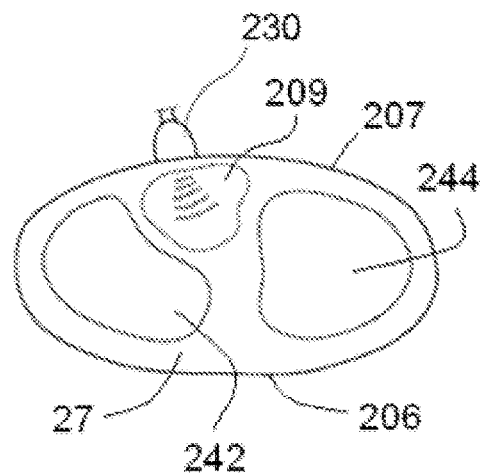
FIG. 24A is a schematic diagram of a shock wave applicator positioned for extracorporeal treatment of a heart in one embodiment of the present invention.
Figure 24B:
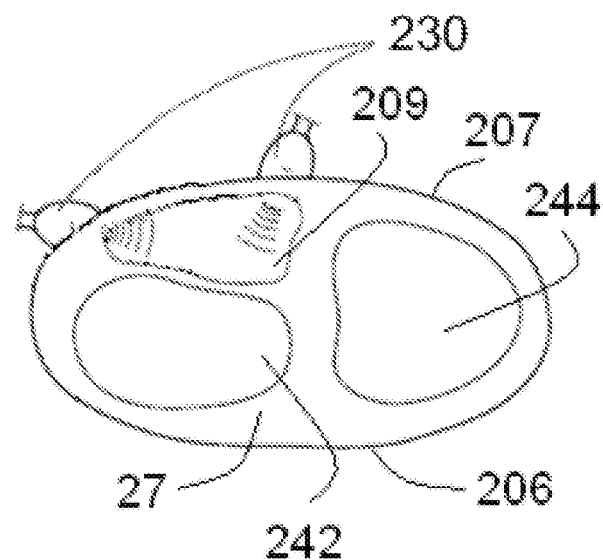
FIG. 24B is a schematic diagram of a shock wave applicator positioned for extracorporeal treatment of a heart in one embodiment of the present invention.

The shape, b/c ratio, and inclination of applicators (any of applicators 200 or 210 or 220 or 230) that treat extracorporeal the heart 209 and pericardium will dictate penetration and how it will be used, as shown in FIGS. 24A and 24B. In the depicted embodiments, it is easier to treat the anterior aspect of the heart 209, pericardium and pericardial cavity, via the contact with chest 207.

It is typically more difficult to treat the posterior part of the heart 209, pericardium and pericardial cavity (against the left lung 242). In posterior treatment tangential pressure shock waves may be used (tangential pathway relatively to the heart 209 muscle instead of perpendicular as can be used for the treatment for the front part of the heart 209).

Another approach to treat the posterior part of the heart 209 is to have extracorporeal pressure shock waves transmitted through the heart 209 chambers from the chest 207 area and precisely focus them only on the posterior part of the heart 209. In general, the penetration of the pressure shock waves in lungs (left lung 242 and the right lung 244) are preferably avoided and including avoiding application of extracorporeal pressure shock waves to the back 206 of the body 27.

Extracorporeal pressure shock waves may also be used for pacemakers leads, implants and prostheses extraction. Pacemakers are devices used to deliver mini-electric shocks to the heart muscle when the natural triggering mechanism of the heart 209 gets irregular (erratic). Pacemakers can identify arrhythmias and eliminate them. Pacemakers have leads that are implanted deep into the heart muscle and the device itself sits subcutaneously. A pacemaker's battery has a limited life up to 10-15 years of functioning. This lifespan is why pacemakers need to be replaced after a long period of time. The leads attached inside the heart have tissue growth around them that sometimes makes their extraction difficult. This growth can lead to injury of the heart muscle due to extraction of tissue together with the leads. To minimize tissue injury, facilitate implantation of a new device without complications, pressure shock waves may be used to loosen the leads before extraction.

Figure 25:
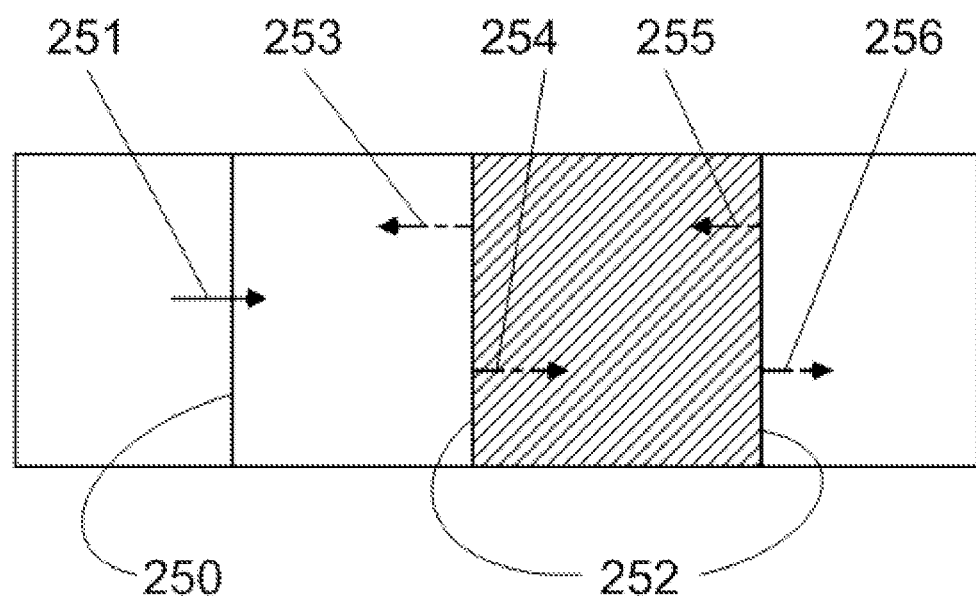
FIG. 25 is a schematic diagram illustrating travel of shock waves through materials of the same and different acoustic impedances in one embodiment of the present invention.

As shown in FIG. 25, when pressure shock waves travel through the separation of substances with the same acoustic impedance 250 (for example water to tissue), the waves are transmitted without any losses (transmitted wave without losses 251). When there is a change of acoustic impedance from one substance to another 252 (tissue to metal or metal to tissue for example) a part of the waves is reflected (reflected wave on the entry surface 253) and another part is transmitted through the hard metal (transmitted wave with losses 254) and then bounce back at the back surface (reflected wave on the back surface 255). Only a small percentage is transmitted afterwards in the adjacent tissue (transmitted wave at the exit surface into adjacent tissue 256).

Figure 26:
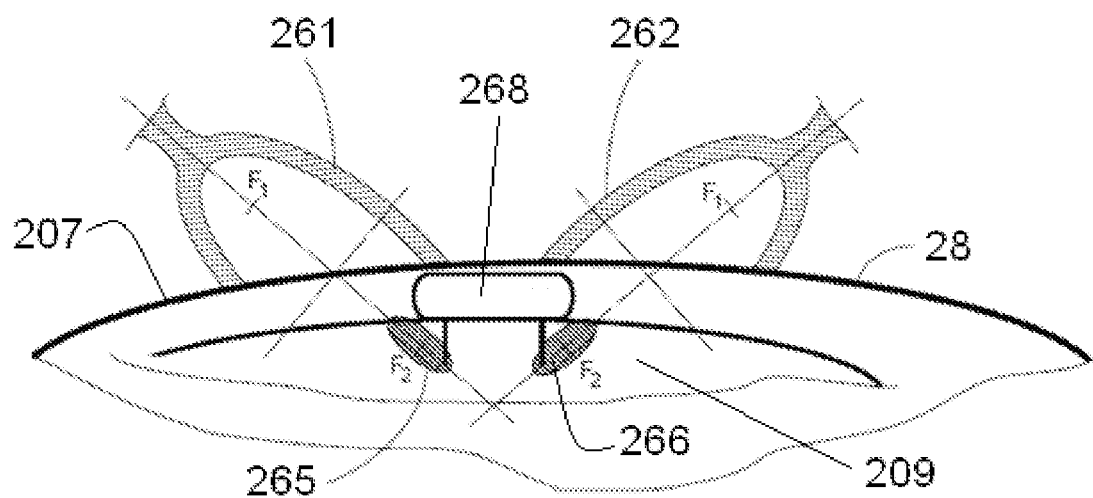
FIG. 26 is a schematic diagram of shock applicators positioned for treating and loosening pacemaker leads from heart tissue in one embodiment of the present invention.

Based on multiple reflections on the surface of the metal lead and inside its structure, shock waves may be used to help to dislodge the leads of the pacemaker 268 from the surrounding tissue, as shown in FIG. 26.

Extracorporeal angled reflectors (reflector 261 and reflector 262) in contact with the skin 28 of the chest 207 are used in the depicted embodiment. Applicator 261 has its focal volume 265 intersecting one of the leads of the pacemaker 268 and second applicator 262 has its focal volume 266 intersecting the other electrode of the pacemaker 268. The triggering of the pressure shock waves preferably occur in accordance with heart beats to generate pressure shock waves during "R" position of the curve representing the peak amplitude during a heart contraction. This triggering is preferable for any pressure shock waves that are applied to the heart 209.

The "loosening" principle utilizing shock waves can also be applied for loosening orthopedic prosthesis from bones (hip or knee replacements) or for removal of any implant from the human body 27 that was encapsulated by the tissue during its service.

If a movable discharge is used (variable voltage discharge on $F_1F_2$ axis for the electrohydraulic devices) then a moveable focal volume 108 can be achieved, which gives treatment flexibility. This concept will be presented in detail later on in this document.

Use of extracorporeal pressure shock waves may also be used for cellulite, body sculpting, skin rejuvenation, "spider veins", burns, acute and chronic wounds, scar tissue, lymph-edema and enhancement of collateral blood flow. Pressure shock waves can be used to liquefy fat (adipose tissue), which then can be pushed together with cellular debris into lymphatic system due to the pressure gradient created by the pressure shock waves.

Also, pressure shock waves can create new collagen structures or reinforce the existing ones through cellular interaction and expression. Stronger collagen structures translate into stronger and more flexible skin 28.

Furthermore, pressure shock waves can produce angiogenesis of small blood vessels (as arterioles and capillaries) that can enhance the blood circulation and stimulate cellular repair in the treated area or allow a better flow of blood towards and from body extremities. This can enhance the overall cosmetic and healthy aspect of the skin 28. For producing enhanced blood circulation in the limbs multiple reflectors or elongated reflectors with multiple points of origin for the pressure shock waves can be incorporated in "braces-like" or "boots-like" constructions that can make the treatment user and patient friendly. Multiple reflector applicators 220 or elongated applicators 210 with multiple points of origin for the pressure shock waves (discharge points 68), which can be used for such constructions, are presented in embodiments shown in FIGS. 21A, 21B, 22, 63, 64A, 64B, 65A, 65B, 65C, 66A and 66B.

Pressure shock waves may be used to activate factors involved in wound repair (acute and chronic wounds including burns) such as VEGF (Vessel Endothelial Growth Factor), TGF β (Transforming Growth Factor β), EGF (Epidermal Growth Factor), FGF (Fibroblast Growth Factor), vWF (von Willenbrand Factor), TNFα (Tumor Necrosis Factor α), PDGF (Platelet Derived Growth Factor), HIF (Hypoxia-Inductive Factor), and the like. The calling of the body repair mechanism through the stimulation of the above-mentioned factors combined with angiogenesis (formation of new small blood vessels from pre-existing ones) and vasculogenesis (formation of new small blood vessels) can create the optimal environment for healing. The angiogenesis and vasculogenesis may create new blood vessels that can enhance the amount of blood that is brought into the treatment area, which provides increased oxygenation of the tissue and brings more nutrients in the area, two critical components to sustain the healing mechanism.

Pressure shock waves can also be used to break down scar tissue and replace with healthy tissue, improving the cosmetic aspect of the skin 28.

Extracorporeal pressure shock waves can also be used to reinforce the wall of the small veins and push stagnant blood from them to reduce the so called "spider veins" aspects of the skin 28 produced by poor venous circulation.

Based on such various embodiments, pressure shock waves can be used to reinforce the skin 28 (a collagen-based structure), rejuvenate it, improve its cosmetic presentation, heal its acute and chronic wounds or to reduce or eliminate the fatty deposits from under the dermis and thus reducing the bumpy skin aspect of the cellulite or to produce body sculpting.

Because cellular debris can be pushed in the lymphatic system by pressure shock waves and because of possible repair of the lymphatic vessels by pressure shock waves, another application for extracorporeal pressure shock waves is treatment of lymph-edema, which is an accumulation of lymph in the body extremities/appendages 25 that produces deformities of the limbs and mobility issues.

The pressure shock waves devices can be used as sole treatment or in conjunction/synergy with other medical devices to treat the above-mentioned target locations or enhance the outcome of the treatment.

The treatment area for various target locations can be found at different depths relative to the skin 28. Exemplary penetration depth of pressure shock waves for cellulite, skin rejuvenation, wound healing, scars and "spider veins" is only superficial in the order of 1-30 mm. Exemplary penetration depth for lymph-edema, improved collateral blood circulation and body sculpting can be up to 100 mm. The penetration depth will dictate the depth of the reflector shape, which can be shallow for superficial applications or very deep for applications where the focus is done deep inside the human body 27.

Figure 27A:
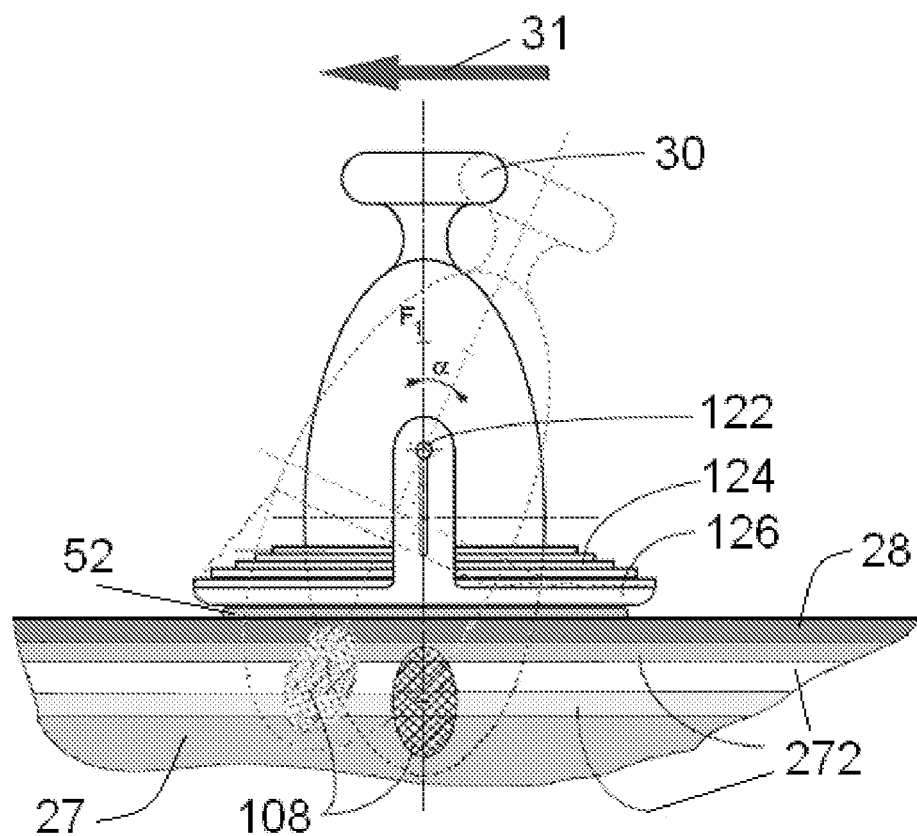
FIG. 27A is a schematic diagram of a pivotable shock wave applicator including bellows in one embodiment of the present invention.
Figure 27B:
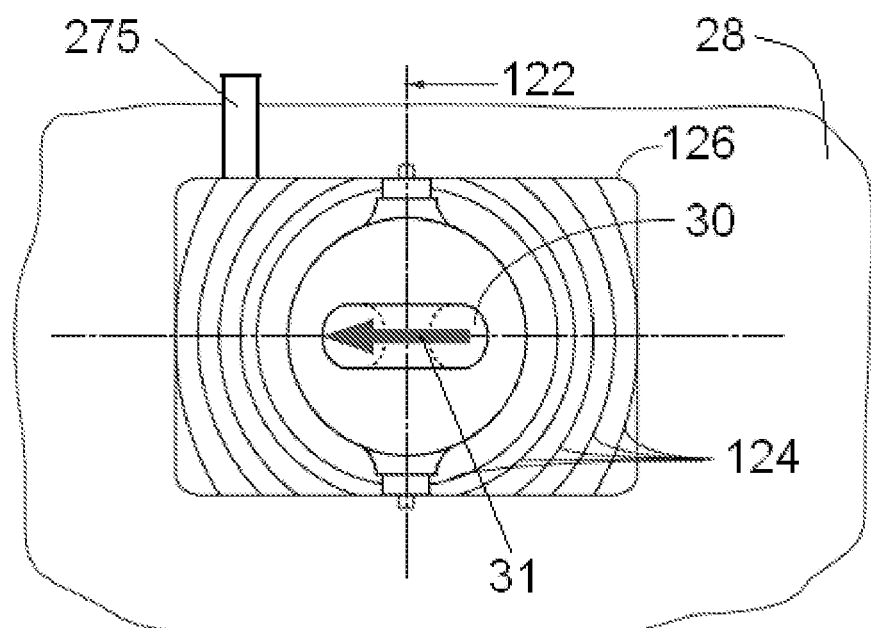
FIG. 27B is a schematic diagram illustrating a bottom plan view a pivotable shock wave applicator including bellows and with vacuum suction in one embodiment of the present invention.

In order to create flexibility regarding the depth penetration during a treatment, embodiments shown in FIGS. 27A and 27B can be used. With varying depth, the treatment can be applied to different subcutaneous tissue layers 272 of the human/animal body 27 as long as the focal volume 108 intersects the desired treatment site. Depending on the quantity and position of fat accumulated under the skin 28, the reflector embodiments presented in FIGS. 27A and 27B may be used for possible cosmetic applications (cellulite, extracorporeal body sculpting, scars, lymph-edema, etc) or for wound healing.

The rotation of the applicator 30 around the pivoting axis 122 allows precise positioning of the focal volume 108 inside the treatment area based on its position relative to the skin 28, the normal curvature of the human body 27 and the shape/thickness of the cushion/gel pad 52.

External frame 126 is longer on the direction of longitudinal movement 31 for the applicator 30 to allow the physician to correctly position of the applicator 30 based on intended treatment procedures. External frame 126 can have many possible shapes. The bellows 124 are constructed to fit inside the external frame 126 and for that reason one preferred shape for the external frame 126 might be circular, which is different from embodiments shown in FIGS. 27A and 27B.

Also, the same embodiments presented in FIGS. 27A and 27B can use the bellows 124 as a sealed chamber from which a vacuum suction 275 can be applied, to enhance the pressure shock waves treatment with a mechanical stimulation by pulling the skin 28 and adjacent tissue layers 272 (including the fat layer) upwards using a pressure from 100 mbar up to 1000 mbar. Pressure shock waves and the mechanical stimulation should work in synergy to increase efficiency of the treatment. Both pressure shock waves and mechanical stimulation are known to produce formation of new collagen fibers into the dermis and enhances localized blood circulation both in dermis/skin 28 and adjacent tissue layers 272, which should enhanced the skin 28 firmness and overall cosmetic aspect.

In the case of wound healing, vacuum suction 275 can be used to extract any exudates out of the wound bed before starting the application of pressure shock waves.

Inclined geometry of the reflector may increase flexibility of the treatment, to equilibrate the applicator 30 from the mass point of view and will not allow the applicator 30 to disengage the treatment area. Mass distribution may account for physicians that should keep their hands out of the treatment regions that might be visualized using a camera, to track treatment progress via sensors.

Figure 28:
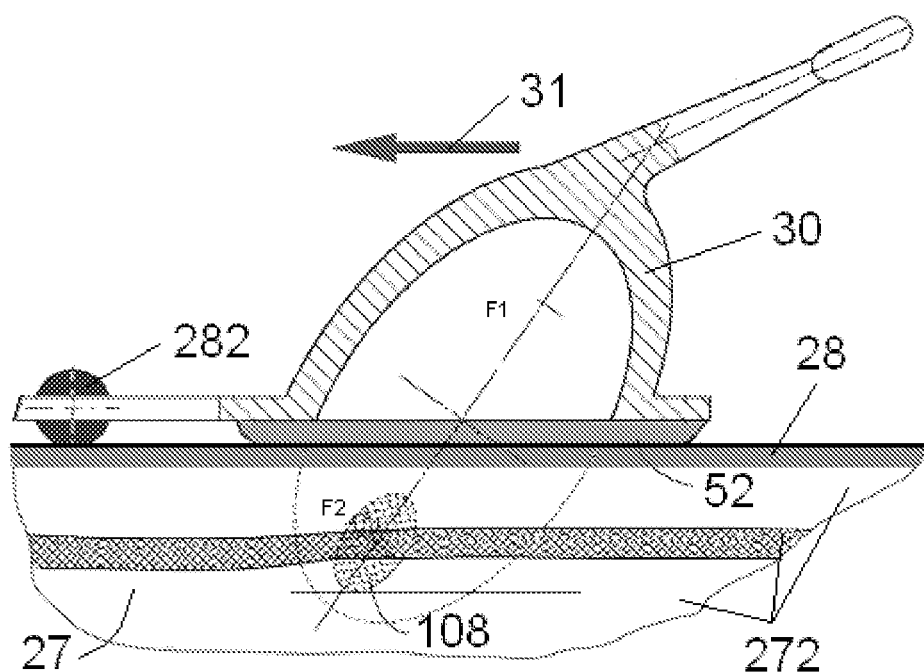
FIG. 28 is a schematic diagram of a movable shock wave applicator including a roller for treating tissue layers in one embodiment of the present invention.

As shown in FIG. 28, a roller 282 can be used to equilibrate the momentum produced by the applicator 30 handle. If necessary, the position of the roller 282 can be adjusted to produce more flexibility for the treatment.

This approach can be used in embodiments for cellulite treatment, skin rejuvenation, scars or body sculpting to allow the easy use of the applicator 30 and coordinate the pressure shock waves with a mechanical massage produce by the roller 282, which can enhance the effects of the pressure shock waves in formation of new collagen fibers, in pushing of liquefied fat into lymphatic system and in enhancing the local blood circulation.

Figure 29:
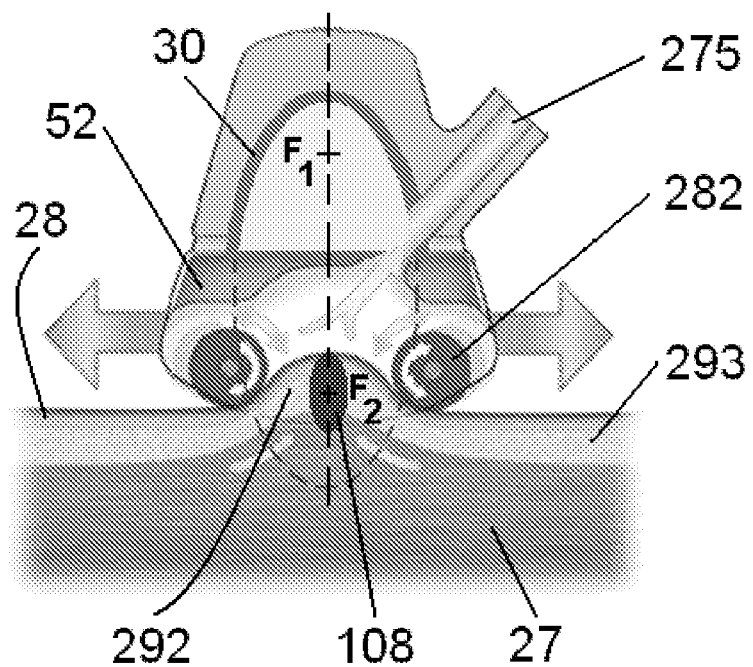
FIG. 29 is a schematic diagram of a movable shock wave applicator including multiple rollers with vacuum suction to treat target tissue in an embodiment of the present invention.

Another embodiment with a combination devices that can use pressure shock waves connected with mechanical double stimulation via vacuum suction 275 and rollers 282 movement is shown in FIG. 29. A reflector is incorporated in this applicator 30 with the focal volume 108 able to intersect sufficient thickness of the treatment area (skin 28 and the fat layer 293 of the body 27), to be sure that the pressure shock waves accomplish their role. Simultaneously, the mechanical stimulation is given to the "rolled and vacuum suction affected tissue" 292. The focal volume 108 positioning during treatment, is preferably considered in view of the raise of the "rolled and vacuum suction affected tissue" 292, which is influencing the intersection of the focal volume with the targeted/treated tissue. The transmission of the pressure shock waves to the tissue occurs via a cushion/gel pad 52 or liquid sack present in between the rollers 282.

Extracorporeal pressure shock waves may further be used for controlled fragmentation of biodegradable stents. In order to allow multiple treatments of the stenotic areas of a vessel 15 (reduction in vessel diameter due to stenotic plaque 130 build-up), a new trend in cardiology is to use biodegradable stents that may be loaded with drugs to block or arrest smooth muscle growth. The advantage of the biodegradable stents is that they can keep the blood vessels 15 open for a sufficient time to allow stenotic plaque breakages and healing, and after that they are absorbed by the body 27 in a period ranging from three months to one year or even more. By disappearing through biodegrading process from the tissue or blood vessel 15 wall in time, biodegradable stents do not leave behind any structure incorporated into the tissue and a new treatment can be applied with a new stent without having on overlap and build-up of foreign structures in the blood vessel 15 wall, as is the case with metallic stents 170.

The difficulties with biodegradable stents include: reduced radial strength of the biodegradable stents when compared with metallic stents 170 translates in less efficacy in treating strong stenosis; the erratic (uncontrolled) degradation of the biodegradable stents might start before total incorporation in the blood vessel 15 wall and thus large parts of the stents can flow down the blood stream 39 and can trigger thrombolytic events, that can then produce cardiovascular problems and even death for the patient; and sometimes the design of the biodegradable stents do not permit total incorporation in the blood vessel 15 wall, which makes these stents prone to let parts of them flowing down the blood stream/flow 39, which can generate cardiovascular problems and even death for the patient, due to the blockage of the blood vessel 15.

To address reduced radial strength of the biodegradable stents, different geometries are proposed by the industry: mechanical interlocks when stents are deployed to their maximal dimensions, increasing the thickness of the stent struts and using stronger materials (combination of biodegradable polymers as poly-L-lactide, polyglycolic acid (PGA), high molecular weight poly-L-lactic acid (PLLA), poly (D, L-lactide/glycolide) copolymer (PDLA), and poly-caprolactone (PCL), with metallic biodegradable materials as magnesium alloys).

Figure 30A:
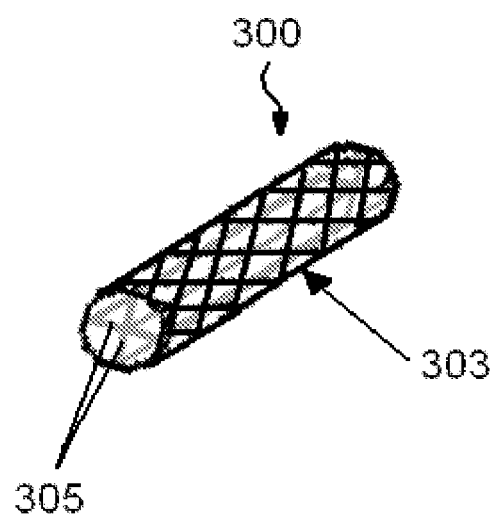
FIG. 30A is a schematic diagram of a biodegradable stent in one embodiment of the present invention.

FIG. 30A presents an embodiment for a biodegradable stent 300 with a knitted pattern or zigzag helical coil for the circumferential design 303 to contact with the vessel 15 wall. The circumferential design 303 is combined with a stent luminal radial reinforcement 305 with two perpendicular and foldable walls inside the biodegradable stent 300, as shown in FIG. 30B.

The perpendicular walls run the length inside the biodegradable stent 300 as they are dimensioned in such way to produce reinforcement in radial strength and in the same time to allow a normal blood flow 39 through the biodegradable stent 300.

Figure 30B:
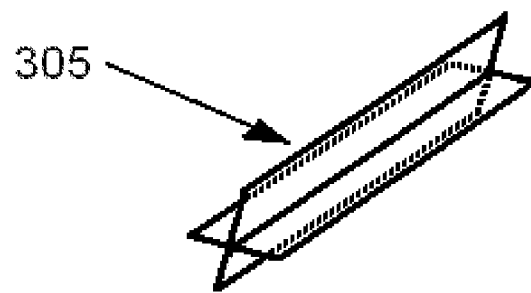
FIG. 30B is a schematic diagram of a stent luminal radial reinforcement having foldable walls in one embodiment of the present invention.
Figure 31:
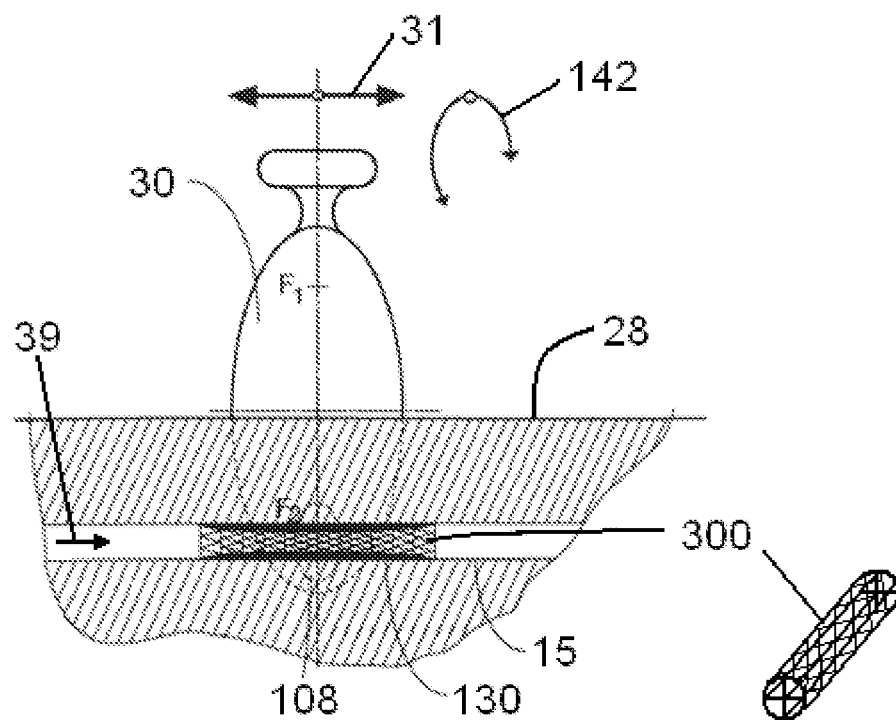
FIG. 31 is a schematic diagram of a shock wave applicator positioned with a focal zone intersecting a stent in a blood vessel in one embodiment of the present invention.

The challenge of embodiments similar to the one presented in FIGS. 30A and 30B includes not all the scaffolding of the biodegradable stent 300 can be incorporated into the blood vessel 15 wall, which during degradation of the biodegradable stent 300 can produce large pieces that have eventual potential of producing blockage down the blood flow 39. For these situations, the degradation of the biodegradable stent 300 can be controlled using pressure shock waves to break at a given timeframe into small particles that cannot produce blockages and can be easily degraded by the body 27 afterwards (see FIG. 31).

By using pressure shock waves to break such biodegradable stent 300 structures after a given timeframe, the patient is provided a biodegradable stent 300 has accomplished its role (push the plaque 130 against the blood vessel 15 wall) and can be safely disintegrated without creating hazardous situations. To cover the whole area of the biodegradable stent 300 during extracorporeal pressure shock wave treatment, the applicator 30 (in contact with the skin 28) can have a longitudinal movement 31 that can be combined with transversal movement 142.

In embodiments to collect the fragments of the biodegradable stent 300 floating inside the blood vessels 15, distal protection systems can be used. The distal protection systems utilize debris collection baskets 35 or flush catheters 91 combined with suction catheters 93 or occlusion balloon 154 or occlusion catheters 96, which can be concomitantly used with extracorporeal pressure shock waves treatment, as shown in FIGS. 15A, 15B, 16A and 16B.

Extracorporeal pressure shock waves can be used in embodiments of the invention for controlled drug delivery. Efficient intracorporeal or percutaneous drug delivery is very important for localized treatment of different diseases. This approach is preferred by many patients when compared with systemic drug delivery, which has reduced efficiency and high probability of side effects.

Local delivery of a drug typically uses high doses that can be very effective without creating a systemic reaction to the increased dose or without loosing high efficacy by delivering the drug through digestive system (systemic delivery). Also, in some cases it is desired to avoid the sanguine system delivery of a drug, to avoid affecting organs and tissues that are not targeted for the treatment.

Local drug delivery can be done via patches or biodegradable pouches/structures/patches incorporated inside the targeted tissue via a percutaneous approach. Biodegradable pouches/structures/patches 320 used for high efficiency drug delivery can include the embodiments depicted in FIGS. 32A and 32B.

Figure 32A:
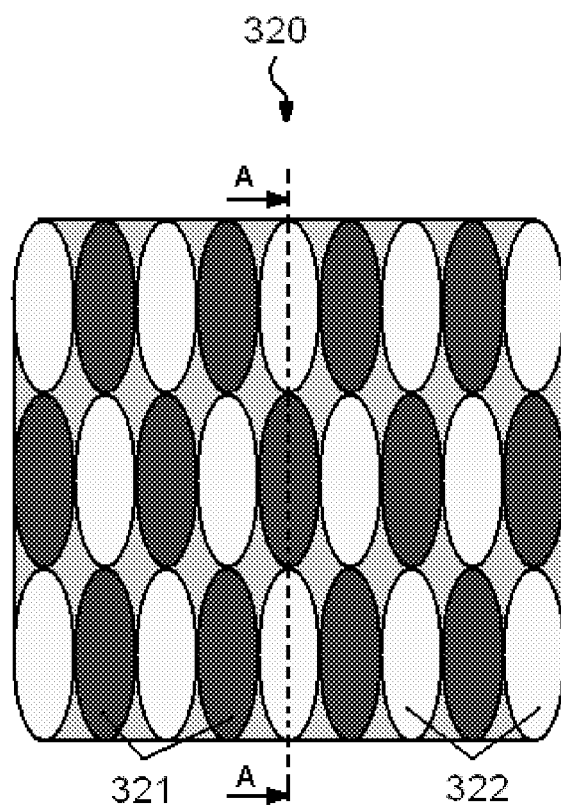
FIG. 32A is a schematic diagram of a top plan view of a drug-releasing pouch system in one embodiment of the present invention.
Figure 32B:
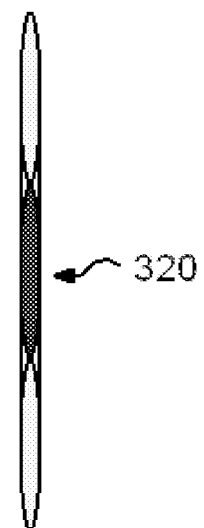
FIG. 32B is a schematic diagram of a side view of a drug-releasing pouch system in one embodiment of the present invention.

The drug delivery system presented in FIGS. 32A and 32B is capable of delivering two different drugs (drug 321 and drug 322) and it presents itself as a thin biodegradable foil that has ellipsoidal pouches filled with drugs (321 or 322) at high concentration. The pouches are created using thin biodegradable films/thin foil and the drugs (321 or 322) are in a fluid form to allow the cavitation formation during extracorporeal pressure shock waves treatment. To perforate the pouches and thus releasing the drugs (321 or 322) into the tissue, the main mechanism is the collapse of the cavitation bubbles generated by the pressure shock waves in the focal volume 108. Cavitation bubbles collapse produces high velocity micro-jets, which can puncture the pouches and thus slowly releasing the drugs (321 or 322) in the treatment targeted tissue.

Figure 33:
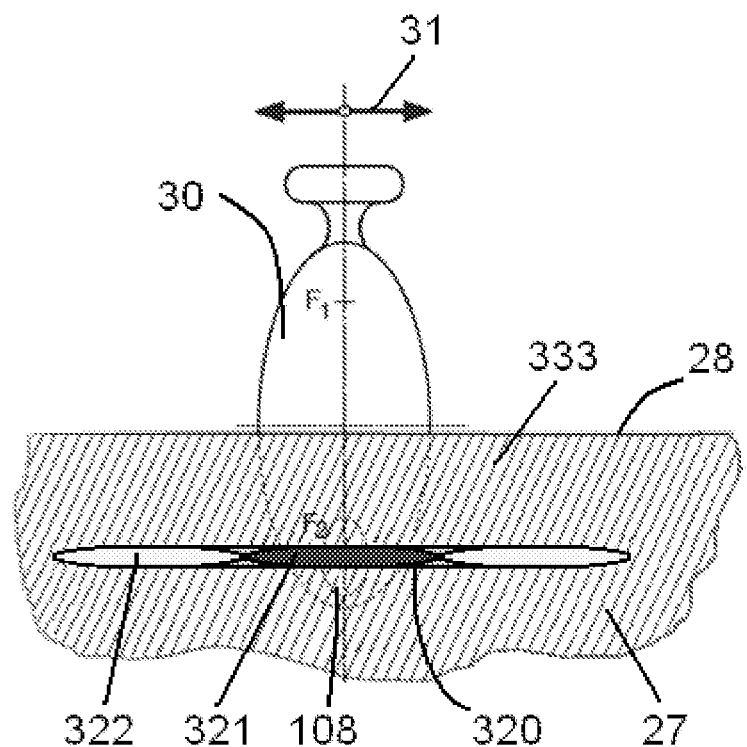
FIG. 33 is a schematic diagram of a side view of a shock wave applicator positioned with a focal zone at a drug-releasing pouch system in a body in one embodiment of the present invention.

In order to be successful in releasing drugs 321 or 322 using extracorporeal pressure shock waves it is very important that the extracorporeal shock wave applicator 30 positioned on the skin 28 to have the focal volume 108 intersecting the biodegradable pouch/structure/patch 320 implanted near or into the tissue 333 that is targeted for the treatment inside the body 27, as shown in FIG. 33.

In embodiments, the biodegradable pouch/structure/patch 320 can be activated via pressure shock waves at any time interval or intervals (multiple activations) after implantation via a percutaneous approach. Based on the depth where the biodegradable pouch/structure/patch 320 is implanted the pressure shock waves reflectors 22 will have different geometries, with shallow reflectors 22 for less subcutaneous depth penetration or deeper reflectors 22 for deep subcutaneous depth penetration.

In order to cover the whole area of a drug delivery biodegradable pouch/structure/patch 320 the applicator 30 may have a longitudinal movement 31 at the surface of the skin 28 following a predetermined pattern that can be monitored by a designated computer program.

The controlled locally activated release of the drugs via pressure shock waves can be very beneficial for the patient to avoid overdoses and to assure high efficiency of the treatment. In the same time, due to the high pressures generated during pressure shock waves the drugs can be pushed in the order of several millimeters away from the delivery system, which gives even more efficiency of the treatment. Also, at the end of the treatment a sufficient number of pressure shocks waves can be delivered to provide a breakage of the biodegradable pouch/structure/patch 320 in small pieces that can be easily absorbed by the tissue 333 and thus allowing a quicker re-implantation of a new drug delivery biodegradable pouch/structure/patch 320 into the area, if needed.

Extracorporeal pressure shock waves may also be used for destruction of tissue hyperplasia, cysts and malignant tumors. Hyperplasia is defined as an abnormal increase in number of cells, which may result in the gross enlargement of an organ, such as the prostate when benign prostate hyperplasia or BPH occurs. The abnormal increase in number of cells can happen to many types of tissues of the human/animal body 27 and can create pain, obstructions and abnormal functioning of certain organs or tissues.

A cyst is a closed sac, having a distinct membrane and division on the nearby tissue. It may contain air, fluids, or semi-solid material. A collection of pus is called an abscess, not a cyst. Once formed, a cyst could go away on its own or may have to be removed through surgery.

Malignant neoplasms (cancer tumors) represent an abnormal mass of tissue as a result of neoplasia. Neoplasia is the abnormal proliferation of cells. The growth of the cells exceeds and is uncoordinated with that of the normal tissues around it. The growth persists in the same excessive manner even after cessation of the stimuli. It usually causes a lump or cancer tumor. Malignant neoplasm can be treated via medication, chemo-therapy, radiation, surgery or ablation.

Typical technologies used to ablate cysts and benign or malignant tumors include using radio-frequency, high intensity focused ultrasound or cryogenic approaches. The main drawback for these technologies is the extreme heat or freezing temperatures generated during treatment that can affect adjacent tissues/organs and blood flow 39 circulation with unwanted side effects. After a procedure, the absorption of ablated tissue by the body 27 is hindered by excessive inflammation, impaired blood circulation/flow 39, fluid accumulation, etc. Also, none of these technologies are known to trigger a body reaction to heal the treated area.

Cavitation bubbles produced by pressure shock waves are collapsing with microjets powerful enough to penetrate the cancerous cellular membrane and thus destroying their integrity. This represents a "normal body temperature ablation" process that not employs high or low temperatures used by the existing ablation technologies. Even more than that, the leakage of the cytoplasm content outside the cells triggers a localized apoptosis mechanism and a immune response, which makes the body 27 to recognize the cancer cells that were invisible before and thus enhancing tumor destruction. Cavitation bubbles can be formed and/or induced by pressure shock waves only in fluids as water, blood, urine, etc. In order to promote/enhance the cavitation inside the body 27, saline solution, contrast solution or drug cocktails can be injected in the targeted treatment area as cysts, benign or malignant tumors. By using the drug cocktails with extracorporeal pressure shock waves, the microjets generated by the collapse of the cavitation bubbles can effectively push the drugs in the adjacent areas at high concentration and thus enhancing their effects on the tumor in general. Furthermore, by applying a high number of shots (more than 2,000 shots per treatment) at high energy to the vasculature that feeds the tumor, the small blood vessels and capillaries can be destroyed, which can be another way to shrink the tumors after the treatment with pressure shock waves.

Pressure shock waves can be also used for treating cancer in conjunction with microparticles or/and nanoparticles, which can be activated or pushed into the tissue via pressure shock waves in order to selectively kill cancer cells or to deliver specific drugs and/or proteins and/or substances that can destroy the cancer cells.

Finally, the high energy pressure shock waves can be used to enhance the sensibility of the tumor cells to certain drugs and thus enhancing their cytotoxicity.

Based on the above observations, using a sufficient number of pressure shock waves (higher than 2000 shots) at high energies (flux densities higher than 0.3 mJ/mm$^2$) and multiple treatments (at least two) applied to a cyst, benign or malignant tumor a "normal body temperature ablation" can be realized using extracorporeal pressure shock waves. Applicators 30 such as those presented in FIGS. 5A, 5B, 6, 7, 10, 12A, 12B, 14A, 14B and 33 may be used for the "normal body temperature ablation" using extracorporeal pressure shock waves. The ablation can be either superficial or deep inside the human body 27 and must be precisely coordinated and monitorized via ultrasound probes 37 or fluoroscopy.

Extracorporeal pressure shock waves may be used for fibrotic tissue, hyperthrophic lesions, organ adhesions, capsular contracture and tissue repair/regeneration. Pressure shock waves used at the proper dosage and treatment setting (medium to high energies, flux densities higher than 0.1 mJ/mm$^2$) are known to break down fibrous tissue or excessive tissue formed post-surgical as reparative or reactive processes of the body 27. This phenomenon can be used to repair: fibrotic tissue (excess fibrous connective tissue in an organ or tissue generated by a reparative or reactive process), hyperthrophic lesions (increase in the volume of an organ or tissue due to the enlargement of its component cells, which is different from hyperplasia where the cells remain approximately the same size but increase in number), organ adhesions (fibrous bands that form between tissues and organs, often as a result of injury during surgery, which may be thought of as internal scar tissue) and capsular contracture (an abnormal response of the immune system to foreign materials, which forms capsules of tightly-woven collagen fibers around a foreign body (breast implants, pacemakers 268, orthopedic joint prosthetics), tending to wall it off followed by the capsule tightening/contracture around the implant.

Pressure shock waves may also trigger body reaction (at low to medium energy settings, flux densities of less than 0.3 mJ/mm$^2$) for healing via growth factors, stem cells activation and enhanced collateral blood circulation through new small arterioles and/or capillaries formation (angiogenesis). Such triggering may be used to produce the following: regeneration of burn tissue, repair of acute and chronic wounds, repair and regeneration of necrotic tissue due to ischemia (bone, soft tissue, skin, etc.), repair of bone fractures (acute or non-unions), repair of partial or total tears of cartilage, muscle, ligaments, tendons, etc., regenerate the lining of the bladder for interstitial cystitis and reduce the symptoms, effects and treat auto-immune diseases as Systemic Lupus Erythematosus, Ankylosing Spondylitis, Crohn's Disease, Scleroderma, Dermatomyositis, etc.

Based on the foregoing descriptions, using a sufficient number of pressure shock waves (higher than 500 shots), appropriate energy flux densities (as mentioned before) and multiple treatments (at least two), the suitable results can be realized using extracorporeal pressure shock waves. Applicator embodiments (30, 200, 210, 220, 230) such as those presented in FIGS. 5A, 5B, 6, 7, 8A, 8B, 10, 12A, 12B, 14A, 14B, 20, 21A, 21B, 22, 23A, 23B and 33 may be used for the treatment of fibrotic tissue, hypertrophic lesions, organ adhesions, capsular contracture and tissue repair/regeneration. The pressure shock waves treatment can be either superficial or deep inside the human body 27 (tuned to each type of tissue treatment mentioned above) and must be precisely coordinated and monitorized via ultrasound probes 37 or fluoroscopy.

Extracorporeal pressure shock waves may also be used for aseptic, bacterial, abacterial and viral infections or of parasites and harmful micro-organisms. When pressure shock waves were used for treating infected wounds it was noticed that they have a bactericidal effect, which helped with the healing and tissue repair. The effect of the pressure shock waves on Gram positive and Gram negative bacteria is enhanced due to the capacity of pressure shock waves to break the biofilms formed by these bacteria. This is a major aspect of the treatment using pressure shock waves due to the fact that they can allow the treatment of most resistant infections, which are produced due to the clustering of bacteria in biofilms and thus making bacterial infections very difficult to treat with antibiotics or any other medical means.

Also, studies have showed that the bacterial and viral capsule walls are more susceptible to be disrupted and/or punctured by the pressure shock waves (especially by the microjets produced during collapse of the cavitational bubbles) when compare to normal cells that make the body tissues.

Furthermore, aseptic (sterile) loosening formed around implants or abacterial inflammation (as in abacterial prostatitis also know as painful pelvic syndrome) can be treated using pressure shock waves for pushing inflammatory cells or inflammatory by-products out of the treatment area and thus eliminate the active ingredients that produce inflammation and body reaction.

Fungal infections can be also treated using pressure shock waves in conjunction with appropriate medication, due to the capacity of pressure shock waves to disrupt the fungal films in places where the access is not so easy—for example at the base of the toe nails.

Finally, parasites or harmful micro-organisms that can develop inside the human/animal body 27 can be eliminated with appropriate pressure shock waves by damaging them or through disruption of their environment.

Depending on where the infection was developed, using a sufficient number of pressure shock waves (higher than 1,000 shots), appropriate energy flux densities (higher than 0.2 mJ/mm$^2$) and multiple treatments (at least two), the appropriate results can be realized using extracorporeal pressure shock waves. Applicators (30, 200, 210, 220, 230) such as those presented in FIGS. 5A, 5B, 6, 7, 8A, 8B, 10, 12A, 12B, 14A, 14B, 20, 21A, 21B, 22, 23A, 23B and 33 can successfully be used for the treatment of aseptic, bacterial, abacterial and viral infections or of parasites and harmful micro-organisms. The pressure shock waves treatment can be either superficial or deep inside the human body 27.

Extracorporeal pressure shock waves may be utilized for stem cells, genes treatment and nerve cells. When pressure shock waves were used for treating infected wounds it was demonstrated that the dormant stem cells are activated to participate in the repair mechanism. Also, scientific studies showed that a stimulation of the stem cells in the harvesting areas from inside the human body 27 (periosteum, bone marrow, etc.) is produced by the pressure shock waves. This allows the harvesting of an increased population of stem cells that can be used for proliferation phase, thus making the process more efficient.

During proliferation phase a moderate mechanical stimuli produced by the pressure shock waves can be used to sustain an increased proliferation and thus a larger population of stem cells can be produced in a shorter period of time.

Based on the type of stem cells (human embryonic stem cells, adult stem cells or induced pluripotent stem cells) the energy generated by the pressure shock waves can be particularly tuned to produce the differentiation of the stem cells into desired cells necessary for implantation into a specific type of tissue (bone, muscle, cartilage, etc.).

Furthermore, before stem cells implantation, during implantation or after implantation the stem cells can be sustained in vivo by the pressure shock waves through enhanced blood flow 39 in the implantation area through angiogenesis and by calling growth and repair factors.

The microjets generated by the collapse of the cavitation bubbles can create transient micro pores on living cells membranes and due to existing pressure gradients produced by the pressure shock waves can establish the optimum situation to push DNA fragments or genes inside the cells. Specific genes can alter the behavior of the cells, which might turn out to be benefic. For example, the pancreatic beta islet cells (produce insulin and amylin) that are dysfunctional for type I diabetic patients, through pressure shock wave gene treatment the restoring of physiological beta cell function could be accomplished.

Nerve cells assist with the correct functioning of the body 27 because they process and transmit information by electrical and chemical signaling from any region of the body 27 to the brain, for a harmonious perception and functionality.

The pain generated by tissue disruptions or inflammation is perceived by the peripheral nerve terminals and pressure shock waves are known to produce an analgesic effect after few hundreds of shots, especially when the energy settings are gradually increased (ramping up process). This analgesic effect can last for hours and may constitute an advantage when treating chronic painful target locations. Furthermore, using special designed micro-tubes to guide severed nerves, when multiple treatment using pressure shock waves are applied, it was observed in animal studies that the nerves can grow from both ends and finally reunite to restore their initial function.

Depending on where the targeted cells (stem cells, nerve cells, etc.) are found inside the human/animal body 27, using a sufficient number of pressure shock waves (higher than 750 shots), appropriate energy flux densities (higher than 0.1 $mJ/mm^2$) and multiple treatments (at least two), the desired results can be realized using extracorporeal pressure shock waves. Applicators (30, 200, 210, 220, 230) such as those shown in FIGS. 5A, 5B, 6, 7, 8A, 8B, 10, 12A, 12B, 14A, 14B, 20, 21A, 21B, 22, 23A, 23B and 33 may be used for the stimulation, proliferation, differentiation of stem cells and their sustainability after implantation, for genes treatment or nerve cells stimulation (analgesic effect) or for nerves regeneration and/or repair. The pressure shock waves treatment can be either superficial or deep inside the human body 27.

Extracorporeal pressure shock waves may be used in embodiments for destruction of unwanted hard tissue. With advance in age and due trauma and different chronic diseases accumulation and/or deposits of hard tissue are created in specific area of the human body 27. Some examples include: Bone spurs—are formed due to the increase in a damaged joint's surface area. This is most commonly seen from the onset of arthritis. Bone spurs usually limit joint movement and typically cause pain; heterotopic ossifications—is the process by which bone tissue forms outside of the skeleton. Studies on heterotopic ossification have suggested that it may be linked to injuries to the spinal cord, along with neurological target locations. The target location often appears in the form of periarticular ossification, especially around the site of hip injuries; and calcifications—is the process in which calcium salts build-up in soft tissue, causing it to harden. Calcifications may be classified on whether there is mineral balance or not, and the location of the calcification.

Debilitating accumulation of hard tissue in unwanted parts of the body 27 can be treated using high energy pressure shock waves (energy flux densities higher than 0.3 $mJ/mm^2$) with high number of shots (more than 2,500 shots) and multiple treatment (more than three). The pressure shock waves treatment can be either superficial or deep inside the human body 27 (tuned to each type of tissue treatment mentioned above) and must be precisely coordinated and monitored via ultrasound probes 37 or fluoroscopy.

Applicators (30, 200, 210, 220, 230) such as those presented in FIGS. 5A, 5B, 6, 7, 8A, 8B, 10, 12A, 12B, 14A, 14B, 20, 21A, 21B, 22, 23A, 23B and 33 may be used for this type of treatment.

In embodiments utilizing shock waves in an intracorporeal approach, shock wave reflector 22 is preferably positioned on a catheter that may have radio-opaque markers 152, transducers, and the like, which help with positioning in the treatment area. The shaft of the catheter may be multi-lumen to allow guide wire 94 access, fluid access in the reflector 22 area, electrical connections, extraction of fluids/body fluids, etc. The intracorporeal approach requires the usage of a blood vessel 15 or natural lumen of the human/animal body 27 or of an artificial created opening/conduit, as is happening in laparoscopic procedures.

Embodiments of intracorporeal applications with pressure shock waves include: treatment of total occlusions for major vessels (limited by the dimension of the catheter that carries the shock wave device inside the blood vessels) as independent intracorporeal pressure shock waves treatment or in conjunction with drugs and/or extracorporeal pressure shock waves treatment; dissolution of blood clots (thrombus or embolus) from blood vessels (arteries and veins) and natural human/animal conduits/lumens as independent intracorporeal pressure shock waves treatment or in conjunction with dissolution agents/drugs and/or extracorporeal pressure shock waves treatment; removal of blood vessels stenotic plaques as independent intracorporeal pressure shock waves treatment or in conjunction with drugs and/or extracorporeal pressure shock waves treatment; treatment to stabilize vulnerable plaques as independent intracorporeal pressure shock waves treatment or in conjunction with drugs and/or extracorporeal pressure shock waves treatment; treatment to reduce inflammation post angioplasty and stenting as an independent intracorporeal pressure shock waves treatment or in conjunctions with drugs and/or extracorporeal pressure shock waves treatment; treatment of blood vessels in-stent restenosis (blockage of the blood vessel after stenting due to regrowth of the smooth muscle stimulated by post stenting inflammation), or in-stent restenosis for any natural human/animal conduit/lumen as an independent intracorporeal pressure shock waves treatment or in conjunctions with drugs and/or extracorporeal pressure shock waves treatment; treatment to enhance drug delivery to blood vessels and natural human/animal body internal conduits/lumens walls; treatment of the heart muscle via intracorporeal approach or transcutaneously as an independent intracorporeal pressure shock waves treatment or in conjunctions with drugs and/or extracorporeal pressure shock waves treatment and/or gene therapy and/or stem cells therapy; treatment to improve the functionality of the muscles that activate heart valves via intracorporeal approach or transcutaneously as an independent intracorporeal pressure shock waves treatment or in conjunctions with drugs and/or extracorporeal pressure shock waves treatment; treatment of aneurysms as an independent intracorporeal pressure shock waves treatment or in conjunctions with drugs; treatment for occluded grafts (artificial or natural/harvested) as an independent pressure shock waves treatment or in conjunctions with drugs and/or extracorporeal pressure shock waves treatment; treatment to reduce inflammation and repair internal lining of human and animal bodies natural conduits and cavities (as an independent intracorporeal pressure shock waves treatment or in conjunctions with drugs and/or extracorporeal pressure shock waves treatment) including repair the lining of the bladder for interstitial cystitis, repair of the all layers of the small intestine in Crohn's Disease, and repair of the superficial lining of the large intestine for ulcerative colitis; treatment to reduce tissue hyperplasia as for benign prostate hyperplasia (BPH) as an independent intracorporeal pressure shock waves treatment or in conjunctions with drugs and/or extracorporeal pressure shock waves treatment; treatment to remove occlusions/obstructions from human and animal bodies natural conduits and cavities (intracorporeal pressure shock waves treatment alone or in conjunction with other substances/drugs and/or extracorporeal pressure shock waves treatment and/or other therapies); liposuction system, which can avoid the side effects of the "golden treatment" HIFU liposuction as an independent intracorporeal pressure shock waves treatment or in conjunctions with extracorporeal pressure shock waves devices; treatment of benign or malignant tumors using cavitation jets that can penetrate/break cellular membranes and thus destroying benign or malignant cells using non-heat producing mechanisms, as an independent pressure shock waves treatment or in conjunctions with drugs and/or extracorporeal pressure shock waves treatment; treatment to produce cellular apoptosis as an independent pressure shock waves treatment or in conjunctions with drugs and/or extracorporeal pressure shock waves treatment; and treatment to kill internal infections produced by Gram positive and Gram negative bacteria, viruses, fungus, etc., or parasites and micro-organisms from all human body tracts that allows of introduction of a intracorporeal pressure shock wave devices, as an independent intracorporeal pressure shock waves treatment or in conjunctions with drugs and/or extracorporeal pressure shock waves treatment including the following: urinary tract infections including (renal infections, bladder infection, bacterial or abacterial prostatitis), gastro-intestinal tract infections and respiratory tract infections.

Figure 34:
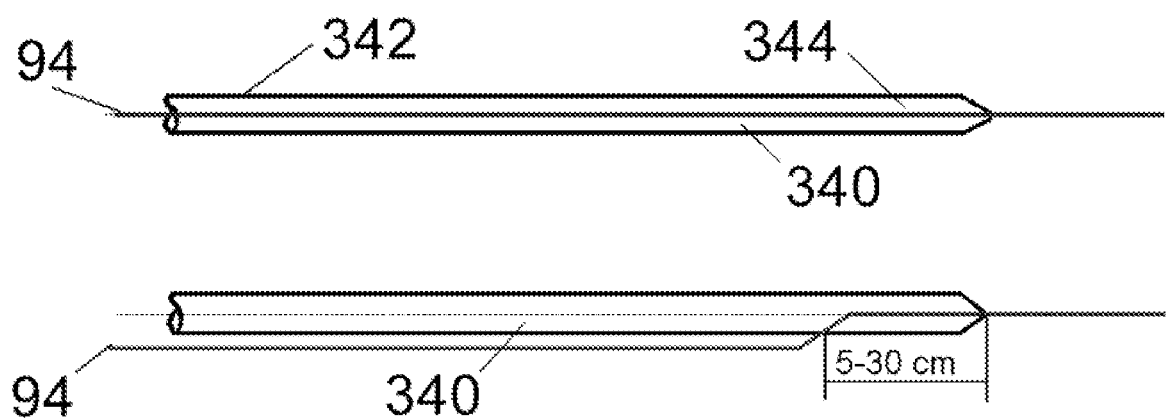
FIG. 34 is a schematic diagram of both over-the-wire and rapid-exchange solutions of guide wires and catheters in one embodiment of the present invention.

In embodiments, the following characteristics may contribute to efficacy of treatment performed using intracorporeal pressure shock waves:

(1) Lateral exposure of the reflector to access cavities/conduits wall
(2) Frontal exposure of the reflector to access treatment area frontally
(3) Reflector aperture can be circular or elongated
(4) The shape of the reflector may be shallow due to dimensional constraints and can be in the form of an ellipsoid, sphere, paraboloid, or planar. Any combination of two or more shapes can also be used.
(5) Reflector dimensions (diametric) may be in the order of 2.5-10 mm, preferably 2.5-5 mm (miniature reflector) to accommodate the vasculature/internal conduits dimensions
(6) Position of the reflector may be in proximity of the distal end of a catheter
(7) The intracorporeal pressure shock wave catheter 340 may be rotated around its central axis of symmetrys. This rotation can be achieved by having over-the-wire (guide wire 94) construction or a rapid exchange solution, as shown in FIG. 34.

An over-the-wire solution has the guide wire 94 going through the whole length of the intracorporeal pressure shock wave catheter 340 (from the proximal end 342 to the distal end 344 of the catheter), which helps with a good guidance of the intracorporeal pressure shock wave catheter 340 inside the vasculature or human body cavities, blood vessels 15 and natural conduits/lumens. A drawback is that the long length (up to 190 cm) can make the exchange of intracorporeal pressure shock wave catheter 340 (retrieval from the guide wire 94 and replace with another intracorporeal pressure shock wave catheter 340) cumbersome. Also the guide wire 94 length must be twice the length of the intracorporeal pressure shock wave catheter 340.

For rapid-exchange solution the guide wire 94 goes inside the intracorporeal pressure shock wave catheter 340 only for 5-30 cm of the distal end 344 of the intracorporeal pressure shock wave catheter 340 and for the rest of the length runs along the intracorporeal pressure shock wave catheter 340 inside the vasculature. This reduces the length of the guide wire 94 (now the length should be a little bid longer than the catheter not double the length) and the exchange of intracorporeal pressure shock wave catheter 340 is done much faster. These constructions complicate the distal end 344 design for the intracorporeal pressure shock wave catheter 340 and may impede centering of the intracorporeal pressure shock wave catheter 340 inside the blood vessels 15 or body conduits/lumens.

(8) The settings may be in the low energy scale (flux densities of less than 0.1 mJ/mm$^2$), due to the dimensions of the reflector and also presence of the intracorporeal pressure shock wave catheter 340 inside the human body 27. The range of actuating voltages may be between few millivolts to hundreds of volts and better in the order of volts. Also, more than 1,000 shocks are preferable to achieve the appropriate results.
(9) Methods to produce pressure shock waves include electrohydraulic, electromagnetic, piezoelectric, laser discharge, explosive, mechanical, etc.
(10) Pressure shock waves can be focused, unfocused, radial, planar, pseudo-planar, etc.
(11) The intracorporeal pressure shock wave catheter 340 will access the vasculature through major arteries vs. femoral artery (femoral access in the groin area) or brachial access (in the appendage area). If needed, other non-traditional access points might be used.

Intracorporeal pressure shock waves may be used for the treatment of vulnerable and stenotic plaques, post angioplasty and post stenting inflammation, in-stent restenosis, heart muscle, drug delivery to human/animal body internal conduits/lumens and blood vessels walls, inflammation of human/animal body internal conduits/lumens and blood vessels, and internal infections. The intracorporeal pressure shock wave catheter 340 can be deployed inside the vasculature and used independently or in conjunction with drug boluses (mixture of medications) to treat vulnerable plaques 135 and stenotic plaques 130, in-stent restenosis 190, inflammation after angioplasty/stenting, blood clots dissolution or to treat the tissue adjacent to the blood vessels 15 (for example heart muscle, muscle that activate heart valves, etc.), as an independent intracorporeal pressure shock waves treatment or in conjunctions with drugs and/or extracorporeal pressure shock waves treatment and/or gene therapy and/or stem cells therapy.

When intracorporeal pressure shock wave catheters 340 are placed inside a natural human/animal conduit/lumen, they can be used independently or in conjunction with drug boluses (mixture of medications) and/or extracorporeal pressure shock waves devices for reducing/eliminating chronic inflammation, eradication of infections, or to promote healing and repair. Chronic inflammations can degenerate in cellular destruction and they are interconnected with infections and thus can have detrimental effects on the human/animal bodies 27 and they need to be eliminated. It is well known that the pressure shock waves can reduce inflammation and also have a bactericidal effect (destroy bacteria), antiviral effect (destroy viruses) or antipathogen effect, which make the intracorporeal pressure shock waves treatment a prime candidate to treat infections and chronic inflammations, as independent treatment or in conjunction with drugs and/or extracorporeal pressure shock waves devices and/or other therapies.

In the case of healing and repair an interstitial cystitis (painful bladder syndrome), intracorporeal pressure shock waves catheters may be used to repair the defects in the lining (epithelium) of the bladder and thus reducing or eliminate the symptoms of this disease. Also, the pressure shock waves can have an analgesic effect on the nerves that transmit the sensation of pain around the bladder, which can also help with the symptoms of this disease.

Artificial conduits may be used with intracorporeal pressure shock waves catheters to treat percutaneously inflammation and infections or to reduce subcutaneous body fat layer, as in the case of liposuction.

When pressure shock waves are used to activate drug boluses an increased concentration of the drugs can be delivered in the treatment area for increased efficiency, and thus avoiding systemic reaction given by the same drug concentration when the boluses are delivered intravenously or orally. Activation of drug boluses with pressure shock waves can be done either intracorporeal or extracorporeal.

For electromagnetic discharge used to produce pressure shock waves, an activator is needed which can increase the size of the intracorporeal pressure shock wave catheter 340. If the intracorporeal pressure shock wave catheter 340 uses piezoelectric generated pressure shock waves, the bulkiness is reduced and thus the intracorporeal pressure shock wave catheter 340 are smaller, which allows them to penetrate deeper into vasculature/blood vessels 15 (away from the heart 209) or in smaller natural/artificial human/animal conduits 17, which can give the advantage of being able to treat areas that are not available for other technologies.

The electrohydraulic activation of the pressure shock waves may be used for any of the intracorporeal applications mentioned above due to their smallest diametric dimension when compared with the electromagnetic or piezoelectric principle used to generate pressure shock waves using an intracorporeal pressure shock wave catheter 340.

Figure 35:
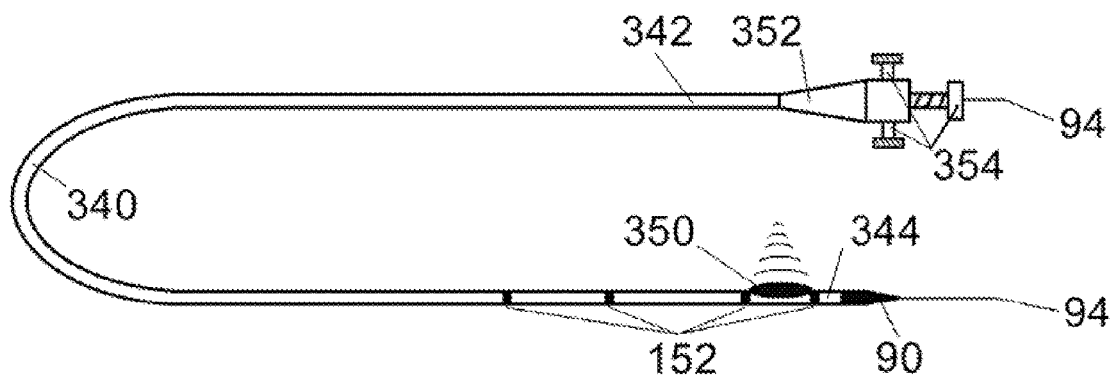
FIG. 35 is a schematic diagram of an intracorporeal shock wave catheter in one embodiment of the present invention.

FIG. 35 shows an intracorporeal pressure shock wave catheter 340 functioning on the electrohydraulic principle. The intracorporeal pressure shock wave catheter 340 has at the proximal end 342, access ports 354 to allow the introduction of the guide wire 94 (for "over-the-wire" construction) and for introduction/extraction of fluid from the intracorporeal catheter shock wave applicator area 350. The strain relief 352 is used to allow the transition from the access ports 354 to the body of the intracorporeal pressure shock wave catheter 340 without kinking. The distal end 344 of the intracorporeal pressure shock wave catheter 340 has the intracorporeal catheter shock wave applicator 350, where the pressure shock waves are produced. Also, for visualization and correct positioning in the treatment area, the distal end 344 of the intracorporeal pressure shock wave catheter 340 has radio-opaque markers 152 and a radio-opaque tip 90.

Figure 36A:
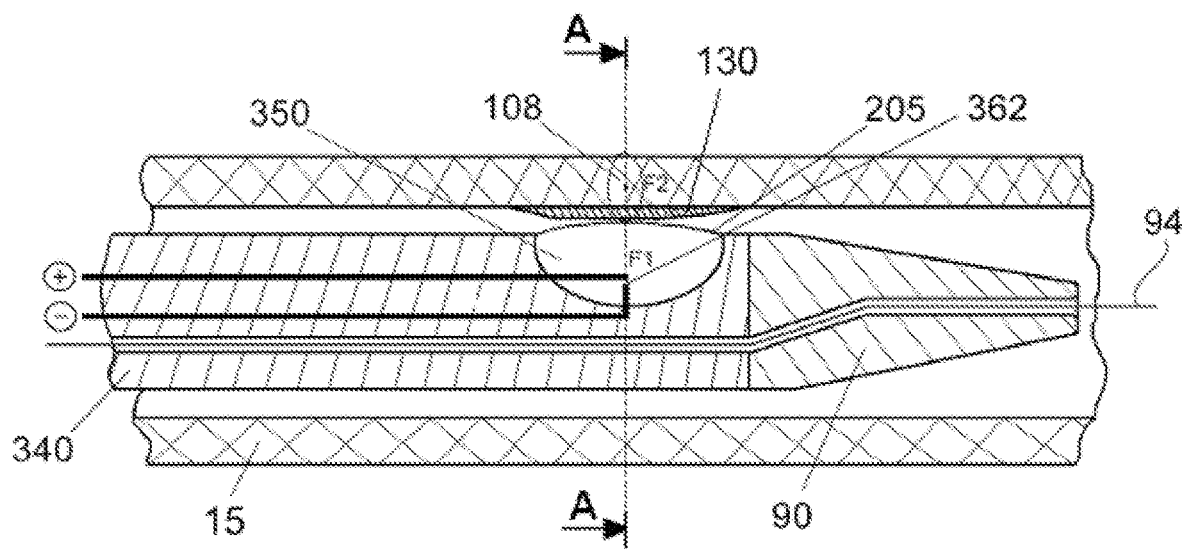
FIG. 36A is a schematic diagram of an intracorporeal shock wave catheter in a blood vessel in one embodiment of the present invention.
Figure 36B:
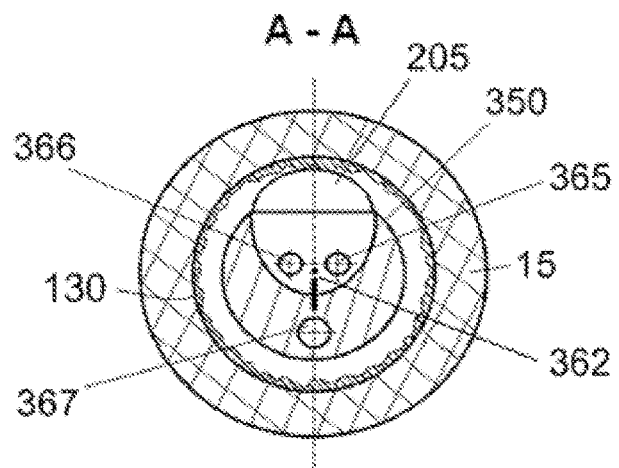
FIG. 36B is a schematic diagram of a cross-sectional view along AA of FIG. 36A of an intracorporeal shock wave catheter in one embodiment of the present invention.

For electrohydraulic principle (FIG. 35), the electrical discharge can be produced directly in blood from blood vessels 15 or in any fluid present in natural human/animal conduits/lumens or in enclosed water filled (saline solution filled) chambers or spaces in the intracorporeal catheter shock wave applicator 350. To have consistency of the discharge, the discharge in water or saline solution is preferred. In embodiments, the intracorporeal catheter shock wave applicator 350 is pre-filled or can be filled with saline solution at "the point of care" using the two saline lumens (saline "IN" lumen 365 and saline "OUT" lumen 366), as shown in FIG. 36B. Filling at "the point of care" is preferred to reduce the size of the intracorporeal pressure shock wave catheter 340 during advancement through vasculatures (blood vessels 15) or natural/artificial human/animal conduits/lumens, as shown in FIGS. 36A and 36B.

In embodiments of the invention, direct contact of the intracorporeal catheter shock wave applicator 350 is made with the plaques 130 (stenotic plaques or vulnerable plaques) or targeted area of natural human/animal conduit/lumen for pressure shock waves treatment. For vasculature treatment this approach can be used for the vessels 15 in the body appendage 25, where the generation of small particles from the plaques 130 (stenotic plaques or vulnerable plaques) can flow down the blood stream without any life threatening consequences. In embodiments to completely treat the plaques 130 (stenotic plaques or vulnerable plaques from blood vessels) or targeted area of natural human/animal conduit/lumen, the intracorporeal pressure shock wave catheter 340 may allow axial movement and rotational movement around the guide wire 94 (the catheter needs to be stir-able) and facilitate the focal volume 108 intersecting the plaques 130 (stenotic plaques or vulnerable plaques from blood vessels 15) or targeted area of natural human/animal conduit/lumen. Shock waves are generated in electrohydraulic embodiments by discharging voltage on the spark gap 362.

Figure 37:
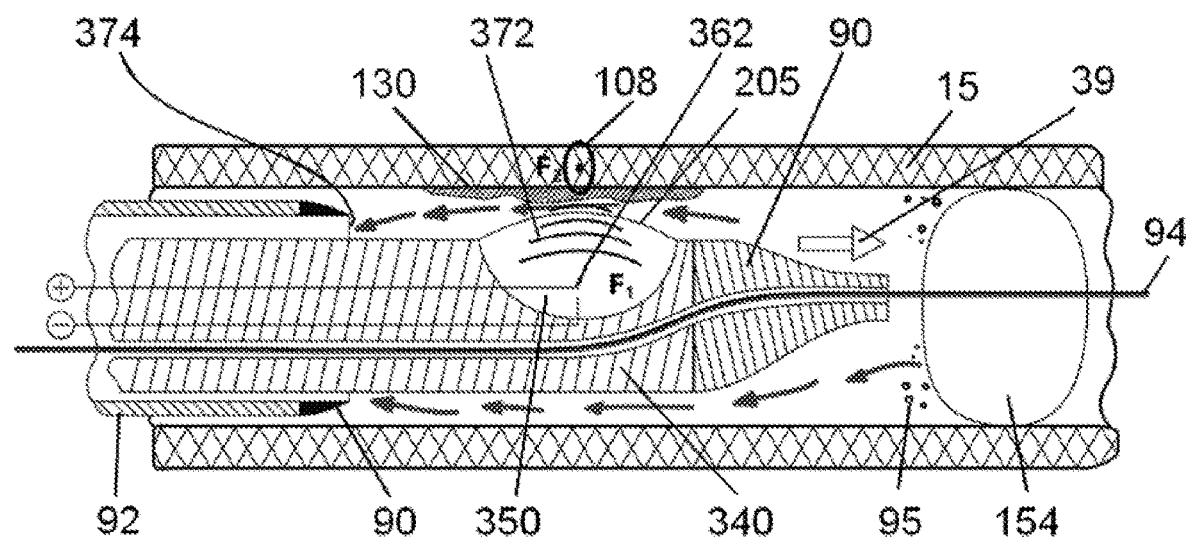
FIG. 37 is a schematic diagram of an intracorporeal shock wave catheter and occlusion balloon system in a blood vessel in one embodiment of the present invention.

In order to protect the distal vasculature from any pieces of plaque 130 (stenotic plaque or vulnerable plaque) that might be dislodged from the blood vessel 15 wall, the treatment with intracorporeal pressure shock waves may be combined with distal protection devices, such as presented in FIG. 37.

The distal protection system shown in FIG. 37 includes an occlusion balloon 154 utilized to collect debris 95 generated during intracorporeal pressure shock wave treatment. The extraction of collected debris 95 is done using passive suction (manual syringe activated—not pumps) to prevent the blood flow 39 or normal flow for natural conduits/lumens to carry the debris 95 down the stream, which might create blockages. The steps to perform such a procedure in one embodiment include:

(A) Guide wire 94 introduction through femoral and brachial access.
(B) Set guide wire 94 in the plaque 130 (stenotic plaque or vulnerable plaque from blood vessels 15) or targeted area of natural human/animal conduit/lumen 17.
(C) Introduce the guide catheter 92 over the guide wire 94 and set the distal end of the guide catheter 92 proximal to the treatment area using the radio-opaque tip 90 of the guide catheter 92.
(D) Using the guide wire 94 slide the intracorporeal pressure shock wave catheter 340 inside the guide catheter 92 towards the treatment area.
(E) Set the intracorporeal pressure shock wave catheter 340 in front of the plaque 130 (stenotic plaque or vulnerable plaque from blood vessels 15) or targeted area of natural human/animal conduit/lumen using the catheter radio-opaque markers 152 (not shown in FIG. 37) and the radio-opaque tip 90. This procedure allows the focal volume 108 to properly intersect the treatment area.
(F) Fill in the intracorporeal catheter shock wave applicator 350. Push saline solution and contrast media mixture through the "IN" lumen 365 and saline until it comes back to the "OUT" lumen 366. Block the "OUT" lumen 366 and fill in the intracorporeal catheter shock wave applicator 350 at the required pressure (1-10 psi) using the "IN" lumen 365. The membrane 205 should now be in contact with plaque 130 (stenotic plaque or vulnerable plaque from blood vessels 15) or targeted area of natural human/animal conduit/lumen.

(G) Inflate the guide wire 94 occlusion balloon 154 with saline solution and contrast media mixture.

(H) Perform the shock wave treatment by discharging voltage on the spark gap 362 in order to create, focused shock waves 372. Move intracorporeal pressure shock wave catheter 340 up and down and rotate it to cover the whole treatment area.

(I) After finishing the treatment retrieve the intracorporeal pressure shock wave catheter 340 and use the guide catheter 92 to perform passive suction through the suction area 374 in order to collect any possible debris 95.

(J) After extraction of 2-3 syringes of 60 ml of blood/fluid from the treatment area through the suction area 374, deflate the guide wire 94 occlusion balloon 154.

(K) Retrieve the guide catheter 92 and the guide wire 94.

(L) Close the access (femoral or brachial).

In embodiments, the suction is done after the treatment with pressure shock waves was finished and after the intracorporeal pressure shock wave catheter 340 is removed from the treatment area, allowing a larger lumen to be used for suction (larger suction area 374 shown in FIG. 37).

Figure 38:
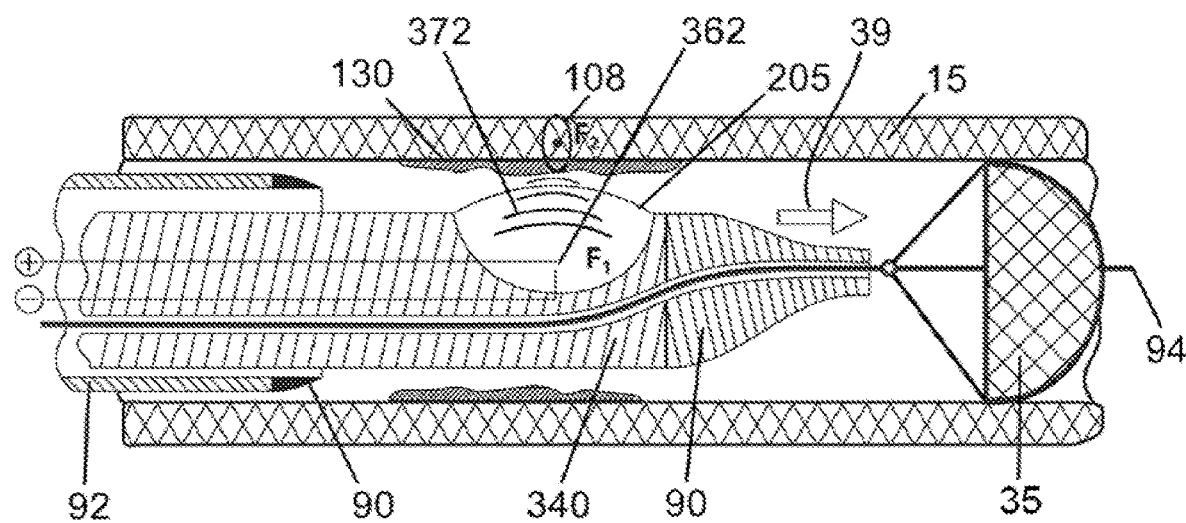
FIG. 38 is a schematic diagram of an intracorporeal shock wave catheter and debris collection basket system in a blood vessel in one embodiment of the present invention.

Another option for distal protection includes use of designed debris collection basket 35 to collect debris 95, as shown in FIG. 38. The debris collection basket 35 opens and closes based on an umbrella mechanism and it is attached to a guide wire 94. In this case the guide catheter 92 is used to guide the intracorporeal pressure shock wave catheter 340 through vasculature and not for suction as in the distal protection solution that uses the occlusion balloon 154 of the vessel 15, as presented in FIG. 37. The big advantage of the debris collection baskets 35 is that they allow blood flow 39 through them during treatment and in the same time the debris 95 collection, in contrast to occlusion balloon 154 solution where no blood flow 39 is allowed until the treatment is finished, and debris 95 collected via suction.

The treatment set-up, generation of the pressure shock waves, positioning under fluoroscopic guidance of the guide catheter 92 and intracorporeal pressure shock wave catheter 340 in the treatment area and post treatment steps are similar to those presented in explanations for the FIG. 37.

Figure 39:
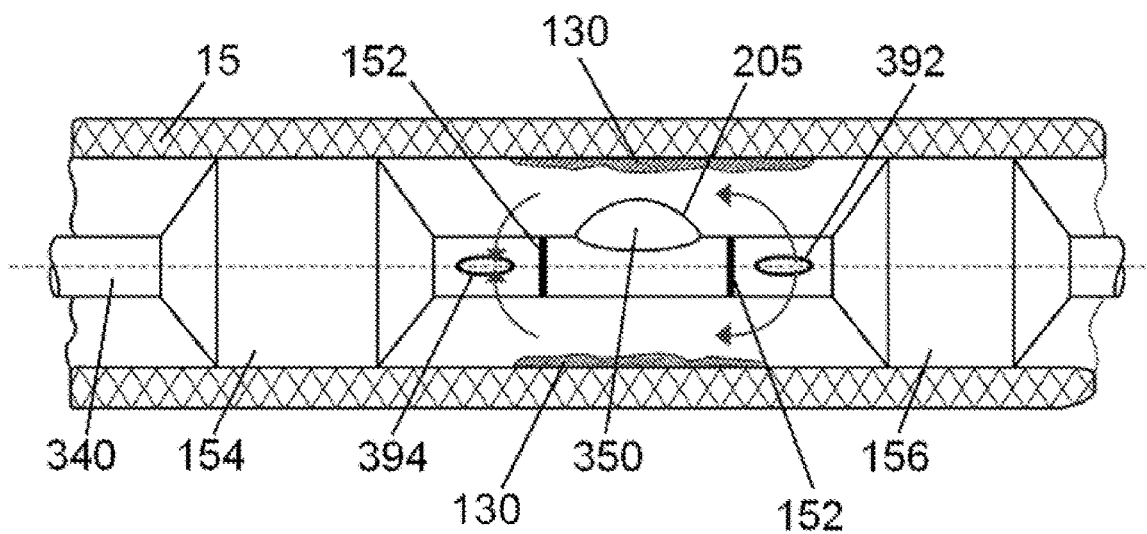
FIG. 39 is a schematic diagram of an intracorporeal shock wave catheter and multiple occlusion balloons system with a membrane protecting a reflector in a blood vessel in one embodiment of the present invention.

Another approach (the third) is provided by the distal protection devices that use multiple occlusion balloons (first occlusion balloon 154 and the second occlusion balloon 156) as presented in FIG. 39, where the catheter shock wave applicator 350 has a membrane 205 and propagation of pressure shock waves is done through blood. Collection of debris 95 is done through active flushing with saline using IN opening 392 and OUT opening 394 positioned in between the two occlusion balloons (154 and 156). The active flushing is done by extracorporeal dedicated pumps. The correct positioning of the intracorporeal pressure shock wave catheter 340 in the treatment area of the blood vessel 15 or natural conduit/lumen is done using the radio-opaque markers 152 and the two occlusion balloons (154 and 156) that are filled with saline and contrast media solutions.

Figure 40:
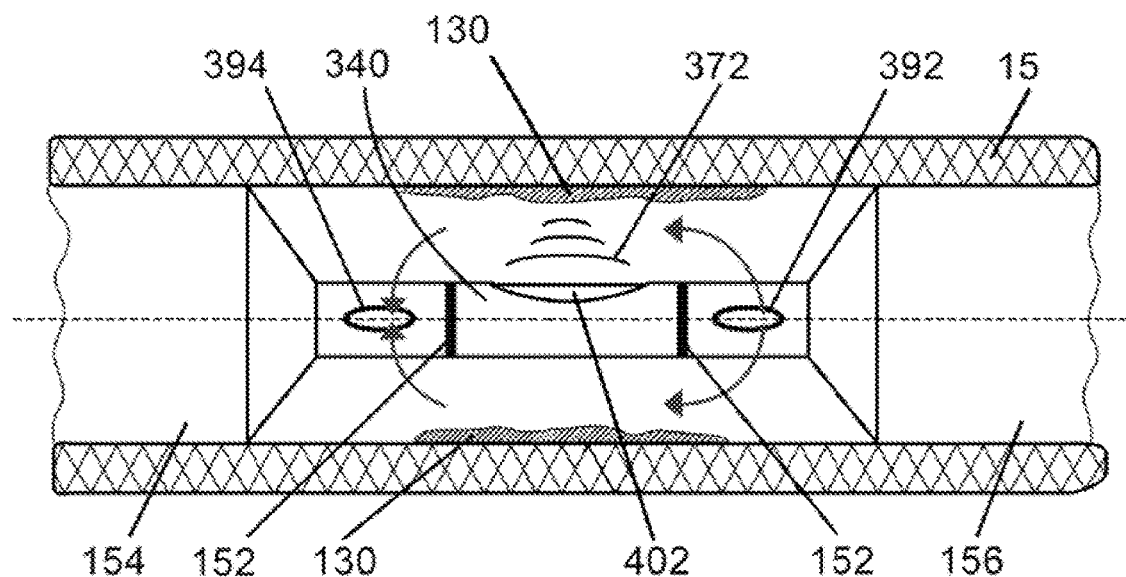
FIG. 40 is a schematic diagram of an intracorporeal shock wave catheter and multiple occlusion balloons system without a membrane protecting a reflector in a blood vessel in one embodiment of the present invention.

In another embodiment presented in FIG. 40, different from those presented in FIGS. 36A, 36B, 37, 38 and 39, a space is created in between first occlusion balloon 154 and the second occlusion balloon 156 and the blood is evacuated from the enclosed space and replaced with saline solution to allow a better formation of cavitation bubbles by the focused pressure shock waves 372. Compared to FIG. 39 where the discharge is produced in a protected space under a membrane 205, the embodiment in FIG. 40 using an electrohydraulic generator permits the voltage discharge to occur in the saline solution trapped between the two balloons 154 and 156 without the protection of a membrane 205. In other words, reflector 402 of the intracorporeal pressure shock wave catheter 340 is exposed to the saline solution trapped between the two balloons 154 and 156.

At the end of the treatment, IN lumen 365 and OUT lumen 366 (FIG. 36B), may be used to bring and extract the saline solution into and from the closed space and can be also used for flushing the area of possible debris 95 via active flushing using dedicated pumps.

Figure 41:
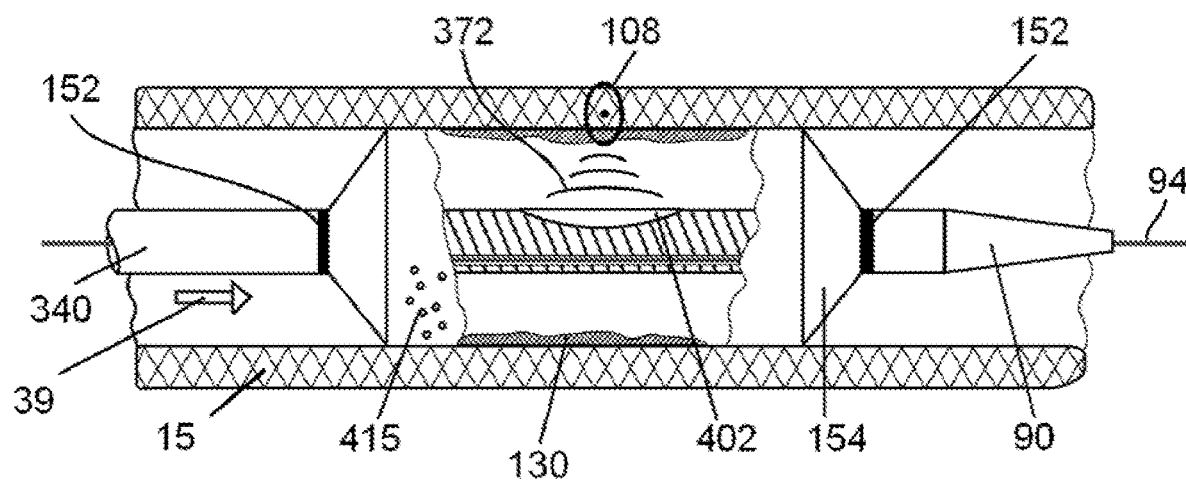
FIG. 41 is a schematic diagram of an intracorporeal shock wave catheter with a reflector incorporated in an occlusion balloon in one embodiment of the present invention.

In another embodiment presented in FIG. 41, reflector 402 is incorporated inside an occlusion balloon 154, which can be filled with high pressure saline solution or saline solution plus contrast for visualization inside the body 27. Thus the occlusion balloon 154 can have a dual treatment purpose of: (1) balloon used to push the plaque 130 (stenotic plaque or vulnerable plaque) or the targeted area radially and thus opening the cross-sectional area of the blood vessel 15 or the conduit/lumen; and (2) usage of the same balloon to treat with pressure shock waves.

In embodiments, the pressure shock waves can be delivered in fully inflated balloons or partially deflated balloons. Additionally, the balloon can be designed in such a way that its diametric dimension at full inflation is less than the blood vessel 15 or the conduit/lumen diameter. In the described embodiment, the catheter is dedicated for pressure shock waves only and can be used to treat plaques 130 (stenotic plaques or vulnerable plaques of a blood vessel 15) or in-stent restenosis 190. The same embodiment presented in FIGS. 39, 40 and 41 can be used to treat chronic inflammation, hyperplasia or in-stent restenosis 190 for any natural human/animal conduits/lumens, as independent intracorporeal pressure shock waves treatment or in conjunction with drugs and/or extracorporeal pressure shock waves devices and/or other therapies.

If the occlusion balloon 154 from FIG. 41 has a controlled porosity 415, medication can be pushed out from the occlusion balloon 154 due to pressure shock waves. This approach can be used to push medication much easier than a passive mean into the plaques 130 (stenotic plaques or vulnerable plaques of a blood vessel 15) or in targeted area for any natural human/animal conduits/lumens. The medication can help with reducing inflammation, blocking smooth muscle cells proliferation, relaxation of vessel 15 or natural human/animal conduit/lumen wall, etc.

The positioning of the intracorporeal pressure shock wave catheter 340 inside the vasculature or natural human/animal conduits/lumens is done using radio-opaque markers 152 incorporated in the catheter body (as part of plastic mixture or by adding metallic bands, dots, etc) and the radio-opaque tip 90 of the intracorporeal pressure shock wave catheter 340.

For the treatment of vulnerable plaque and stenotic plaque, post angioplasty and post stenting inflammation, in-stent restenosis 190, heart muscle, drug delivery to human/animal body internal conduits/lumens and blood vessels 15 walls, inflammation of human/animal body internal conduits/lumens and blood vessels 15, and internal infections, the settings of the intracorporeal pressure shock waves catheter 340 should be for the dosage of more than 500 shots, at energy flux densities higher than 0.001 $mJ/mm^2$ and frequencies of the pulses between 1 Hz and 10 Hz.

Intracorporeal pressure shock waves may be further used to treat aneurysms of the blood vessels. When the radial and tangential strength is lost, the blood vessels 15 start to balloon, which creates aneurysms The reduced strength of the blood vessels 15 wall makes them prone to balloon that can ultimately results in the blood vessels 15 burst/rupture under normal blood pressure, which can be fatal especially for major blood vessels as aorta. When an aneurysm develops it is typically treated via surgery or endovascular approach with multiple combinations of stents 170 covered with graft material. Based on demonstration efficacy of the pressure shock waves to grow tissue, there is a favorable possibility of reinforcing the wall of the aneurysm using an intracorporeal pressure shock waves device.

Aneurysms can form in brain (genetic predispositions and anomalies). Due to the sensitive area and the very small dimensions of the blood vessels, the intracorporeal pressure shock waves catheters 340 are not preferable for brain aneurysms. If pressure shock waves are needed to treat brain area, the device should preferably be extracorporeal.

Big blood vessels walls (especially aorta, iliacs, femoral arteries, etc.) can lose their radial strength due to genetic problems, nutrition, age, etc. If aneurysms in aorta grow too big, they can rupture, which can be fatal if not treated immediately. The aneurysms in the iliacs are not fatal, but they create important health problems.

Aortas are big blood vessels 15 up to 35 mm and iliacs can get close to 18 mm in diameter. This gives the advantage of using larger intracorporeal pressure shock waves catheters 340 with bigger reflectors for pressure shock waves that can be introduced into vasculature via femoral access.

Figure 42:
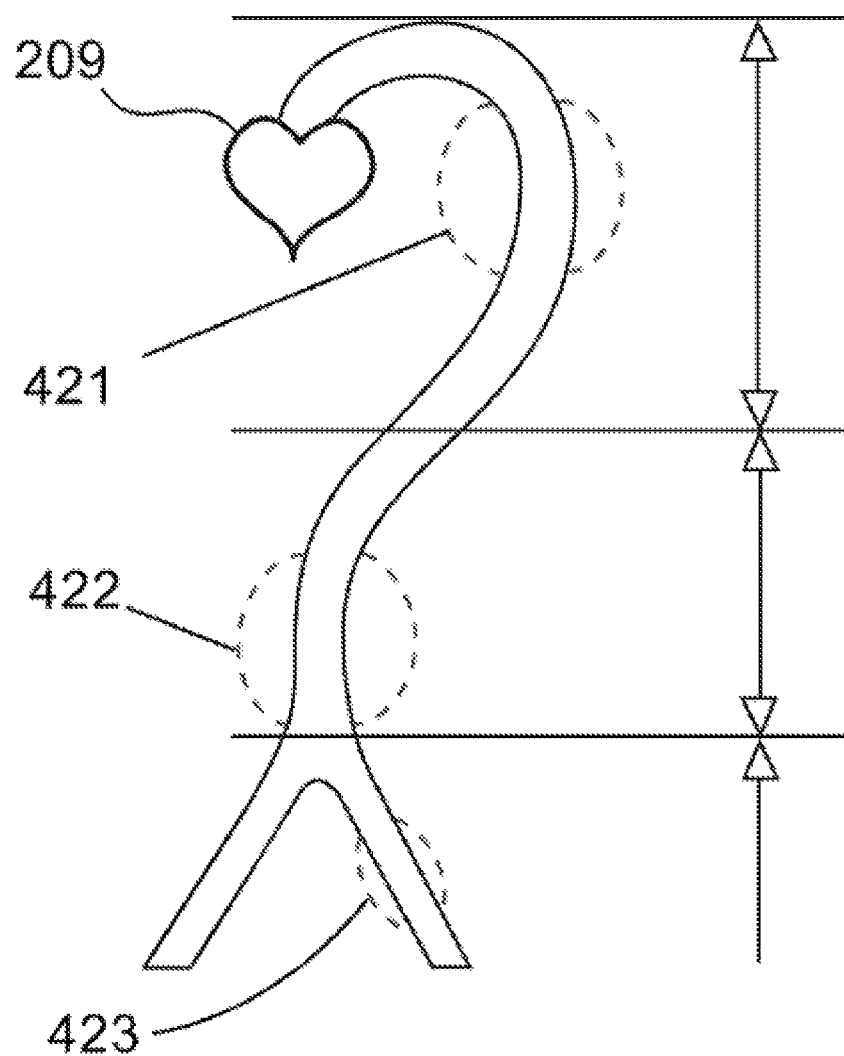
FIG. 42 is a schematic diagram of aneurysms' locations in one embodiment of the present invention.

Most aneurysms 420 are found in aorta (thoracic aneurysms 421 and abdominal aneurysms 422) and in the iliacs (iliac aneurysms 423), as shown in FIG. 42. The intracorporeal pressure shock waves catheter 340 can reach an outer diameter of about 7-8 mm for the treatment of aortic aneurysms (421 and 422) and iliac aneurysms 423.

Aneurysms' 420 treatment with any of the intracorporeal pressure shock waves' catheters 340 presented previously in FIGS. 35, 36A, 36B, 37, 38, 39, 40 and 41 may be used. Due to increased dimensions for the intracorporeal pressure shock waves catheter 340 and the necessary increase in efficiency, multiple reflectors (402 and 404) may also be used, as presented in FIG. 43.

Reflector 402 and reflector 404 are in communication to allow the saline solution to move "in" and "out" for both reflectors 402 and 404 simultaneously.

Figure 43:
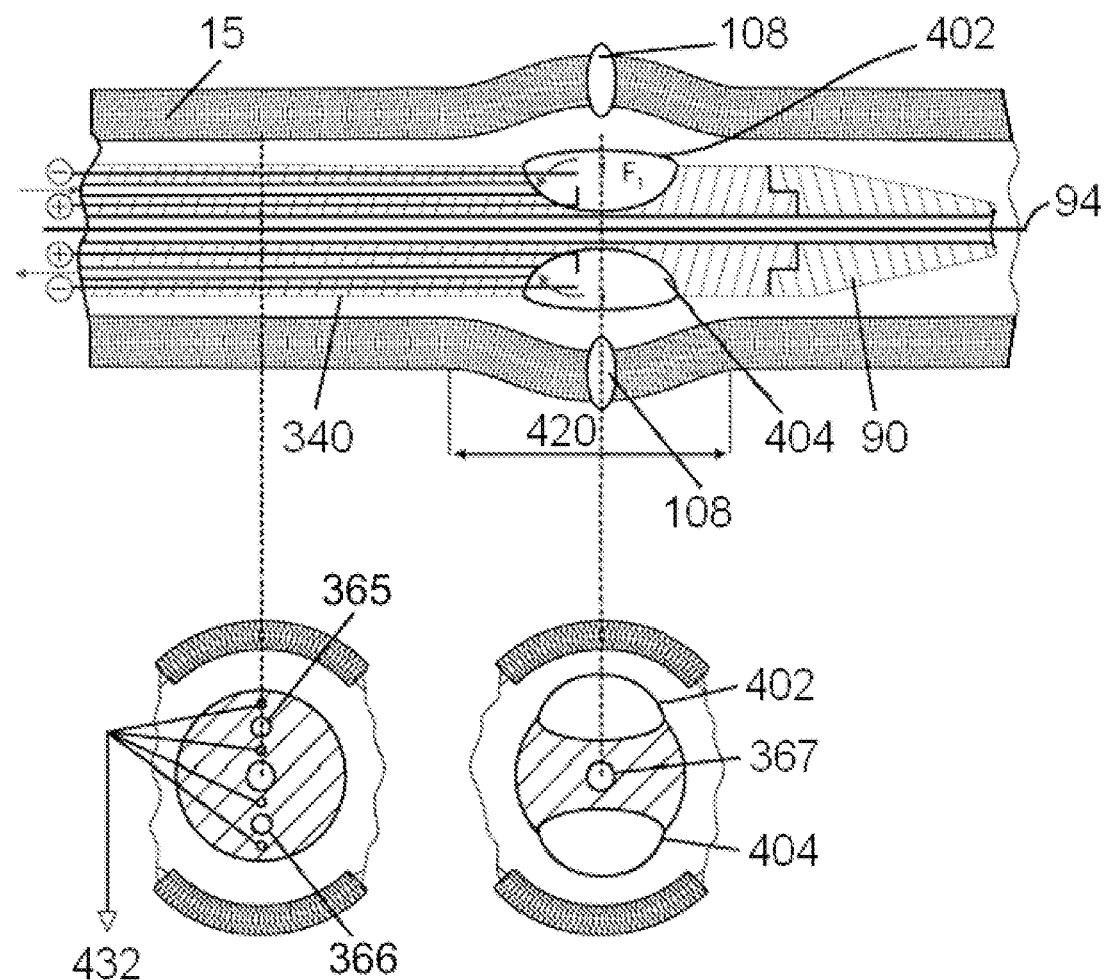
FIG. 43 is a schematic diagram of an intracorporeal shock wave catheter including multiple reflectors in one embodiment of the present invention.
Figure 44:
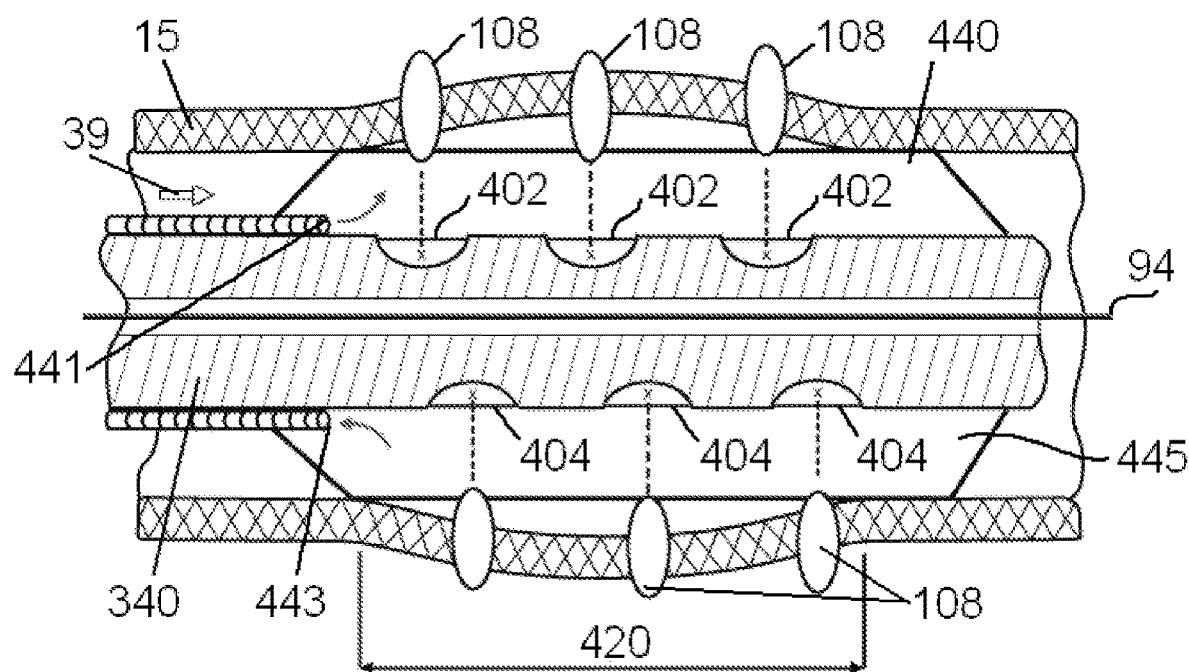
FIG. 44 is a schematic diagram of an intracorporeal shock wave catheter including multiple reflectors disposed in a non-occlusion balloon in one embodiment of the present invention.

Multiple reflectors can increase efficiency as the treatment is given simultaneously in multiple points of the aneurysm 420, where the focal volumes 108 intersect the aneurysm 420 wall. Referring to FIGS. 43 and 44, independent reflectors (402 and/or 404) are disposed 180° apart (opposite). Electrical wires 432 are provided within catheter 340. If the environment permits, the reflectors can be at 120° angle separation and even better at 90° angle separation. FIG. 44 shows an embodiment where multiple reflectors (three reflectors 402 and three reflectors 404) are disposed inside a dedicated non-occlusion balloon 440 that allows the electrohydraulic discharge in saline solution 445 instead of blood, which can increase the efficiency of the pressure shock waves treatment. The length of the non-occlusion balloon 440 that incorporates the pressure shock waves reflectors (402 and 404) is dictated by the size of the aneurysm 420 that must be treated and can vary from 5-15 cm. The saline solution 445 is brought IN and OUT via small tubes of plastic (saline "IN" tube 441 and saline "OUT" tubing 443), glued on the body of the intracorporeal pressure shock waves catheter 340. The material of the non-occlusion balloon 440 should be able to sustain high pressures (for example nylon or other materials used for angioplasty balloons).

Figure 45:
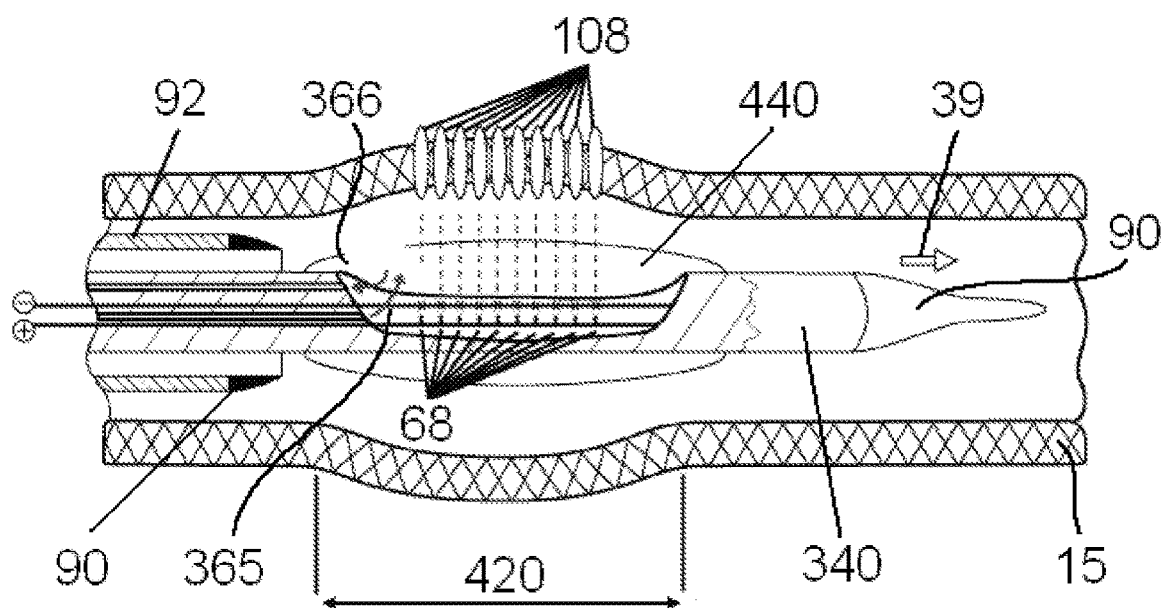
FIG. 45 is a schematic diagram of an intracorporeal shock wave catheter including multiple reflectors disposed in a non-occlusion balloon without contacting an aneurysm in one embodiment of the present invention.

In FIG. 44 the non-occlusion balloon 440 is illustrated in direct contact with the aneurysm 420, although the design could be done in such way to not push against the wall of the aneurysm 420, as presented in FIG. 45. The only role for the non-occlusion balloon 440 is to provide an enclosed chamber in which the pressure shock waves can be generated in more efficient way. For both FIGS. 44 and 45 the material of the non-occlusion balloon 440 should be a very good acoustic transmission material, to not impede in pressure shock waves propagation and focusing. The controlled pressure inside the non-occlusion balloon 440 may maintain a certain dimension of the balloon, its integrity and in the same time optimal propagation of the pressure shock waves.

Referring to FIG. 45 the difference between the shaft of the intracorporeal pressure shock waves catheter 340 and the outer diameter of the non-occlusion balloon 440 may be minimal (difference of 2-5 mm radial). In this way, the non-occlusion balloon 440 will not contact the aneurysm 420 wall. In some embodiments, the intracorporeal pressure shock waves catheter 340 is centered inside the blood vessel 15 to allow the treatment of the aneurysm 420 wall. In other words it is wanted that the focal volumes 108 to intersect the aneurysm 420 wall to provide a good treatment.

Note that the solution presented in FIG. 45 does not have a guide wire lumen 367 (FIG. 43). The guiding of the intracorporeal pressure shock waves catheter 340 into the treatment area is made by the guide catheter 92. Initially a guide wire 94 was used to allow the correct positioning and advancement of guide catheter 92 inside vasculature by gliding over the guide wire 94. After this step, the guide wire 94 was retrieved and finally the intracorporeal pressure shock waves catheter 340 is set in place by sliding it inside the guide catheter 92.

As shown in FIG. 45, multiple points of origin (discharge points 68) for pressure shock waves can be used in a single cavity (such as pipe with ellipse cross-section) used for reflection and focusing of the pressure shock waves. In this embodiment, the efficiency is improved in treating the aneurysm 420 with multiple focal volumes 108. To cover the whole aneurysm 420 the intracorporeal pressure shock waves catheter 340 must be moved axially and rotate 360°, under fluoroscopic guidance using catheters' radio-opaque markers 152 (not shown in FIG. 45) and the radio-opaque tip 90. The intracorporeal pressure shock waves catheter 340 is introduced and guided inside the blood vessel 15 via a guide catheter 92. The non-occlusion balloon 440 is inflated and deflated with saline solution via the "IN" lumen 365 and "OUT" lumen 366.

Figure 46:
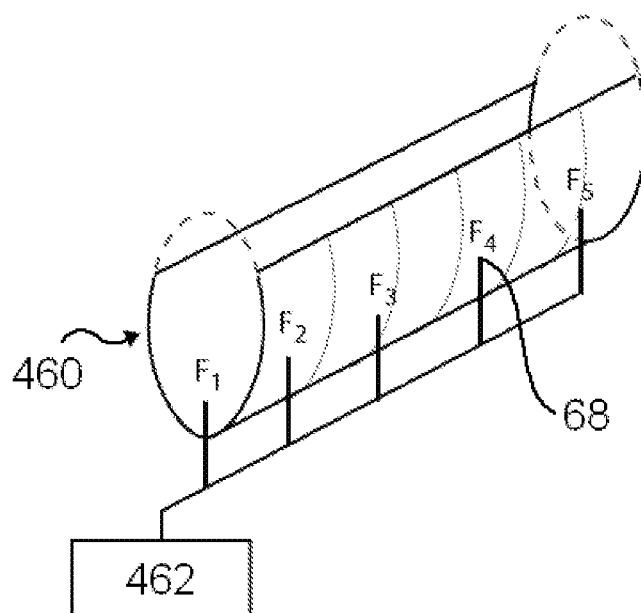
FIG. 46 is a schematic diagram of a catheter reflector having multiple discharge points in one embodiment of the present invention.

In a further embodiment, the body of the intracorporeal pressure shock waves catheter 340 can be made in the form of a reflective geometry shown in FIG. 46. The catheter reflector 460 is made of a hypotube (thin metal tube) shaped in the form of a pipe with ellipse or a parabola cross-section that can focus away pressure shock waves generated by the discharge points 68 ($F_1, F_2, F_3, F_4$, and $F_5$).

A radio-opaque key/marker 152 (as shown in FIGS. 40 and 41) on the proximal end of the intracorporeal pressure shock waves catheter 340, in the form of a line or a marker point, will allow the user to know the proper alignment of the intracorporeal pressure shock waves catheter 340 against the vessel 15 wall needing treatment.

For embodiments shown in FIGS. 43, 44, 45, and 46, the multiple points of origin for the shock waves (multiple reflectors 402 and/or 404 or multiple discharge points 68, in one reflector) can be controlled via software, which allows the firing simultaneously of each point of origin or sequentially in a predetermined pattern by the controller 462.

For the treatment of aneurysms 420 in blood vessels the settings of the intracorporeal pressure shock waves catheter 340 should be for the dosage more than 2000 shots, at energy flux densities higher than 0.01 mJ/mm² and frequencies of the pulses higher than 2 Hz.

Figure 47A:
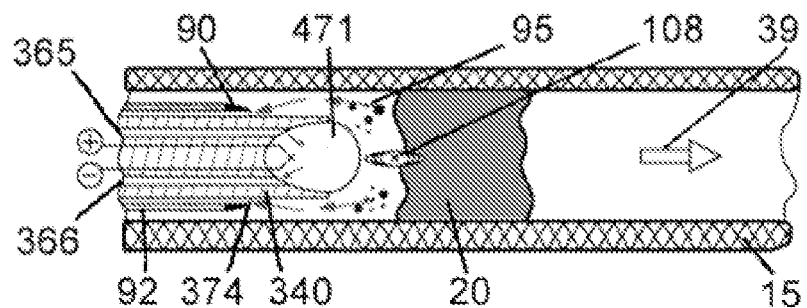
FIG. 47A is a schematic diagram of an intracorporeal shock wave catheter with a frontal reflector positioned for treating an occlusion in a blood vessel in one embodiment of the present invention.
Figure 47B:
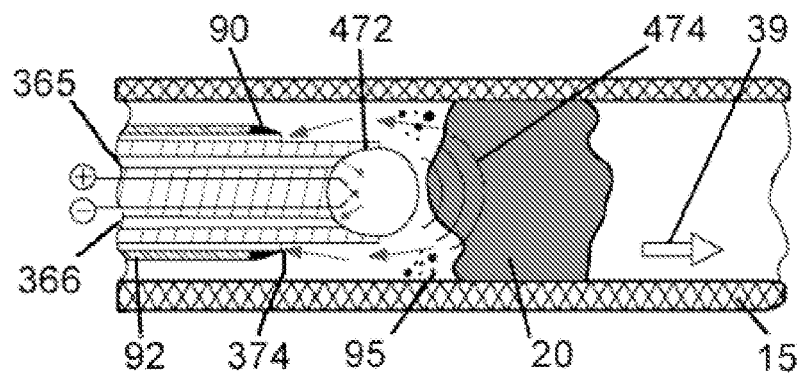
FIG. 47B is a schematic diagram of an intracorporeal shock wave catheter with a frontal reflector positioned for treating an occlusion in a blood vessel in one embodiment of the present invention.
Figure 47C:
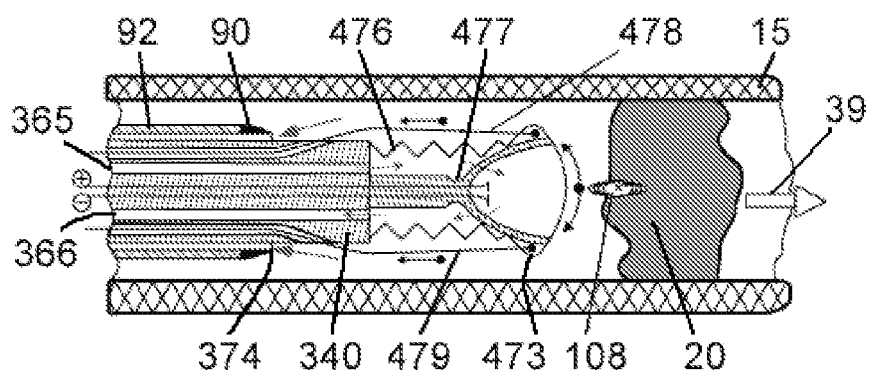
FIG. 47C is a schematic diagram of an intracorporeal shock wave catheter with an extendible frontal reflector positioned for treating an occlusion in a blood vessel in one embodiment of the present invention.

The following characteristics may contribute to successful treatment of occlusions 20 and blood clots with intracorporeal pressure shock waves treatment (as seen in FIGS. 47A, 47B and 47C):

1) Frontal exposure of the pressure shock waves reflectors (471, 472 or 473), positioned at the intracorporeal pressure shock waves catheter 340 distal end.
2) Microjets produced by collapse of the cavitation bubbles represent a main mechanism of action to treat occlusions 20 and blood clots.
3) The focal volume 108 of the intracorporeal pressure shock waves catheter 340 (where the cavitation is formed) must intersect the occlusion 20 or the blood clot in order for the intracorporeal pressure shock waves treatment to be efficient.
4) The dimensions of the reflectors (471, 472 or 473) and their optimal orientation (perpendicular to the occlusion 20 or blood clot) will dictate the efficiency of the intracorporeal pressure shock waves.
5) The small area available to focus intracorporeal pressure shock waves (dictated by the blood vessel 15, conduit/lumen or artificial vessel 184 cross sectional area) can reduce the amount of energy delivered in one shot by the intracorporeal pressure shock waves catheter 340, when compared to extracorporeal pressure shock waves devices (larger area at their disposal to focus pressure shock waves). This is why the intracorporeal pressure shock waves catheter 340 may need to use an increased number of shots per treatment.
6) The voltage used for actuating the intracorporeal pressure shock waves catheter 340 is in the range of millivolts to hundreds of volts.
7) If the actuating voltage for the intracorporeal pressure shock waves catheter 340 used for occlusions 20 and blood clots is small enough, battery operating devices may be used in such applications.
8) The reflectors (471, 472 or 473) may be created from materials such as, but not limited to metal, hard plastics or ceramics/glass.
9) Combination of pressure shock waves and drugs can be used to enhance treatment efficiency by using the synergy of pressure shock waves with the drugs.
10) Various methods to produce pressure shock waves include electrohydraulic, electromagnetic, piezoelectric, laser discharge, micro-explosion/discharge or mechanical vibrations.
11) The electrohydraulic discharge, laser discharge or micro-explosion/discharge may be made in water, and avoid blood, for increased efficiency
12) The shape of the reflector can be elliptical, paraboloid, sphere or planar, or combinations of them.
13) The intracorporeal pressure shock waves catheter 340, due to the position of the reflectors 471, 472 or 473 (frontal exposure), do not allow guide wires 94 usage. The guidance of the intracorporeal pressure shock waves catheter 340 may be done through guide catheters 92. If a guide wires 94 is used that will reduce the dimensions of the reflectors 471, 472 or 473 and the reflective area necessary to focus pressure shock waves.
14) Consistent with described exemplary embodiments, the construction of the intracorporeal pressure shock waves catheter 340 walls preferably allows electrical insulation of that patient.
15) The access of the intracorporeal pressure shock waves catheter 340 for blood vessels 15 or grafts/artificial vessels 184 to treat occlusions 20 and/or blood clots may occur through femoral or brachial points.
16) For occlusions 20 and blood clots of the natural human/animal conduits/lumens, access to the occlusion 20 or blood clot may be via the conduit/lumen.
17) The size of the intracorporeal pressure shock waves catheter 340 might restrict the use of the intracorporeal pressure shock waves technology for certain sizes of blood vessels 15 ort conduits/lumens or grafts/artificial vessels 184.
18) If possible in embodiments, a pivotal movement of the reflectors (471, 472 or 473) may allow the orientation of the cavitation microjets on a larger area of the occlusion 20 or blood clot and thus improved efficiency can be achieved.
19) If needed, the debris 95 generated during elimination of the occlusion 20 or blood clots using the intracorporeal pressure shock waves catheter 340 can be collected using passive or active suction. Distal protection baskets 35 can be also used, although they need a point of access distal to occlusion 20 or blood clot, which is more difficult to achieve. For treating vascular occlusions 20 or blood clots in body appendages 25, the danger of debris 95 going down the blood flow 39 stream is less important in comparison to carotid or coronary arteries.

When an ellipsoid is used for pressure shock waves reflecting area (FIG. 47A) the intracorporeal pressure shock waves catheter 340 will have an ellipsoidal reflector 471. For the ellipsoidal reflectors 471, the ratio of semi axis should be larger than 2.0 (c/b≥2). This ratio will allow the focusing and formation of the cavitation in front and on occlusion 20. A higher ratio of semi axes will also allow having a deeper ellipsoidal reflectors 471 incorporated into the tip of the intracorporeal pressure shock waves catheter 340, which translates into a larger reflecting area and higher efficiency for the intracorporeal pressure shock waves.

When a sphere is used as a reflector, the intracorporeal pressure shock waves catheter 340 may have a spherical reflector 472, as seen in FIG. 42B. These types of reflectors create radial wave 474. Cavitation may still be developed by the spherical reflector 472, although the penetration of the compressive pressure waves is reduced, when compared with focused pressure shock waves. The energy of the radial pressure waves is the highest in the center of the sphere and it dissipates very fast during propagation away from the point of origin (center of the sphere). In this case, a close proximity or contact of the intracorporeal pressure shock waves catheter 340 with the occlusion 20 or blood clot is needed.

Note that for each situation presented above, to eliminate debris 95 generated during pressure shock waves treatment, a passive or active suction can be realized through the guide catheter 92 (using the space in between the interior surface of the guide catheter 92 and external surface of the intracorporeal pressure shock waves catheter 340, which define a suction area 374). Passive suction is done using syringes (manual) for extraction of debris 95 trapped in front of the occlusion 20 or blood clot. Active suction is generated using dedicated pumps that continuously extract the mixture of debris 95 generated during treatment with blood or fluid present inside blood vessel 15, graft or artificial vessel 184 or human/animal body conduit/lumen, during intracorporeal pressure shock waves treatment. To facilitate an easy discharge, the reflectors (471, 472 or 473) have a thin membrane 205 (not shown in FIG. 47A, 47B or 47C) on top of them, which creates an enclosed space filled with a fluid. The fluid can be degassed water, saline solution or saline/contrast mixture and can be filled at the manufacturer (pre-filled catheter) or can be done at "the point of care". When the reflector (471, 472 or 473) is pre-filled at the manufacturer, additional substances might be added into the water/saline solution to improve efficiency of the pressure shock waves generation or for improved visualization of the catheter head inside the human body 27 (any contrast agent). As can be seen from FIGS. 47A, 47B and 47C, there are two distinctive channels (inlet lumen 365 and outlet lumen 366) that can be used to fill in the reflectors (471, 472 or 473) and to allow the clearing of air from the intracorporeal pressure shock waves catheter 340. If air is not cleared from the reflectors (471, 472 or 473) the efficiency of the pressure shock waves can be greatly reduced.

FIG. 47C presents a solution of a movable pressure shock waves reflector or bellowed reflector 473. The angular movement of the bellowed reflector 473 is realized by pulling at the proximal end of the intracorporeal pressure shock waves catheter 340 the two sutures 478 and 479 that run through the catheter body length and are connected to the lateral ears of the reflector. If suture 478 is pulled, then the bellowed reflector 473 will rotate upwards. If suture 479 is pulled, then the bellowed reflector 473 will rotate downwards. The rotation takes place around the "living hinge" 477 through which the bellowed reflector 473 is connected to the intracorporeal pressure shock waves catheter 340 body. The bellows 476 act as a spring, which brings back the bellowed reflector 473 in straight position when the sutures (478 and 479) are released from the tensional (pull) position.

Radio-opaque markers 152 (not shown in FIGS. 47A, 47B and 47C) on the intracorporeal pressure shock waves catheter 340 can be used to position the catheter in the desired position relatively to the occlusion 20 or blood clot. In general, the pressure shock waves should be started away from the occlusion 20 or blood clot and gradually close in.

To further increase efficiency of the intracorporeal pressure shock waves treatment, the reflective area can be increased in embodiments of the invention by using a nitinol reflector that flowers inside the body 27 at 37° C. (body temperature), although at the introduction in the blood vessel 15 or body conduit or lumen its dimension is relatively small. Nitinol (alloy of nickel and titanium) is a temperature memory metal that was used in the last decades successfully in the construction of self-expandable stents 170. Practically, using lasers different patterns are cut on nitinol small diametric tubes (hypo tubes), which then are expended gradually to the desired functional dimension. This final achieved shape and dimension is kept only at body temperature, due to the memory of the nitinol.

Figure 48:
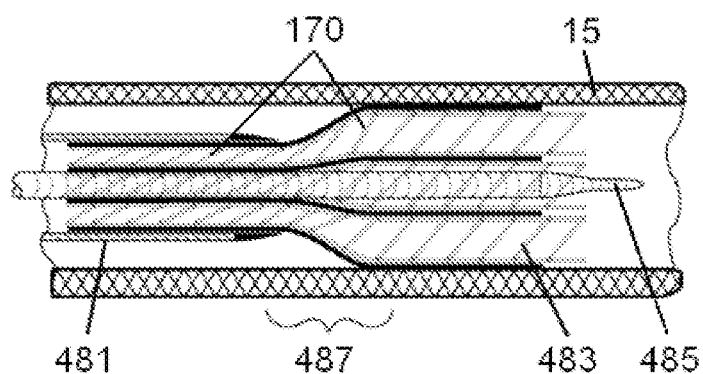
FIG. 48 is a schematic diagram of an expandable stent and intracorporeal shock wave catheter in one embodiment of the present invention.

If the tube is cooled down it will get back to the initial shape and dimension. This process is used to crimp the stents 170 on the transporting catheters (process of capture the stents 170 at their lowest diameter inside a sheath 481 and on a delivery/transporting catheter shaft called catheter inner member 485), as can be seen from FIG. 48. This figure shows a crimped nitinol stent 170 underneath the sheath 481 that is deploying inside a blood vessel 15 or a natural human/animal conduit/lumen 17. After the intracorporeal pressure shock waves catheter 340 is advanced in the treatment area, the sheath 481 that covers the stent 170 is moved backwards using a push-pull mechanisms or screw-nut mechanisms. By pulling the sheath 481 from the top of nitinol stent 170, the stent reacts to the body temperature and gets immediately from the crimped state to full temperature pre-programmed dimension and shape (deployed shape 483). The zone of transition from crimped state to the largest dimension is called "flowering region" 487.

Figure 49A:
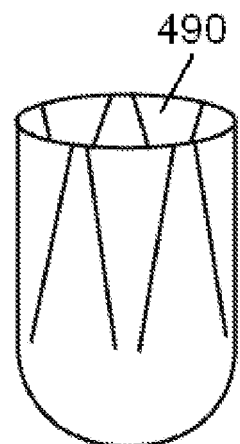
FIG. 49A is a schematic diagram of an expandable tulip reflector of an intracorporeal shock wave catheter in closed position in one embodiment of the present invention.

Based on the same principle, a nitinol reflector can be created that can be crimped on an inner member 485 of the intracorporeal pressure shock waves catheter 340 and stays in that folded position until the desired treatment area is reached. At that point, the sheath 481 is pulled back and allows the extension of additional surface for the pressure shock waves reflector, which can increase its efficiency. This reflector called "tulip reflector" 490 (as seen in FIGS. 49A and 49B) can penetrate small blood vessels 15 or grafts/artificial vessels 184 or small natural conduits/lumens 17 due to its reduced diametric dimension in the crimped state. After the usage/treatment, the "tulip reflector" 490 can be retracted in the sheath 481 to allow the safely removal of the intracorporeal pressure shock waves catheter 340 from blood vessels 15 or grafts/artificial vessels 184 or small natural conduits/lumens.

The "tulip reflector" represents an advantageous embodiment for intracorporeal pressure shock waves treatment of occlusions 20 and blood clots. The nitinol "tulip reflector" 490 design/approach can be mainly used with the electrohydraulic principle for generating pressure shock waves, although the piezoelectric principle can be also used, if the leaves of the reflector are covered with a thin piezoelectric layer (crystals or fibers).

For the electrohydraulic devices, a laser discharge is used to create the pressure shock waves. The discharge is done in blood for vascular occlusions 20 and lysis of the blood clots, which is not as efficient as the voltage discharge in water. This is why is much better to isolate a space in front the occlusion 20, evacuate the blood and replace it with saline solution. For that an occlusion balloon 154 must be present on the guide catheter 92 to create an enclosed chamber in between the balloon and occlusion 20.

For the occlusions 20 and blood clots of the natural human/animal conduits/lumens, the saline solution may be injected in the targeted area to facilitate the electrohydraulic discharge.

The "tulip reflector" 490 presented in FIGS. 49A and 49B is preferably made of nitinol and in order to better preserve dimensional integrity during pressure shock waves emission and focusing, may have a thin polymeric membrane on the outside of the reflector that can easily fold during crimping process without adding significant to diametric dimension of the delivery catheter. Similar thin polymeric membranes may also be used in the distal protection baskets 35 in embodiments. A polymeric thin membrane (on the outside of the "tulip reflector" 490) seeks to ensure the "tulip reflector" 490 will not over extend its leaves under the dynamic pressure generated by the shock waves, which translates in preserving its precise focusing ability.

Figure 49E:
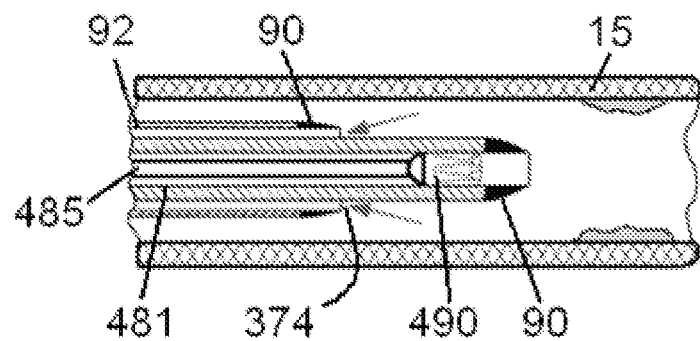
FIG. 49E is a schematic diagram of an expandable tulip reflector of an intracorporeal shock wave catheter in closed position in a blood vessel and relative to a treated occlusion one embodiment of the present invention.

FIGS. 49C, 49D and 49E show the usage of the "tulip reflector" 490 to treat occlusions 20 and blood clots inside blood vessels 15 or grafts/artificial vessels 184 or small natural conduits/lumens.

FIG. 49C shows how the positioning relative to the occlusion 20 or blood clot is accomplished using the radio-opaque tips 90 of the sheath 481 and of the guide catheter 92. The crimped "tulip reflector" 490 being a metallic alloy is preferably visible under fluoroscopy.

In FIG. 49D the deployed "tulip reflector" 490 is shown to generate focused shock waves 372 during treatment of occlusion 20 or blood clot. Sheath 481 is pulled back in order to allow the flowering of the "tulip reflector" 490 that is attached to the inner member 485. The potential debris 95 generated during treatment can be extracted via active or passive suction through the suction area 374 created in between the guide catheter 92 and the sheath 481.

The capture of the "tulip reflector" 490 inside the sheath 481 and retrieval from the blood vessel 15 or grafts/artificial vessels 184 or small natural conduits/lumens is shown in FIG. 49E. Suction is continued through the suction area 374 even after the pressure shock waves treatment was finished in order to avoid the flowing of the debris 95 (not shown in FIG. 49E) down the stream.

Eight (8) steps are used in one embodiment of the invention for advancing the tandem of guide catheter 92 and the "tulip reflector" 490 inside the sheath 481 in order to create an enclosed chamber for pressure shock waves in the treatment area, for performing the treatment of an occlusion 20 or blood clot using the "tulip reflector" 490, and finally for retrieval of the guide catheter 92 and "tulip reflector" 490 from the blood vessel 15 or graft/artificial vessel 184 or small natural conduit/lumen are presented in detail in FIGS. 50A, 50B, 50C and 50D.

Figure 50A:
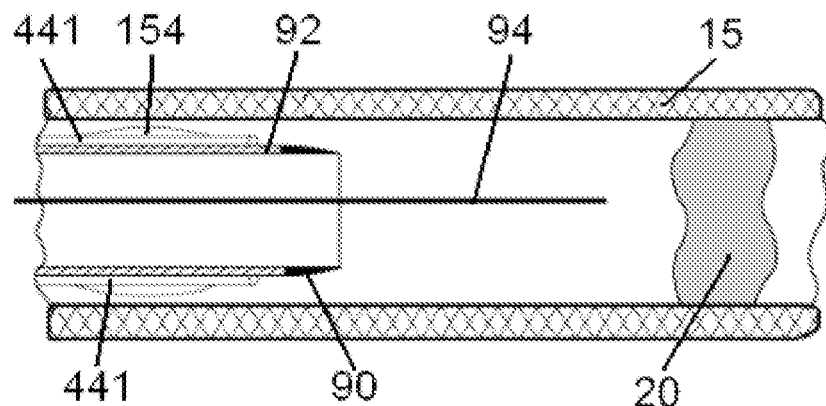
FIG. 50A is a schematic diagram of a first step of advancing a tandem of guide catheter and tulip reflector in one embodiment of the invention.

Step (1) is shown in FIG. 50A where: guide catheter 92 is inserted in the blood vessel 15 or graft/artificial vessel 184 or small natural conduit/lumen over a guide wire 94. When the desired position is reached using fluoroscopy guidance, the radio-opaque tip 90 of the guide catheter 92 should be 3-7 cm before the occlusion 20 or blood clot. In this position the occlusion balloon 154 of the guide catheter 92 is inflated (with saline solution or saline and contrast mixture) and an enclosed chamber is created.

Figure 50B:
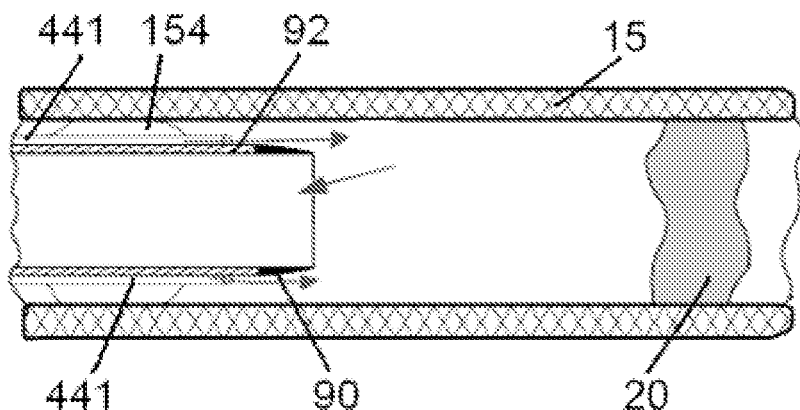
FIG. 50B is a schematic diagram of a second step of advancing a tandem of guide catheter and tulip reflector in one embodiment of the invention.

Step (2) is shown in FIG. 50B, in which the blood from the enclosed chamber crated in Step (1) is emptied via guide catheter 92 lumen and replaced with saline solution introduced via "IN" tubes 441. Guide wire 94 is retrieved in one embodiment before starting the process of replacing the blood with saline solution or mixture of saline and contrast agents.

Figure 50C:
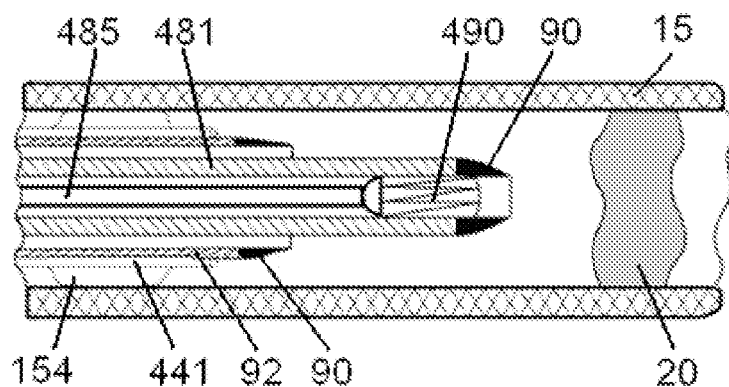
FIG. 50C is a schematic diagram of a third step of advancing a tandem of guide catheter and tulip reflector in one embodiment of the invention.

FIG. 50C shows Step (3) in which the intracorporeal pressure shock waves catheter 340 (composed out of the sheath 481, inner member 485 with the "tulip reflector" 490 at its distal end) is introduced in the treatment area in close proximity of the occlusion 20 or blood clot. The correct positioning should be distal from the guide catheter 92 and can be determined using the radio-opaque tips 90 of the sheath 481 and guide catheter 92.

Figure 50D:
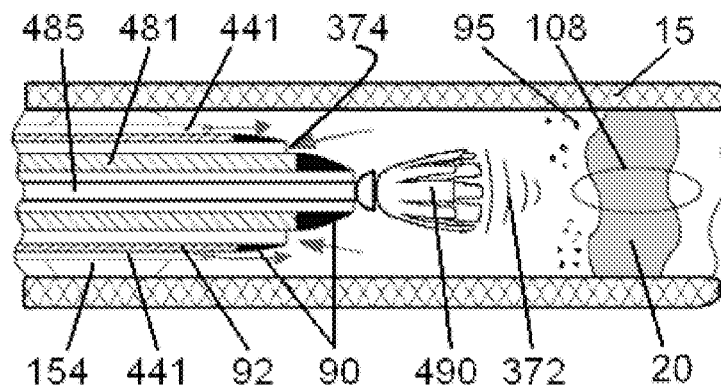
FIG. 50D is a schematic diagram of a fourth step of advancing a tandem of guide catheter and tulip reflector in one embodiment of the invention.

Step (4) is shown in FIG. 50D, in which the "tulip reflector" 490 was deployed by retrieving the sheath 481 and focused pressure shock waves 372 are generated by the "tulip reflector" 490. In order for the treatment to be efficient, the focal volume 108 should intersect the occlusion 20 or blood clot. The debris 95 generated during pressure shock waves treatment can be extracted through suction area 374 (in between the guide catheter 92 and the sheath 481), via a passive or active suction. Concomitantly, saline solution is introduced into enclosed chamber via "in" tubes 441, in order to create enough fluid to flush the debris 95.

Step (5) is similar to step (3), with the difference that the actions are made in reversed order (after elimination of the occlusion 20 or blood clot, the tulip reflector" 490 is retrieved inside the sheath 481 and the assembly is retrieved from the blood vessel 15 or graft/artificial vessel 184 or natural conduit/lumen).

In Step (6) the introduction of saline solution via "IN" tubes 441 and extraction of saline solution with debris 95 occurs through the lumen of the guide catheter 92 few minutes after the end of the pressure shock waves treatment to be sure that no debris 95 is left behind in the blood vessel 15 or graft/artificial vessel 184 or natural conduit/lumen.

In step (7) the occlusion balloon 154 is deflated and the normal blood/fluid circulation is restored.

In step (8) the guide catheter 92 is retrieved from the blood vessel 15 or graft/artificial vessel 184 or natural conduit/lumen.

The intracorporeal pressure shock waves catheter 340 (composed in this case out of the sheath 481, inner member 485 with the "tulip reflector" 490 at its distal end), used for treating occlusions 20 and blood clots, may preferably use more than 2500 shots, energy flux densities higher than 0.05 mJ/mm$^2$ and frequencies of the pulses higher than 2 Hz. The dissolution (lysis) of the blood clots and destruction of occlusions 20 can be done as an independent intracorporeal pressure shock waves treatment or in conjunctions with specialized drugs and/or extracorporeal pressure shock waves devices.

Intracorporeal pressure shock waves may also be used to treat hyperplasia, benign and malignant tumors or to produce cellular apoptosis. The intracorporeal pressure shock waves catheter 340 may also be used to treat hyperplasia (abnormal proliferation of cells that produces enlargement of organs). Hyperplasia needs to be treated because it can produce obstruction of the natural lumens (benign prostatic hyperplasia or BPH can produce obstruction of the urethra), functional deficiencies of the organs/glands (as in adrenal hyperplasia), pain, or can be an early neoplastic process that can lead to cancer.

For ablation of hyperplastic, benign or malignant tumors that can be accessed via a natural conduit/lumen of the human or animal body 27 or by using an artificial conduits (laparoscopic approach), the most treatment technologies are radio-frequency, high intensity focused ultrasound or cryotherapy (usage of low/freezing temperatures). The main drawback for these technologies is the extreme heat or freezing temperatures generated during treatment that can affect adjacent tissues/organs and blood flow 39 circulation with unwanted side effects. After such procedures the absorption of ablated tissue by the body 27 is hindered by excessive inflammation, impaired blood circulation, fluid accumulation, etc. produced by the extreme heat or freezing. Also, none of these technologies are known to trigger a body reaction to heal the treated area.

Cavitation bubbles produced by special tailored pressure shock waves collapses with microjets powerful enough to penetrate the hyperplastic, benign or malignant cells membrane and thus destroying their integrity. This represents a "normal body temperature ablation" process not employing high or low temperatures used by the existing ablation technologies and targets only the hyperplastic, benign or malignant cells without having damaging influences on the healthy adjacent tissue.

For the cancer cells, the leakage of the cytoplasm content outside triggers a localized apoptosis mechanism and an immune response, which makes the body 27 to recognize the cancer cells that were invisible before and thus enhancing tumor destruction.

Pressure shock waves can be also used for treating cancer in conjunction with microparticles or/and nanoparticles, which can be activated or pushed into the tissue via pressure shock waves in order to selectively kill cancer cells or to deliver specific drugs at high concentration and/or proteins and/or substances that can destroy cancer cells. Furthermore, the pressure shock waves can be used to enhance the sensibility of the tumor cells to certain drugs and thus enhancing their cytotoxicity.

The construction of intracorporeal pressure shock waves catheter 340 is done in such way to allow the formation, propagation and focusing of the pressure shock waves. The precise targeting of the tumor is done using fluoroscopic or ultrasound guidance. Furthermore, in order to facilitate propagation and focusing of the shock waves from the intracorporeal pressure shock waves catheter 340 to the targeted tumor, saline and/or contrast and/or drug cocktails can be injected in the treatment area via natural conduits/lumens or percutaneously (artificial conduits). Examples of construction for the intracorporeal pressure shock waves catheters 340 that can be used to ablate benign or malignant tumors and promote apoptosis are shown in FIGS. 35, 36A, 36B, 39, 40, 41, 43, 44, 45, 46, 47A, 47B, 47C, 49A, 49B, 49C, 49D and 49E.

The weeping balloons (with controlled porosity 415) shown in FIG. 41 combined with pressure shock waves can be used to treat tissue malformation that develop close or away from blood vessels 15 or natural human/animal conduits/lumens. If such malformation or unwanted tissue growth is too far away from a blood vessel 15 or a body cavity/conduit/lumen, then a percutaneously approach can be used (via a small incision in the skin 28).

Based on the above observations, using a sufficient number of pressure shock waves (higher than 3500 shots), at energy flux densities higher than 0.05 mJ/mm$^2$, with frequencies of the pulses between 1 to 8 Hz in one or multiple treatments applied to a hyperplastic/benign or malignant tumor a "normal body temperature ablation" can be realized using extracorporeal pressure shock waves. The treatment of hyperplastic/benign or malignant tumors can be done as independent intracorporeal pressure shock waves treatment or in conjunction with drugs or drug cocktails that can be injected in the targeted treatment area and/or with other extracorporeal pressure shock waves devices.

Intracorporeal pressure shock waves may be used in embodiments of the invention for "cold" liposuction and/or body sculpting. Liposuction is used to eliminate the excess fat from under the skin 28 in general in the middle section of the body 27. A typical treatment includes the use of ultrasound to liquefy the fat and extracted via a wand. One big drawback of this technology is that ultrasound produces heat, which helps with the fat melting, but also can heat up the tip of the wand, which can produce sub-dermal burning, with important cosmetic and healing drawbacks for the patient. This is why a technology that can avoid the heating and produce a "cold" melting is an improvement over liposuction or body sculpting.

Pressure shock waves produce cavitation and the microjets created by the collapse of the cavitation bubbles can break the fatty cells and the fatty tissue in invention embodiments without producing localized excess heat that was observed with ultrasound. The micro-cracks in the fatty tissue created by the microjets during collapse of the cavitation bubbles can be amplified by the compressive portion of the pressure shock waves and thus producing macro-tears of the fatty tissue, which will help to eliminate it during liposuction. These mechanisms are why the pressure shock waves technology can be used to produce a "cold" liposuction, which eliminates the unnecessary side effects, observed with the "Golden Therapy" that uses ultrasound technology.

Figure 51:
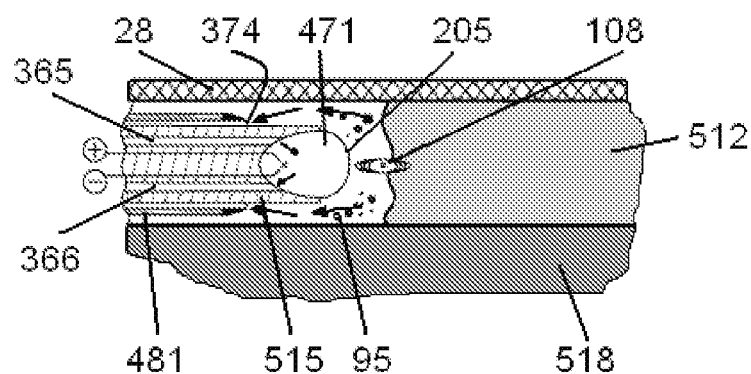
FIG. 51 is a schematic diagram of an intracorporeal shock wave device treating a fat deposit in one embodiment of the present invention.

A device that can be used for liposuction and body sculpting is presented in FIG. 51.

Figure 52A:
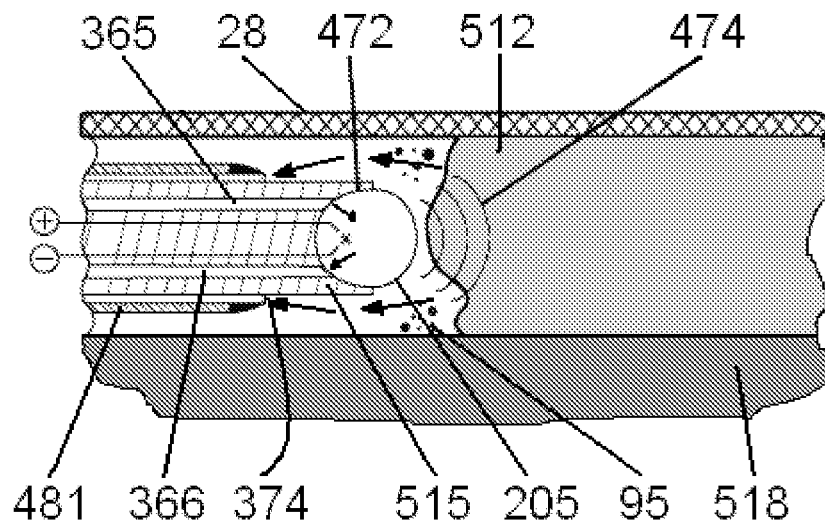
FIG. 52A is a schematic diagram of an intracorporeal shock wave device treating a fat deposit with a spherical reflector in one embodiment of the present invention.
Figure 52B:
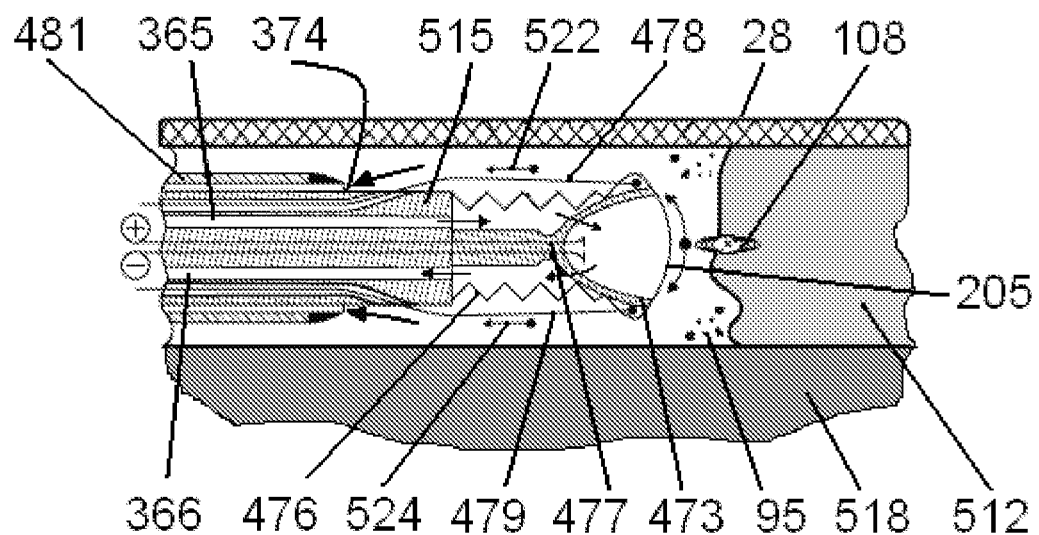
FIG. 52B a schematic diagram of an intracorporeal shock wave device treating a fat deposit with an extendible reflector in one embodiment of the present invention.

The following characteristics are considerations for an intracorporeal pressure shock waves device used to dissolve the fat cells in embodiments of the invention (as seen in FIGS. 51, 52A and 52B):

1) Frontal exposure of the pressure shock waves reflectors (ellipsoidal reflector 471 presented in FIG. 51, spherical reflector 472 presented in FIG. 52A and bellowed reflector 473 presented in FIG. 52B), which are positioned at the distal end of the treatment wand 515.
2) Cavitation is a preferable mechanism of action to break the fat cells and fat deposits 512 in general. This mechanism why the focal volume 108 (where the cavitation bubbles are formed) for the applicators (471, 472 and 473) must intersect the fatty cells clusters (fat deposits 512).
3) The dimensions of the reflector (471, 472 and 473) and its optimal orientation (perpendicular to the targeted fatty tissue) will dictate the efficiency of the intracorporeal pressure shock waves.
4) The voltage used for actuating the applicators (471, 472 and 473) is in the range of millivolts to hundreds of volts.
5) If the actuating voltage for the intracorporeal pressure shock waves reflectors (471, 472 and 473) is small enough, battery operating devices can be developed.
6) The reflectors (471, 472 and 473) can be created from metal or hard plastics or ceramics/glass and it sits at the distal end of the treatment wand 515.
7) The method to produce pressure shock waves can be electrohydraulic, electromagnetic, piezoelectric, laser discharge, micro-explosion/discharge or mechanical vibrations, with the pressure shock waves carried towards the target via an aqueous environment.
8) The shape of the reflectors (471, 472 and 473) can be elliptical, paraboloid, sphere or planar, or combinations of them.
9) The construction of the wand 515 (metal wall) and the associated plastic sheath 481 (made of plastic) preferably allows electrical insulation of the patient and in the same time a reduction in abrasion of the sub-dermal tissue.
10) The suction of fatty cells that were dissolved or broken from the fatty clusters can be done via wand 515 or in between the wand 515 and the sheath 481, which is defined as suction area 374).
11) To increase efficiency a pivotal movement of the applicator 473 (as seen in FIG. 52B) will allow the orientation of the cavitation on a larger area.
12) The electrohydraulic discharge, laser discharge or micro-explosion/discharge should be made in degassed water or saline solution or mixtures of saline solution with contrast, enclosed in a special designed membrane 205 that allows the formation of the cavitation cluster outside it.
13) To enhance the pressure shock waves transmission and the possibility of the onset of in vivo cavitation, saline should be injected in the front of the wand 515 to create a fluid layer in between the applicators (471, 472 and 473) and the targeted fatty cells.

When an ellipsoid is used the ratio of semi axes should be larger than 2.0 (c/b≥2). In this way the focusing and formation of the cavitation will be done at a sufficient distance in front of the applicators (471, 472 and 473), with the whole focal volume 108 formed outside the applicators (471, 472 and 473) and exclusively on the fatty cells. A higher ratio of semi axes will also allow having a deeper reflector (471, 472 and 473) incorporated into the tip of the treatment wand 515, which translates into a larger reflecting area and thus a higher efficiency. There is a direct correlation between the surface of the applicators (471, 472 and 473) and the amount of energy deposited in the focal volume 108. A larger reflecting area translates in higher efficiency for the pressure shock waves.

When a sphere is used as a reflector (FIG. 52A) radial waves 474 are created. Cavitation still may be created with radial waves 474, although the penetration of the compressive waves is reduced, which will reduce eventual macrotear in the fat deposit 512 after the onset of micro-cracks due to the cavitation microjets. The energy of the radial pressure waves 474 is the highest in the center of the sphere and it dissipates very fast during propagation away from the point of origin (center of the sphere).

When a significant amount of fat deposit 512 needs to be eliminated (for a successful liposuction and/or body sculpting) special designed suction catheters 93 or wands 515 or suction areas 374 (in between the interior surface of the sheath 481 and external surface of the treatment wand 515) can be used via an active suction. The active suction is generated by using dedicated pumps that continuously inject saline solution in front of the wand 515 and in the same time extract the mixture of debris 95 generated during treatment (mixture of saline, fatty cells and blood). To facilitate an easy generation and propagation of the pressure shock wave s, the reflectors have a thin membrane 205 on top of them that creates an enclosed space filled with degassed water. The water can be filed at the manufacturer (pre-filled catheter) or can be done at the point of care. As can be seen from FIGS. 51, 52A and 52 there are two distinctive channels (inlet lumen 365 and outlet lumen 366) to fill in the reflectors (471, 472 and 473). This construction also allows the clearing of air from the reflectors (471, 472 and 473). If air is not cleared, the efficiency of the pressure shock waves can be significantly reduced.

FIG. 52B presents a pressure shock waves reflector (bellowed reflector 473) which is movable in an angular fashion. The movement of the bellowed reflector 473 is realized by pulling at the proximal end of the wand 515 the two sutures (478 and 479) that run through the wand 515 body and are connected to the lateral ears of the reflector. If suture 478 is pulled (movement 522) then the bellowed reflector 473 will rotate upwards. If suture 479 is pulled (movement 524) then the bellowed reflector 473 will rotate downwards. The rotation takes place around the "living hinge" 477 through which the bellowed reflector 473 is connected to the wand 515 body.

The bellows 476 act as a spring, which brings back the bellowed reflector 473 in straight position when the sutures are released from the tensional (pull) position.

The cavity of the reflectors (471, 472 and 473) is filled with degassed water, medical saline solution or any mixture of fluids with additives to enhance pressure shock waves formation and durability of the applicators (471, 472 and 473) and wand 515.

Figure 53:
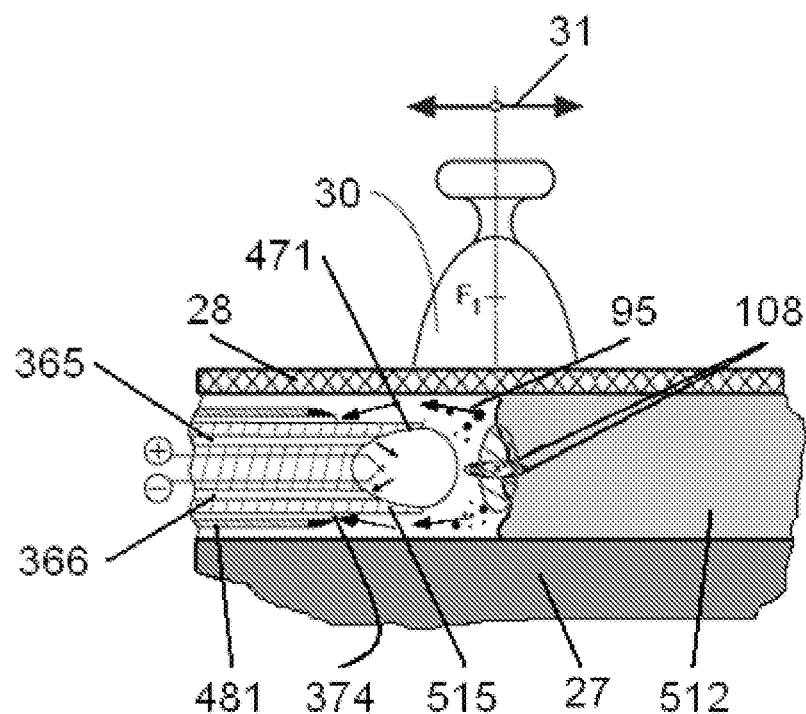
FIG. 53 is a schematic diagram of an intracorporeal shock wave device and extracorporeal shock wave device treatment system in one embodiment of the present invention.

When liposuction is accomplished with pressure shock waves devices, both intracorporeal and extracorporeal devices can be used as seen in FIG. 53. The two devices can be used concomitantly or sequential and they can be con-focal (as seen in FIG. 53, where the focal volumes 108 intersect) or non-con-focal. The use of both devices can speed up the process of dissolving the fat deposits 512 and thus is increasing the treatment efficiency.

The pressure shock waves applicators (30 and 471) can be controlled by different consoles or by one single console. The single console approach is preferable for high degree of coordination of focal volumes 108 spatial placement (via longitudinal movement 31) for the external applicator 30 (in contact with skin 28) and the treatment wand 515 (introduced under the skin 28 via small incisions). The sequence of firing the pressure shock waves into the treatment area between the external applicator 30 and internal applicator 471 can be coordinated to achieve maximum efficiency.

The settings for the intracorporeal pressure shock waves wand 515 used for liposuction should be for the dosage more than 5000 shots, at energy flux densities higher than 0.15 $mJ/mm^2$ and frequencies of the pulses higher than 2 Hz.

The extraction of the mixture of debris 95 generated during treatment (mixture of saline, fatty cells and blood) is done via suction area 374 created for the intracorporeal system in between the sheath 481 and wand 515.

Embodiments of the invention also produce intracorporeal pressure shock waves that are non-focused. If no reflector is used radial and planar non-focused waves can be created. By eliminating the reflector more room is created for the catheter inner construction, which can lead to the increase in the energy delivered per one shock and also it makes the catheter construction less complicated.

Figure 54A:
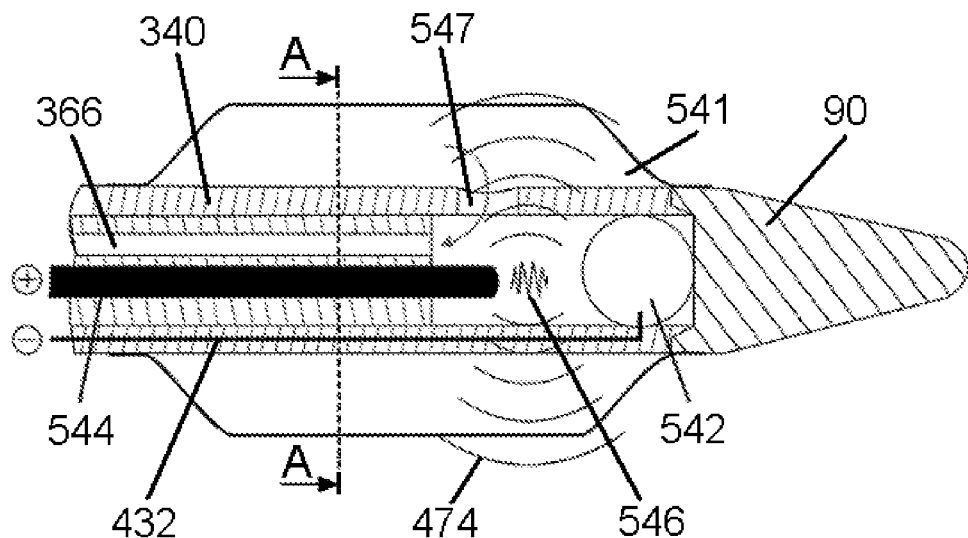
FIG. 54A is a schematic diagram of an intracorporeal shock wave catheter having radially generated shock waves in one embodiment of the present invention.
Figure 54B:
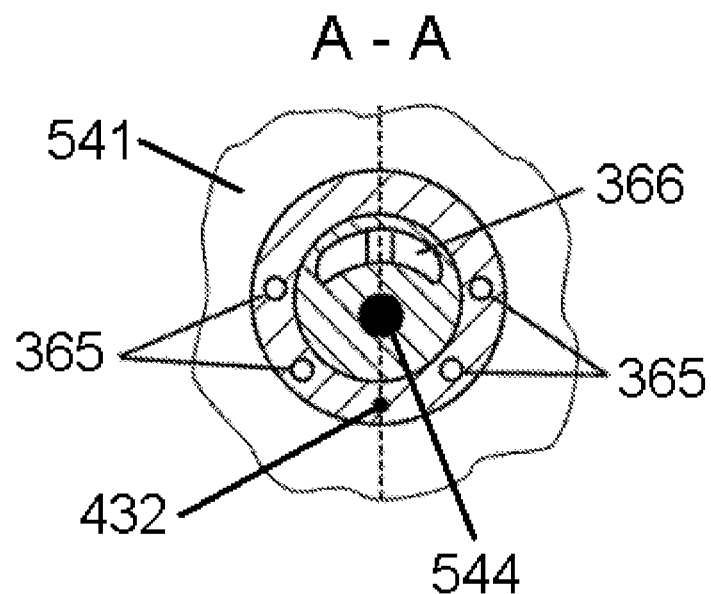
FIG. 54B a schematic diagram with a front cross-sectional view along AA of FIG. 54A of an intracorporeal shock wave catheter having non-focused, radially generated shock waves in one embodiment of the present invention.

As shown in FIGS. 54A and 54B, radial shockwaves can be generated by the discharge in between the two electrodes in a balloon enclosure 541 filled with degassed water or saline solution or saline solution/contrast mixture, positioned at the distal end of the intracorporeal pressure shock waves catheter 340. The IN lumen 365 and OUT lumen 366 are used to fill in the space with degassed water or saline solution or saline solution/contrast mixture, at required pressure and volume. OUT hole 547 provides a conduit to OUT lumen 366.

As shown in FIG. 54A, the uniformity of the discharge is accomplished by making one of the electrodes in the form of a sphere 542 (connected via electrical wire 432 to voltage source) and the other one as a wire electrode 544, which facilitates an easy voltage discharge 546 anytime the device is fired. The waves generated in such embodiment are radial 474 and non-focused.

Figure 55A:
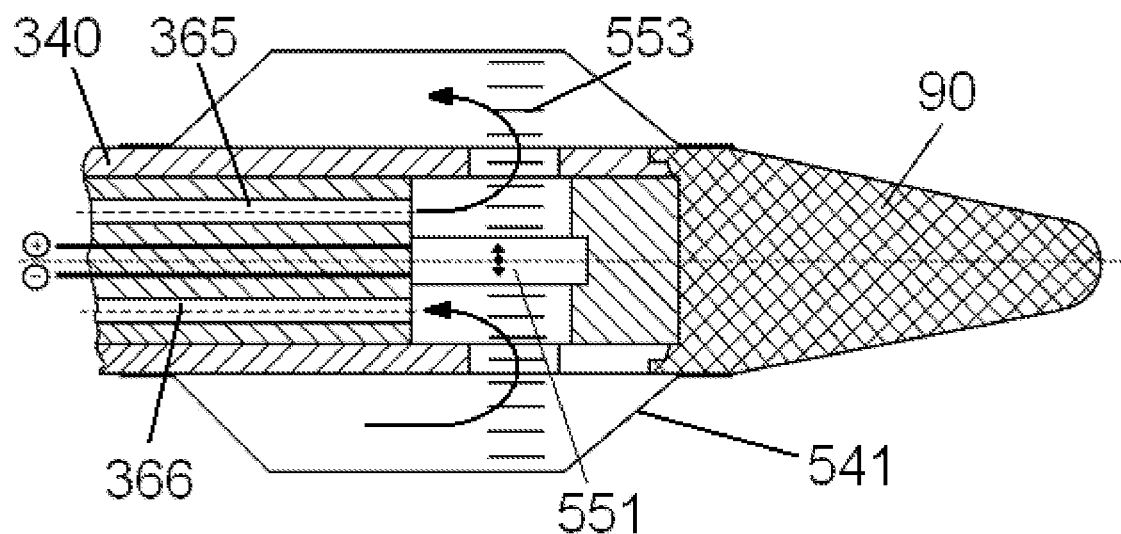
FIG. 55A is a schematic diagram of an intracorporeal shock wave catheter having planar generated shock waves in one embodiment of the present invention.

If a piezo crystals or piezo fiber or piezo films 551 are used to generate the intracorporeal pressure shock waves inside a balloon enclosure 541 filled with degassed water or saline solution or saline solution/contrast mixture, a planar wave 553 can be generated, as seen in FIG. 55A.

Figure 55B:
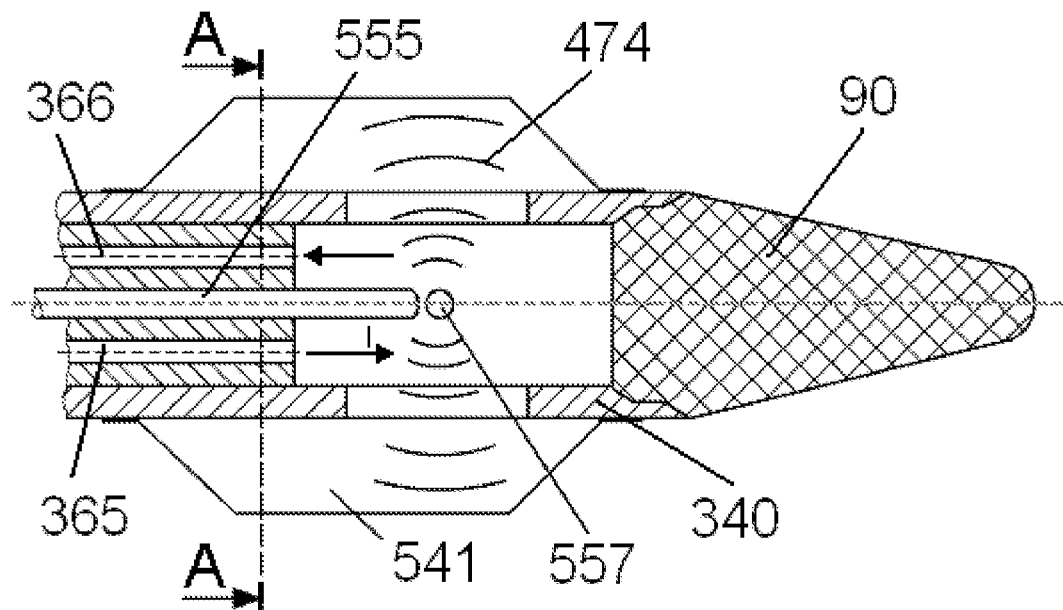
FIG. 55B is a schematic diagram of an intracorporeal shock wave catheter having radially generated shock waves in one embodiment of the present invention.

When a laser discharge 557 in degassed water or saline solution is used inside a balloon enclosure 541, the laser will create a plasma bubble that during its growth and collapse will be able to generate a radial wave 474, as can be seen also in FIG. 55B. Laser fiber 555 for laser discharge 557 runs within catheter 340.

Figure 55C:
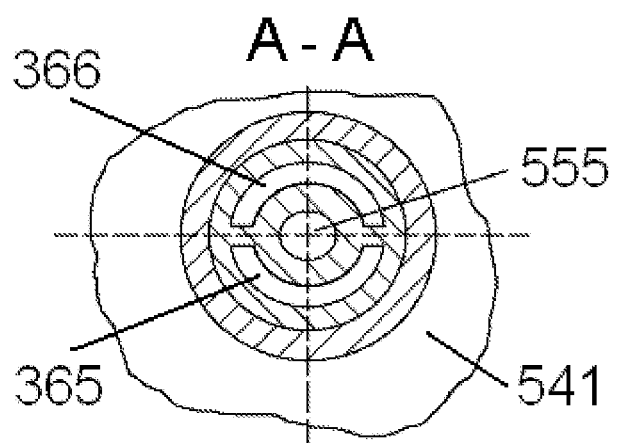
FIG. 55C is a schematic diagram of a cross-section front view along AA of FIG. 55B of n intracorporeal shock wave catheter having radially generated shock waves in one embodiment of the present invention.

The embodiment of FIG. 55C depicts intracorporeal pressure shock waves catheters 340 shown in FIGS. 55A and 55B, that have dedicated distinctive channels (inlet lumen 365 and outlet lumen 366, with different shapes when compared to the ones in FIG. 54B) that can be used to fill in the balloon enclosure 541 and to allow the clearing of air from the intracorporeal pressure shock waves catheters 340. If air is not cleared from the reflector, the efficiency of the pressure shock waves can be greatly reduced.

For intracorporeal pressure shock waves catheters 340 shown in FIGS. 54A, 54B, 55A, 55B and 55C, the waves will, in embodiments, travel without reflections if the materials used in the construction of the intracorporeal pressure shock waves catheters 340 have an acoustic impedance that matches/or is close enough to the water acoustic impedance value. As mentioned previously, the waves are generated inside balloon enclosure 541 inflated with degassed water or saline solution or saline solution/contrast mixture. The balloon enclosure 541 can be filled at the manufacturer (pre-filled catheter) or can be done at the "point of care". When the balloon enclosure 541 is pre-filled at the manufacturer, additional substances may be added into the water/saline to improve efficiency of the pressure shock waves generation and propagation or for improved visualization of the intracorporeal pressure shock waves catheters 340 inside the human body 27 by using any contrast agents. Also, for easy visualization of the intracorporeal pressure shock waves catheter 340 inside the body 27, the tip 90 will be made of radio-opaque materials and the position of the point of origin of the pressure shock waves can be identified via specific radio-opaque markers 152 (bands, dots or combination of them). The radio-opaque markers 152, radio-opaque tips 90 combined with balloon enclosures 541 filled with mixtures of saline solution and contrast agents will allow the precise positioning of the intracorporeal pressure shock waves catheter 340 relatively to the treatment targeted area 145, under ultrasound or fluoroscopic guidance.

There are different methods to improve the efficiency and productivity of the pressure shock waves treatments and the majority focus on treating a larger area and by increasing the amount of energy deposited into the tissue in one position of the pressure shock waves applicators 30.

Increasing the treated area in one position of the applicator 30 can be accomplished by extending the focal volume 108 dimension or by intersecting the treatment targeted area 145 with focal volume 108 longitudinally instead of transversally.

The amount of energy delivered to the focal volume 108 can be increased by extending the reflective area of the reflector 22, by moving the point of origin/discharge of the pressure shock waves from $F_1$ on the direction of $F_1F_2$ and thus creating a pseudo focal volume as an extension of the normal focal volume 108, or by overlapping multiple focal volumes 108. Exemplary solutions are subsequently presented.

The theory of the pressure shock waves for medical treatment was developed for lithotripsy. Based on this theory, the ellipse has a unique property of having two focal points ($F_1$ and $F_2$), which can be interconnected in energy generation and receiving.

Figure 56:
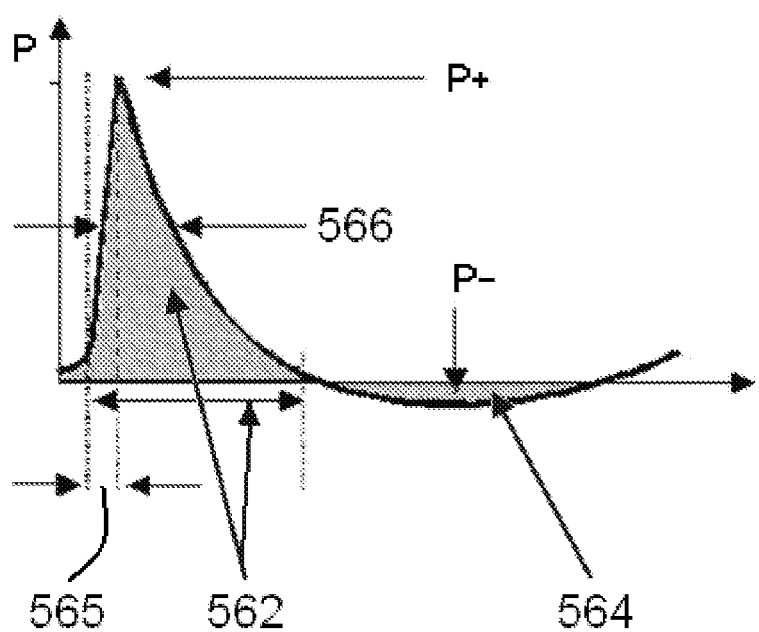
FIG. 56 is a graph of pressure phases of a shock wave in an embodiment of the present invention.

Thus, if a 3D geometry is created (an ellipsoid) the kinetic energy (in the form of pressure shock waves) generated in the first focal point $F_1$ will be reflected with minimal loss in the second focal point $F_2$ when the whole ellipsoid surface is used. During focusing process of the pressure shock waves from $F_1$ to $F_2$, a focal volume 108 is created around $F_2$, with a cigar shape where high compressive pressures are generated (compressive phase 562 that produces macro effects) together with a tensile phase 564 that produces cavitation (action at micro level), as seen in FIG. 56. The compressive phase start with a sharp rise in pressure characterized by the rise time 565 and the pulse width 566 (for −6 dB) determines the amount of energy deposited in the focal volume 108.

The voltages used for discharge in $F_1$ for electrohydraulic devices are 12-30 kV. This discharge produces a plasma bubble in $F_1$ that can rapidly move the liquid around it to create pressure shock waves that are then focused on the full ellipsoidal reflector 471 to generate a spherical focal volume 108, as presented in FIG. 57A. Other ways to produce pressure shock waves are electromagnetic, piezoelectric, explosive or projectile means.

Figure 57A:
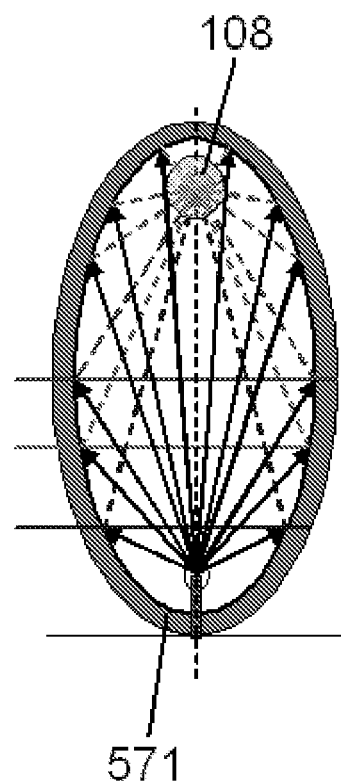
FIG. 57A is a schematic diagram of a full ellipsoidal reflector generating a spherical focal volume in one embodiment of the present invention.

For the focused pressure waves, practically the full solid ellipsoid 571 (whole ellipsoid) cannot be use to do a treatment with pressure shock waves in $F_2$, based on the fact that the treatment area needs to be positioned in $F_2$ (see FIG. 57A). This is why in practice only half of the ellipsoid is used to generate and focus the pressure shock waves, towards $F_2$, as presented in FIG. 57B.

The amount of energy delivered to a target area is directly proportional to the surface area of the reflector. As presented in FIGS. 57A, 57B, 57C and 57D, in medical pressure shock waves applications the reflectors represent only percentages of a full ellipsoid. The more area is used for focusing, the larger the focal volume 108 will be and thus energy deposited inside the treatment area.

Usually the most commons reflectors represent 50% of a full ellipsoid, which means that the available area for reflecting the pressure shock waves is only 50%. That means that the pressure shock waves are reflected on only half of the surface and thus in theory only half of the energy is found in the focal volume 108, when compared to a full ellipsoid 571. Of course the efficiency is reduced below 50% due to other losses on the pathway of the pressure shock waves towards $F_2$. Even with this reduced efficiency the treatments using extracorporeal pressure shock waves were proven to be very efficacious for breaking kidney stones, or to treat bones and soft tissue afflictions.

Figure 57B:
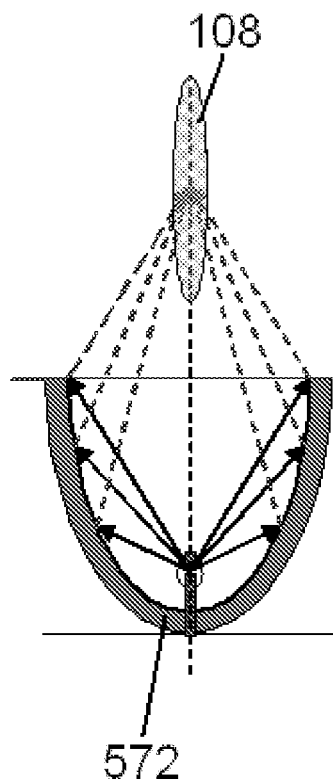
FIG. 57B is a schematic diagram of a 50% ellipsoidal reflector generating a focal volume in one embodiment of the present invention.
Figure 57C:
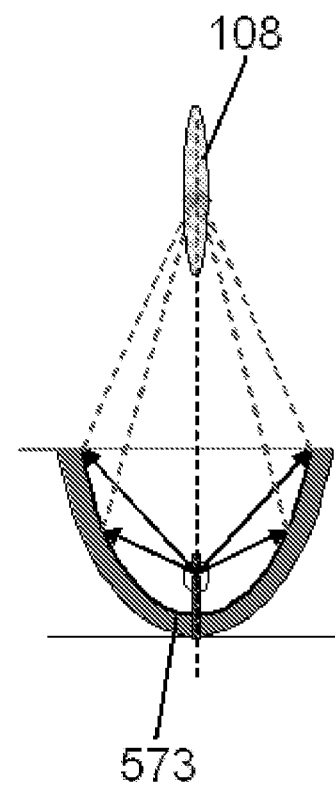
FIG. 57C is a schematic diagram of a 35% ellipsoidal reflector generating a focal volume in one embodiment of the present invention.
Figure 57D:
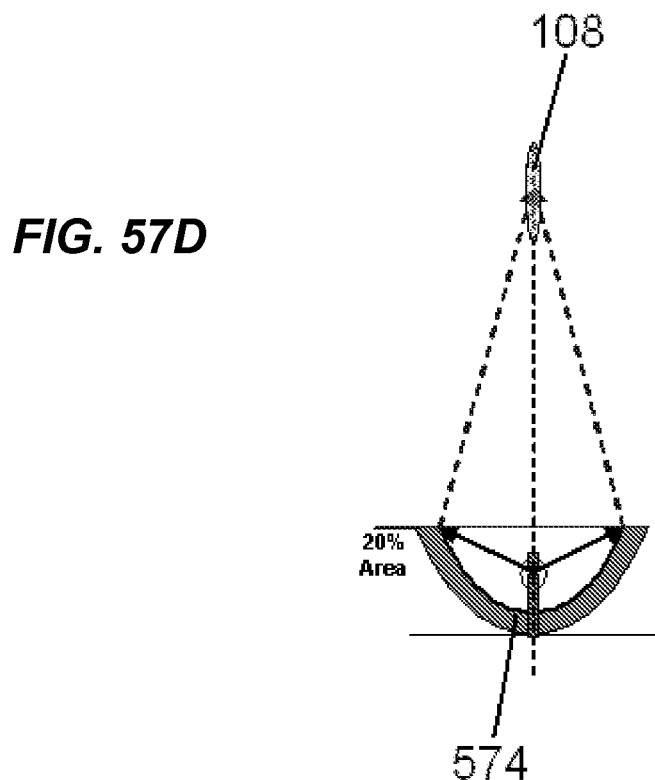
FIG. 57D is a schematic diagram of a 20% ellipsoidal reflector generating a focal volume in one embodiment of the present invention.

As can be seen from FIG. 57B, when 50% of the ellipsoid area reflector 572 is used the focal volume 108 is larger in size when compared to the focal volume 108 of the 35% of the ellipsoid area reflector 573 from FIG. 57C. Even more when 50% of the ellipsoid area reflector 574 is used the reduction in the focal volume 108 is even more significant, as seen from FIG. 57D. This shows that the smaller the available reflective area for the pressure shock waves translates besides smaller quantities of energy in the treatment area as well as in smaller focal volumes 108, which finally means less efficiency for the treatment.

Figure 58A:
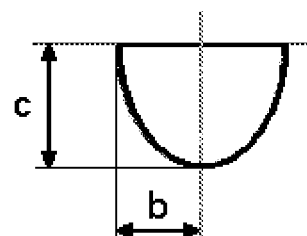
FIG. 58A is a schematic illustration of a reflector having a large semi-axis (c) and small semi-axis (b) with a c/b ratio between 1.1 and 1.6 in one embodiment of the present invention.
Figure 58B:
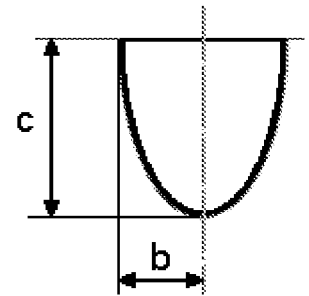
FIG. 58B is a schematic illustration of a reflector having a large semi-axis (c) and small semi-axis (b) with a c/b ratio between 1.6 and 2.0 in one embodiment of the present invention.

The pressure shock waves devices will generate a wide range of energies in the focal volume 108 depending on reflector geometry, which is characterized by the ratio of "c" the large semi-axis of the reflector and "b" the small semi-axis of the reflector (c/b), as can be seen from FIGS. 58A, 58B and 58C.

The c/b~1.1 geometry (FIG. 58A) in one embodiment has a shallow reflector that has $F_2$ very close to its edge and has less reflective area at its disposal. This geometry can be used to treat targets close to the surface of the body 27 (underneath the skin 28) and with medium to low energies.

The c/b~1.6 geometry (FIG. 58B) may be used to treat targets deeper underneath the skin 28 and has more reflective area at its disposal. The travel distance for the pressure shock waves is longer, which might increase losses. The energies generated are medium to high.

The c/b~2 geometry (FIG. 58C) allows the treatment of deep structures from inside the human body 27 and has the largest reflective area at its disposal, which translates in increased amounts of energy (high energy) deposited inside the tissue.

The c/b ratio or reflector area, voltage discharge in $F_2$, materials from which the reflector is made and frequency of the shots (voltage discharge) per second represent important parameters for generation of pressure shock waves. All these parameters have a great influence on the dimensions of the focal volume 108 and the total energy deposited inside the focal volume 108.

FIG. 59 shows that at the same depth of the reflector, one with a larger aperture area 592 (larger diameter) will produce higher pressures in the focal volume 108, a larger focal volume 108 and a greater quantity of energy deposited in the treatment area. A reflector with smaller area 591 when compared with the reflector with larger area 592, generates at "c/2" distance from the aperture a pressure gradient/distribution 593 that is reduced when compared with the pressure gradient distribution 594 generated by the reflector with larger area 592. The same phenomenon is recorded at the distance "c" from the aperture, where the pressure distribution 595 for the reflector with smaller area 591 is reduced when compared with the pressure gradient distribution 596 generated by the reflector with larger area 592. This trend is also found inside the focal volume 109 where the pressure distribution 597 for the reflector with smaller area 591 is reduced when compared with the pressure gradient distribution 598 generated by the reflector with larger area 592.

FIGS. 57A, 57B, 57C, 58A, 58B, 57C and 59 illustrate that the shallower reflectors deposit less energy and at a smaller depth into the tissue compared with the deeper reflectors that deposit more energy and at a deeper depth into the tissue, regardless of larger losses on the pathway to the treatment targeted area.

Figure 60:
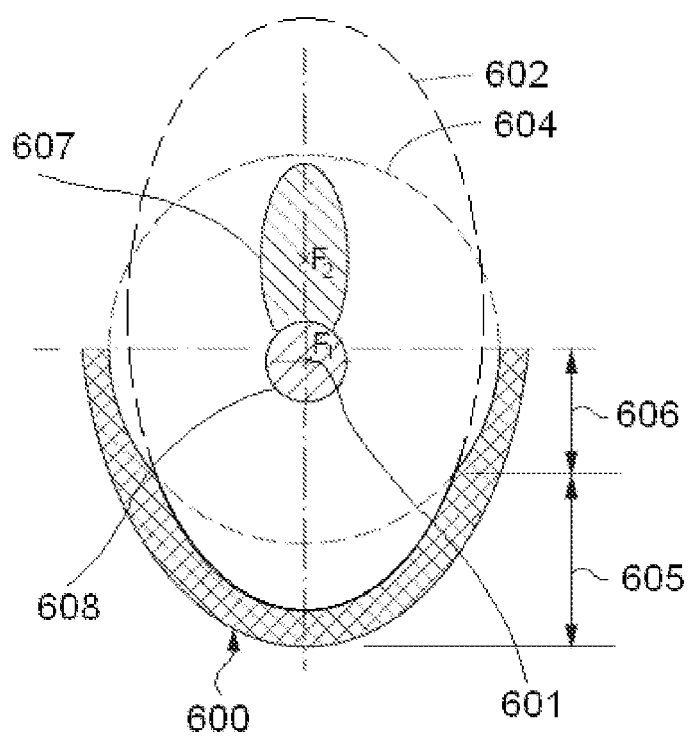
FIG. 60 is a schematic diagram of a reflector with a combination of geometries in one embodiment of the present invention.

Besides the dimension of the reflective area, another way to increase efficiency of the pressure shock waves devices is to increase their focal volumes 108 by combining different geometries for the reflectors. Combinations of elliptical, paraboloid or sphere geometries can be used in one reflector with combined geometries 600 having the spark gap discharge 601 produced in $F_1$ (center of the sphere 604) for an electrohydraulic system. In other embodiments a piezoelectric reflector can be constructed with piezo films, piezo fibers, or piezo crystals arranged in the form of an ellipsoid 602, sphere 604, paraboloid or a combination of them, as shown in FIG. 60.

A reflector with combined geometries 600, including ellipsoidal reflector segment 605 and spherical reflector segment 606 can increase the focal volume length by combination of the focal volume of the ellipsoid segment 607 and focal volume of the sphere segment 608, which can cover more superficial or deep tissue during treatment. This combination can increase the treatment efficiency for cosmetic applications or for lymph-edema treatment for example.

Similar geometries can be also used with devices that produce pressure shock waves using electrohydraulic, electromagnetic, laser discharge, explosive, mechanical means.

To create improved reflectors a combination of ellipsoids 602, spheres 603 and paraboloids can be used including: two geometries in one reflector (FIG. 60), or three or more geometries in one reflector.

In one embodiment, a preferred geometry for the ellipsoids used in reflectors with combined geometries 600 is given by ellipsoids generated from ellipses with a semi axis ratio (c/b) between 1.1 and 1.5.

Such geometrical combinations can generate different types of pressure shock waves, including focused or unfocused, multiple and larger focal volumes (607 and 608) and the like.

Figure 61A:
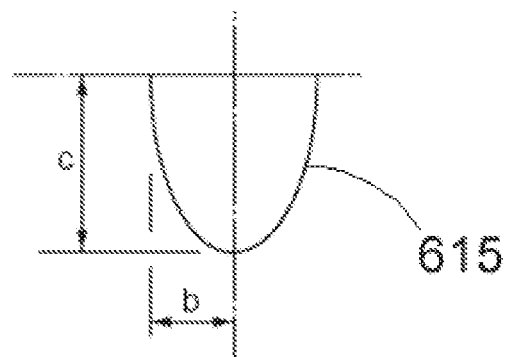
FIG. 61A is a schematic diagram of a conventional reflector geometry with a long axis of symmetry in one embodiment of the present invention.
Figure 61B:
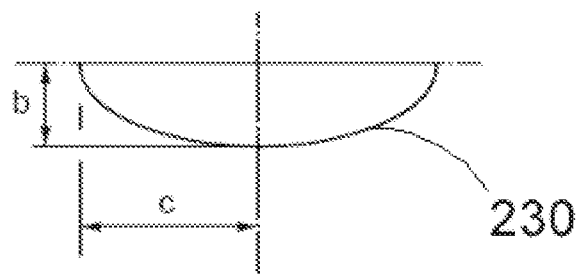
FIG. 61B is a schematic diagram of a reversed reflector geometry with a short axis of symmetry in one embodiment of the present invention.

Due to combination of elliptical, parabolic or spherical geometries in one reflector, focal volume distribution is for the "reversed reflector" 230 shown in FIG. 23A and FIG. 23B presents various embodiments of the invention. In one embodiment, the reversed reflector 230 has a geometry symmetrical around the small, axis of symmetry (FIG. 61B), which is different from the classical reflector geometry 615 that uses the long axis as axis of symmetry, as shown in FIG. 61A.

Figure 62A:
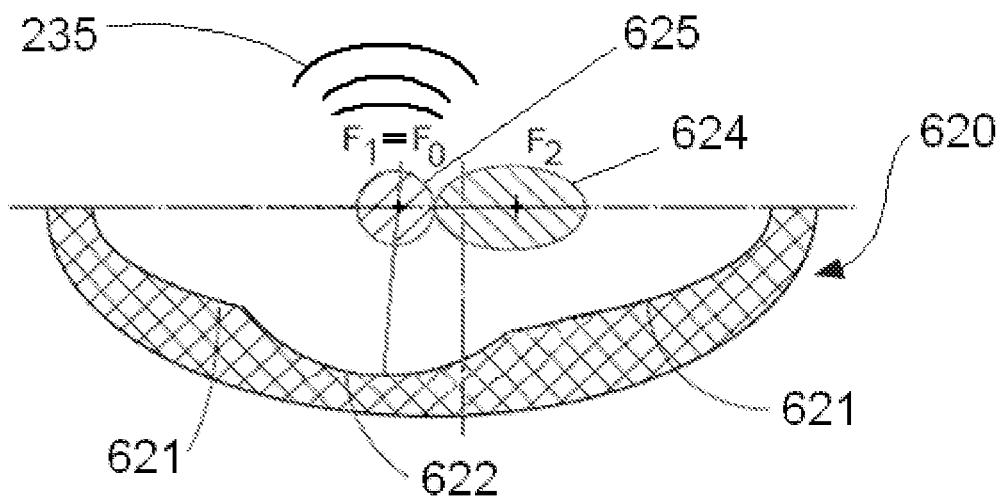
FIGS. 62A and 62B are schematic diagrams of a reversed reflector with a combination of geometries in embodiments of the present invention.
Figure 62B:
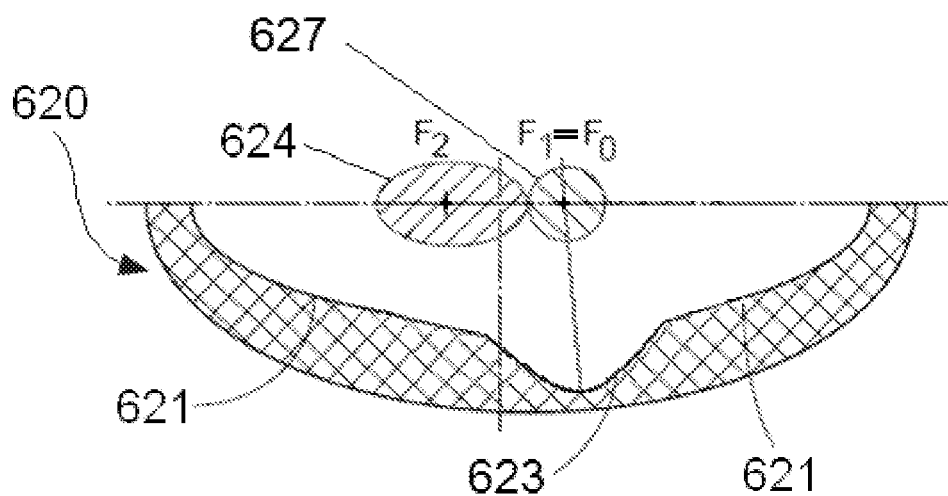

For the combination reflector of FIG. 60, a reversed reflector with combined geometries 620 will be similar to the reflector shown in FIGS. 62A and 62B. The increased length of the focal volume, which in depicted embodiments is a combination of the focal volume 624 of the ellipsoid segment 621 and focal volume 625 of the sphere segment 622 creates a great advantage when the treatment is superficial.

Also, in embodiments reversed reflector 620 generates in $F_1$ a radial wave 235 (produced by the spherical reflector segment 622) and in $F_2$ a focused wave, which means that this kind of reflector has "dual pressure shock waves" (radial and focused). This duality can be beneficial for different phases of the treatment due to the fact that radial pressure shock waves 235 have lower pressures and tissue penetration when compared to the focused waves that have higher pressures and tissue penetration.

Figure 63:
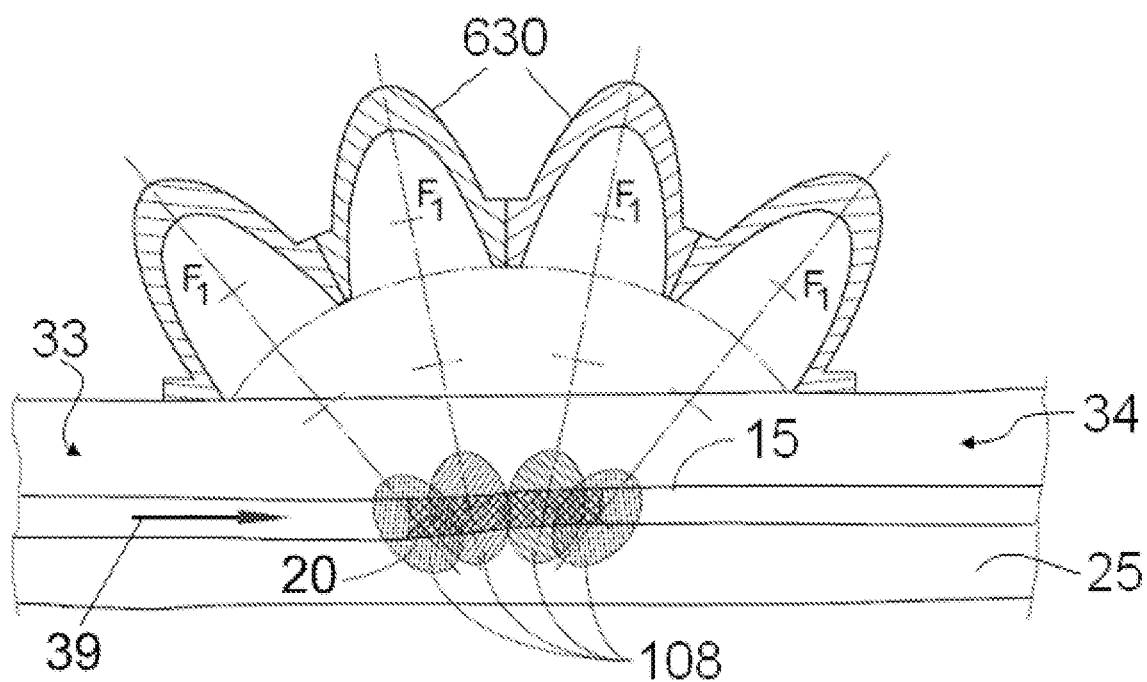
FIG. 63 is a schematic diagram of a multiple combined reflectors in one embodiment of the present invention.

Multiple (combined) reflectors 630 can be used to increase efficiency by increasing focal volume 108, spatial distribution and overlap of the focal volumes 108 in one position during the treatment, shown in FIG. 63.

The discharge in $F_1$ can be done simultaneously or sequentially for the four (4) reflectors in the depicted embodiment, which can be a setting in the software of the control console. The four (4) reflectors share a common contact membrane 205 (not shown in FIG. 63) that gets in contact with body appendage 25 or body 27 generally. The membrane 205 can be also used to adjust tissue penetration in the order of millimeters by inflating and deflating it.

Figure 64A:
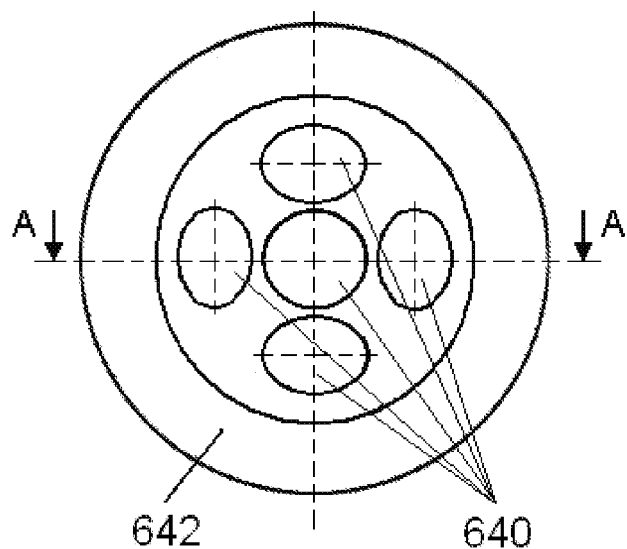
FIG. 64A is a schematic diagram of a shock wave applicator including multiple reflectors in two perpendicular directions in one embodiment of the present invention.
Figure 64B:
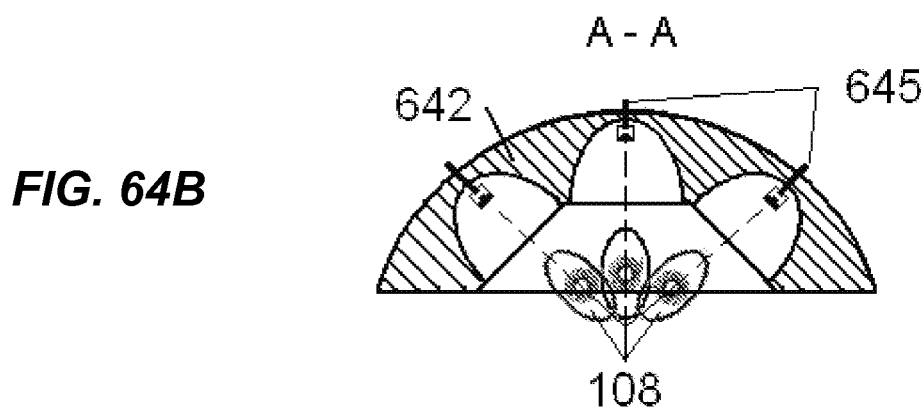
FIG. 64B is a schematic diagram of a cross-sectional side view along AA of FIG. 64A of a shock wave applicator including multiple reflectors in two perpendicular directions in one embodiment of the present invention.

Another embodiment shown in FIGS. 64A and 64B includes an applicator with multiple reflectors 640 on two perpendicular directions producing overlap of the focal volumes 108 on two perpendicular directions/dimensions in the treatment area, which yields a three-dimensional spread of the focal volumes 108. Due to the spatial orientation of the reflectors arranged on a spherical calotte dish 642, this embodiment creates a distribution of the focal volumes 108 on two different and perpendicular directions, which is different from the embodiment presented in FIG. 63 where the focal volumes 108 align only in one direction. Each reflector has its independent electrodes 645 to produce electrohydraulic generated pressure shock waves.

Figure 65A:
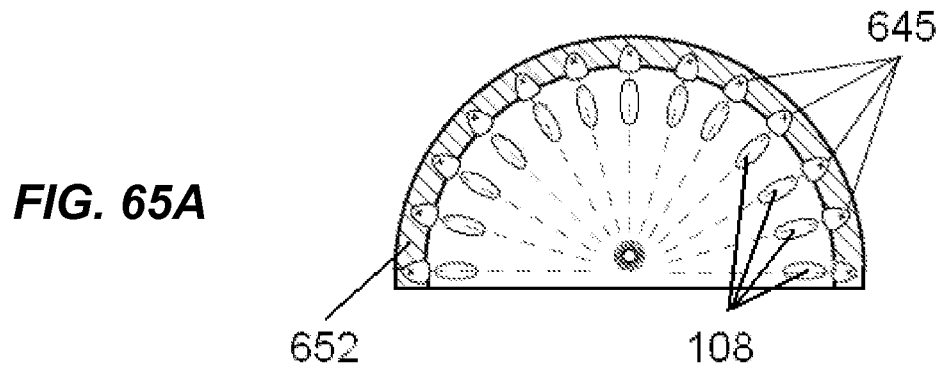
FIG. 65A is a schematic diagram of a cross-sectional side view of a half sphere dish having multiple reflectors and discharge points in one embodiment of the present invention.
Figure 65B:
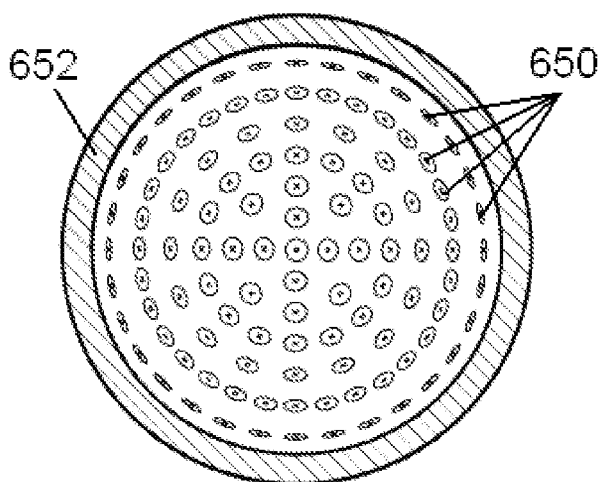
FIG. 65B is a schematic diagram of a bottom plan view of a half sphere dish having multiple reflectors and discharge points in one embodiment of the present invention.
Figure 65C:
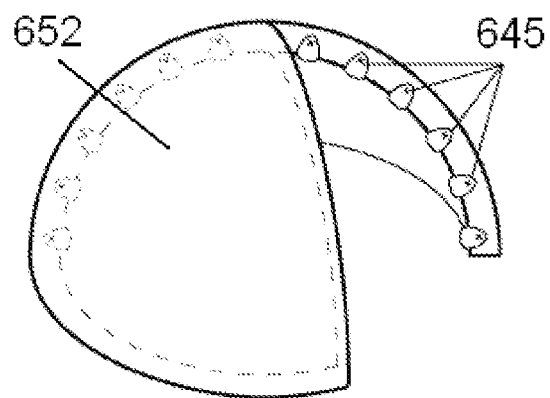
FIG. 65C is a schematic diagram of a partial perspective view from above of a half sphere dish having multiple reflectors and discharge points in one embodiment of the present invention.

For a curved three-dimensional treatment area another embodiment can be used, wherein numerous reflectors 650 (with distinctive electrodes 645 for spark discharge) are arranged on a half sphere dish 652 that creates a spatial distribution of the focal volumes 108, as shown in FIGS. 65A, 65B and 65C. Depending on the dish geometry (hemisphere, or a spherical calotte, or a semi-ellipsoid, or a paraboloid, or a cylinder) the spatial distribution of the focal volumes 108 can be modified accordingly, depending on treatment scope. The flexibility of these embodiments can be used to produce multi focal devices in the form of bandages, boots, straps, braces, helmets, belts, etc., for increased efficiency of the pressure shock waves treatments. Finally, the materials used in the construction of such devices should be biocompatible and/or sterilizable depending on the specific application.

Embodiments of the invention shown in FIGS. 65A, 65B and 65C use a hemisphere dish 652. Depending on the total energy that needs to be delivered during one treatment and the depth inside the tissue where the focal volumes 108 should be positioned during treatment for the applicators presented in FIGS. 60, 62, 63, 64A, 64B, 65A, 65B and 65C at the same diametric dimension of the reflector opening, the geometry of the reflector can be shallower (to deliver smaller energies into treatment area and provide less tissue penetration) or deeper (for larger energies deposited into treatment area and more tissue penetration), as presented in FIGS. 57A, 57B, 57C, 57D, 58A, 58B, 58C and 59.

Figure 66A:
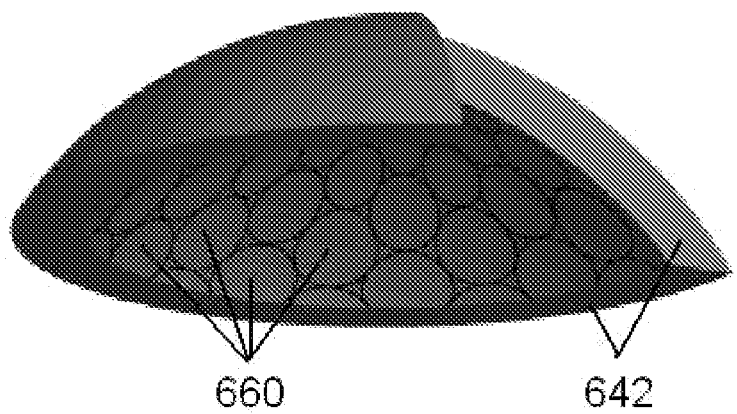
FIG. 66A is a schematic diagram of multiple reflectors arranged on a dish in one embodiment of the present invention.
Figure 66B:
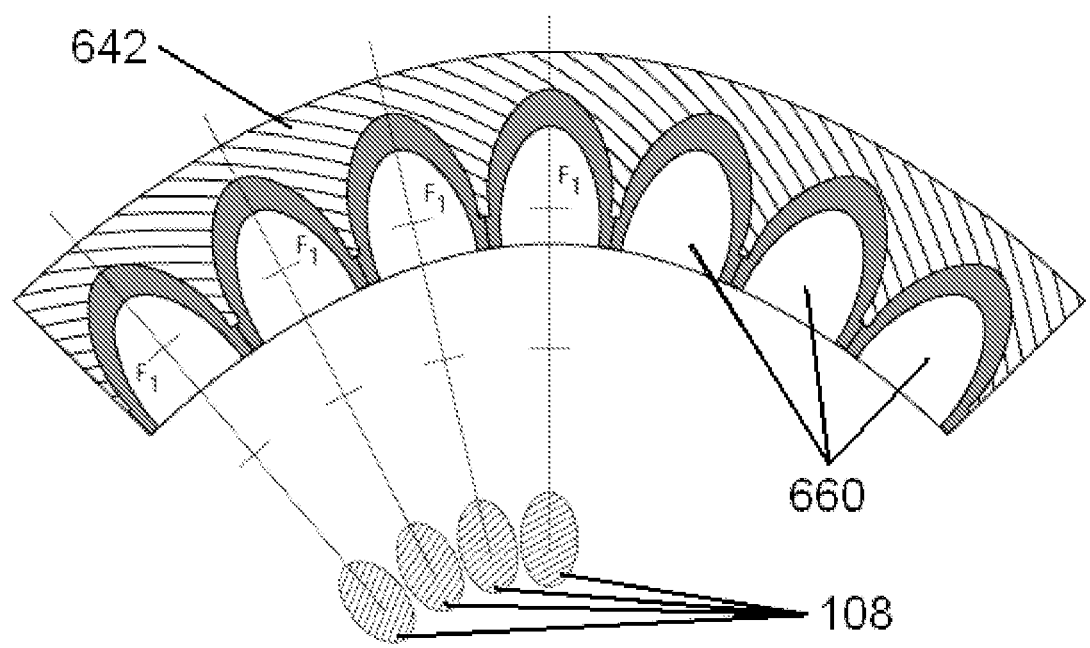
FIG. 66B is a schematic diagram of multiple reflectors arranged on a dish in one embodiment of the present invention.

FIGS. 66A and 66B show an embodiment where multiple reflectors 660 arranged on a dish 642 that creates the spatial (3-D) distribution with all the focal volumes 108 found outside of the dish 642 and not inside the dish 642, as shown in FIGS. 65A, 65B and 65C.

Another approach that provides flexibility and increased efficiency for treatment with pressure shock waves applicators 30 (or any of the variation and applicators special geometries presented in the body of this patent) is given by the automatically control of applicators' movements when necessary to change position in the course of one treatment session.

Figure 67:
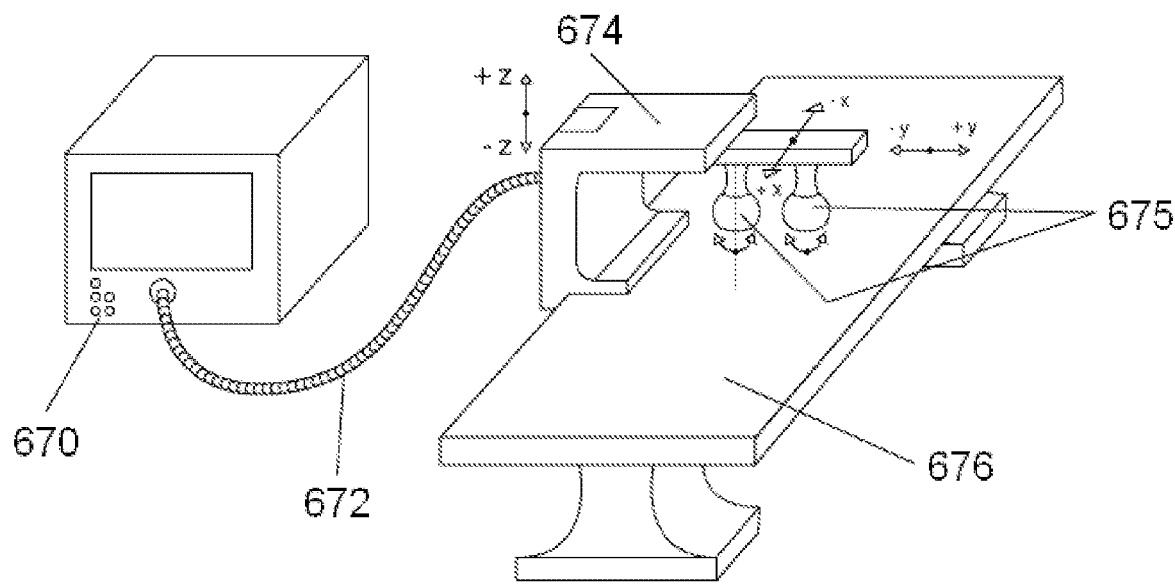
FIG. 67 is a schematic diagram of a multiple shock wave applicator treatment system in one embodiment of the present invention.

A motorized holding fixture 674 may be provided for the multiple applicators 675, as shown in FIG. 67. This holding fixture 674 is controlled by a computerized main console 670 that includes the components that can generate pressure shock waves, user interface, security systems, power supply, high voltage cable 672 and software, as seen in FIG. 67.

Figure 68A:
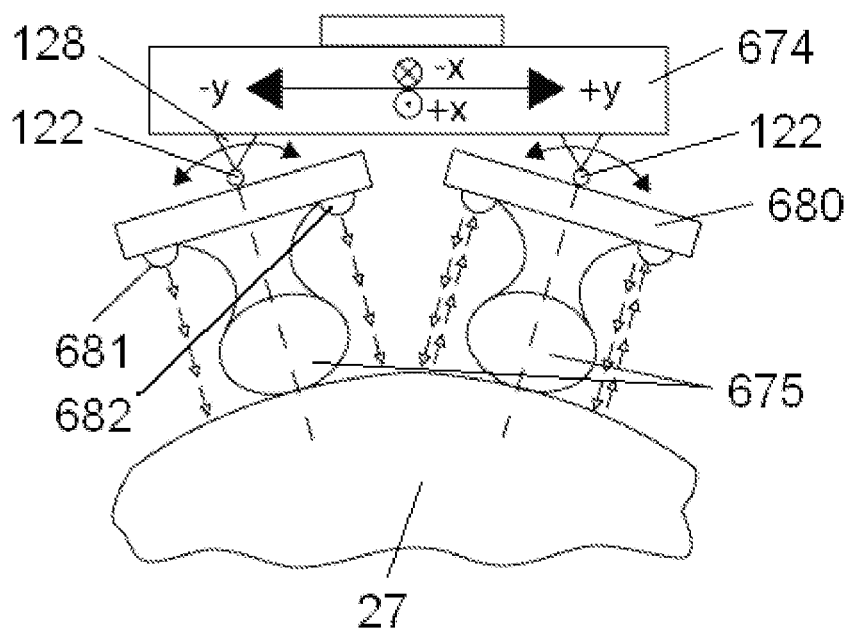
FIG. 68A is a schematic diagram of a multiple shock wave applicator treatment system having positioning sensors in one embodiment of the present invention.

The holding fixture 674 can be installed in embodiments on treatment table 676 and can offer flexibility of attaching one or more applicators 675, as the specific treatment requires. Also, this fixture should be able to move applicators 675 on ±X, ±Y, ±Z, to focus the applicators 675 on the desired treatment area. Additionally, the applicators 675 may include angular movement around a hinge 128 mounted on the holding fixture 674 that provides a pivoting axis 122 for the applicators 675, as shown in FIG. 68A. All these movements can be controlled by software based on feedback from different sensors applied to the fixtures. In certain embodiments, motors are the step motors that can be precisely controlled by software using angles values as part of rotational movement. DC or AC motors are other types of motors can also be used in other embodiments.

To achieve efficiency, a correct orientation of the applicators 675 relatively to the treated area is maintained by keeping the axis of the applicators 675 perpendicular to the plane of the targeted area. The applicators 675 orientation adjustments necessary during a treatment is realized using step motors controlled by software that receives continuous feedback from the sensors' readings.

The automatic adjustment can be also done for individual applicators 675 used in a manual movement during treatment provided by the physician (audible signals can be generated, which will trigger manual adjustments by the user) or can be used as part of an automatic fixture controlled by computer, as presented in FIG. 67.

Figure 68B:
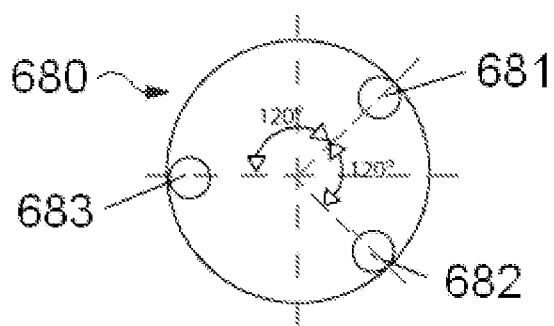
FIG. 68B is a schematic diagram of a sensor block and positioning sensors of a shock wave applicator in one embodiment of the present invention.
Figure 68C:
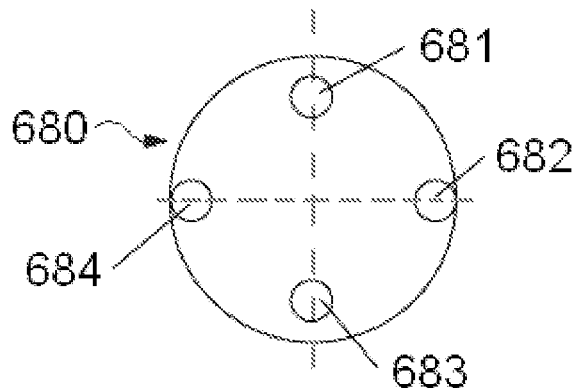
FIG. 68C is a schematic diagram of a sensor block and positioning sensors of a shock wave applicator in one embodiment of the present invention.
Figure 69:
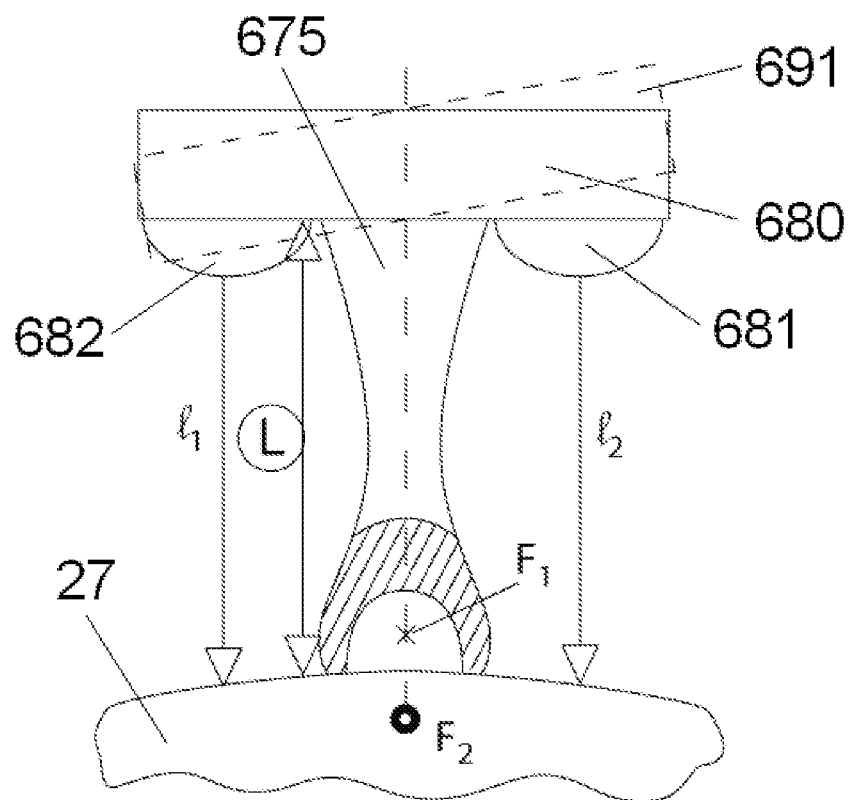
FIG. 69 is a schematic diagram of a shock wave applicator system with positioning sensors in one embodiment of the present invention.

Individual sensors 681 can be mounted directly on the sensors block 680 of the applicators 675 (as seen in FIGS. 68A, 68B and 68C). The readings from the sensors 681 mounted around the applicators 675 (two sensors 681 and 682 at 180° apart as seen in FIG. 68A or three sensors 681, 682 and 683 at 1200 apart as seen in FIG. 68B or four sensors 681, 682, 683 and 684 at 90° apart as seen in FIG. 68C) are averaged and compared. When a significant difference occurs the adjustments are made by computer for automatic fixtures or by the user in case of manual adjustment. For the manual adjustment, a beeper in the controlling console for the applicators 675 might be triggered by the abnormal position, beeper that stops when the correct position is finally found.

Schematic representation of positioning is presented in detail in FIGS. 69, 70A, 70B and 70C. For the systems presented in FIGS. 68A, 68B, 68C, 69 70A, 70B and 70C the sensors 681, 682, 683 and 684 are measuring the distance to the target and the computer of main console 670 averages the readings (from 2, 3 or 4 sensors that are present on sensors block 680). The averaged values can be compared with other averages from other sensors blocks 680 or against a preset nominal value and thus the position of the applicators 675 can be corrected from a tilted position 691 to the correct position as can be seen in FIGS. 69 and 70A-C.

Figure 70A:
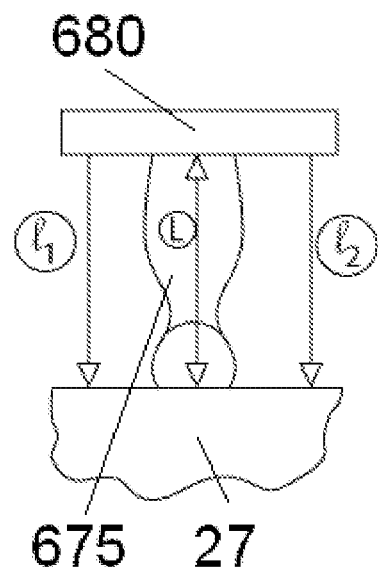
FIG. 70A is a schematic diagram of a shock wave applicator system with positioning sensors in one embodiment of the present invention.
Figure 70B:
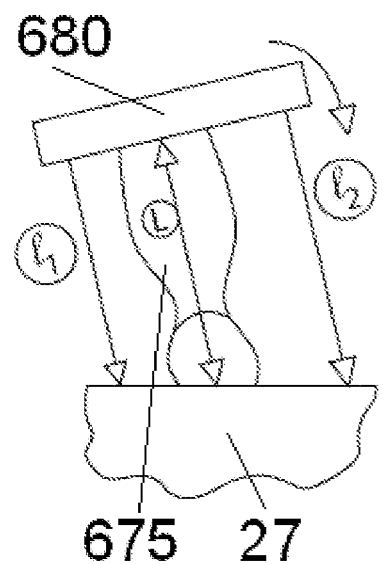
FIG. 70B is a schematic diagram of a shock wave applicator system with positioning sensors in one embodiment of the present invention.
Figure 70C:
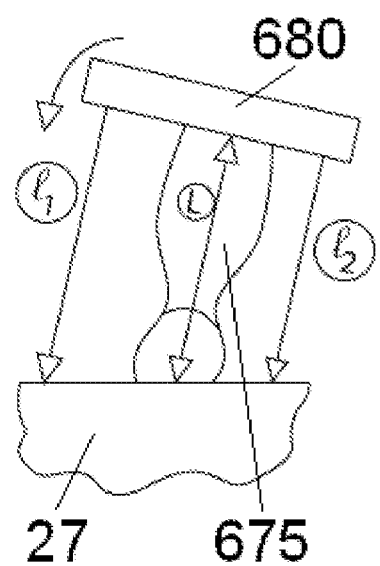
FIG. 70C is a schematic diagram of a shock wave applicator system with positioning sensors in one embodiment of the present invention.

Based on the sensors 681, 682, 683 and 684 readings and the computing algorithm the adjustments are done "on the fly", as presented in FIGS. 70A, 70B and 70C. In the depicted embodiments, an exemplary algorithm for triggering adjustment includes calculation of distances (L), ($l_1$) and ($l_2$). If L–$l_1$=±1 mm no adjustment is considered necessary. If L–$l_1$ is greater than 1.1 mm then adjustment is made to $l_2$ to appropriately level and correct the discrepancy. Similarly, if L–$l_2$=±1 mm no adjustment is considered necessary. If L–$l_2$ is greater than 1.1 mm then adjustment is made to $l_1$ to appropriately level and correct the discrepancy for such side.

Figure 71:
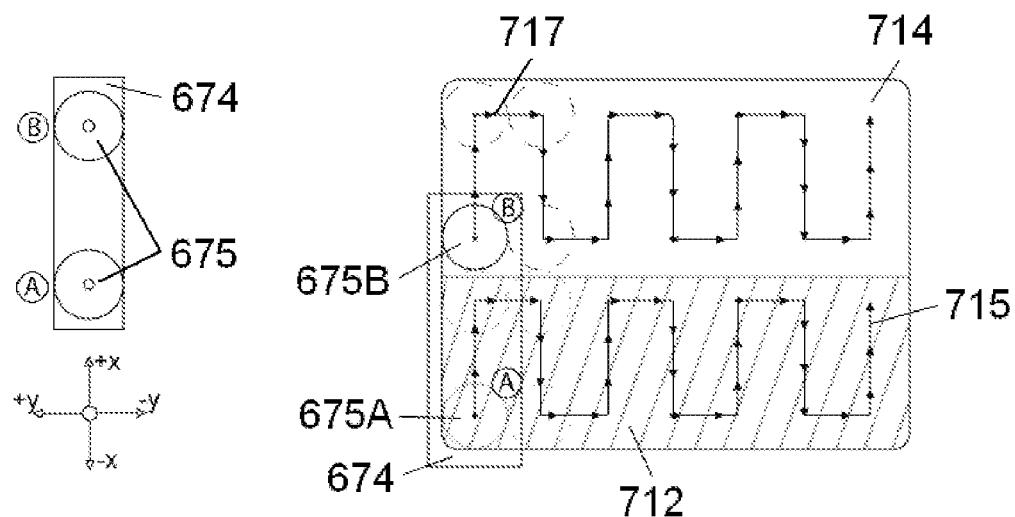
FIG. 71 is a schematic diagram of a shock wave applicator system including software-controlled positioning patterns in one embodiment of the present invention.

To optimize the process of treating larger areas (for example cellulite or burns) the software of the main console 670 can move the holding fixture 674 for applicators 675 in optimum patterns (715 within area 712 for applicator 675A and 717 within area 714 for applicator 675B) and thus adding the area treated by applicator 675A with the area treated by applicator 675B, which translates in high efficiency for the treatment with minimal movement for the holding fixture 674, as shown in FIG. 71.

In such embodiment, the distance between applicators 675A and 675B heads is preferably larger than (1.5–2.0)×d, where d=diameter of the applicators 675A and 675B.

Figure 72:
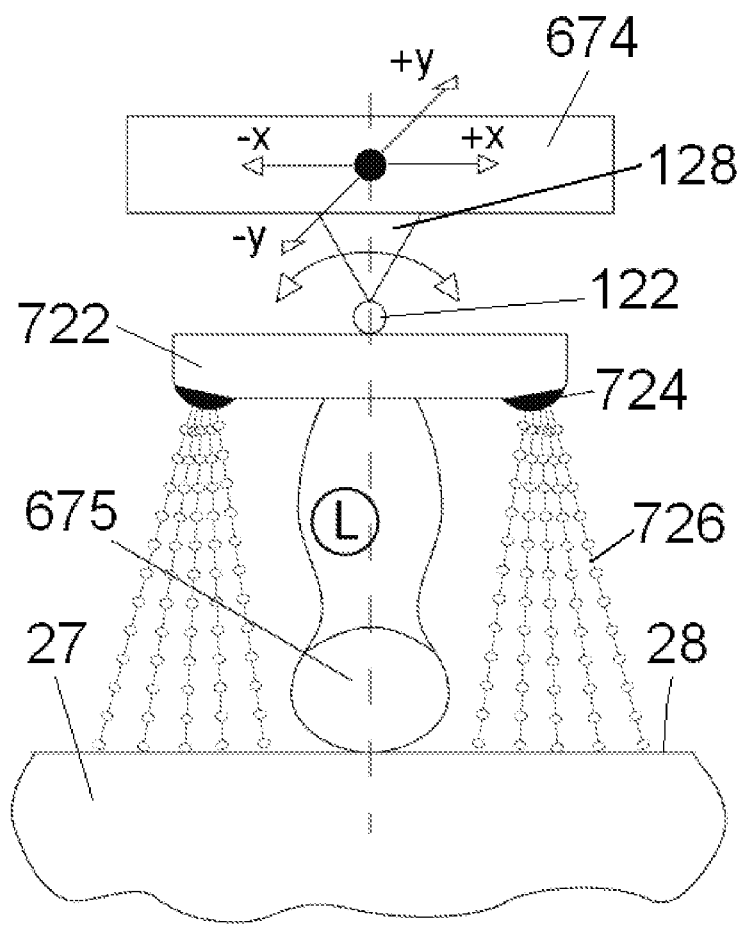
FIG. 72 is a schematic diagram of a shock wave applicator system including liquid sprayer in one embodiment of the present invention.

The use of the holding fixture 674 for the sensors 681, 682, 683 and 684 can also generate other advantages as presented in FIG. 72.

As seen from this embodiment, the holding fixture 674 for the applicator 675 could contain pressurized reservoirs 722 with different liquids that can be sprayed during treatment over the skin 28 or targeted area 145 (not shown in FIG. 72) from the body 27. The same liquid substances can be pulverized via nozzles 724 on the treatment area using air and thus creating aerosols. The medication combined with air movement can have on analgesic effect. During one treatment, different substances can be sprayed (via spray jets 726) on the treatment area based on necessities and physician's indications. Also, the front spray (placed in the front of the applicator 675) could contain a different substance from the back spray (placed in the back of the applicator 675). Substances that might be used with this design can be analgesics, antibiotics, saline solution, liquid gel, and the like.

Figure 73:
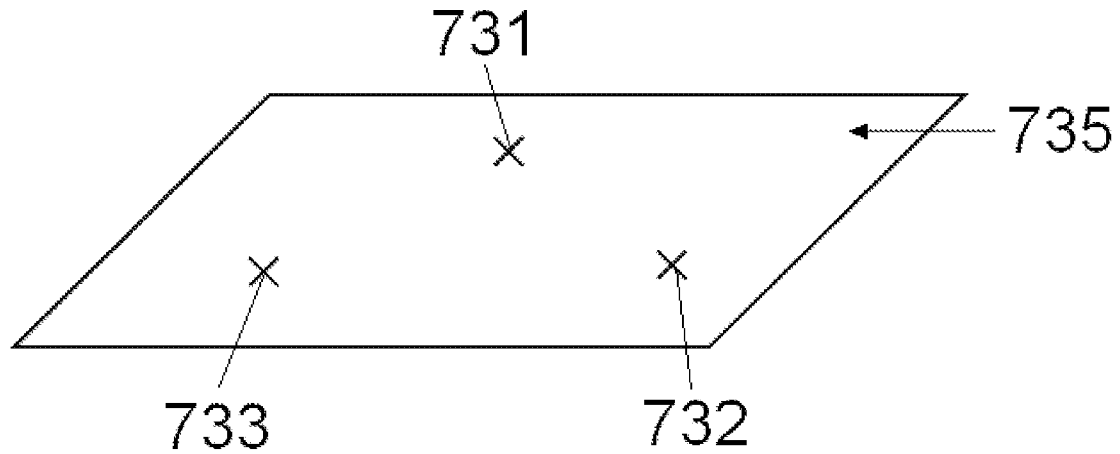
FIG. 73 is a schematic diagram illustrating points on a plane in one embodiment of the present invention.

On treatments performed on body appendages 25 (smaller areas when compared to the torso) manual coordination/positioning of the applicators 675 may be utilized in some embodiments. To avoid the misalignment of the applicators 675 to the treatment area (applicators 675 are non-perpendicular per targeted surface), the applicators 675 can be mounted in a special designed holder, to provide stability and good alignment. The whole concept is based on creating a plane by having at least three (3) points of contact with the skin 28. The laws of geometry state that at least 3 points (731, 732 and 733) can determine/define a plane 735 and its position in space, as presented in FIG. 73 (Prior art).

Based on this theory, the holder will have three points of contact with the skin 28 (thus creating a stable plane 735) and in the middle of the plane 735 the applicator 675 will be held in place, in the right position to the treatment areas ($F_2$ in the treatment zone without tilts of the applicator that can modify focal zone positioning relatively to the skin 28 and the correct deposit of treatment energy in the treatment area).

Figure 74A:
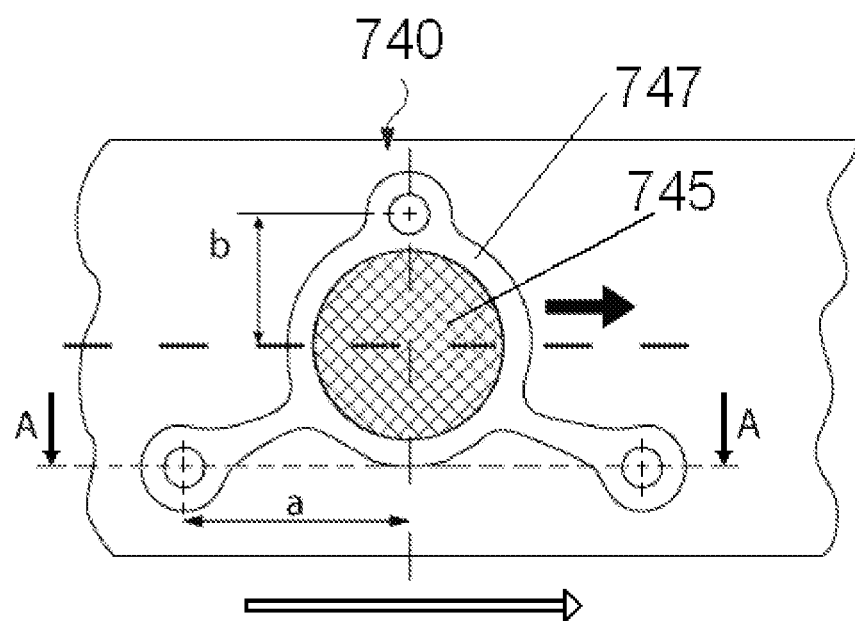
FIG. 74A is a schematic diagram of a shock wave applicator system with an applicator and positioning holder in one embodiment of the present invention.
Figure 74B:
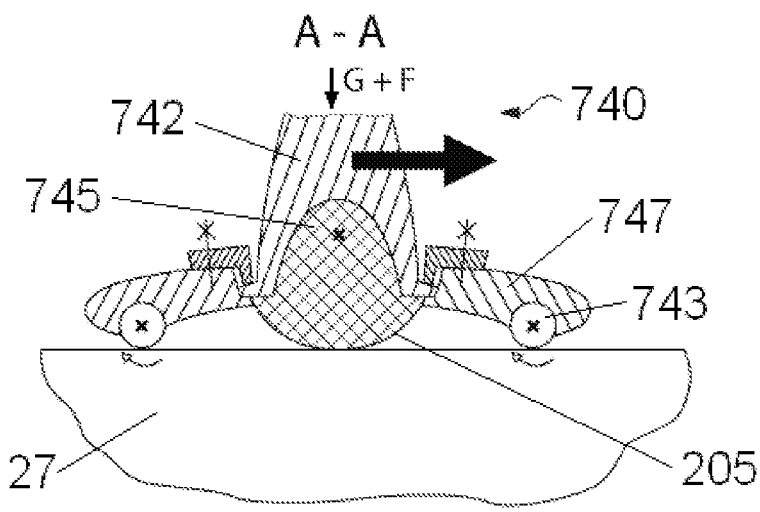
FIG. 74B is a schematic diagram of a shock wave applicator system with an applicator and positioning holder in one embodiment of the present invention.

Based on this theory, the applicator 675 may be a special designed applicator holder 740, as presented in FIGS. 74A and 74B. From this figure it can be seen that a>b with the longitudinal movement of the assembly along the "a" dimension shown by the black arrow.

This applicator embodiment can be used for extended treatment areas especially on body appendages 25 (small and curved surfaces). Embodiments of the invention can be used in non-limiting examples on the torso, buttocks and for the front of body 27. The applicator 675 stays in place due to its own weight (G) and under the force (F) that the user applies on applicator 675 during treatment.

As shown in FIGS. 74A and 74B, the applicator holder 740 holds the applicator body 742, which allows the correct positioning of the applicator reflector cavity 745 relative to the body appendage 25 or body 27 generally. The applicator reflector cavity 745 is isolated with the membrane 205, which also facilitates the smooth contact with the body appendage 25 or body 27 generally.

Figure 75A:
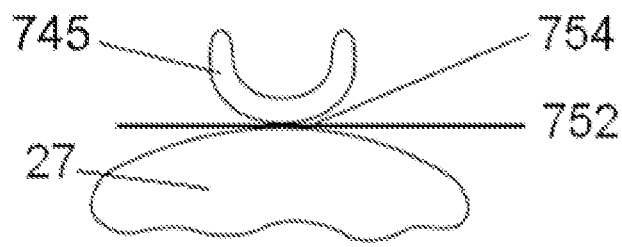
FIG. 75A is a schematic diagram of a positioning holder plane of a shock wave applicator system at a surface of a body in one embodiment of the present invention.
Figure 75B:
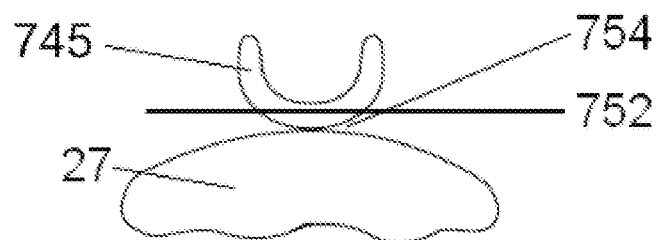
FIG. 75B is a schematic diagram of a positioning holder plane of a shock wave applicator system above a surface of a body in one embodiment of the present invention.
Figure 75C:
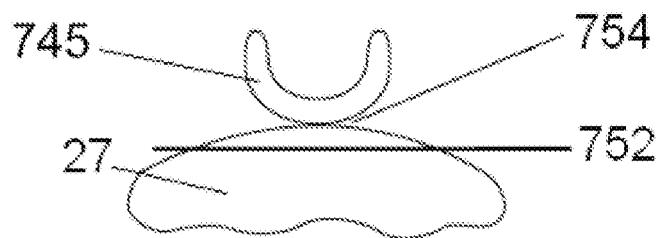
FIG. 75C is a schematic diagram of a positioning holder plane of a shock wave applicator system below a surface of a body in one embodiment of the present invention.

The applicator holder 740 can be delivered in different versions that allow the reflector cavity 745 and membrane 205 (marked as 745 on the FIGS. 75A, 75B and 75C) to have the contact 754 in the same plane (see FIG. 75A) nested by the holder 740 three (3) points 743 (defining holder plane 752) of contact or in another plane-such as after the plane (as presented in FIG. 75B) or before the plane (as can be seen from FIG. 75C). Holder contact points 743 may include rollers, wheels and like elements for movement of the holder 740 in embodiments of the invention.

To accomplish the positioning of the reflector cavity 745 and membrane 205 in the holder plane 752 or before or after holder plane 752, the holder 740 can be provided in different embodiments, based on the targeted treatment area that dictates the necessary penetration depth inside the body 27. Using fixed reflector geometry, when the contact 754 with the body 27 is made after the holder plane 752 a deeper penetration is accomplished. For shallower penetrations the contact of the contact 754 with the body 27 is made before the holder plane 752.

To accomplish the variability in tissue penetration, a holder 740 in embodiments includes a latch mechanism or a screw-nut mechanism to adjust where the contact 754 with the body 27 is made ("before", "in" or "after" the holder plane 752).

Figure 76A:
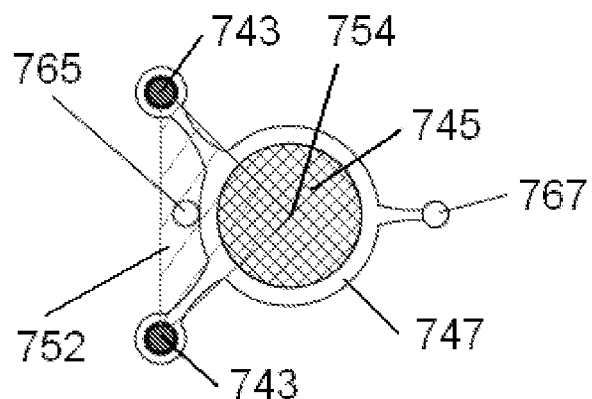
FIG. 76A is a schematic diagram of a shock wave applicator system holder with a connector to connect to another holder in one embodiment of the present invention.
Figure 76B:
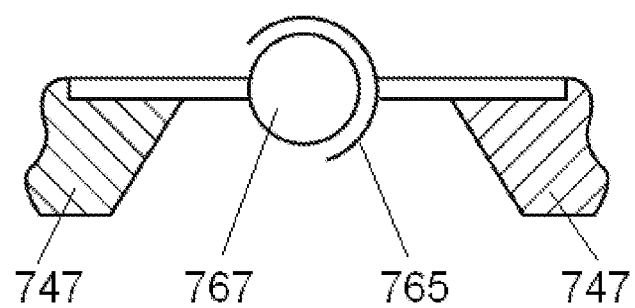

Much larger areas of treatment embodiments may utilize in embodiments a "bracelet design" 780 (FIGS. 78A and 78B), which includes attaching multiple applicators 675 sitting in holders 740. The holders 740 for the bracelet design 780 are connected, such as in non-limiting embodiments via female ball hinges 765 combined with male ball hinges 767, that allow the applicators 675 and associated holders 740 to interconnect (FIGS. 76A and 76B). For these holders 740, two points 743 of the holder plane 752 come from the holder body 747 and the third point is given by the applicator contact 754 with the body 27, as seen in FIG. 76A. This means that the applicator 675 is preferably in the holder plane 752.

Figure 77:
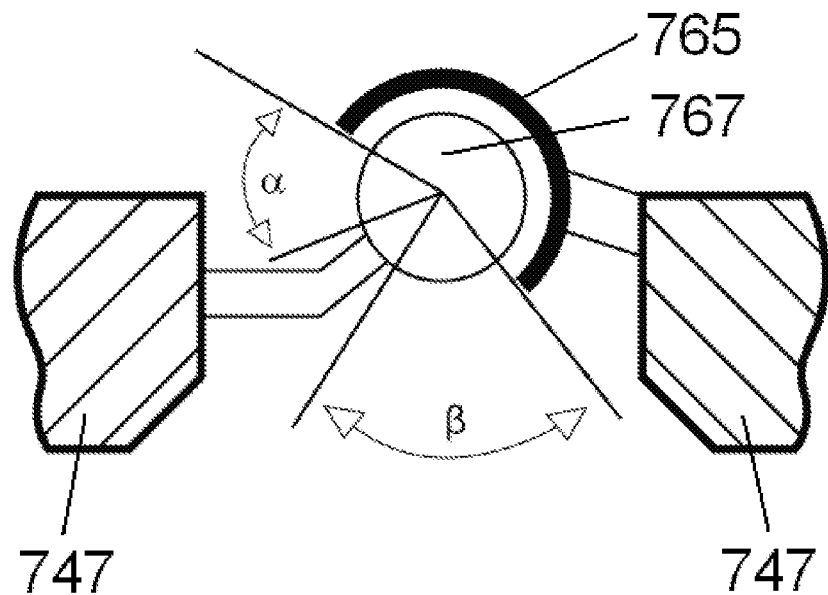

In FIG. 77, a and B are the possible angles of rotation for consecutive holders 740 (only the holder body 747 seen in the FIG. 77 and not including the entire holder assembly 740) to allow their relative movement in the female ball hinges 765 and male ball hinges 767 area, in order to conform to the body 27 curves.

Figure 78A:
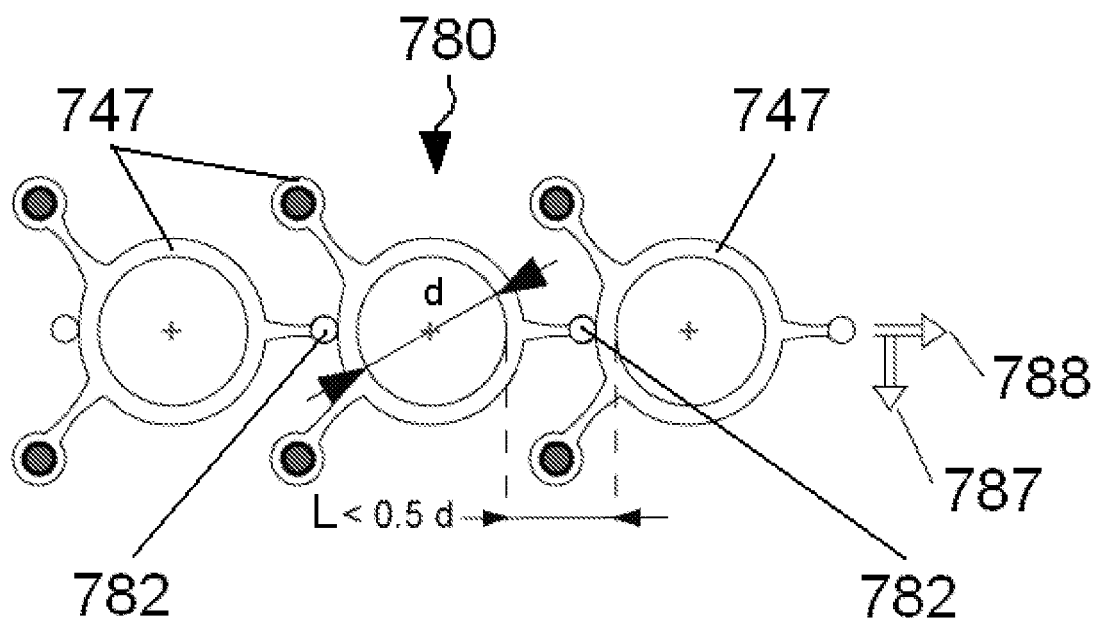
Figure 78B:
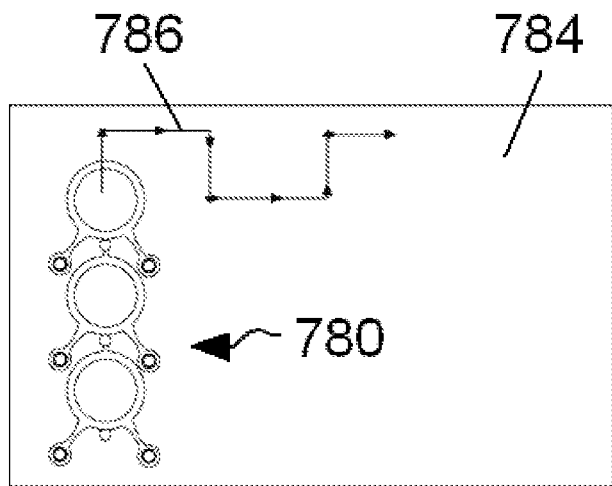

In FIGS. 78A and 78B, the "bracelet design" 780 is presented in further detail. The smaller "L" distance between consecutive holder bodies 747, the smaller the distance that the bracelet design 780 needs to be moved longitudinally ("bracelet" chain secondary movement 788). The transversal movement (main movement 787) will be with a distance equal to the diameter of the focal volume 108 (not the same as applicator's diameter "d"). The combination of the main movement 787 and secondary movement 788 gives the movement pattern 786 of the bracelet design 780 in the treatment area 784.

The shape of holder bodies 747 can be a triangle or any other shape that facilitates a stabilizing plane combined with hinge connection (connection points 782).

Holder bodies 747 preferably stay close to the body 27 and the connection to the applicators 675 is preferably as close as possible to applicator's distal end (in the applicator reflector cavity 745 area).

The connection of the applicators 675 to the body 27 occurs in various embodiments via gels or gel pads 52 designed to conform to body curvature and to control tissue penetration (thicker gel pads 52 can reduce tissue penetration and vice versa).

The stability is again realized with the applicator's 675 own weight (G) and the force F that the user can apply on applicator 675 (FIGS. 74A and 74B).

As illustrated in FIG. 78B, the bracelet design 780 can be used with a computerized system, such as depicted in FIG. 67, where the two-dimensional movements of the connected applicators 675 (main movement 787 perpendicular on the axis of the bracelet assembly and the secondary movement 788 along the axis of the bracelet assembly) is controlled via a dedicated software. The computerized movement pattern 786 can be done in any geometry and kinds of directions of motion, including beyond the embodiments of FIGS. 71, 78A and 78B. For example, a spiral movement can be used to uniformly cover a treatment area in other embodiments.

Figure 79A:
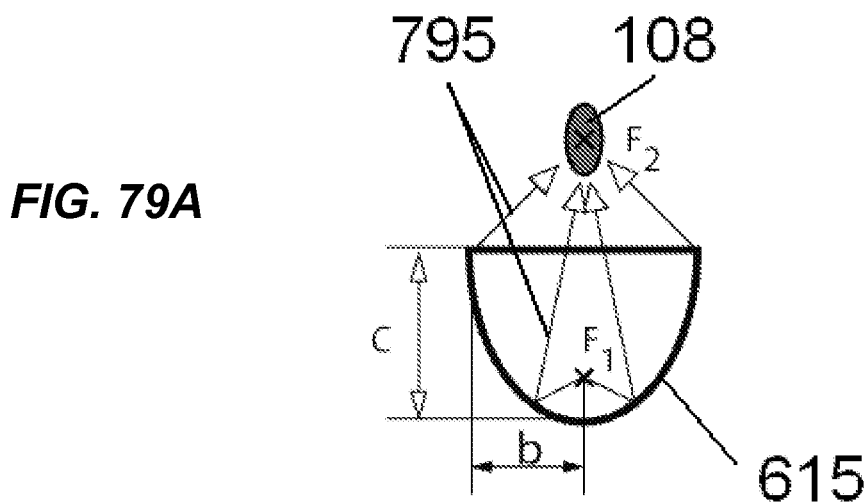
Figure 79B:
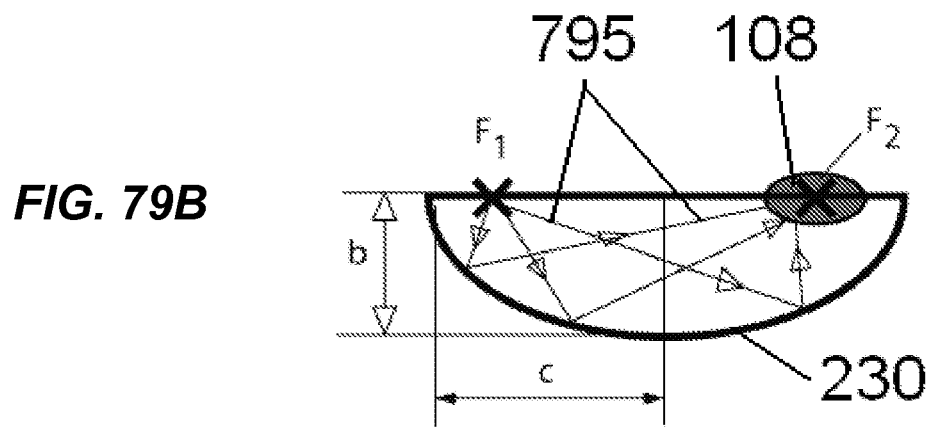

Another approach to increase the treatment area in one applicator 675 position is given by the increase of the cross-section of the focal volume 108 in a tangential direction (parallel to the skin 28). The reflector geometry can be "reversed" as shown in FIGS. 79A and 79B (with further reference to FIGS. 23A, 23B, 61A and 61B).

Figure 80:
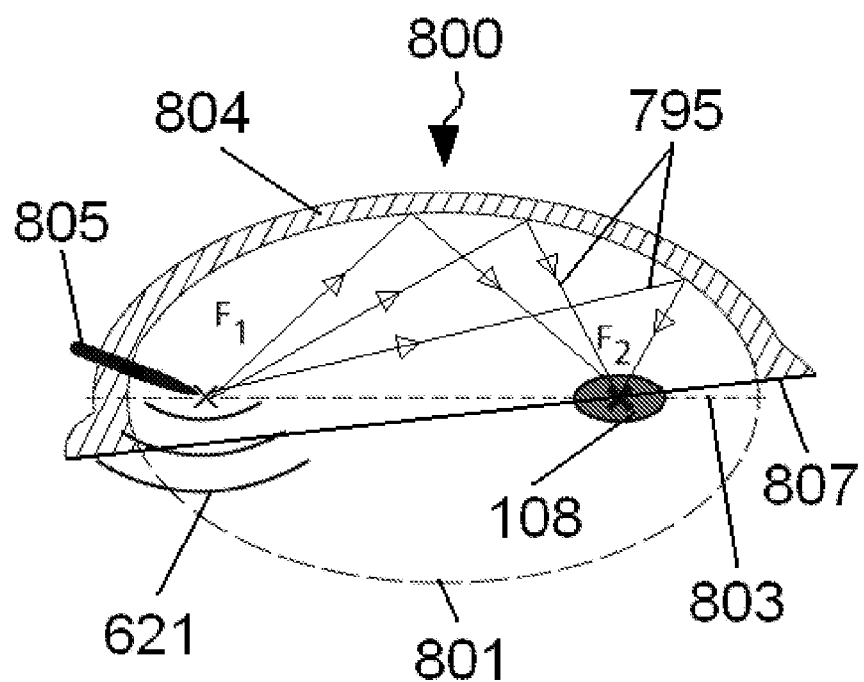

The reversed reflector 800 embodiment presented in FIG. 80 has the following advantages:

A radial pressure shock waves is generated from $F_1$ at electrode 805 where the high voltage discharge is produced, due to the fact that the radial wave 621 that propagates below the reflector does not have any surface to bounce back. Thus the waves propagate into a body 27 in the treatment area.

Focused pressure shock waves are also produced by the radial wave 795 generated in $F_1$ and is reflected by the upper portion of the reflector and then focused towards $F_2$.

Treatment area longitudinally slices the focal volume 108 and not transversally as with classic reflector designs, which also translates into increased efficiency of the treatment in one fixed position.

The reversed reflector 800 has the advantage in various embodiments of creating radial and focused pressure shock waves in the treatment area using only one reflector. The "double punch" pressure shock waves can increase the efficiency of the treatment for superficial areas of the body 27 such as wounds, burns, cellulite, and the like.

Figure 81:
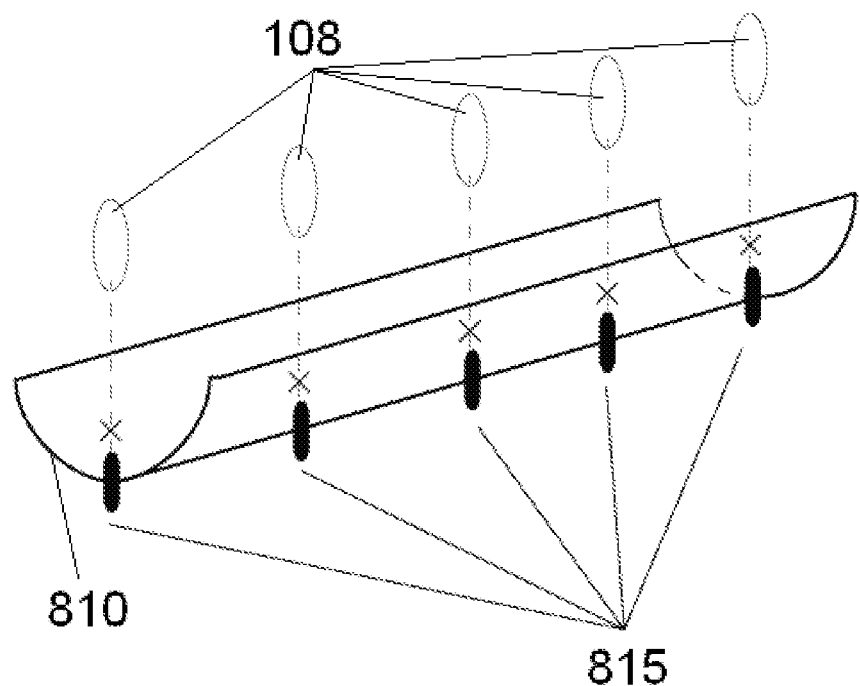

Another embodiment includes a "pipe reflector" 810 shown in FIG. 81, which has multiple focal points of electrodes 815 and focal volumes 108, to increase the area that is treated in one position of the reflector (the summation of multiple focal volumes 108). A reduction of the surface of reflection for the pressure shock waves (only slices of the half ellipsoid are used) is expected to reduce the energy delivered by the pressure shock waves in each individual focal volume 108 in comparison to classical design (half ellipsoid). Such embodiments are beneficial for longer treatment areas that require low energies to be deposited into the tissue.

Another embodiment for generating pressure shock waves includes creating a movable pressure shock waves electrode (pressure shock waves originating source), which can be moved out of focus (move up or down from $F_1$ that represents the normal geometrical position for the first focal point of an ellipsoid). In this way a change in the geometry of the focal volume 108 can be achieved.

A shift in the spark discharge 601 produces (for both −z and +z) a change in the second focal point from geometrical $F_2$ to a pseudo focal point $F_2'$.

From a focal shift, a change in pressure distribution and values in the focal volume 108 will be reflected in modification of energy values and their distribution. For an electrohydraulic device this means that with a certain voltage discharge in $F_1'$, different levels of energies can be achieved in $F_2$ and $F_2'$, when compared with normal discharge in $F_1$.

The advantages of generating different energy values in $F_2$ and different energies' distributions in the focal volume 108 (normal and extended) using the same voltage discharge in $F_1$ or in the shifted point $F_1'$ include simplified construction of control console and possibility to tune the energy for many treatments using one range of discharge voltages.

Figure 82A:
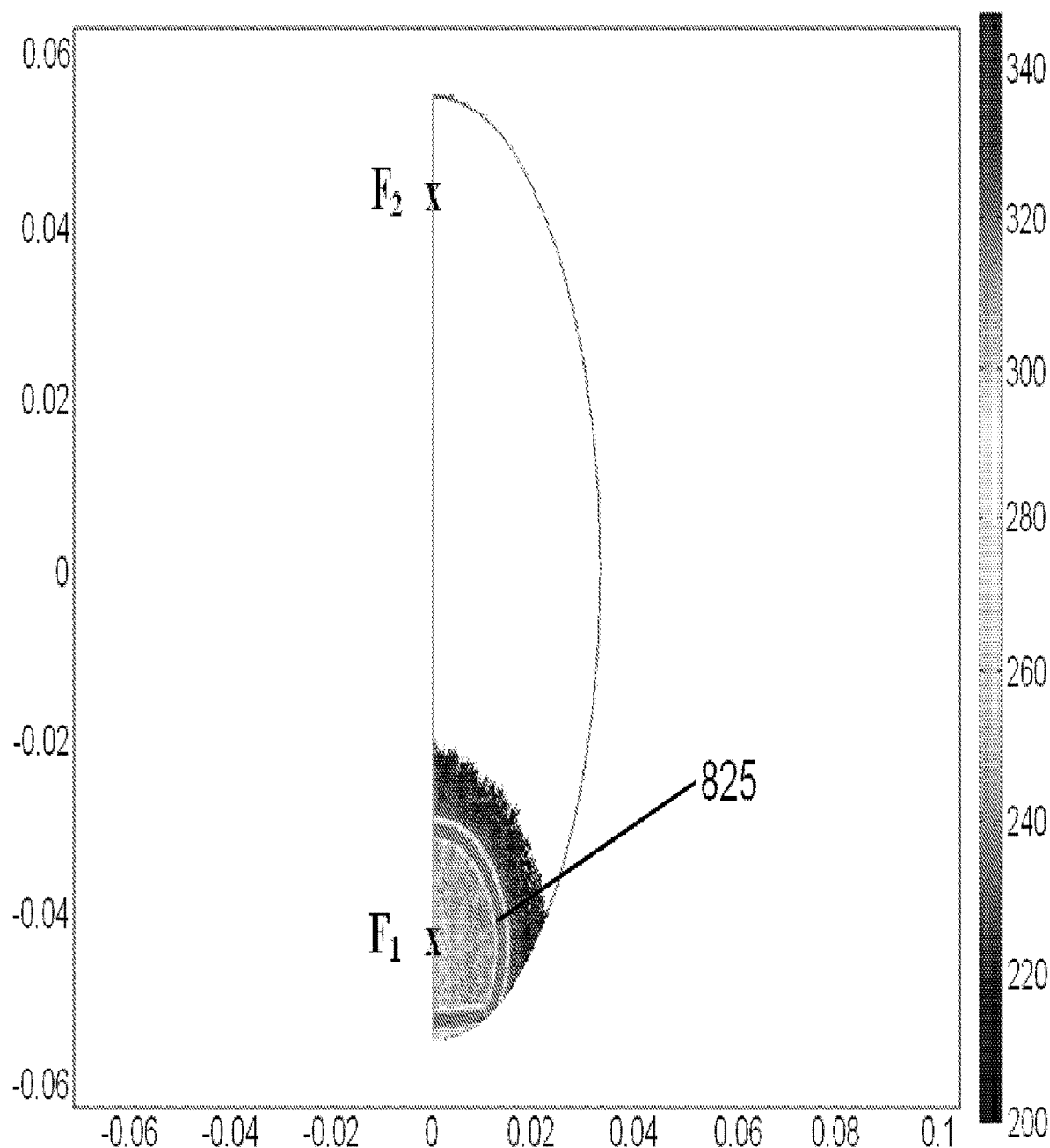
Figure 82B:
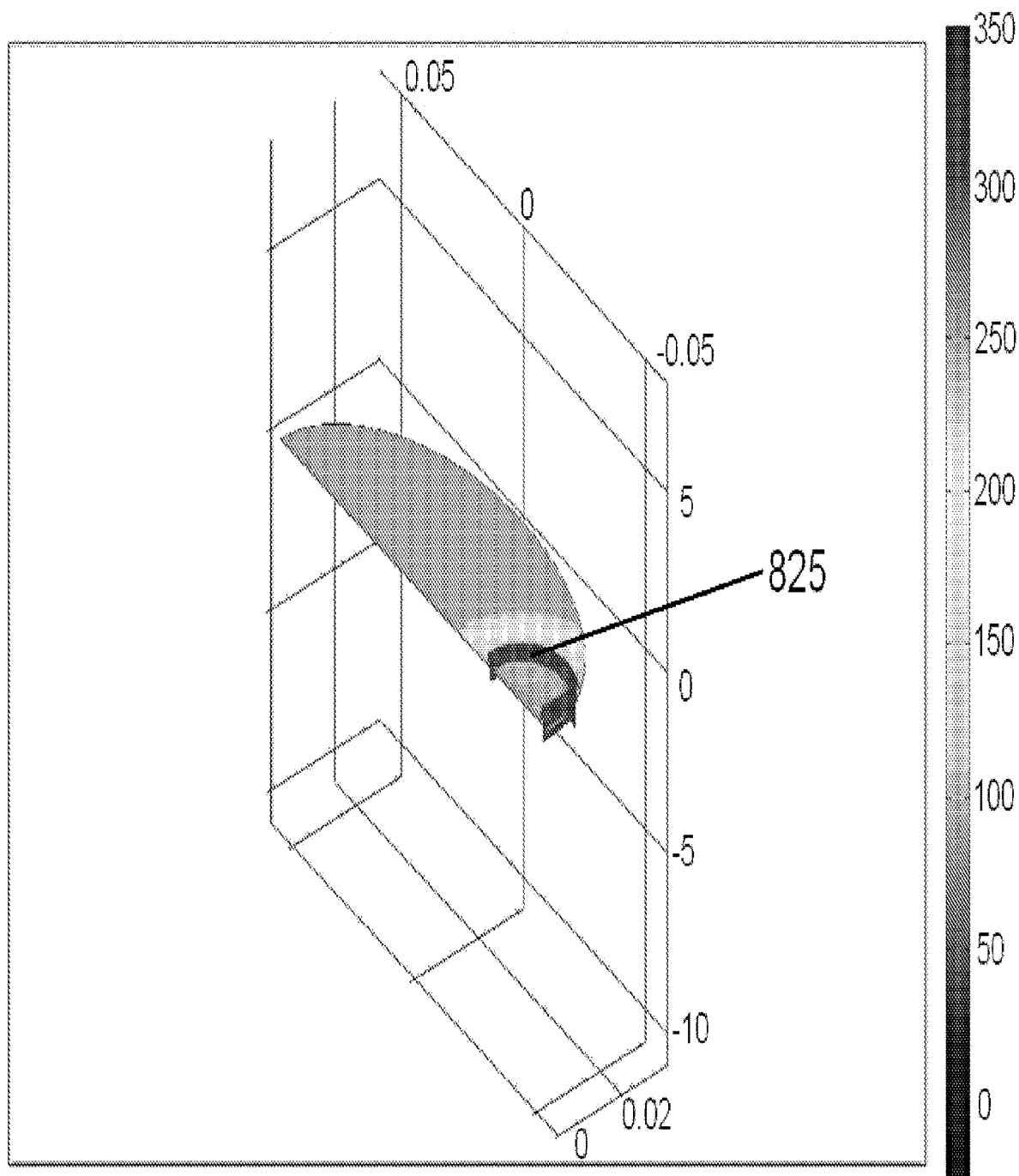

Simulation with COMSOL acoustic propagation software package shows the following results (for all corresponding figures the top image (A) shows is showing pressure amplitudes correlated with the pressure shock waves front propagation and the bottom image (B) shows the 2-D view of the top image):

FIGS. 82A and 82B shows the normal discharge in geometrical focal point $F_1$, which is starting the pressure shock waves propagation 825 towards the second geometrical focal point $F_2$.

Figure 83A:
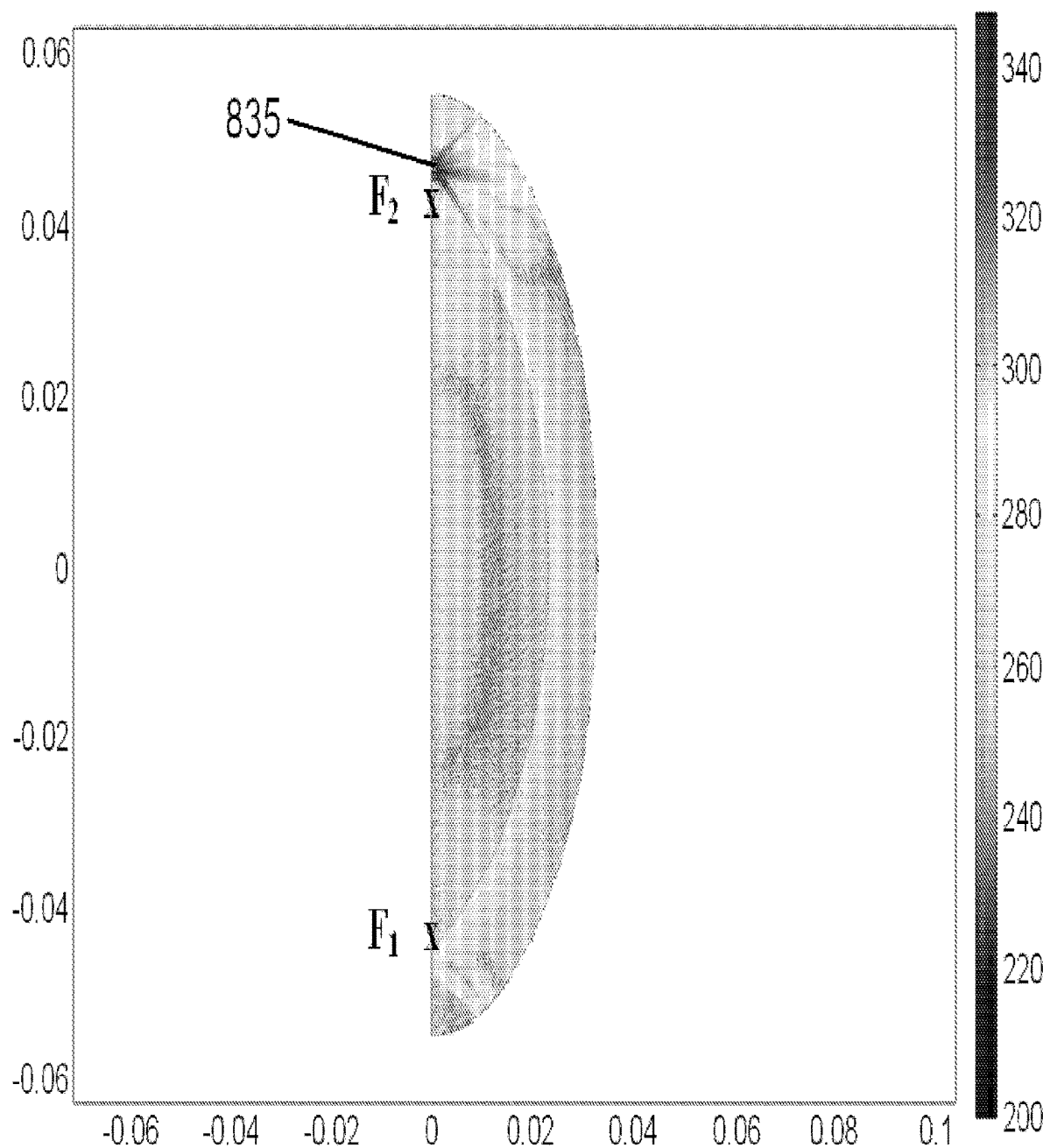
Figure 83B:
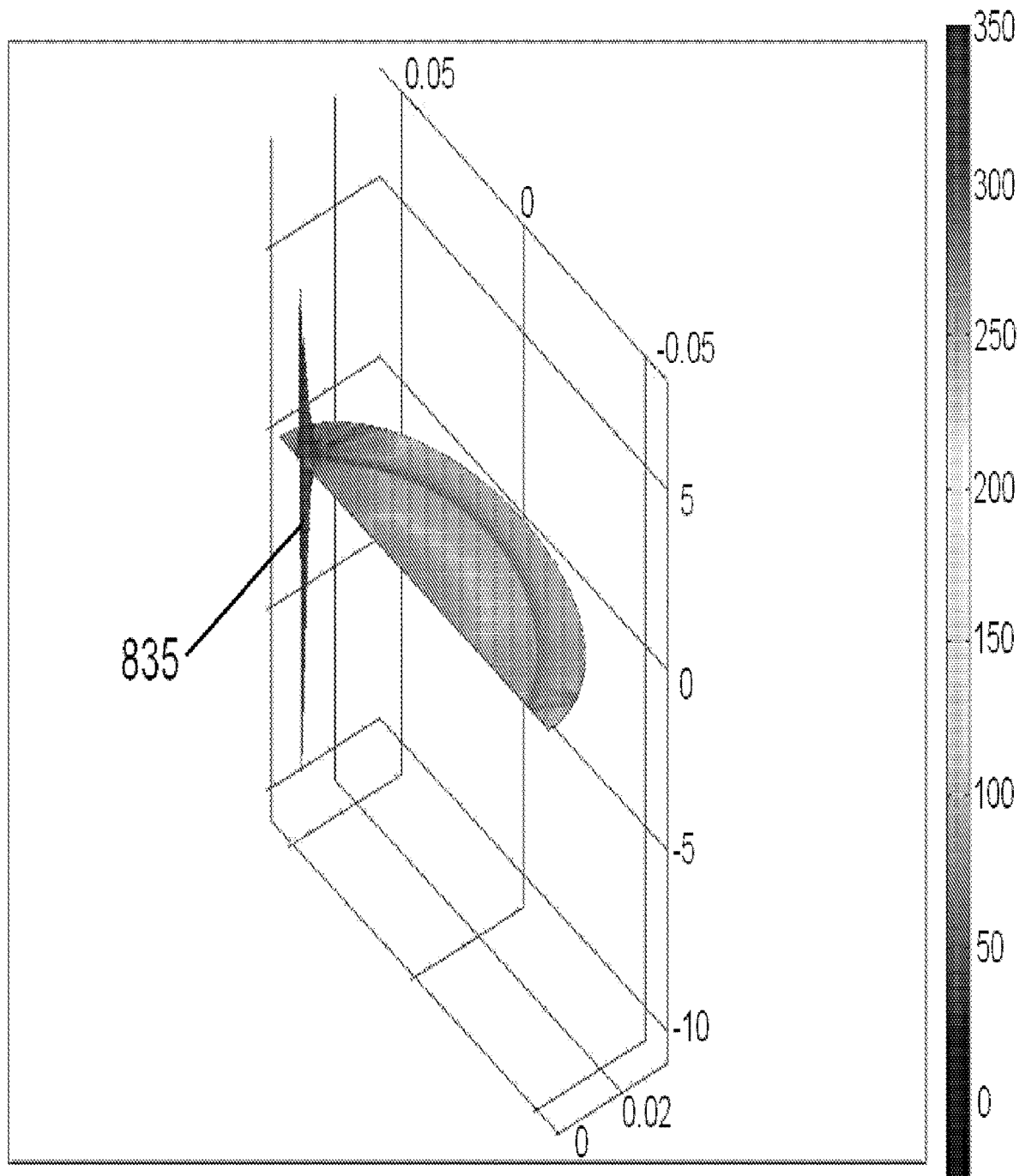

FIGS. 83A and 83B shows the reach of the pressure shock waves 835 in the second geometrical focal point $F_2$ after a normal discharge in the first geometrical focal point $F_1$. High amplitude pressures are generated in $F_2$, where the bottom peak represents the compressive pressure corresponding to compressive phase and the top one the negative pressure corresponding to tensile phase that generates cavitation.

Figure 84A:
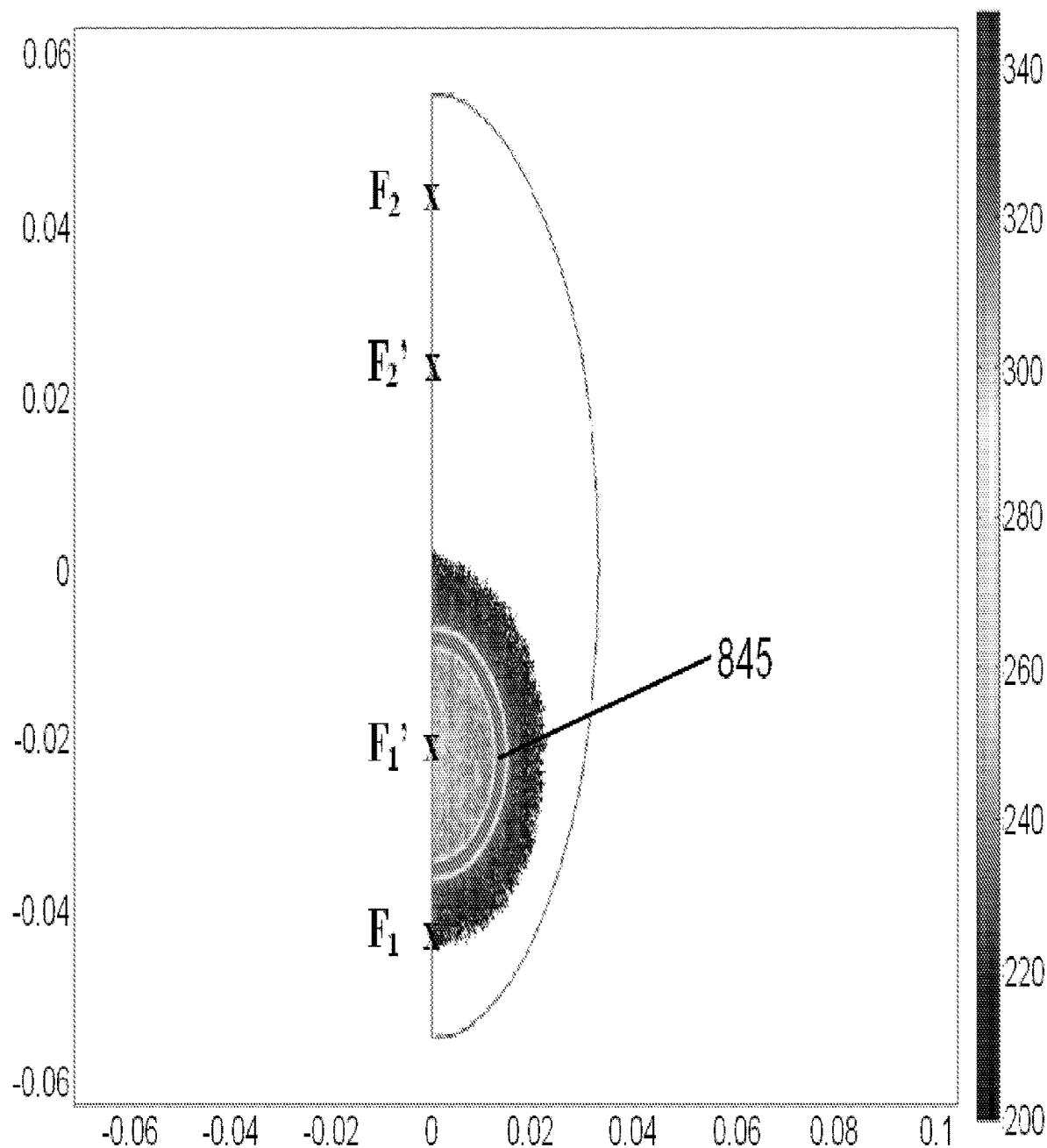
Figure 84B:
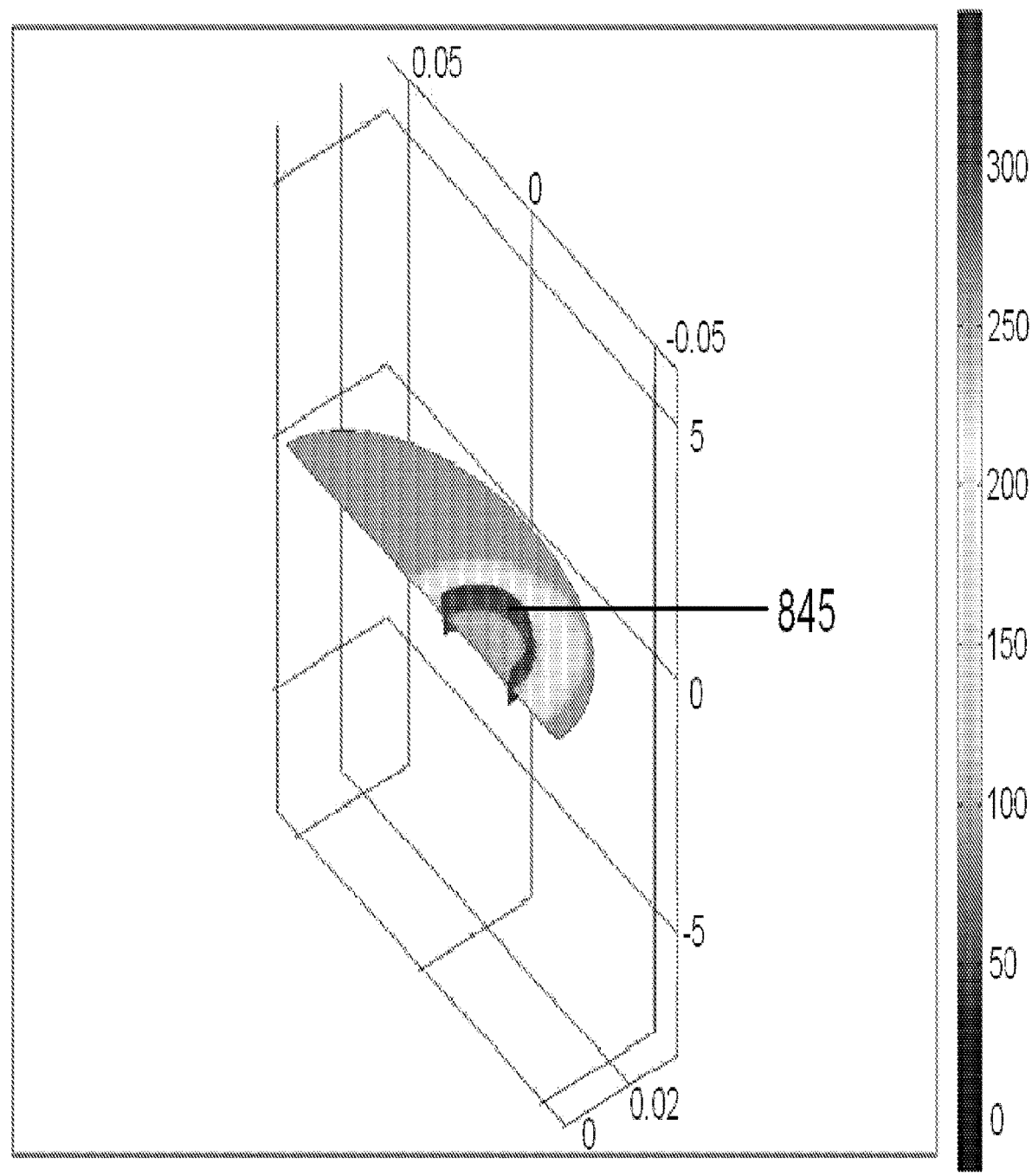

FIGS. 84A and 84B shows the discharge at a shifted point $F_1'$ (22 mm up from the first geometrical point $F_1$), which is starting the pressure shock waves propagation 845 towards the second geometrical focal point $F_2$ and pseudo second focal point $F_2'$, symmetric to $F_1'$ regarding the small semi-axis of the ellipsoid.

Figure 85A:
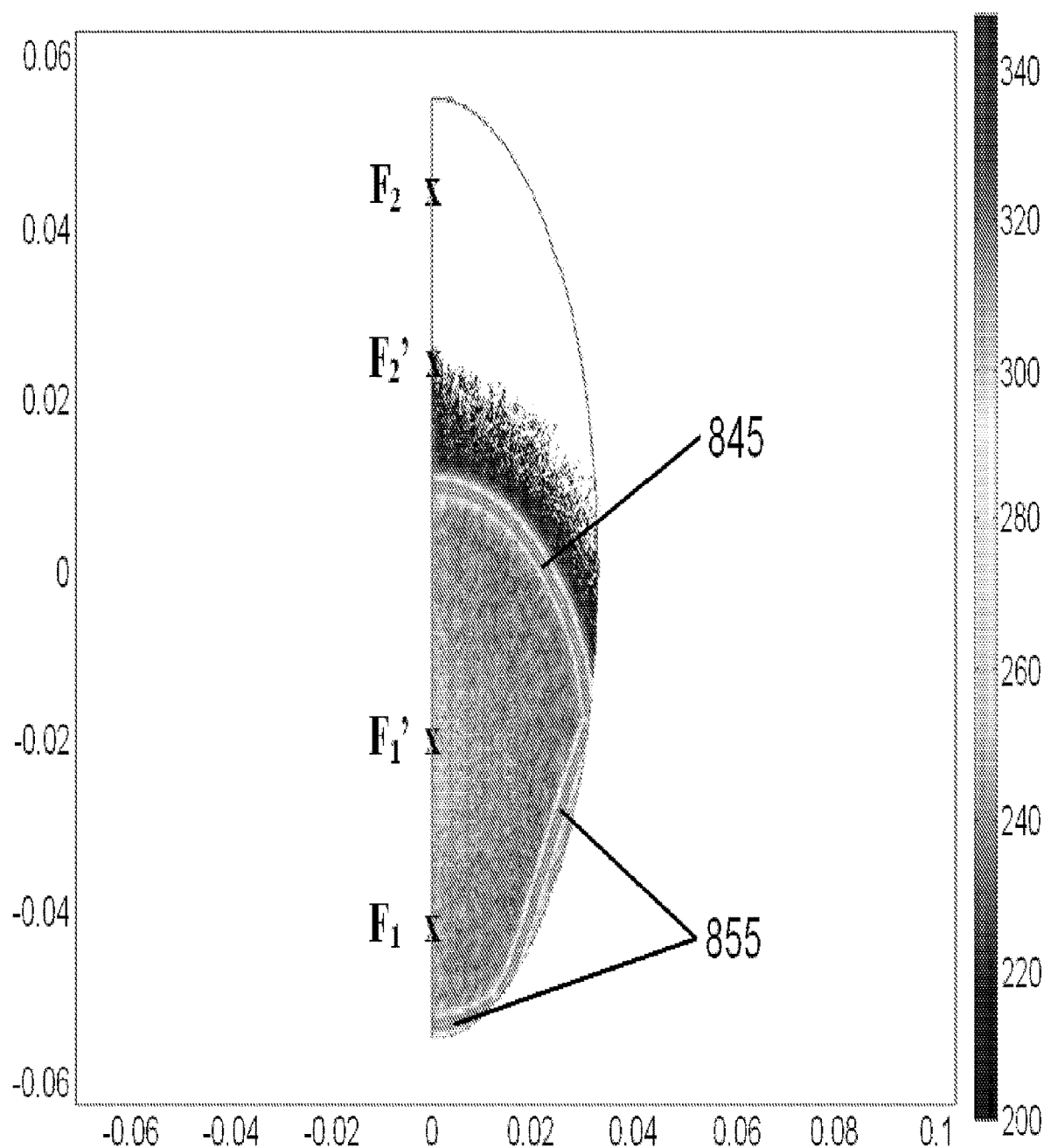
Figure 85B:
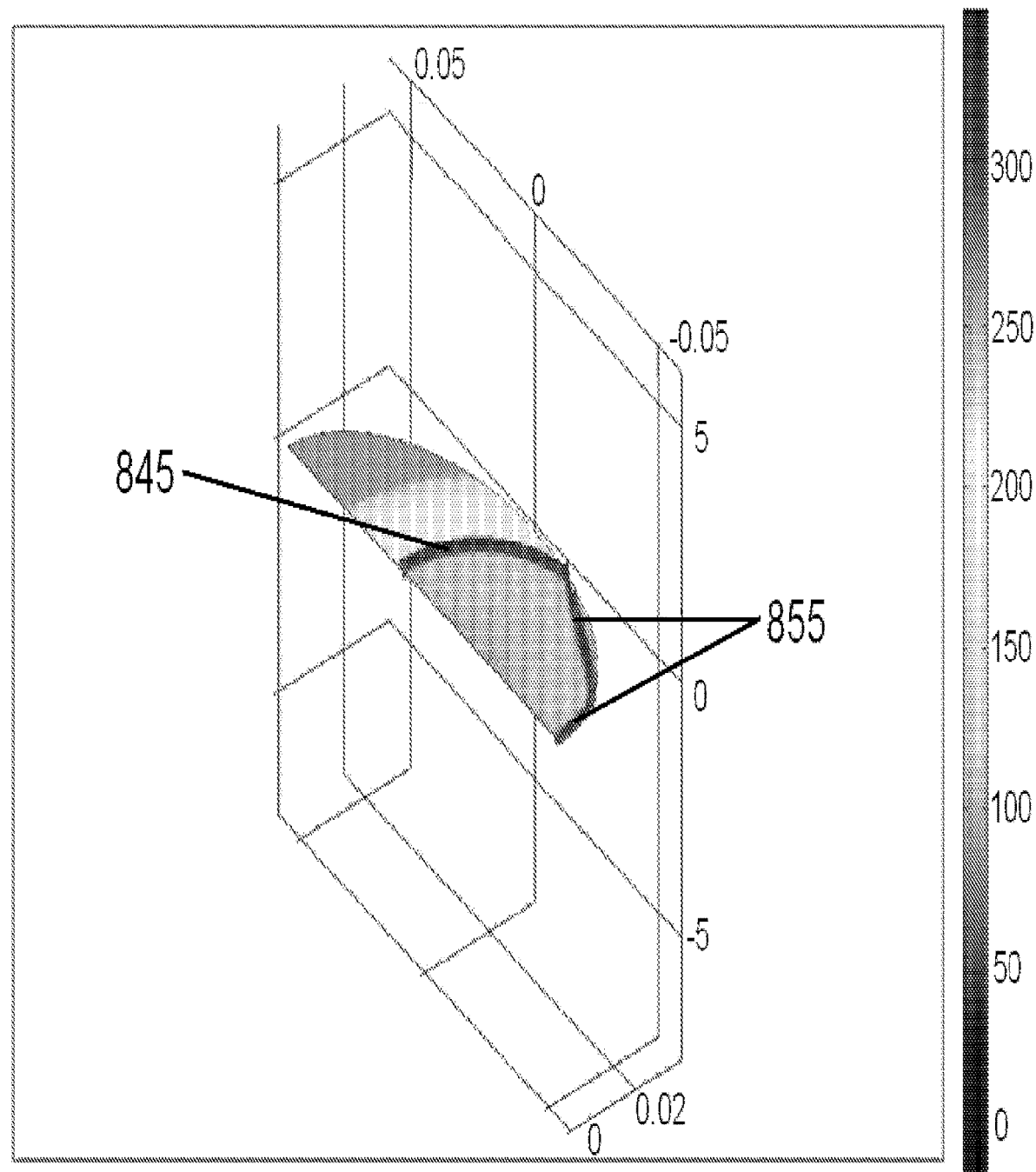

FIGS. 85A and 85B shows the movement of the primary shock waves front 845 towards the $F_2'$ and $F_2$ and the reflection at the bottom of the reflector, which creates a secondary shock waves front 855, which has a large delay from the primary shock waves front and has enough energy to produce a pressure spike when will pass through $F_1$.

Figure 86A:
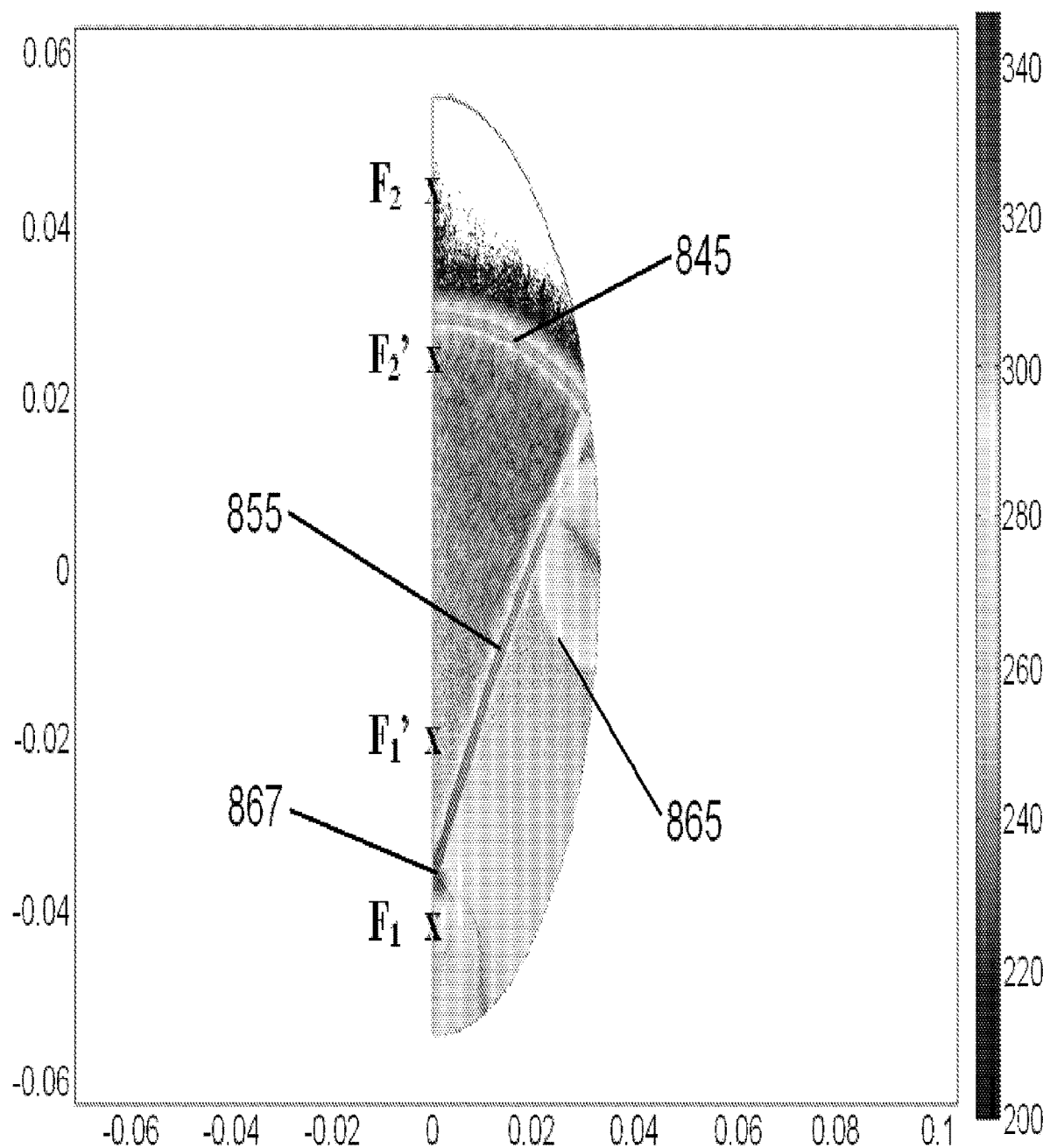
Figure 86B:
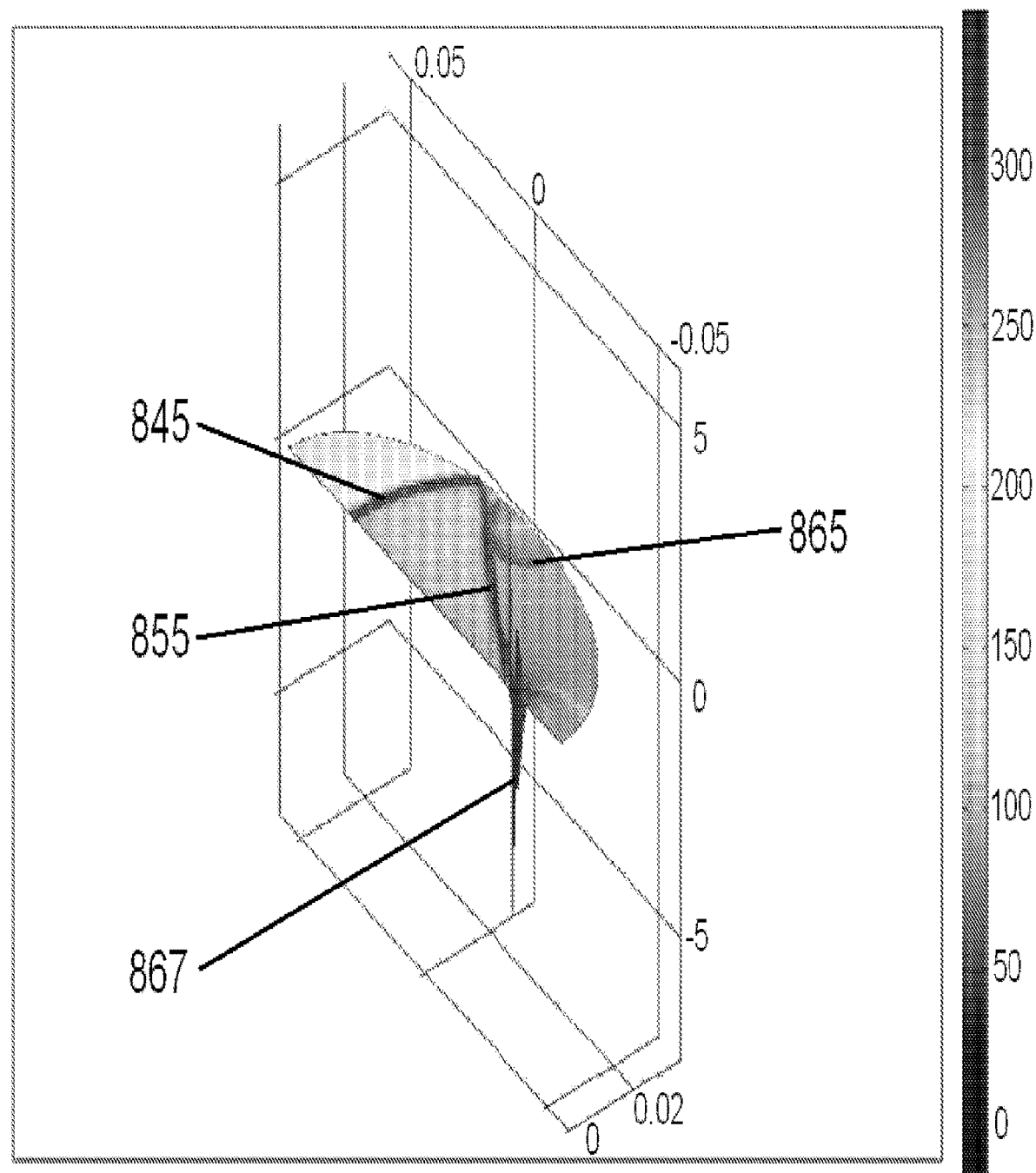

FIGS. 86A and 86B shows the secondary shock waves front (shown in FIGS. 85A and 85B) passing through $F_1$, which due to the spike in pressure 867 acts as a secondary pressure source for a new wave front (tertiary shock waves pressure front 875) with the origin in $F_1$. Also a spherical wave 865 is generated by the reflector's right edge/top rim.

Figure 87A:
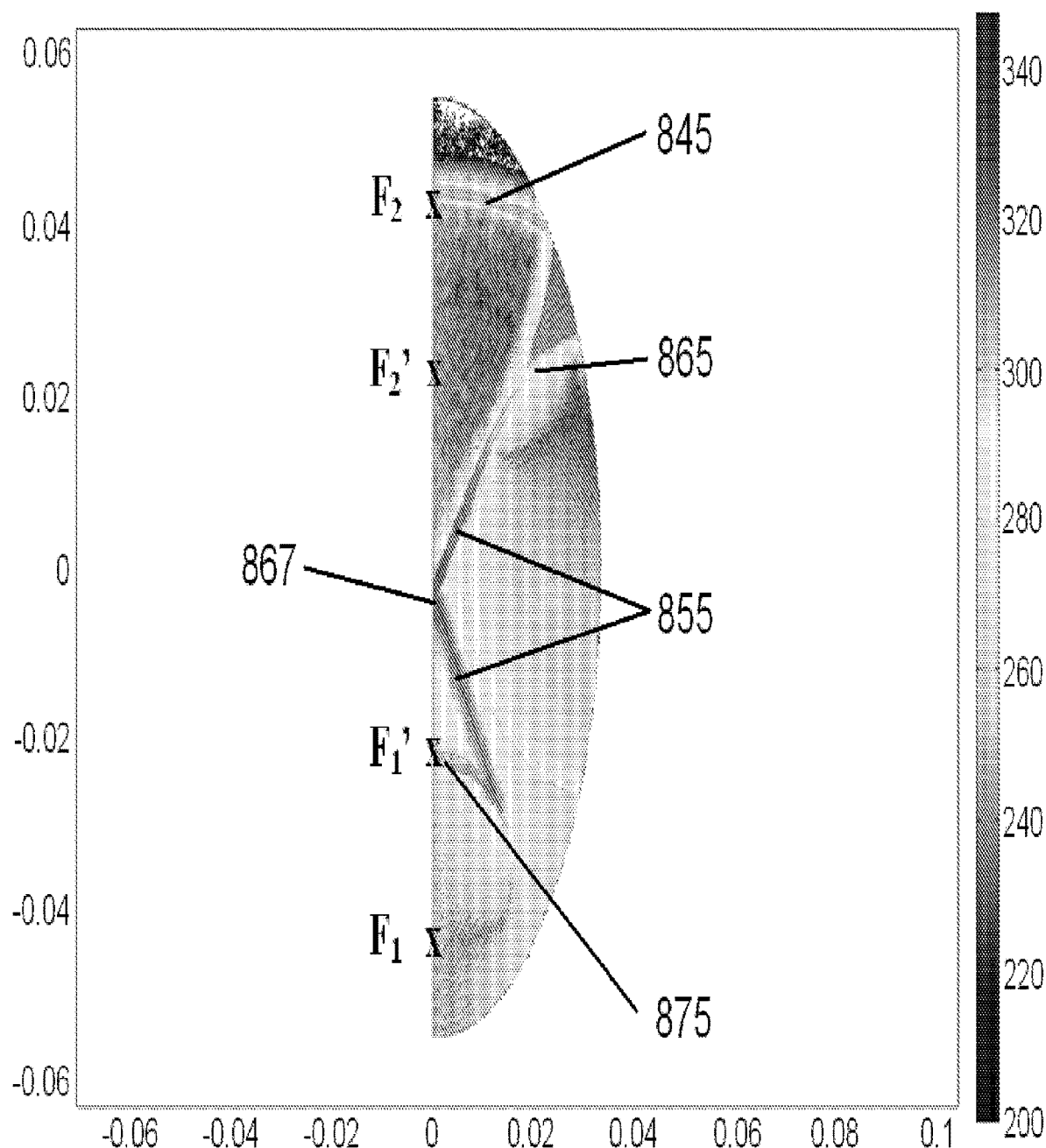
Figure 87B:
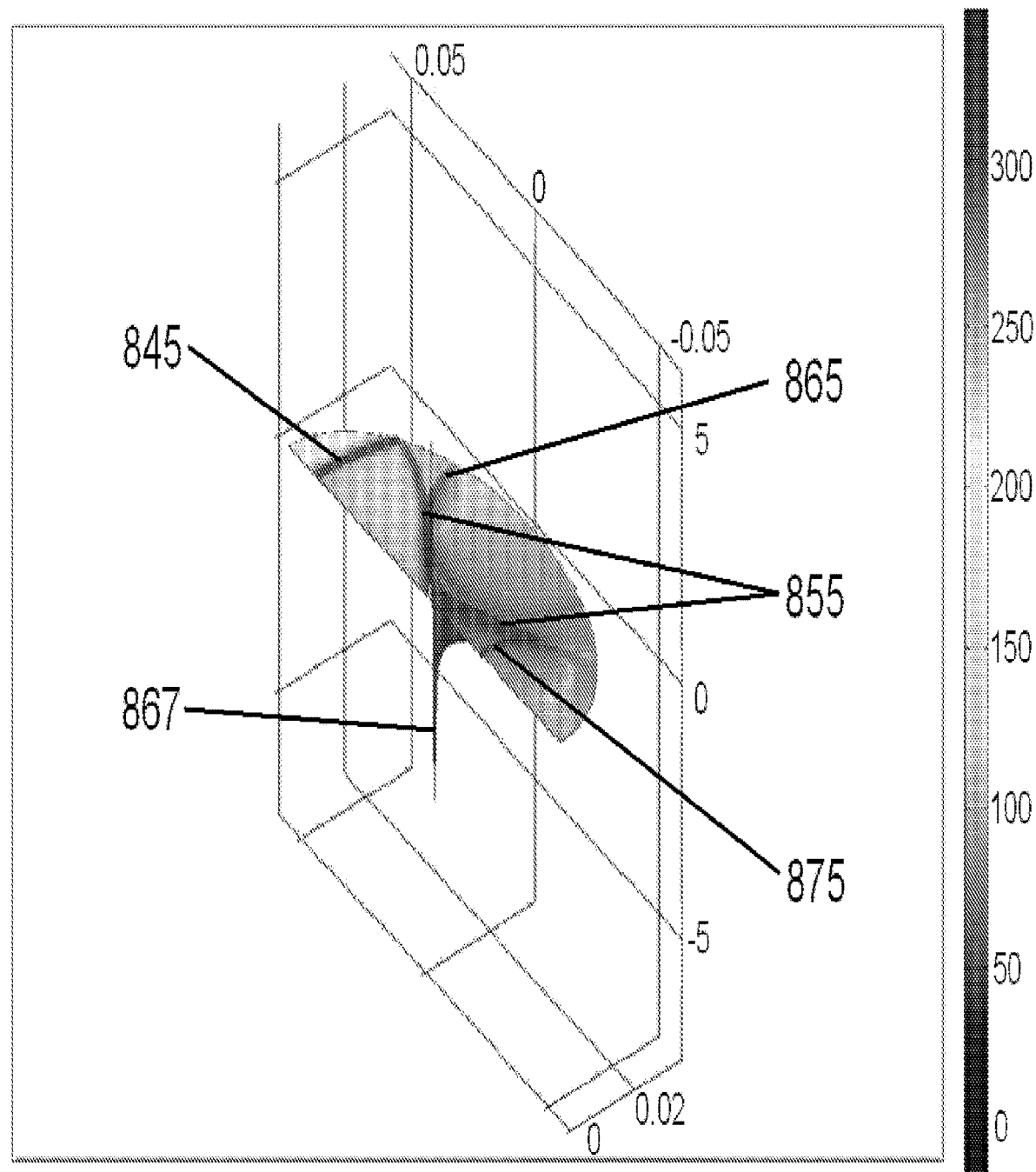

FIGS. 87A and 87B shows the spatial distribution and the time delay between the primary shock waves front (passing through $F_2$ with no spike in pressure), secondary shock waves front (almost a straight line starting to interfere with the reflector's right top rim wave shown in FIGS. 86A and 86B) and the tertiary shock waves front 875.

Figure 88A:
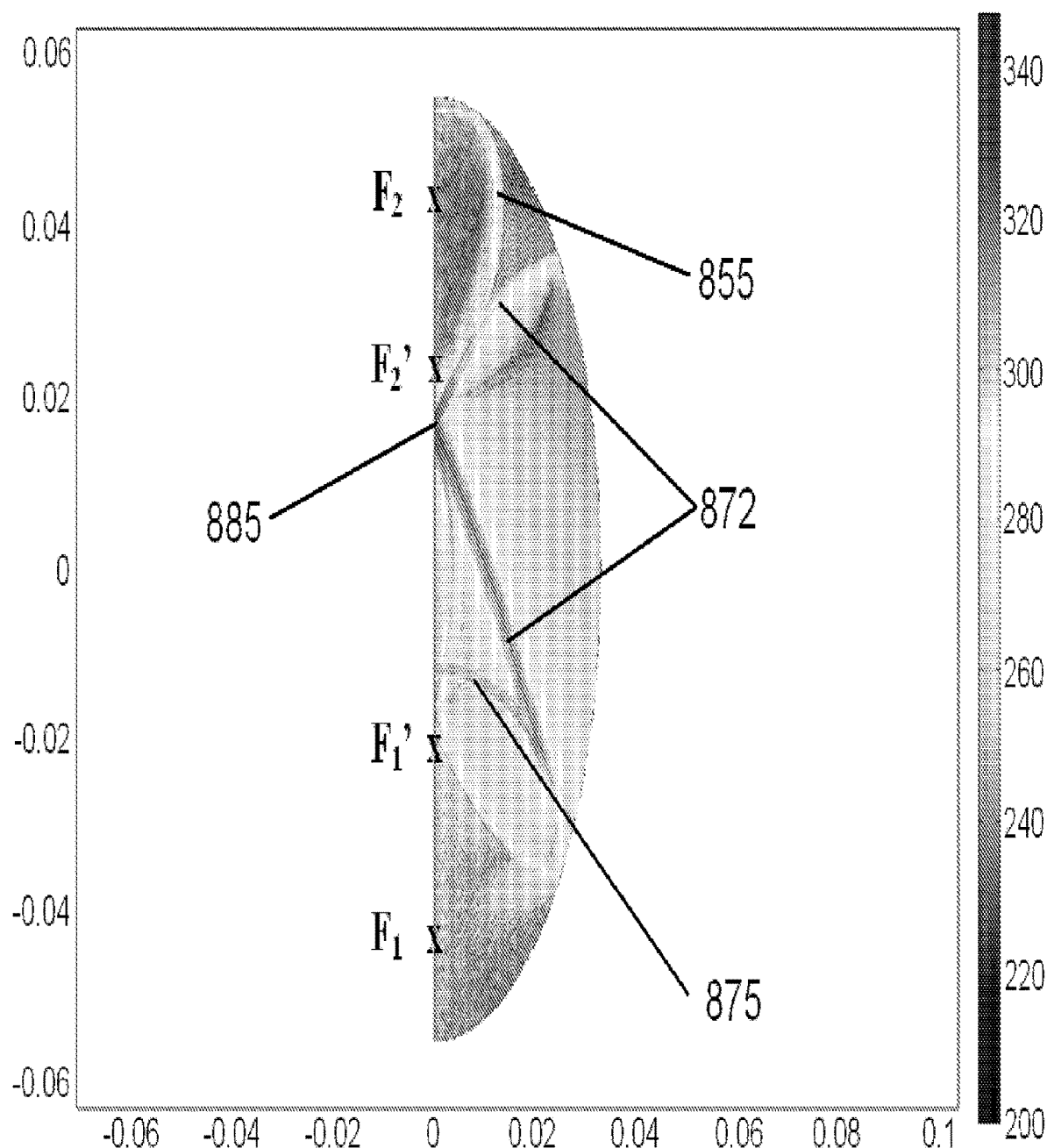
Figure 88B:
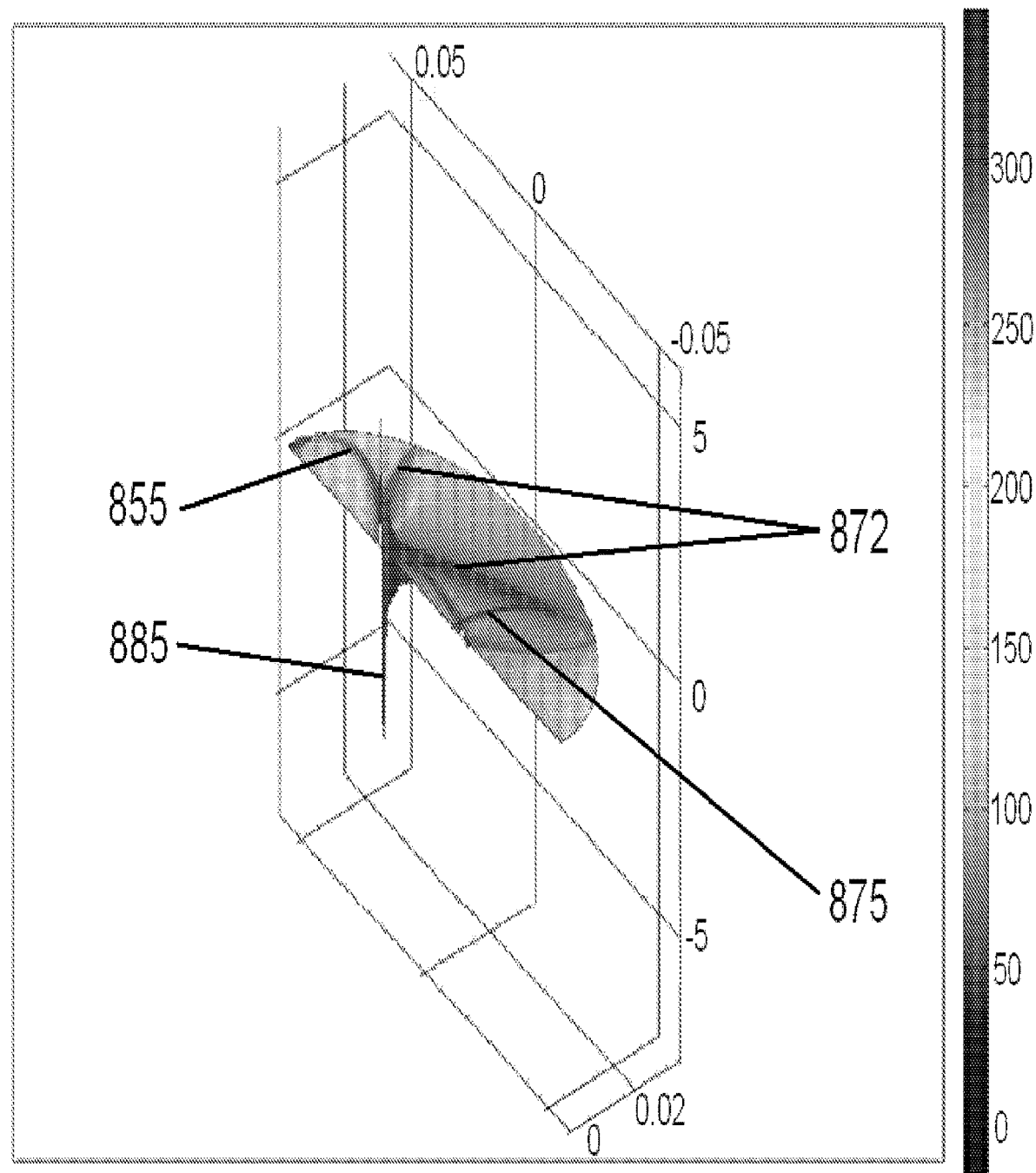

FIGS. 88A and 88B shows the reach of the secondary shock waves front in $F_2'$ (pseudo second focal point), which shows significant pressure spikes 885. Also as seen from FIGS. 86A-87B, the secondary shock waves front 855 brings significant increases in pressure between $F_1$ and $F_2'$, which suggests increased focal volume length. A secondary shock waves front 872 is shown that originates from the left side of the reflector.

Figure 89A:
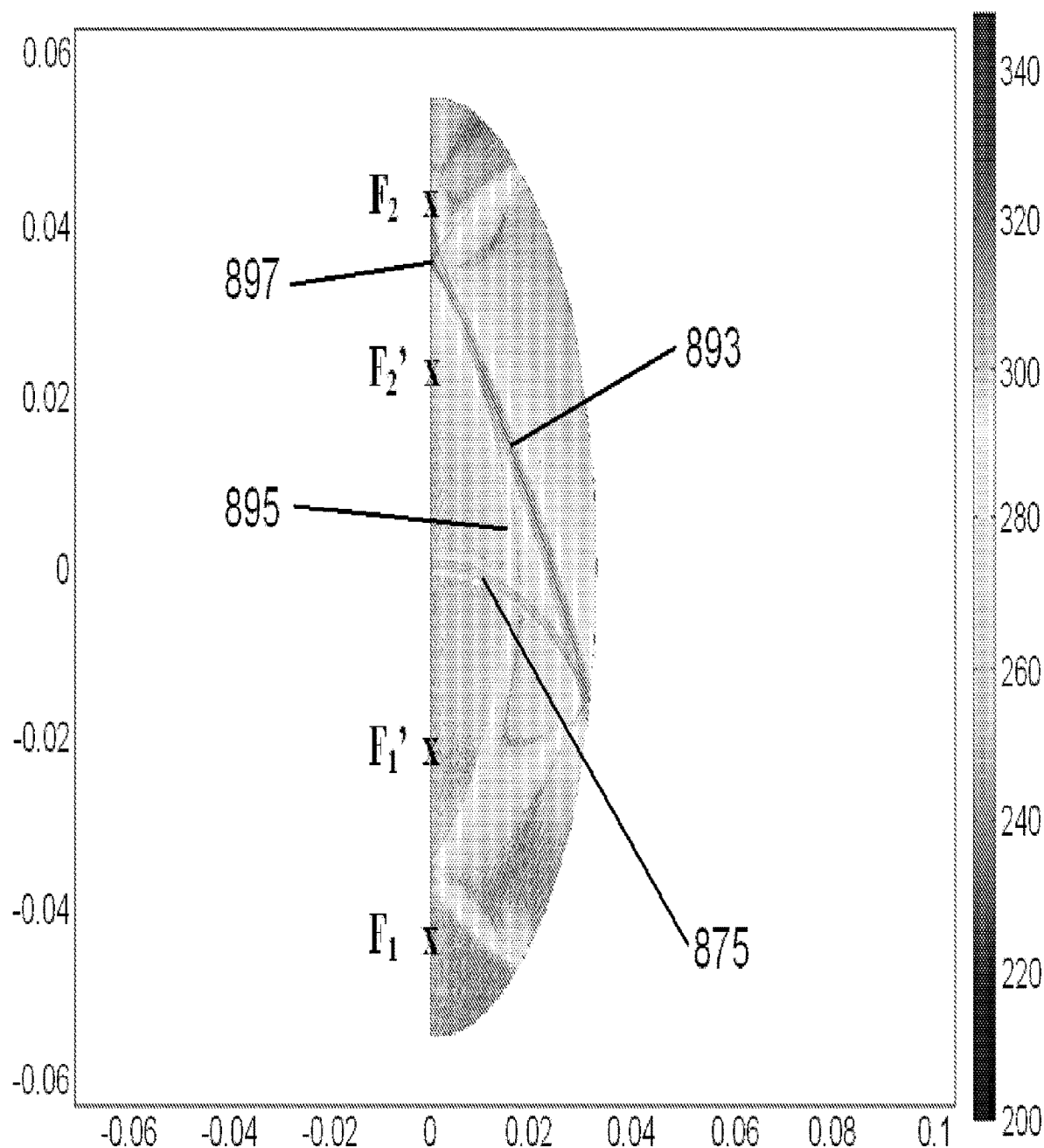
Figure 89B:
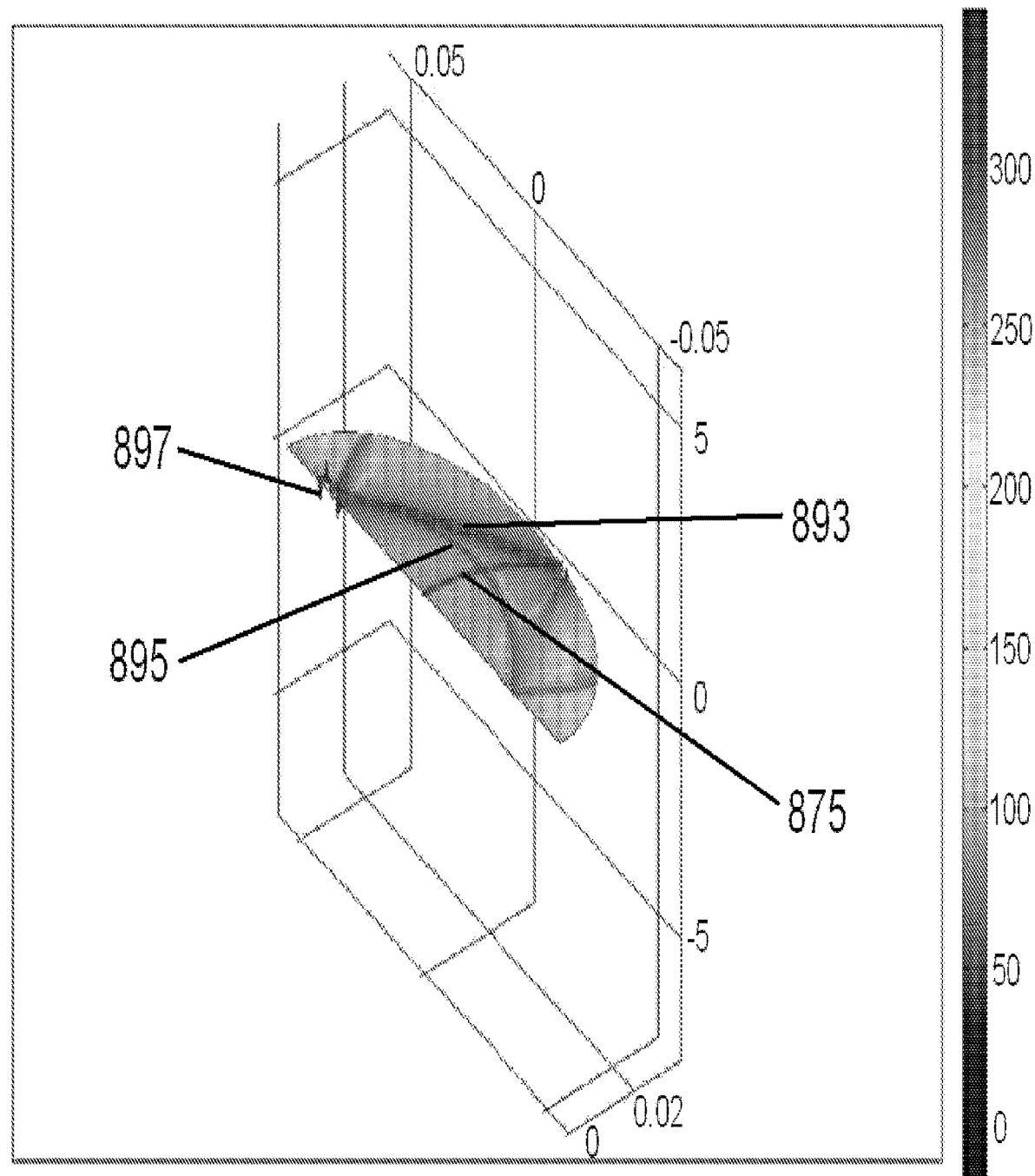

FIGS. 89A and 89B shows the reach of secondary shock waves front in $F_2$ resulting in pressure spike 897. The "remaining secondary shock wave front" 893 formed by interaction of secondary front with the wave produced by reflector's right top rim is pushed away from the axis of the reflector by the tertiary front and the front from left side reflector's rim 895.

Figure 90A:
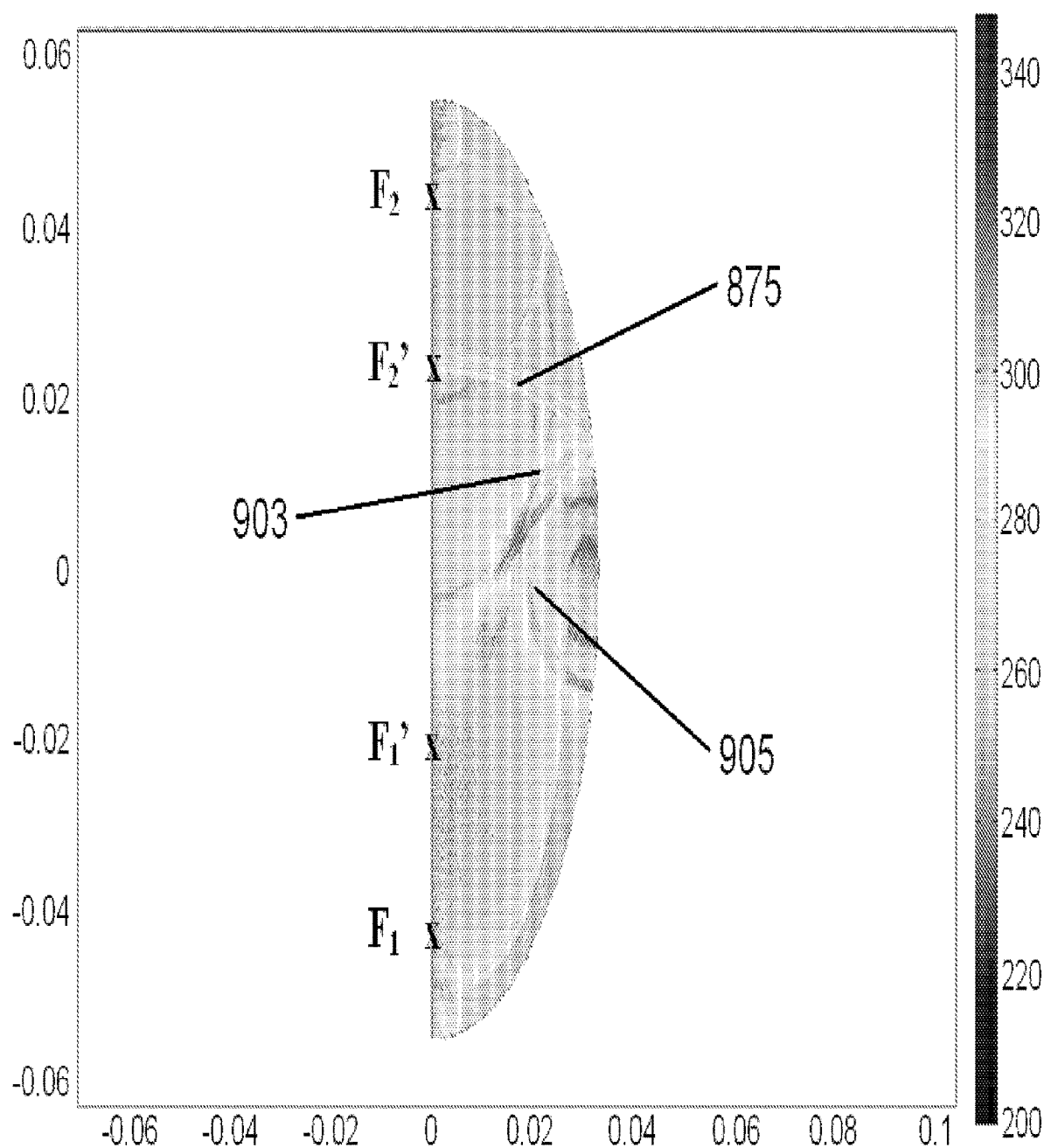
Figure 90B:
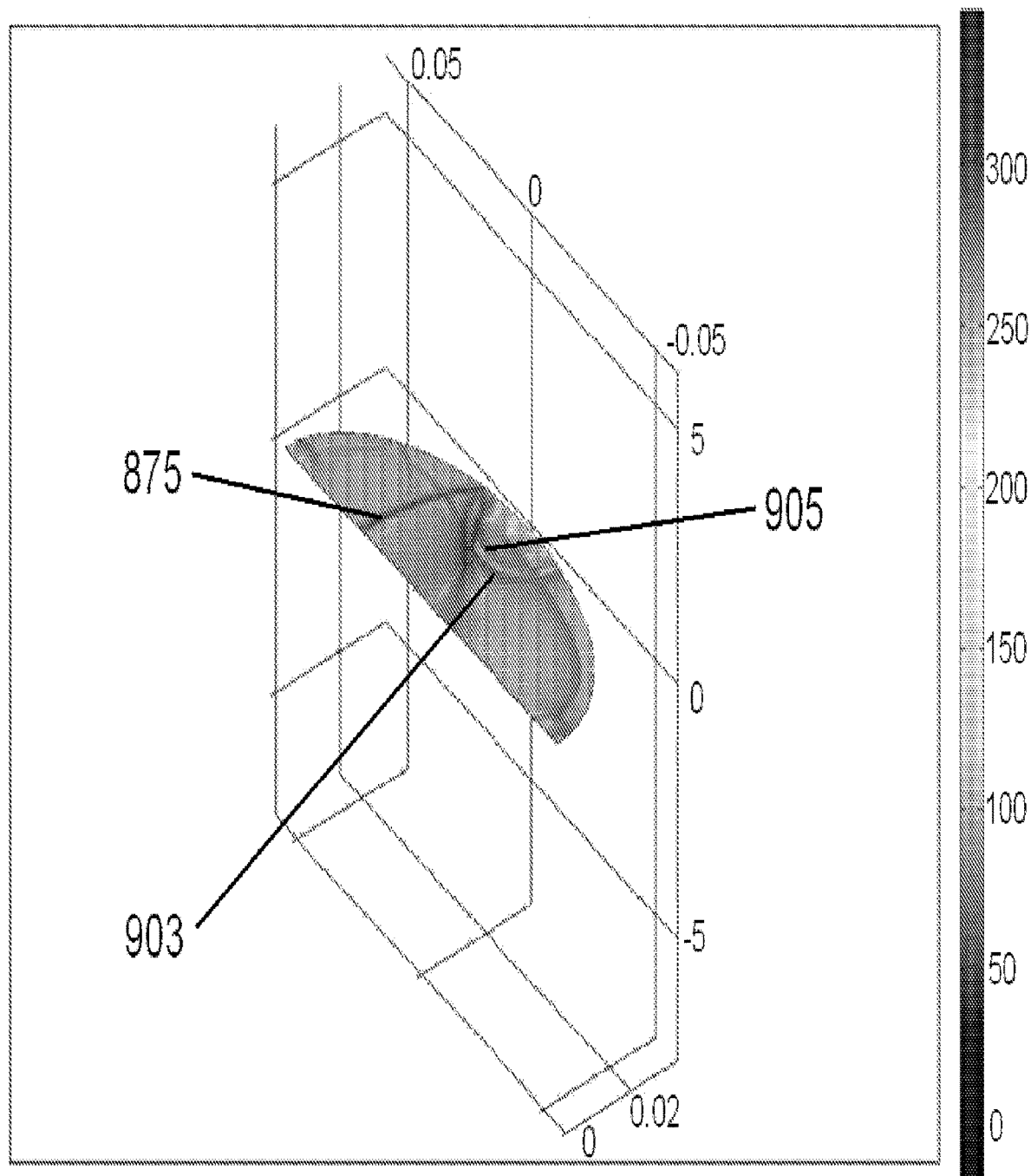

FIGS. 90A and 90B shows the formation of two new fronts from the top rim of the reflector (secondary 903 and tertiary 905), produced by the interaction with remaining secondary shock waves front shown on FIGS. 89A and 89B and with the tertiary wave. The short delay between these fronts makes them prone to interaction.

Figure 91A:
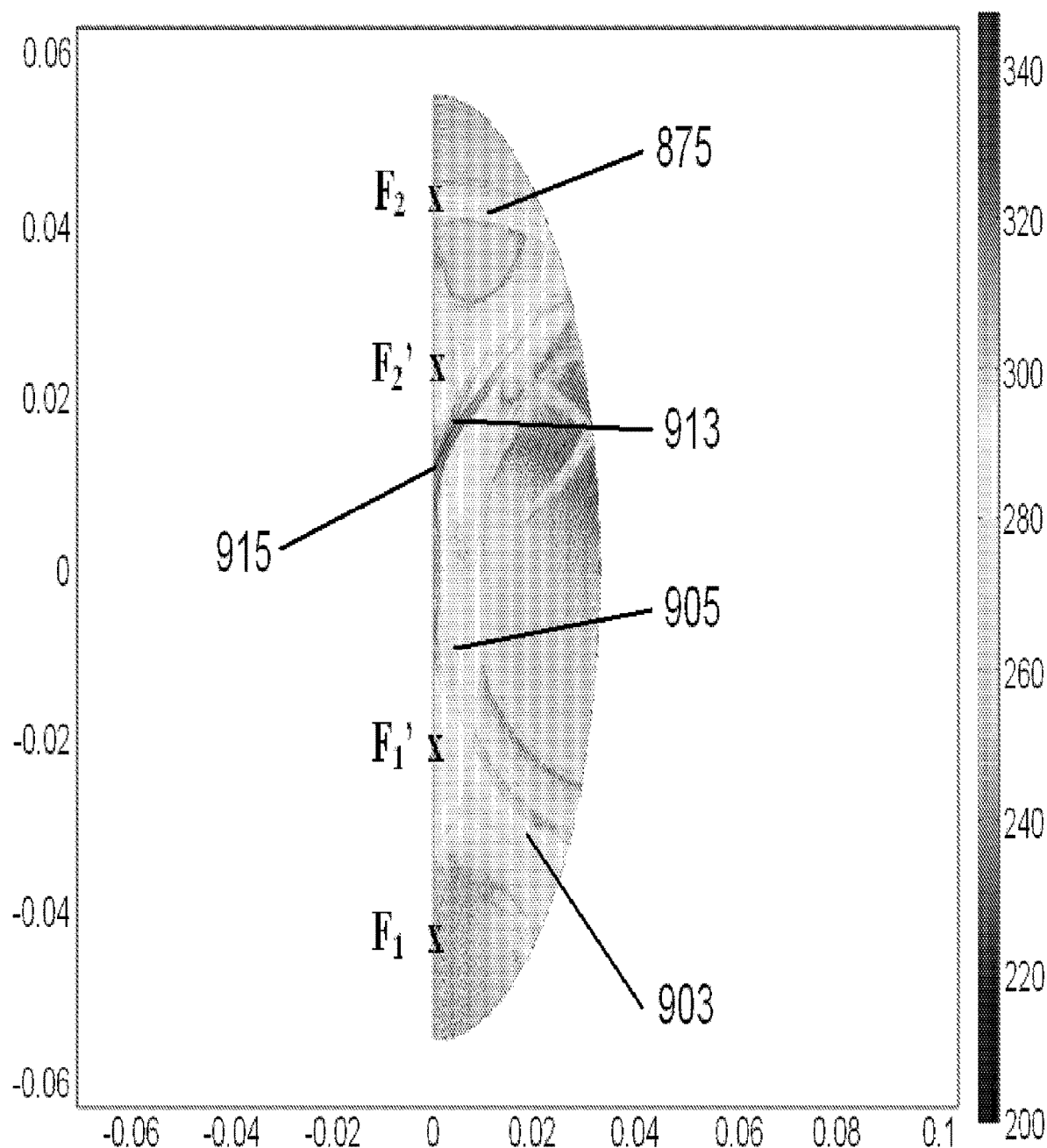
Figure 91B:
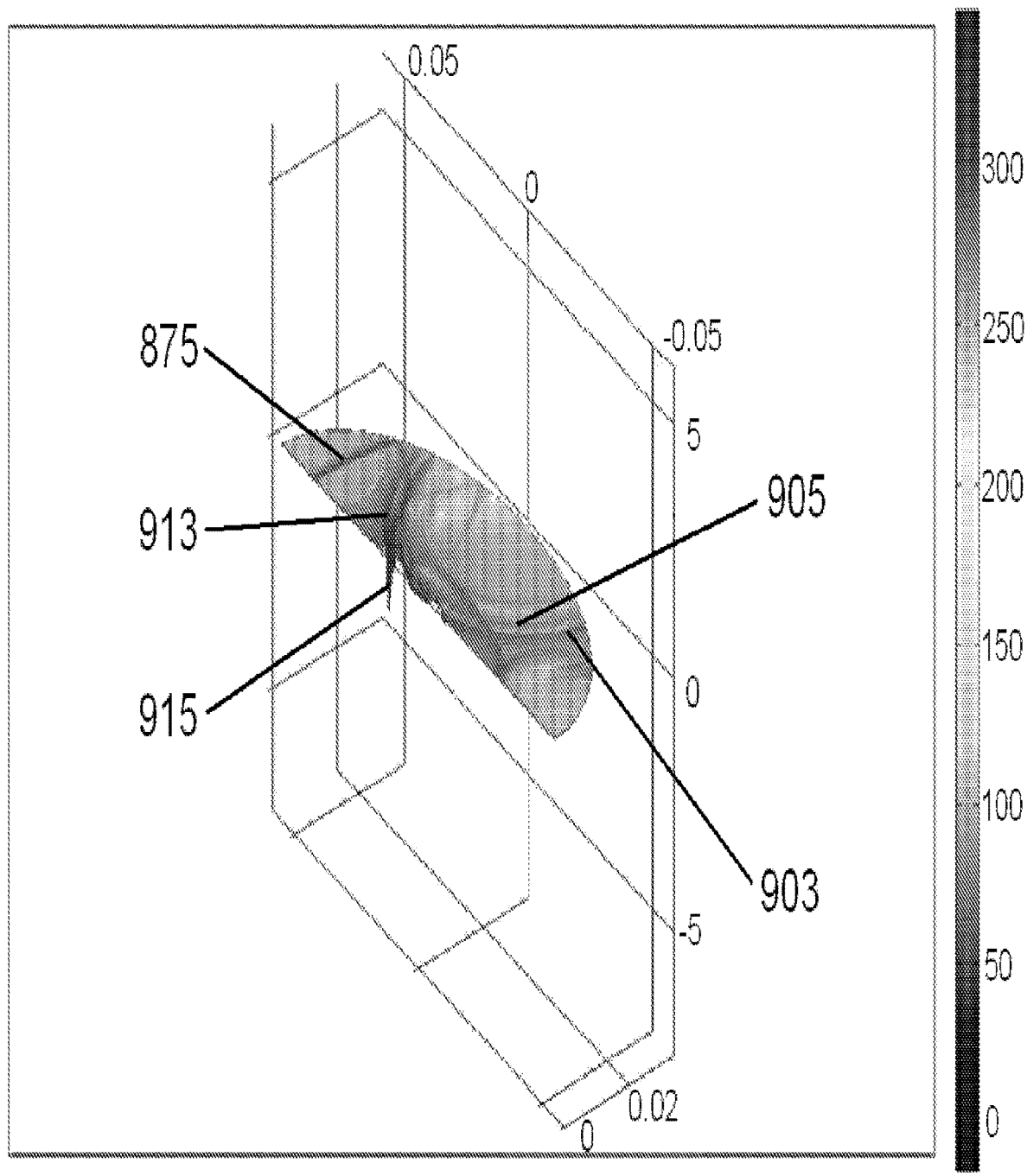

FIGS. 91A and 91B shows the interaction 913 of secondary and tertiary waves close to pseudo focal point $F_2'$. Due to their small time delay the two waves were pushed into each other by the wave coming from left produced by reflector's rim from the left side (see FIGS. 90A and 90B). A new (secondary) spike 915 in pressure results.

Figure 92A:
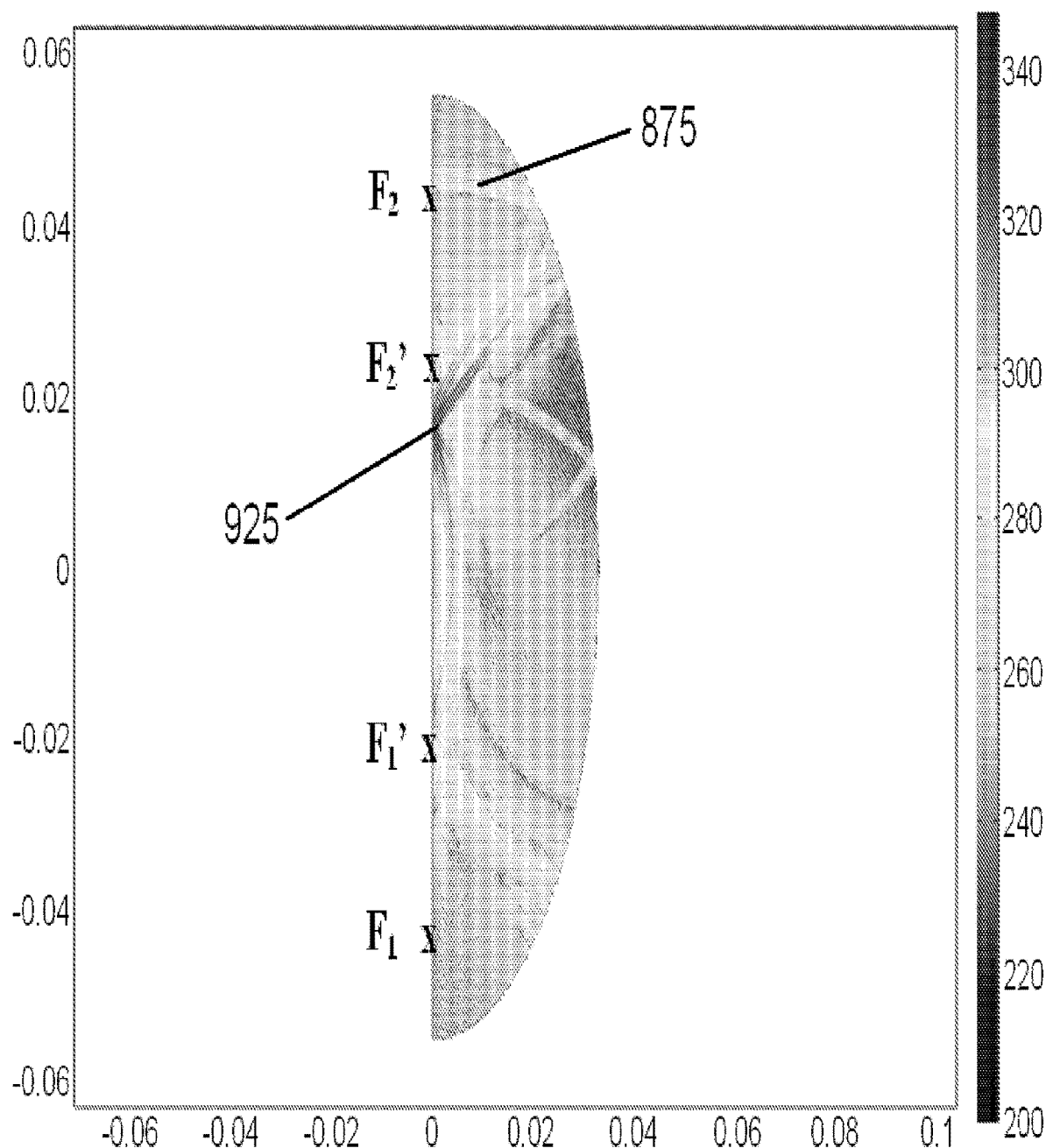
Figure 92B:
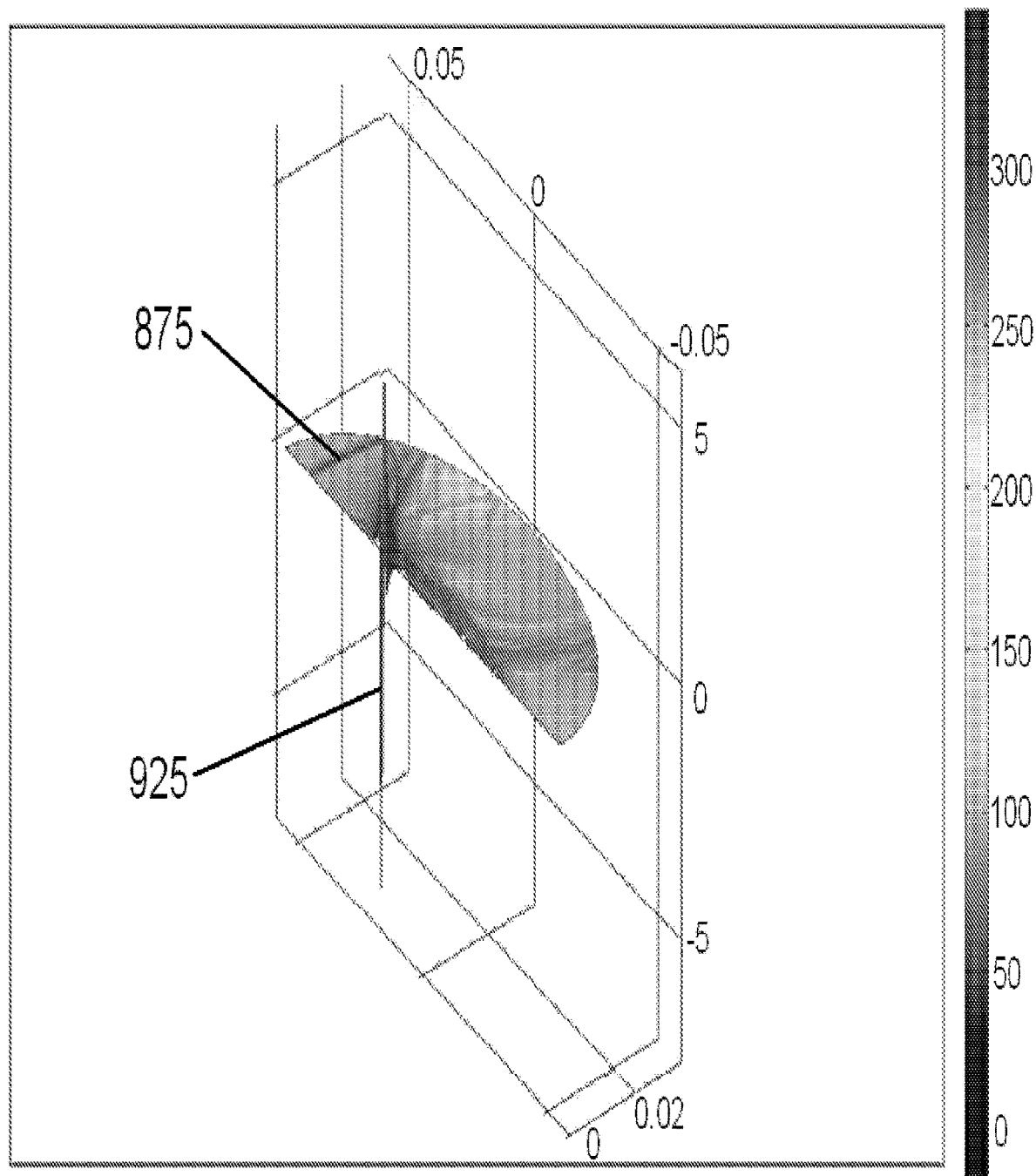

FIGS. 92A and 92B shows that the spike 925 in pressure observed in FIGS. 91A and 91B becomes significant when it reaches $F_2'$ (the second pseudo focal point). That means that besides focal volume 108 extension along the $F_1F_2$ axis, a secondary spike in pressure can be seen in $F_2'$ (the first one was seen in FIG. 88).

Figure 93A:
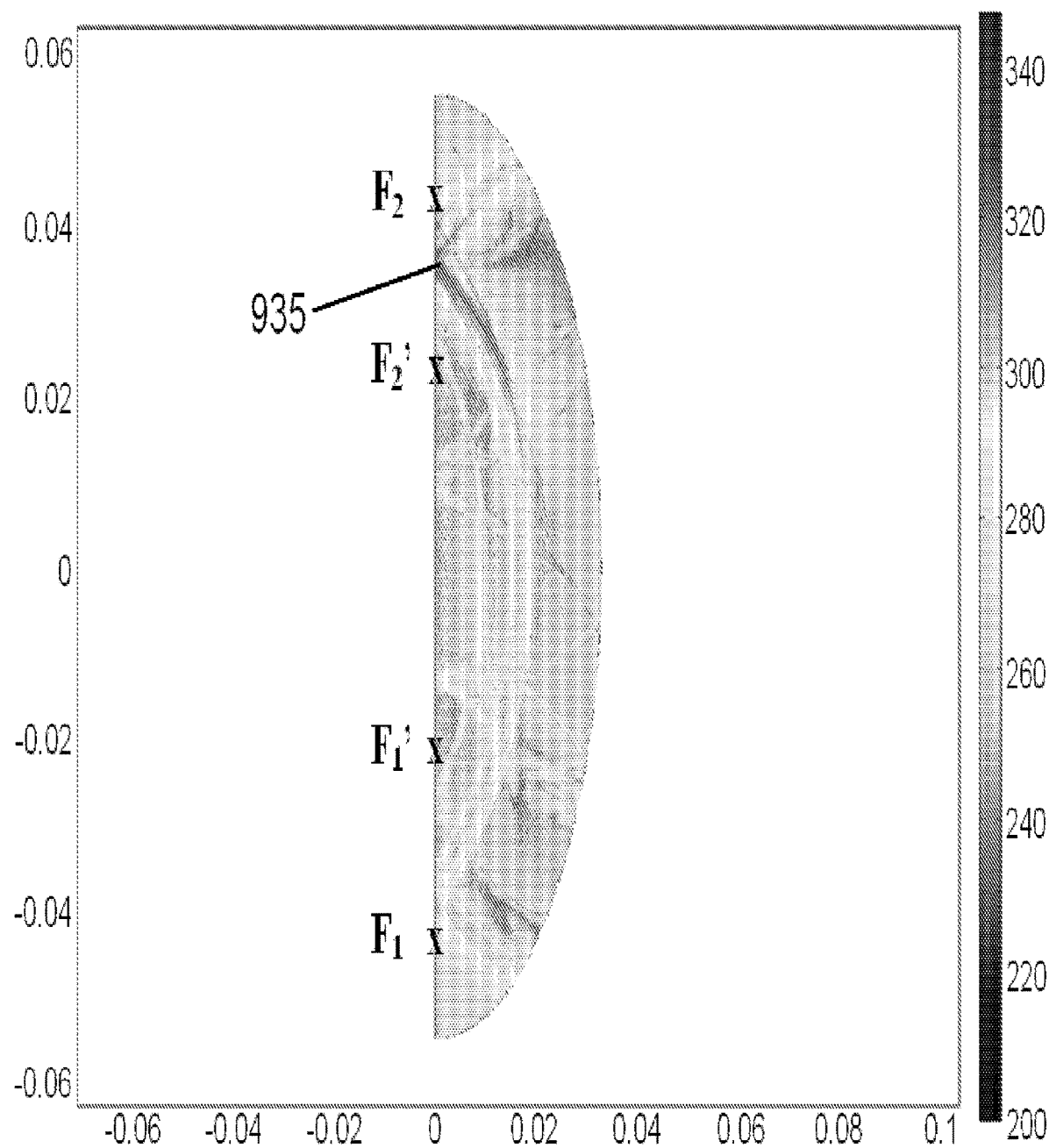
Figure 93B:
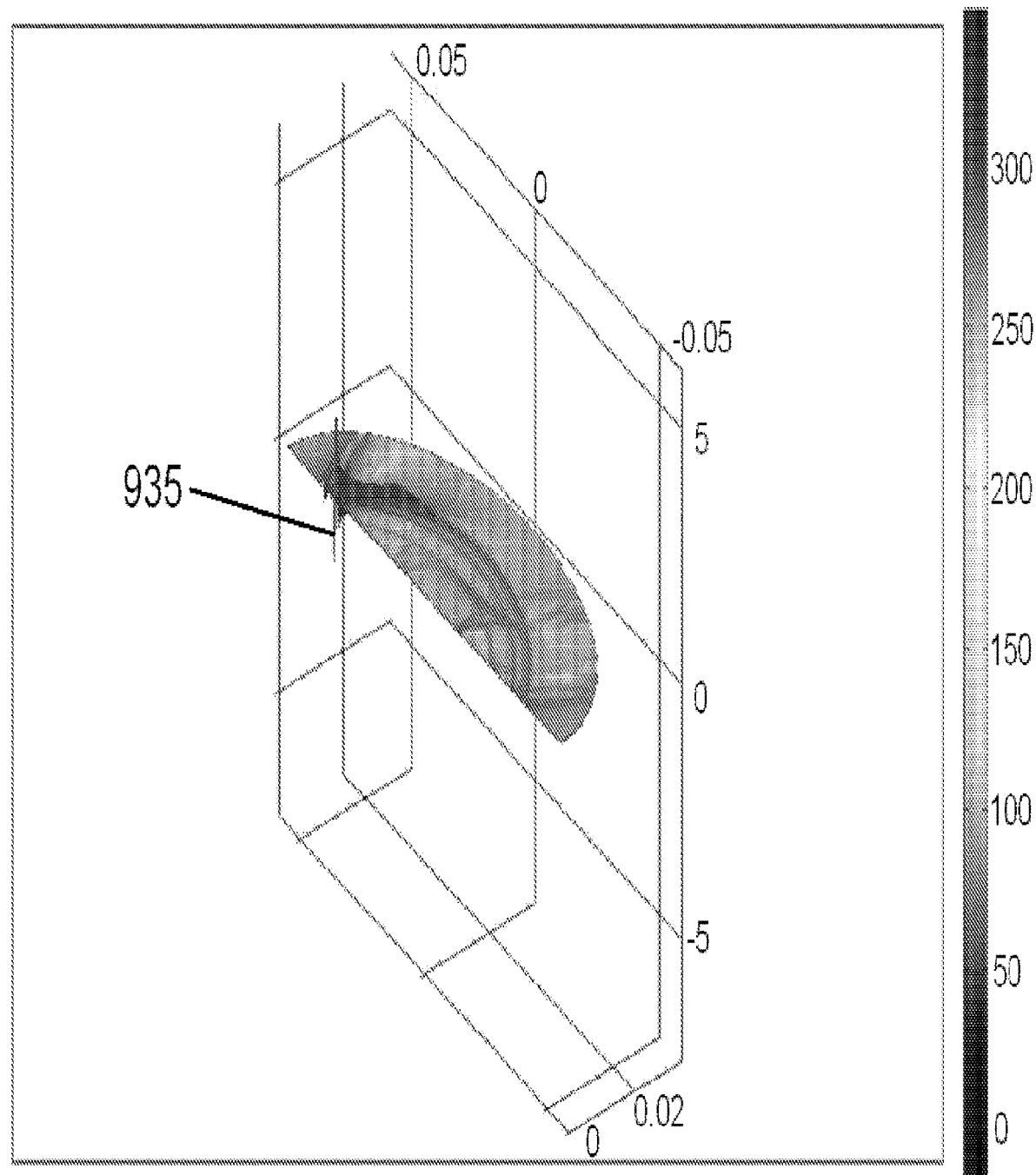

FIGS. 93A and 93B shows that the 935 spike in pressure observed in FIGS. 92A and 92B continues to be seen when it reaches $F_2$ (the second geometrical focal point), which confirms the focal volume 108 extension along the $F_1F_2$ axis.

The foregoing results and graphs show significant difference between the discharge in $F_1$ and in $F_1'$ including:

10 ns after discharge a difference in spatial distribution of the discharge between normal discharge in $F_1$ and the shifted discharge in $F_1'$ is visible.

The direct wave and reflected wave can be clearly distinguished. The time delay between waves is dictated by the distance between the discharge points to the bottom of the reflector.

The reflected wave (that follows closely the direct compression wave) gets distorted due to the reflections on the edge of the reflector. Also, the focusing occurs after the wave passes the edge of the reflector.

The simulation shows that a discharge in $F_1'$ creates a symmetric focal point $F_2'$ situated before $F_2$ (normal geometric second focal point). Also, there are two distinctive peaks that pass through $F_2'$—the first one at 50-60 µs after discharge and the second one at 90 µs. Also, the pressure values are lower than the pressure values generated in the normal way when the discharge takes place in $F_1$.

The focal volume 108 seems to be enlarged when the discharge takes place in $F_1'$ or at least shifted with the distance between $F_1$ and $F_1'$. High pressures are developed before $F_2'$ and in between $F_2'$ and $F_2$.

Figure 94A:
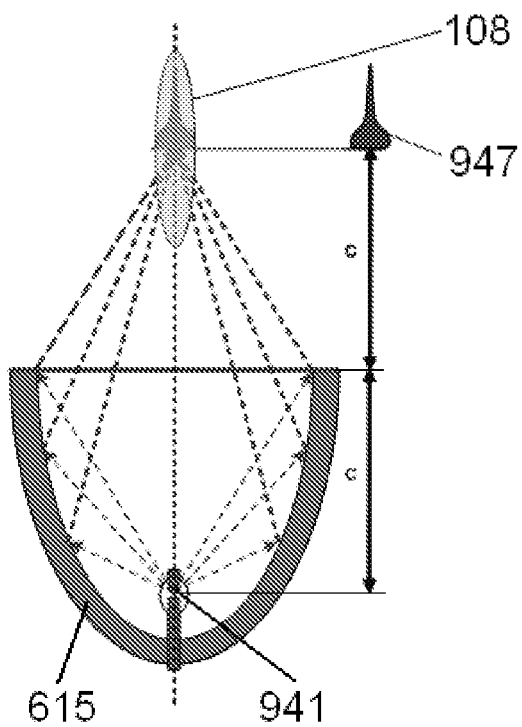
Figure 94B:
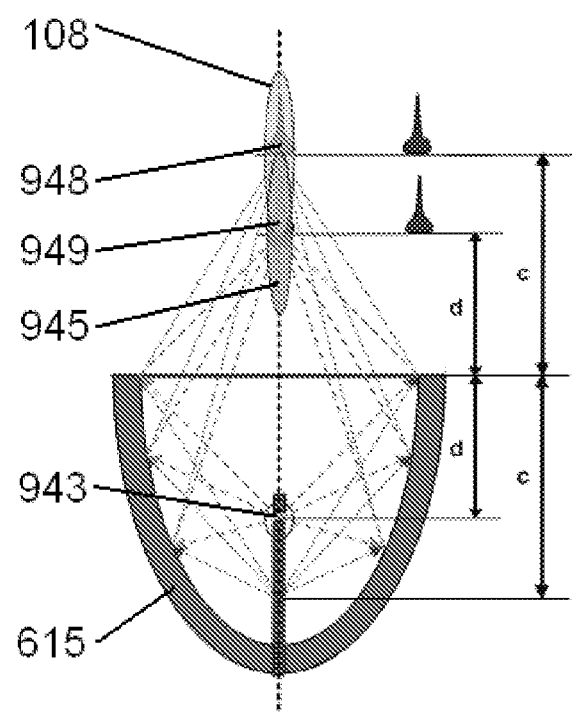

These observations and the interaction shown from the graphs of FIGS. 82A-93B suggest with reference to FIGS. 94A and 94B:

Desirable focusing is realized with the normal discharge in $F_1$ (941) (normal first geometric focal point of the ellipsoid), resulting in pressure distribution 947 in focal volume 108.

Referring to FIGS. 94A and 94B, a discharge away from $F_1$ (941) at discharge point 943 (FIG. 94B) and on the $F_1F_2$ line creates focused pressure shock waves in a pseudo focal point $F_2'$ (949) symmetric with the small axes of symmetry of the ellipsoid. High pressures are still present in $F_2$ (although smaller when compared with the normal discharge in the first geometrical focal point $F_1$), which suggests an elongation of the focal volume 108 or an overlap between a reduced normal focal volume 108 with a pseudo focal volume 945.

In $F_2'$ there are two distinctive pressure shock waves, a primary one 948 in focal volume 108 generated by the discharge in $F_1'$ and a secondary one 949 in pseudo focal volume 945. The second wave seems to be a complex interaction of waves oriented from the edge of the reflector towards the pseudo focal point $F_2'$.

The amount of energy (connected to pressure values show in FIGS. 82A-93B) seems to be lower in the pseudo focal volume 945 centered in $F_2'$ when compared to the energy in the focal volume 108 centered in $F_2$ generated by the normal discharge in $F_1$. A defocused discharge reduces the amount of energy in the corresponding second focal point. If a discharge of 20 kV is used in the first pseudo focal point ($F_1'$) the amount of energy in the second focal point ($F_2$) and the second pseudo focal point ($F_2'$) may be similar to a 15 kV discharge. A broader range of energy can be delivered during treatment using a narrow discharge range for the controlling device. In other words with a 20-28 kV high voltage source, it can be delivered in $F_2$ and $F_2'$ energies equivalent to 8-18 kV, when shifting from $F_1$ to $F_1'$.

The change in focal volume 108 combined with an increased range of energies that can be delivered for the treatment using the same source and reflector geometry, represents two advantages of focal point shifting.

Figure 95:
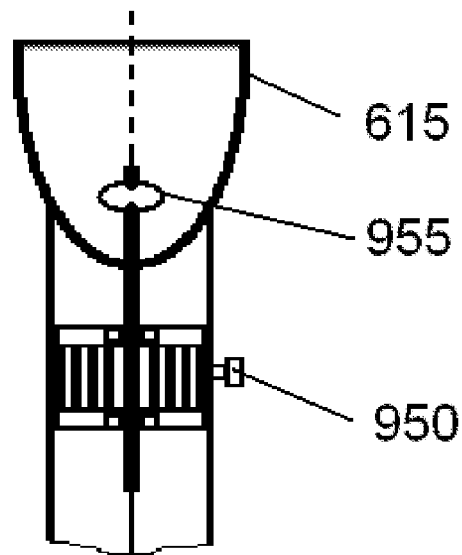

The movement of the electrode 955 inside a reflector with classical geometry 615 as shown in FIG. 95 can be done manually or automatically using an adjustment mechanism 950 such as a screw/nut mechanism, a gear mechanism, sliding mechanism and the like.

The change in focal volume 108 dimension and the enlargement of the bandwidth of energies that can be delivered using a unique high voltage source, and one reflector geometry may be beneficial for treatments using pressure shock waves.

For example, sometimes it is difficult to provide a proper electrohydraulic discharge of voltages lower than 16 kV. The variation from shock to shock can be higher than 50%. By using the shifted focus the discharge can be produced at 20 kV (which provides a more repeatable and consistent discharge) with the advantage of delivery in $F_2'$ an energy equivalent to a 16 kV discharge, other new treatments requiring lower energies from a few kilowatts up to 18 kV may be facilitated.

The high voltage discharge from 18 kV to 30 kV used in conventional electrohydraulic devices and are capable of providing the energy required for pressure shock waves treatments. With a shifted discharge, the range of treatments can range from a few kilovolts up to 30 kV, using one of the existing/commercial available high voltage sources incorporated in the existing commercial available devices.

The foregoing approaches can also be applied in embodiments with reversed reflector geometry 804 as shown in FIG. 96.

In a reflector with reversed reflector geometry 804, the area treated in one shock is much larger due to the fact that the treatment area is crossed longitudinally by the focal volume 108 instead of transversely. The significant longitudinal increase in the focal volume 108 length (due the combination of normal focal volume 965 with pseudo focal volume 967) may further improve the efficiency of the treatment for superficial treatment areas. Specifically, electrode 961 ($F_1$) to selectively generate electrode 962 ($F_2$) may shift normal focal volume 965 and pseudo focal volume 967 that intersect the body contact plane 807. Volume 965 arises from wave front 963 that originates at electrode 961 and pseudo focal volume 967 arises from wave front 964 that originates at electrode 962. In the reverse reflector embodiment of FIG. 96, the longitudinal axis of symmetry 803 of the ellipsoid 801 is shown to intersect all points $F_1$-$F_4$ without coinciding with the contact plane 807. This improved efficiency translates in reduced number of movements per treatment necessary to cover a large treatment area.

While the invention has been described with reference to exemplary structures and methods in embodiments, the invention is not intended to be limited thereto, but to extend to modifications and improvements within the scope of equivalence of such claims to the invention.

What is claimed is:

1. A method for treating a target location of a blood vessel, comprising the steps of:
   providing an apparatus comprising:
      a catheter sized to fit in a blood vessel including a proximal end and distal end; and
      multiple shock wave discharge points within a balloon positioned along the catheter between the proximal end and the distal end, wherein the distal end extends distally beyond the balloon and the proximal end extends proximally beyond the balloon;
   placing a guidewire into the blood vessel;
   advancing a guidewire lumen over the guidewire to advance the balloon to the target location of the blood vessel;
   inflating the balloon with fluid;
   producing non-focused shock waves by activating an electronic controller connected to at least one electrode at each shock wave discharge point of the multiple shock wave discharge points;
   applying the non-focused shock waves through the balloon to treat the target location with the shock waves;
   deflating the balloon; and
   withdrawing the catheter from the blood vessel.

2. The method of claim 1, further comprising producing the non-focused shock waves substantially simultaneously at the shock wave discharge points via the electronic controller.

3. The method of claim 2, wherein each of the shock wave discharge points include a spark gap.

4. The method of claim 3, further comprising activating the electronic controller multiple times to generate multiple shock waves from each spark gap of each of the shock wave discharge points to provide multiple treatments to the target location.

5. The method of claim 4, wherein a first shock wave discharge point including a spark gap is spaced apart from a second shock wave discharge point including a spark gap along a longitudinal axis of the catheter.

6. The method of claim 5, wherein the balloon is non-perforated.

7. The method of claim 1, further comprising producing the non-focused shock waves sequentially at the shock wave discharge points via the electronic controller.

8. The method of claim 7, wherein each of the shock wave discharge points include a spark gap.

9. The method of claim 1, further comprising producing the non-focused shock waves in a predetermined pattern at the shock wave discharge points via the electronic controller.

10. The method of claim 9, wherein each of the shock wave discharge points include a spark gap.

11. The method of claim 1, further comprising producing radial shock waves by activating the electronic controller.

12. The method of claim 11, wherein each of the shock wave discharge points include a spark gap.

13. The method of claim 1, further comprising using radiopaque markers to position the balloon to the target location of the blood vessel.

14. The method of claim 13, wherein each of the shock wave discharge points include a spark gap.

15. The method of claim 1, wherein each of the shock wave discharge points include a spark gap.

16. The method of claim 15, further comprising activating the electronic controller multiple times to generate multiple shock waves from each spark gap of each of the shock wave discharge points to provide multiple treatments to the target location.

17. The method of claim 16, wherein a first shock wave discharge point including a spark gap is spaced apart from a second shock wave discharge point including a spark gap along a longitudinal axis of the catheter.

18. The method of claim 1, further comprising activating the electronic controller multiple times to generate multiple shock waves from each of the shock wave discharge points to provide multiple treatments to the target location.

19. The method of claim 18, wherein a first shock wave discharge point including a spark gap is spaced apart from a second shock wave discharge point including a spark gap along a longitudinal axis of the catheter.

20. The method of claim 1, wherein the balloon is non-perforated.

21. A method for treating a target location of a blood vessel, comprising the steps of:
providing an apparatus comprising:
a catheter sized to fit in a blood vessel including a proximal end and distal end; and
a first shock wave discharge point including a spark gap and a second shock wave discharge point including a spark gap within a non-perforated balloon positioned along the catheter between the proximal end and the distal end, wherein each shock wave discharge point is positioned along a longitudinal axis of the catheter and each shock wave discharge point is spaced apart from one another, and wherein the distal end extends distally beyond the balloon and the proximal end extends proximally beyond the balloon;
placing a guidewire into the blood vessel;
advancing a guidewire lumen over the guidewire to advance the balloon to the target location of the blood vessel;
visualizing that the ballon has reached the target location with radiopaque markers;
inflating the balloon with fluid;
producing non-focused shock waves at the first and second shock wave discharge points by activating an electronic controller;
applying the non-focused shock waves through the balloon to treat the target location with the shock waves;
deflating the balloon; and
withdrawing the catheter from the blood vessel.

22. A method for treating a target location of a blood vessel, comprising the steps of:
providing an apparatus comprising:
a catheter sized to fit in a blood vessel including a proximal end and a distal end; and
a first spark gap with a first electrode and a second spark gap with a second electrode within a balloon, wherein each spark gap is positioned along a longitudinal axis of the catheter between the proximal end and the distal end;
placing a guidewire into the blood vessel;
advancing a guidewire lumen over the guidewire to advance the balloon to the target location of the blood vessel;
visualizing that the ballon has reached the target location with radiopaque markers;
inflating the balloon with fluid;
producing non-focused shock waves by activating an electronic controller connected to the first electrode of the first spark gap and to the second electrode of the second spark gap;
applying the non-focused shock waves through the balloon to treat the target location with the shock waves;
deflating the balloon; and
withdrawing the catheter from the blood vessel.

23. The method of claim 22, further comprising producing the non-focused shock waves substantially simultaneously at each of the first and second spark gaps via the electronic controller.

24. The method of claim 23, further comprising producing radial shock waves by activating the electronic controller.

25. The method of claim 22, further comprising producing radial shock waves by activating the electronic controller.

26. The method of claim 22, further comprising activating the electronic controller multiple times to generate multiple shock waves from each of first and second spark gaps to provide multiple treatments to the target location.

27. The method of claim 26, wherein the first spark gap is spaced apart along a longitudinal axis of the catheter from the second spark gap.

28. The method of claim 22, wherein the first spark gap is spaced apart along a longitudinal axis of the catheter from the second spark gap.

29. The method of claim 22, wherein the balloon is non-perforated.

* * * * *